US008802597B2

(12) United States Patent
Clark et al.

(10) Patent No.: US 8,802,597 B2
(45) Date of Patent: Aug. 12, 2014

(54) HERBICIDAL PYRIMIDINES

(75) Inventors: David Alan Clark, Landenberg, PA (US); Bruce Lawrence Finkelstein, Newark, DE (US); Gregory Russell Armel, Knoxville, TN (US); Vernon Arie Wittenbach, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 348 days.

(21) Appl. No.: 12/963,231

(22) Filed: Dec. 8, 2010

(65) Prior Publication Data

US 2011/0077156 A1 Mar. 31, 2011

Related U.S. Application Data

(63) Continuation of application No. 10/581,897, filed as application No. PCT/US2004/042302 on Dec. 16, 2004, now Pat. No. 7,863,220.

(60) Provisional application No. 60/531,300, filed on Dec. 19, 2003, provisional application No. 60/598,397, filed on Aug. 3, 2004.

(51) Int. Cl.
*C07D 239/42* (2006.01)
*A01N 43/54* (2006.01)

(52) U.S. Cl.
USPC ........... 504/225; 504/239; 504/242; 544/122; 544/329

(58) Field of Classification Search
USPC .................. 544/122, 329; 504/225, 239, 242
See application file for complete search history.

(56) References Cited

U.S. PATENT DOCUMENTS

| | | | |
|---|---|---|---|
| 4,014,677 A | 3/1977 | Fischer | |
| 4,490,375 A | 12/1984 | Hoegerle et al. | |
| 4,674,229 A | 6/1987 | Burdeska et al. | |
| 5,138,058 A | 8/1992 | Geisen et al. | |
| 5,324,710 A | 6/1994 | Ort et al. | |
| 5,525,724 A | 6/1996 | Hunds | |
| 5,631,038 A | 5/1997 | Kurtz et al. | |
| 5,631,122 A | 5/1997 | Mihayashi et al. | |
| 5,631,231 A | 5/1997 | Kurtz et al. | |
| 5,646,122 A | 7/1997 | Kurtz et al. | |
| 5,654,311 A | 8/1997 | Kurtz et al. | |
| 5,668,140 A | 9/1997 | Schaper et al. | |
| 5,700,792 A | 12/1997 | Kurtz et al. | |
| 5,859,020 A | 1/1999 | Preuss et al. | |
| 6,090,815 A | 7/2000 | Masuda et al. | |
| 6,281,358 B1 | 8/2001 | Meyer et al. | |
| 6,297,197 B1 | 10/2001 | Fields et al. | |
| 6,528,513 B2 | 3/2003 | Cushing et al. | |
| 6,559,307 B2 | 5/2003 | Meyer et al. | |
| 6,706,740 B2 | 3/2004 | Ricks et al. | |
| 6,784,137 B2 | 8/2004 | Balko et al. | |
| 6,835,726 B2 | 12/2004 | Cushing et al. | |
| 7,144,903 B2 | 12/2006 | Collins et al. | |
| 7,235,571 B2 | 6/2007 | Beckmann et al. | |
| 7,291,580 B2 | 11/2007 | Balko et al. | |
| 7,300,907 B2 * | 11/2007 | Epp et al. ..................... 504/239 |
| 7,314,849 B2 | 1/2008 | Balko et al. | |
| 7,432,227 B2 | 10/2008 | Balko et al. | |
| 7,538,214 B2 * | 5/2009 | Epp et al. ..................... 544/329 |
| 7,642,220 B2 * | 1/2010 | Epp et al. ..................... 504/239 |
| 7,888,287 B2 * | 2/2011 | Epp et al. ..................... 504/239 |
| 7,915,200 B2 * | 3/2011 | Epp et al. ..................... 504/239 |

(Continued)

FOREIGN PATENT DOCUMENTS

DE 3807532 A 9/1989
EP 136976 A2 4/1985
(Continued)

OTHER PUBLICATIONS

J Clark et al. "Heterocyclic Studies, Part VIII. 2 Phenylpteridine and Some Related Compounds" J. Chem. Soc. C: Organic 1969 (10), pp. 1408-1412.
J.L. Hilton et al., Mechanisms of Herbicide Action, Crops Research Division, Agricultural Research Service, U.S. Department of Agriculture, Beltsville, Maryland, 1963, pp. 353-384.
Pesticide Manual, British Crop Protection Council, Thirteenth Edition, 2003, pp. 254-258.
Pesticide Manual, British Crop Protection Council, Thirteenth Edition, 2003, pp. 610-614.
Pesticide Manual, British Crop Protection Council, Thirteenth Edition, 2003, pp. 782-785.
Schtilman et al., Correlation between Plant Growth Regulator Rlease Rate and Bioactivity for the Series of Newly Synthesized Phyoactive Polymers, Journal of Plant Growth Regulation, 2006, 25, 211-218.
Harvey, Biological Activity of 2,4-D Esters on Rubber Vine (Crptostegia graniflora) Dependence on Vapour Pressure and Molecular Weight and Isomerism of the Alcohol Substituent, Australian Journal of Agricultural Research, 1989, 40 (3), 685-690.
Aizawa, Metabolic Maps of Pesticides, 1982, pp. 93 and 95, Academic Press.
Collette, Environmental Science and Technology, 1990, 24(11), pp. 1671-1676.
W. J. Middleton et al. "Cyanocarbon Chemistry IX, Heterocyclic Compounds from Dicyanoketene Acetals" J. of the Amer. Chem. Soc. vol. 80, Jun. 5, 1958 pp. 2829-2832.
Tu et al., Weed Control Methods Handbook, The Nature Convervancy, Apr. 2001, pp. 6.1-6.13.

*Primary Examiner* — Deepak Rao
(74) *Attorney, Agent, or Firm* — Reed A Coats

(57) ABSTRACT

Compounds of Formula I, and their N-oxides and agriculturally suitable salts, are disclosed which are useful for controlling undesired vegetation

I

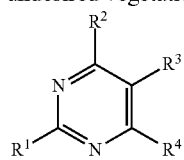

wherein
R$^1$ is cyclopropyl optionally substituted with 1-5 R$^5$, isopropyl optionally substituted with 1-5 R$^6$, or phenyl optionally substituted with 1-3 R$^7$;
R$^2$ is ((O)$_j$C(R$^{15}$)(R$^{16}$))$_k$R;
R is CO$_2$H or a herbicidally effective derivative of CO$_2$H;
R$^3$ is halogen, cyano, nitro, OR$^{20}$, SR$^{21}$ or N(R$^{22}$)R$^{23}$;
R$^4$ is —N(R$^{24}$)R$^{25}$ or —NO$_2$;
j is 0 or 1; and k is 0 or 1; provided that when k is 0, then j is 0;
and R$^5$, R$^6$, R$^7$, R$^{15}$, R$^{16}$, R$^{20}$, R$^{21}$, R$^{22}$, R$^{23}$, R$^{24}$ and R$^{25}$ are as defined in the disclosure.

Also disclosed are compositions comprising the compounds of Formula I and a method for controlling undesired vegetation which involves contacting the vegetation or its environment with an effective amount of a compound of Formula I. Also disclosed are compositions comprising a compound of Formula I and at least one additional active ingredient selected from the group consisting of an other herbicide and a herbicide safener.

38 Claims, No Drawings

(56) References Cited

U.S. PATENT DOCUMENTS

| | | | |
|---|---|---|---|
| 2002/0013316 A1 | 1/2002 | Furuta et al. | |
| 2003/0130264 A1 | 7/2003 | Jaen | |
| 2003/0171218 A1 | 9/2003 | Bojack et al. | |
| 2004/0039035 A1 | 2/2004 | Collins et al. | |
| 2008/0091016 A1 | 4/2008 | Epp et al. | |

FOREIGN PATENT DOCUMENTS

| | | |
|---|---|---|
| EP | 0426476 A | 1/1990 |
| EP | 0472113 A | 8/1991 |
| GB | 1501935 A | 2/1978 |
| GB | 1 585 950 A | 3/1981 |
| GB | 2281295 A | 3/1995 |
| JP | 2000001460 A | 1/2000 |
| JP | 2001247411 A | 9/2001 |
| JP | 2003171370 A | 6/2003 |
| WO | 9205159 A | 4/1992 |
| WO | 9941253 A | 11/1999 |
| WO | 0151468 A | 4/2001 |
| WO | 0168614 A | 9/2001 |
| WO | 02064096 A | 8/2002 |
| WO | 02094264 A | 11/2002 |
| WO | 03011853 A | 2/2003 |
| WO | 2004111014 A | 12/2004 |
| WO | 2006124874 A | 11/2006 |

* cited by examiner

HERBICIDAL PYRIMIDINES

FIELD OF THE INVENTION

This invention relates to certain pyrimidines, their N-oxides, agriculturally suitable salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

World Patent Application Publication WO 92/05159-A discloses pyrimidines useful as plant protectants, especially fungicides. European Patent Application Publication EP-136976-A2 discloses pyrimidines as plant growth regulators. U.S. Pat. No. 5,324,710 discloses sulfonated heterocyclic carboxamide derivatives of pyrimidines as herbicides and growth regulators.

SUMMARY OF THE INVENTION

This invention is directed to a compound of Formula I including all geometric and stereoisomers, N-oxides or agriculturally suitable salts thereof, agricultural compositions containing them and their use as herbicides:

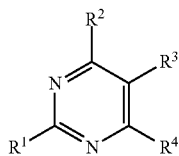

I wherein
$R^1$ is cyclopropyl optionally substituted with 1-5 $R^5$, isopropyl optionally substituted with 1-5 $R^6$, or phenyl optionally substituted with 1-3 $R^7$;
$R^2$ is $((O)_jC(R^{15})(R^{16}))_kR$;
R is $CO_2H$ or a herbicidally effective derivative of $CO_2H$
$R^3$ is halogen, cyano, nitro, $OR^{20}$, $SR^{21}$ or $N(R^{22})R^{23}$;
$R^4$ is $-N(R^{24})R^{25}$ or $-NO_2$;
each $R^5$ and $R^6$ is independently halogen, $C_1$-$C_6$ alkyl, $C_1$-$C_6$ haloalkyl, $C_2$-$C_6$ alkenyl, $C_2$-$C_6$ haloalkenyl, $C_1$-$C_3$ alkoxy, $C_1$-$C_2$ haloalkoxy, $C_1$-$C_3$ alkylthio or $C_1$-$C_2$ haloalkylthio;
each $R^7$ is independently halogen, cyano, nitro, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ hydroxyalkyl, $C_2$-$C_4$ alkoxyalkyl, $C_2$-$C_4$ haloalkoxyalkyl, $C_2$-$C_4$ alkenyl, $C_2$-$C_4$ haloalkenyl, $C_3$-$C_4$ alkynyl, $C_3$-$C_4$ haloalkynyl, hydroxy, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkenylthio, $C_2$-$C_4$ haloalkenylthio, $C_2$-$C_4$ alkenylsulfinyl, $C_2$-$C_4$ haloalkenylsulfinyl, $C_2$-$C_4$ alkenylsulfonyl, $C_2$-$C_4$ haloalkenylsulfonyl, $C_3$-$C_4$ alkynylthio, $C_3$-$C_4$ haloalkynylthio, $C_3$-$C_4$ alkynylsulfinyl, $C_3$-$C_4$ haloalkynylsulfinyl, $C_3$-$C_4$ alkynylsulfonyl, $C_3$-$C_4$ haloalkynylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl, phenyl, phenoxy and 5- or 6-membered heteroaromatic rings, each phenyl, phenoxy and 5- or 6-membered heteroaromatic ring optionally substituted with one to three substituents independently selected from $R^{45}$; or
two adjacent $R^7$ are taken together as $-OCH_2O-$, $-CH_2CH_2O-$, $-OCH(CH_3)O-$, $-OC(CH_3)_2O-$, $-OCF_2O-$, $-CF_2CF_2O-$, $-OCF_2CF_2O-$ or $-CH=CH-CH=CH-$;
$R^{15}$ is H, halogen, $C_1$-$C_4$ alkyl, $C_1$-$C_4$ haloalkyl, hydroxy, $C_1$-$C_4$ alkoxy or $C_2$-$C_4$ alkylcarbonyloxy;
$R^{16}$ is H, halogen, $C_1$-$C_4$ alkyl or $C_1$-$C_4$ haloalkyl; or
$R^{15}$ and $R^{16}$ are taken together as an oxygen atom to form, with the carbon atom to which they are attached, a carbonyl moiety;
$R^{20}$ is H, $C_1$-$C_4$ alkyl or $C_1$-$C_3$ haloalkyl;
$R^{21}$ is H, $C_1$-$C_4$ alkyl or $C_1$-$C_3$ haloalkyl;
$R^{22}$ and $R^{23}$ are independently H or $C_1$-$C_4$ alkyl;
$R^{24}$ is H, $C_1$-$C_4$ alkyl optionally substituted with 1-2 $R^{30}$, $C_2$-$C_4$ alkenyl optionally substituted with 1-2 $R^{31}$, or $C_2$-$C_4$ alkynyl optionally substituted with 1-2 $R^{32}$; or $R^{24}$ is $C(=O)R^{33}$, nitro, $OR^{34}$, $S(O)_2R^{35}$, $N(R^{36})R^{37}$ or $N=C(R^{62})R^{63}$;
$R^{25}$ is H, $C_1$-$C_4$ alkyl optionally substituted with 1-2 $R^{30}$ or $C(=O)R^{33}$; or
$R^{24}$ and $R^{25}$ are taken together as a radical selected from $-(CH_2)_4-$, $-(CH_2)_5-$, $-CH_2CH=CHCH_2-$ and $-(CH_2)_2O(CH_2)_2-$, each radical optionally substituted with 1-2 $R^{38}$; or
$R^{24}$ and $R^{25}$ are taken together as $=C(R^{39})N(R^{40})R^{41}$ or $=C(R^{42})OR^{43}$;
each $R^{30}$, $R^{31}$ and $R^{32}$ is independently halogen, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl;
each $R^{33}$ is independently H, $C_1$-$C_{14}$ alkyl, $C_1$-$C_3$ haloalkyl, $C_1$-$C_4$ alkoxy, phenyl, phenoxy or benzyloxy;
$R^{34}$ is H, $C_1$-$C_4$ alkyl, $C_1$-$C_3$ haloalkyl or $CHR^{66}C(O)OR^{67}$;
$R^{35}$ is $C_1$-$C_4$ alkyl or $C_1$-$C_3$ haloalkyl;
$R^{36}$ is H, $C_1$-$C_4$ alkyl or $C(=O)R^{64}$;
$R^{37}$ is H or $C_1$-$C_4$ alkyl;
each $R^{38}$ is independently halogen, $C_1$-$C_3$ alkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl;
$R^{39}$ is H or $C_1$-$C_4$ alkyl;
$R^{40}$ and $R^{41}$ are independently H or $C_1$-$C_4$ alkyl; or
$R^{40}$ and $R^{41}$ are taken together as $-(CH_2)_4-$, $-(CH_2)_5-$, $-CH_2CH=CHCH_2-$ or $-(CH_2)_2O(CH_2)_2-$;
$R^{42}$ is H or $C_1$-$C_4$ alkyl;
$R^{43}$ is $C_1$-$C_4$ alkyl;
each $R^{45}$ is independently halogen, cyano, nitro, $C_1$-$C_4$ alkyl, $C_1$-$C_4$ haloalkyl, $C_3$-$C_6$ cycloalkyl, $C_3$-$C_6$ halocycloalkyl, $C_2$-$C_4$ alkenyl, $C_2$-$C_4$ haloalkenyl, $C_3$-$C_4$ alkynyl, $C_3$-$C_4$ haloalkynyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{62}$ is H, $C_1$-$C_4$ alkyl or phenyl optionally substituted with 1-3 $R^{65}$;

$R^{63}$ is H or $C_1$-$C_4$ alkyl; or $R^{62}$ and $R^{63}$ are taken together as —$(CH_2)_4$— or —$(CH_2)_5$—;

$R^{64}$ is H, $C_1$-$C_{14}$ alkyl, $C_1$-$C_3$ haloalkyl, $C_1$-$C_4$ alkoxy, phenyl, phenoxy or benzyloxy;

each $R^{65}$ is independently $CH_3$, Cl or $OCH_3$;

$R^{66}$ is H, $C_1$-$C_4$ alkyl or $C_1$-$C_4$ alkoxy;

$R^{67}$ is H, $C_1$-$C_4$ alkyl or benzyl;

j is 0 or 1; and k is 0 or 1;

provided that:

(a) when k is 0, then j is 0;

(b) when $R^2$ is $CH_2OR^a$ wherein $R^a$ is H, optionally substituted alkyl or benzyl, then $R^3$ is other than cyano;

(c) when $R^1$ is phenyl substituted by Cl in each of the meta positions, the phenyl is also substituted by $R^7$ in the para position;

(d) when $R^1$ is phenyl substituted by $R^7$ in the para position, said $R^7$ is other than tert-butyl, cyano or optionally substituted phenyl;

(e) when $R^1$ is cyclopropyl or isopropyl optionally substituted with 1-5 $R^6$, then R is other than C(=W)N($R^b$)S(O)$_2$—$R^c$—$R^d$ wherein W is O, S, $NR^e$ or $NOR^e$; $R^b$ is hydrogen, $C_1$-$C_4$ alkyl, $C_2$-$C_6$ alkenyl or $C_2$-$C_6$ alkynyl; $R^c$ is a direct bond or $CHR^f$, O, $NR^e$ or $NOR^e$; $R^d$ is an optionally substituted heterocyclic or carbocyclic aromatic radical having 5 to 6 ring atoms, the radical being optionally condensed with an aromatic or nonaromatic 5- or 6-membered ring; each $R^e$ is independently H, $C_1$-$C_3$ alkyl, $C_1$-$C_3$ haloalkyl or phenyl; and $R^f$ is H, $C_1$-$C_3$ alkyl or phenyl; and (f) the compound of Formula I is other than diethyl 6-amino-5-nitro-2-phenyl-4-pyrimidinemalonate.

More particularly, this invention pertains to a compound of Formula I, including all geometric and stereoisomers, N-oxides or agriculturally suitable salts thereof. This invention also relates to a herbicidal composition comprising a herbicidally effective amount of a compound of Formula I and at least one of a surfactant, a solid diluent or a liquid diluent. This invention further relates to a method for controlling the growth of undesired vegetation comprising contacting the vegetation or its environment with a herbicidally effective amount of a compound of Formula I (e.g., as a composition described herein). This invention also relates to a herbicidal mixture comprising a herbicidally effective amount of a compound of Formula I and an effective amount of at least one additional active ingredient selected from the group consisting of an other herbicide and a herbicide safener. This invention further relates to a herbicidal composition comprising a herbicidally effective amount of a compound of Formula I, an effective amount of at least one additional active ingredient selected from the group consisting of an other herbicide and a herbicide safener, and at least one of a surfactant, a solid diluent or a liquid diluent.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$ and $CH_3CH_2OCH_2CH_2$. "Alkenyloxy" includes straight-chain or branched alkenyloxy moieties. Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HC\equiv CCH_2O$ and $CH_3C\equiv CCH_2O$. "Alkylthio" includes branched or straight-chain alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl. Examples of "cycloalkylalkyl" include cyclopropylmethyl, cyclopentylethyl, and other cycloalkyl moieties bonded to straight-chain or branched alkyl groups. "Alkylcycloalkyl" denotes alkyl substitution on a cycloalkyl moiety. Examples include 4-methylcyclohexyl and 3-ethylcyclopentyl. The term "heteroaromatic ring" includes fully aromatic heterocycles. Aromatic indicates that each of the ring atoms is essentially in the same plane and has a p-orbital perpendicular to the ring plane, and in which (4n+2) π electrons, when n is 0 or a positive integer, are associated with the ring to comply with Hückel's rule. The term carbocyclic aromatic radical is synonymous with the term isocyclic aromatic radical. A wide variety of synthetic methods are known in the art to enable preparation of aromatic heterocyclic rings; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996. The 5- and 6-membered heteroaromatic rings described for $R^7$ typically comprise 1 to 4 heteroatom ring members, the heteroatom members selected from 0-4 N, 0-1 O and 0-1 S atoms. Exhibit 1 shows examples of heteroaromatic rings; H-1 through H-55 are to be construed as illustrative rather than limiting of the heteroaromatic rings within the scope of the present invention.

Exhibit 1

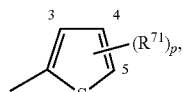
H-1

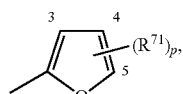
H-2

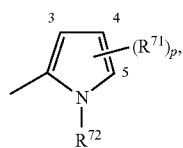
H-3

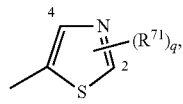
H-4

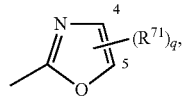
H-5

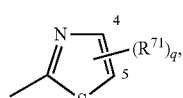
H-6

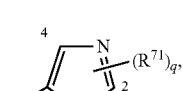
H-7

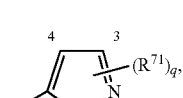
H-8

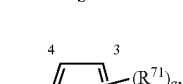
H-9

-continued

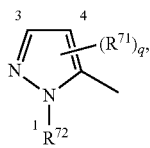
H-10

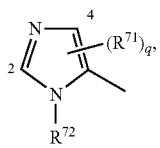
H-11

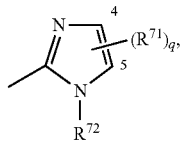
H-12

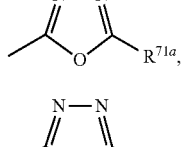
H-13

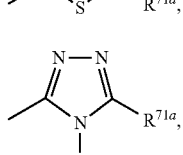
H-14

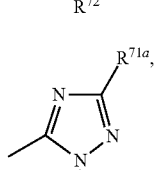
H-15

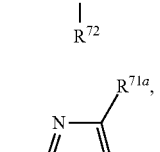
H-16

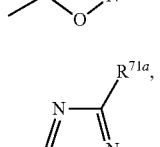
H-17

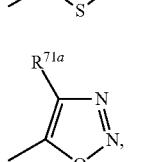
H-18

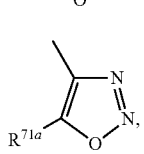
H-19

H-20

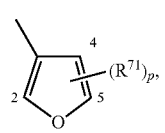 H-21
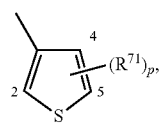 H-22
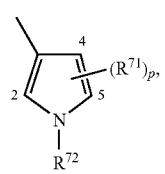 H-23
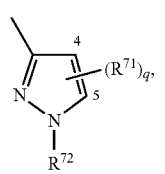 H-24
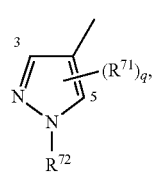 H-25
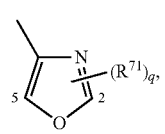 H-26
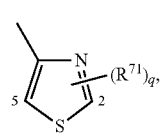 H-27
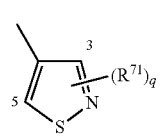 H-28
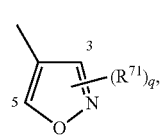 H-29
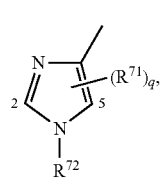 H-30
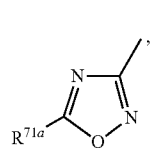 H-31
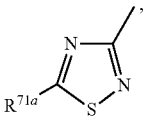 H-32
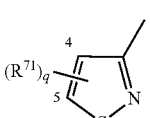 H-33
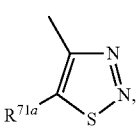 H-34
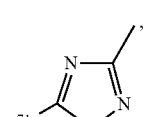 H-35
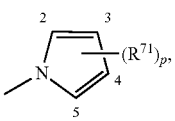 H-36
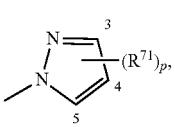 H-37
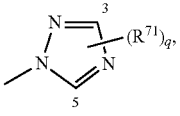 H-38
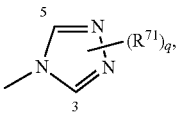 H-39
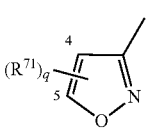 H-40
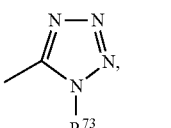 H-41
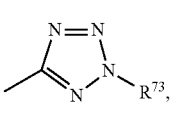 H-42

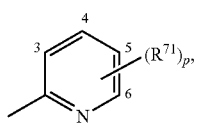 H-43

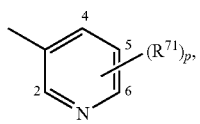 H-44

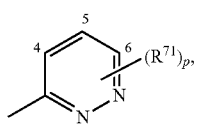 H-45

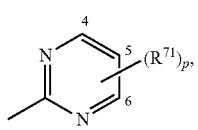 H-46

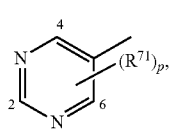 H-47

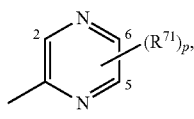 H-48

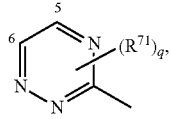 H-49

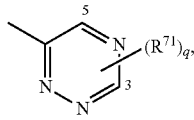 H-50

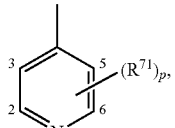 H-51

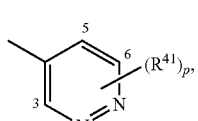 H-52

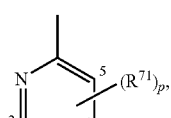 H-53

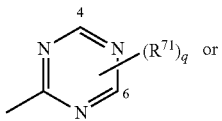 H-54

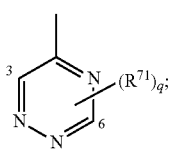 H-55 wherein
each $R^{71}$ is independently $R^{45}$;
$R^{71a}$, $R^{72}$ and $R^{73}$ are independently H or $R^{45}$;
p is an integer from 0 to 3; and
q is an integer from 0 to 2.

References herein to $R^7$ groups H-1 through H-55 refer to those shown in Exhibit 1.

One skilled in the art will appreciate that not all nitrogen-containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$-$C_j$" prefix where i and j are numbers from 1 to 14. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2OC(=O)$, $CH_3CH_2CH_2C(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript (e.g., $(R^d)_{1-3}$) that indicates the number of instances (i.e. occurrences) of said substituent can vary or the substituent is preceded with a numeric range (e.g., 1-3 $R^d$) indicating the number of instances of said substituent can vary, then when the number of said instances is greater than 1, each instance is independently selected from the group of radicals defined for the substituent. Further, when the subscript indicates a range, e.g., $(R^d)_{i-j}$, then the number of substituent instances may be selected from the integers between i and j inclusive.

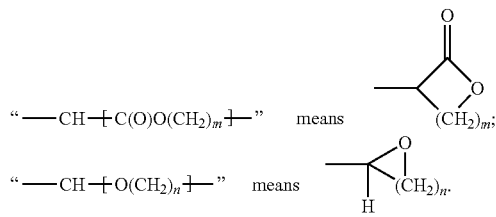

When a group contains a substituent which can be hydrogen, for example $R^{15}$ or $R^{34}$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The compounds of Formula I wherein R is $CO_2H$ (i.e. a carboxylic acid function) are believed to be the compounds that bind to an active site on a plant enzyme or receptor causing herbicidal effect on the plant. Other compounds of Formula I wherein the substituent R is a group that can be transformed within plants or the environment to a carboxylic acid function (i.e. $CO_2H$) provide similar herbicidal effects and are within the scope of the present invention. Therefore "a herbicidally effective derivative of $CO_2H$" when used to describe the substituent R in Formula I is defined as any salt, ester, carboxamide, acyl hydrazide, imidate, thioimidate, amidine, acyl halide, acyl cyanide, acid anhydride, ether, acetal, orthoester, carboxaldehyde, oxime, hydrazone, thioacid, thioester, dithiolester, nitrile or any other carboxylic acid derivative known in the art which does not extinguish the herbicidal activity of the compound of Formula I and is or can be hydrolyzed, oxidized, reduced or otherwise metabolized in plants or soil to provide the carboxylic acid function, which depending upon pH, is in the dissociated or the undissociated form.

Agriculturally suitable salts of the compounds of the invention are salts formed by contact with acids or bases or through ion exchange such that the derived salts retain sufficient water solubility for bioavailability and thus herbicidal efficacy and that the counterions of the salts are suitable for use in agriculture. The agriculturally suitable salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The agriculturally suitable salts of the compounds of the invention also include those formed with strong bases (e.g., hydroxides of sodium, potassium, lithium or quaternary ammonium) or amines. One skilled in the art recognizes that because in the environment and under physiological conditions salts of the compounds of the invention are in equilibrium with their corresponding nonsalt forms, agriculturally suitable salts share the biological utility of the nonsalt forms.

Particularly useful are agriculturally suitable salts of compounds of Formula I wherein R is $CO_2H$ (including wherein $R^2$ is $CO_2H$) formed with strong bases or amines. As is well known in the art, contact of a carboxylic acid group ($CO_2H$) with a base causes deprotonation to give the corresponding carboxylate ion ($CO_2^-$) and a typically positively charged counterion derived from the base. An extensive range of counterions form agriculturally suitable salts of compounds of Formula I wherein R is $CO_2H$, as most of the derived salts have sufficient water solubility for bioavailability. Illustrative and of particular note are salts of compounds of Formula I in which R is $CO_2H$ wherein the counterion ion is an alkali metal cation such as lithium, sodium or potassium, quarternary ammonium such as tetramethylammonium, ternary sulfonium such as trimethylsulfonium, or derived from an amine such as dimethylamine, diethanolamine (diolamine), triethanolamine (trolamine).

Also particularly useful are ester and thioester derivatives of $CO_2H$ as R in the compounds of Formula I. As is well known in the art, ester groups (i.e. $CO_2R^{AL}$) result from condensation of a carboxylic acid function ($CO_2H$) with an alcohol (i.e. $R^{AL}OH$) wherein $R^{AL}$ is the radical derived from the alcohol; a wide range of methods are known to prepare such esters. Analogously, thioester groups of formula $C(O)SR^{AL}$ may be conceptually viewed as the condensation product of a carboxylic acid function with a thioalcohol (often called a mercaptan) of formula $R^{AL}SH$; a variety of methods are known to prepare such thioesters. As compounds of Formula I wherein R is $CO_2H$ are herbicidally active and their derived esters and thioesters are susceptible to hydrolysis (to R being $CO_2H$) particularly in the presence of hydrolytic enzymes, the compounds of Formula I wherein $R^1$ is an ester (i.e. $CO_2R^{AL}$) or thioester (i.e. $C(O)SR^{AL}$) are generally useful as herbicides. Of the herbicidally effective derivatives of $CO_2H$, the ester and thioester derivatives, particularly ester derivatives, are among the most conveniently prepared and useful. If the radical $R^{AL}$ has more than one OH or SH function, the radical may then be condensed with more than one pyrimidine ring system of Formula I having $CO_2H$ as R. As the derived multiply esterified derivatives can be hydrolyzed to the compound of Formula I having $CO_2H$ as R, said multiply esterified derivatives are among the herbicidally effective derivatives of $CO_2H$. Illustrative and of note are ester and thioester compounds of Formula I in which R being $CO_2H$ is esterified with methanol, ethanol, butanol, 2-butoxyethanol, 2-ethylhexanol, isopropanol, 2-methylpropanol (isobutanol), octanol isomers (isoctanol) and ethanethiol to form methyl, ethyl, butyl, 2-butoxyethyl, 2-ethylhexyl, isopropyl, 2-methypropyl, isoctyl and ethylthio esters, respectively. Of particular note are the methyl and ethyl esters.

Embodiments of the present invention include:

Embodiment 1. A compound of Formula I wherein j is 0.

Embodiment 2. A compound of Formula I wherein k is 0.

Embodiment 3. A compound of Formula I wherein $R^{15}$ is H.

Embodiment 4. A compound of Embodiment 3 wherein $R^{16}$ is H.

Embodiment 5. A compound of Formula I wherein
R is $CO_2R^{12}$, $CH_2OR^{13}$, $CH(OR^{46})(OR^{47})$, CHO, $C(=NOR^{14})H$, $C(=NNR^{48}R^{49})H_5C(=O)N(R^{18})R^{19}$, $C(=S)OR^{50}$, $C(=O)SR^{51}$, $C(=S)SR^{52}$ or $C(=NR^{53})YR^{54}$;

$R^{12}$ is H, $-CH+C(O)O(CH_2)_m+$, $-N=C(R^{55})R^{56}$; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl, $C_2$-$C_{14}$ alkynyl and phenyl, each radical optionally substituted with 1-3 $R^{27}$; or $R^{12}$ is a divalent radical linking the carboxylic ester function $CO_2R^{12}$ of each of two pyrimidine ring systems of Formula I, the divalent radical selected from $-CH_2-$, $-(CH_2)_2-$, $-(CH_2)_3-$ and $-CH(CH_3)CH_2-$;

$R^{13}$ is H, $C_1$-$C_{10}$ alkyl optionally substituted with 1-3 $R^{28}$, or benzyl;

$R^{14}$ is H, $C_1$-$C_4$ alkyl, $C_1$-$C_4$ haloalkyl or benzyl;

$R^{18}$ is H, $C_1$-$C_4$ alkyl, hydroxy, $C_1$-$C_4$ alkoxy or $S(O)_2R^{57}$;

$R^{19}$ is H or $C_1$-$C_4$ alkyl;

each $R^{27}$ is independently halogen, cyano, hydroxycarbonyl, $C_2$-$C_4$ alkoxycarbonyl, hydroxy, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ dialkylamino, $-CH+O(CH_2)_n+$ or phenyl optionally substituted with 1-3 $R^{44}$; or two $R^{27}$ are taken together as $-OC(O)O-$ or $-O(C(R^{58})(R^{58}))_{1-2}O-$; or two $R^{27}$ are taken together as an oxygen atom to form, with the carbon atom to which they are attached, a carbonyl moiety;

each $R^{28}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino; or two $R^{28}$ are taken together as an oxygen atom to form, with the carbon atom to which they are attached, a carbonyl moiety;

each $R^{44}$ is independently halogen, $C_1$-$C_4$ alkyl, $C_1$-$C_3$ haloalkyl, hydroxy, $C_1$-$C_4$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or nitro;

$R^{46}$ and $R^{47}$ are independently $C_1$-$C_4$ alkyl or $C_1$-$C_3$ haloalkyl; or $R^{46}$ and $R^{47}$ are taken together as $-CH_2CH_2-$, $-CH_2CH(CH_3)-$ or $-(CH_2)_3-$;

$R^{48}$ is H, $C_1$-$C_4$ alkyl, $C_1$-$C_4$ haloalkyl, $C_2$-$C_4$ alkylcarbonyl, $C_2$-$C_4$ alkoxycarbonyl or benzyl;

$R^{49}$ is H, $C_1$-$C_4$ alkyl or $C_1$-$C_4$ haloalkyl;

$R^{50}$, $R^{51}$ and $R^{52}$ are H; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl and $C_2$-$C_{14}$ alkynyl, each radical optionally substituted with 1-3 $R^{27}$;

Y is O, S or $NR^{61}$;

$R^{53}$ is H, $C_1$-$C_3$ alkyl, $C_1$-$C_3$ haloalkyl, $C_2$-$C_4$ alkoxyalkyl, OH or $C_1$-$C_3$ alkoxy;

$R^{54}$ is $C_1$-$C_3$ alkyl, $C_1$-$C_3$ haloalkyl or $C_2$-$C_4$ alkoxyalkyl; or $R^{53}$ and $R^{54}$ are taken together as $-(CH_2)_2-$, $-CH_2CH(CH_3)-$ or $-(CH_2)_3-$;

$R^{55}$ and $R^{56}$ are independently $C_1$-$C_4$ alkyl;

$R^{57}$ is $C_1$-$C_4$ alkyl, $C_1$-$C_3$ haloalkyl or $NR^{59}R^{60}$;

each $R^{58}$ is independently selected from H and $C_1$-$C_4$ alkyl;

$R^{59}$ and $R^{60}$ are independently H or $C_1$-$C_4$ alkyl;

$R^{61}$ is H, $C_1$-$C_3$ alkyl, $C_1$-$C_3$ haloalkyl or $C_2$-$C_4$ alkoxyalkyl;

m is an integer from 2 to 3; and n is an integer from 1 to 4.

Embodiment 6. A compound of Formula I wherein when $R^1$ is optionally substituted cyclopropyl, then $R^2$ is other than alkoxyalkyl or alkylthioalkyl.

Embodiment 7. A compound of Formula I wherein $R^2$ is other than alkoxyalkyl or alkylthioalkyl.

Embodiment 8. A compound of Embodiment 5 wherein
$R^2$ is $CO_2R^{12}$, $CH_2OR^{13}$, $CH(OR^{46})(OR^{47})$, CHO, $C(=NOR^{14})H$, $C(=NNR^{48}R^{49})H$, $(O)_jC(R^{15})(R^{16})CO_2R^{17}$, $C(=O)N(R^{18})R^{19}$, $C(=S)OR^{50}$, $C(=O)SR^{51}$, $C(=S)SR^{52}$ or $C(=NR^{53})YR^{54}$;

$R^{17}$ is $C_1$-$C_{10}$ alkyl optionally substituted with 1-3 $R^{29}$, or benzyl; and each $R^{29}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino.

Embodiment 9. A compound of Embodiment 8 wherein when $R^3$ is $CH_2OR^{13}$, then $R^{13}$ is other than alkyl.

Embodiment 10. A compound of Embodiment 8 wherein when $R^3$ is $CH_2OR^{13}$, then $R^{13}$ is other than optionally substituted alkyl.

Embodiment 11. A compound of Embodiment 8 wherein $R^3$ is other than $CH_2OR^{13}$.

Embodiment 12. A compound of Embodiment 8 wherein j is 0.

Embodiment 13. A compound of Embodiment 12 wherein $R^2$ is $CO_2R^{12}$, $CH_2OR^{13}$, CHO or $CH_2CO_2R^{17}$.

Embodiment 14. A compound of Embodiment 13 wherein $R^2$ is $CO_2R^{12}$.

Embodiment 15. A compound of Embodiment 14 wherein $R^{12}$ is H, $C_1$-$C_8$ alkyl or $C_1$ alkyl substituted with phenyl optionally substituted with 1-3 $R^{44}$.

Embodiment 16. A compound of Embodiment 15 wherein $R^{12}$ is H, $C_1$-$C_4$ alkyl or $C_1$ alkyl substituted with phenyl optionally substituted with 1-3 $R^{44}$.

Embodiment 17. A compound of Embodiment 16 wherein $R^{12}$ is H, $C_1$-$C_4$ alkyl or benzyl.

Embodiment 18. A compound of Formula I wherein $R^2$ is $CO_2H$, an agriculturally suitable salt or an ester or thioester derivative thereof.

Embodiment 19. A compound of Embodiment 18 wherein $R^2$ is $CO_2H$, an agriculturally suitable salt or an ester derivative thereof.

Embodiment 20. A compound of Formula I wherein $R^1$ is cyclopropyl optionally substituted with 1-5 $R^5$.

Embodiment 21. A compound of Formula I wherein $R^1$ is isopropyl optionally substituted with 1-5 $R^6$.

Embodiment 22. A compound of Formula I wherein $R^1$ is phenyl optionally substituted with 1-3 $R^7$.

Embodiment 23. A compound of Formula I wherein $R^1$ is cyclopropyl optionally substituted with 1-5 $R^5$ or isopropyl optionally substituted with 1-5 $R^6$.

Embodiment 24. A compound of Formula I wherein $R^1$ is cyclopropyl optionally substituted with 1-5 $R^5$ or phenyl optionally substituted with 1-3 $R^7$.

Embodiment 25. A compound of Formula I wherein $R^1$ is isopropyl optionally substituted with 1-5 $R^6$ or phenyl optionally substituted with 1-3 $R^7$.

Embodiment 26. A compound of Formula I wherein $R^1$ is other than cyclopropyl.

Embodiment 27. A compound of Formula I wherein $R^1$ is cyclopropyl optionally substituted with 1-2 $R^6$ or phenyl optionally substituted with 1-3 $R^7$.

Embodiment 28. A compound of Embodiment 27 wherein $R^1$ is cyclopropyl optionally substituted with 1-2 $R^6$.

Embodiment 29. A compound of Embodiment 27 wherein $R^1$ is cyclopropyl or phenyl optionally substituted with 1-3 $R^7$.

Embodiment 30. A compound of Embodiment 28 wherein $R^1$ is cyclopropyl.

Embodiment 31. A compound of Embodiment 27 wherein $R^1$ is phenyl optionally substituted with 1-3 $R^7$.

Embodiment 32. A compound of Embodiment 27 wherein $R^1$ is cyclopropyl or phenyl substituted with a $R^7$ radical in the para position and optionally with 1-2 $R^7$ in other positions.

Embodiment 33. A compound of Embodiment 32 wherein $R^1$ is cyclopropyl or phenyl substituted with a halogen, methyl or methoxy radical in the para position and optionally with 1-2 radicals selected from halogen and methyl in other positions.

Embodiment 34. A compound of Embodiment 33 wherein $R^1$ is cyclopropyl or phenyl substituted with a halogen radical in the para position and optionally with 1-2 radicals selected from halogen and methyl in other positions.

Embodiment 35. A compound of Embodiment 34 wherein $R^1$ is cyclopropyl or phenyl substituted with a Br or Cl radical in the para position and optionally with 1-2 radicals selected from halogen and methyl in other positions.

Embodiment 36. A compound of Embodiment 35 wherein $R^1$ is phenyl substituted with a Br or Cl radical in the para position and optionally with 1-2 radicals selected from halogen and methyl in other positions.

Embodiment 37. A compound of Embodiment 35 wherein $R^1$ is cyclopropyl or phenyl substituted with a Br or Cl radical in the para position.

Embodiment 38. A compound of Embodiment 37 wherein $R^1$ is phenyl substituted with a Br or Cl radical in the para position.

Embodiment 39. A compound of Formula I wherein $R^7$ is other than cyano.

Embodiment 40. A compound of Formula I wherein $R^7$ selected from other than optionally substituted phenyl, phenoxy and 5- and 6-membered heteroaromatic rings.

Embodiment 41. A compound of Formula I wherein each $R^7$ is independently selected from halogen, $C_1$-$C_2$ alkyl, $C_1$-$C_2$ haloalkyl, $C_1$-$C_2$ alkoxy or $C_1$-$C_2$ haloalkoxy; or two adjacent $R^7$ are taken together as —$OCH_2O$—, —$CH_2CH_2O$—, —$OCH(CH_3)O$—, —$OC(CH_3)_2O$—, —$OCF_2O$—, —$CF_2CF_2O$—, —$OCF_2CF_2O$— or —CH=CH—CH=CH—.

Embodiment 42. A compound of Embodiment 41 wherein each $R^7$ is independently selected from halogen, $C_1$-$C_2$ alkyl, $C_1$-$C_2$ haloalkyl, $C_1$-$C_2$ alkoxy or $C_1$-$C_2$ haloalkoxy; or two adjacent $R^7$ are taken together as —$OCH_2O$—, —$CH_2CH_2O$—, —$OCH(CH_3)O$— or —$OCF_2O$—.

Embodiment 43. A compound of Embodiment 42 wherein each $R^7$ is independently selected from halogen, $C_1$-$C_2$ alkyl, $C_1$ fluoroalkyl, $C_1$-$C_2$ alkoxy or $C_i$ fluoroalkoxy.

Embodiment 44. A compound of Formula I wherein each $R^7$ is independently selected from halogen, methyl and methoxy.

Embodiment 45. A compound of Embodiment 44 wherein each $R^7$ is independently selected from halogen and methyl.

Embodiment 46. A compound of Embodiment 45 wherein each $R^7$ is independently selected from F, Cl and Br.

Embodiment 47. A compound of Embodiment 46 wherein each $R^7$ is independently selected from Cl and Br.

Embodiment 48. A compound of Formula I wherein $R^3$ is other than cyano.

Embodiment 49. A compound of Formula I wherein $R^3$ is other than nitro.

Embodiment 50. A compound of Formula I wherein $R^3$ is halogen, nitro, $OR^{20}$, $SR^{21}$ or $N(R^{22})R^{23}$.

Embodiment 51. A compound of Embodiment 50 wherein $R^3$ is halogen.

Embodiment 52. A compound of Embodiment 51 wherein $R^3$ is Br or Cl.

Embodiment 53. A compound of Embodiment 52 wherein $R^3$ is Cl.

Embodiment 54. A compound of Formula I wherein $R^4$ is —$N(R^{24})R^{25}$.

Embodiment 55. A compound of Formula I wherein $R^{24}$ is other than $C_2$-$C_4$ alkynyl optionally substituted with 1-2 $R^{32}$.

Embodiment 56. A compound of Formula I wherein $R^{24}$ is H, $C(O)R^{33}$ or $C_1$-$C_4$ alkyl optionally substituted with $R^{30}$; $R^{25}$ is H or $C_1$-$C_2$ alkyl; or $R^{24}$ and $R^{25}$ are taken together as =$C(R^{39})N(R^{40})R^{44}$.

Embodiment 57. A compound of Embodiment 56 wherein $R^{24}$ is H, $C(O)CH_3$ or $C_1$-$C_4$ alkyl optionally substituted with $R^{30}$; and $R^{25}$ is H or $C_1$-$C_2$ alkyl.

Embodiment 58. A compound of Embodiment 57 wherein $R^{24}$ and $R^{25}$ are independently H or methyl.

Embodiment 59. A compound of Embodiment 58 wherein $R^{24}$ and $R^{25}$ are H.

Embodiment 60. A compound of Formula I wherein $R^{30}$ is halogen, methoxy, $C_1$ fluoroalkoxy, methylthio, $C_1$ fluoroalkylthio, amino, methylamino, dimethylamino or methoxycarbonyl.

Embodiment 61. A compound of Formula I wherein $R^{33}$ is H or $C_1$-$C_3$ alkyl.

Embodiment 62. A compound of Embodiment 61 wherein $R^{33}$ is $CH_3$.

Embodiment 63. A compound of Formula I wherein $R^{39}$ is H or $C_1$-$C_2$ alkyl.

Embodiment 64. A compound of Formula I wherein $R^{40}$ and $R^{41}$ are independently H or $C_1$-$C_2$ alkyl.

Embodiment 65. A compound of Formula I wherein $R^3$ is other than OH.

Embodiment 66. A compound of Formula I wherein $R^3$ is other than $OR^{20}$.

Embodiment 67. A compound of Formula I wherein when j is 1, and $R^1$ is isopropyl substituted with at least one $R^6$ being halogen, then $R^{24}$ and $R^{25}$ are each H.

Embodiment 68. A compound of Formula I wherein when j is 1, $R^1$ is optionally substituted isopropyl, the $R^{24}$ and $R^{25}$ are each H.

Embodiment 69. A compound of Formula I wherein when j is 1, then $R^{24}$ and $R^{25}$ are each H.

Embodiment 70. A compound of Formula I wherein when j is 1, then $R^6$ is other than halogen.

Embodiment 71. A compound of Formula I wherein when j is 1, then $R^1$ is other than optionally substituted isopropyl.

Embodiment 72. A compound of Formula I wherein when j is 1, then $R^1$ is cyclopropyl optionally substituted with 1-5 $R^5$, isopropyl, or phenyl optionally substituted with 1-3 $R^7$.

Embodiment 73. A compound of Formula I wherein when j is 1, then $R^1$ is cyclopropyl, isopropyl, or phenyl optionally substituted with 1-3 $R^7$.

Embodiment 74. A compound of Formula I wherein when $R^1$ is phenyl optionally substituted with 1-3 $R^7$ then R is other than cyano.

Embodiment 75. A compound of Formula I wherein R is other than cyano.

Embodiment 76. A compound of Embodiment 5 wherein when $R^1$ is phenyl optionally substituted with 1-3 $R^7$ then R is $CO_2R^{12}$.

Embodiment 77. A compound of Embodiment 5 wherein R is $CO_2R^{12}$.

Embodiment 78. A compound of Embodiment 8 wherein when $R^1$ is phenyl optionally substituted with 1-3 $R^7$ then $R^2$ is $CO_2R^{12}$.

Embodiment 79. A compound of Embodiment 8 wherein $R^2$ is $CO_2R^{12}$.

Embodiment 80. A compound of Formula I wherein when $R^1$ is phenyl optionally substituted with 1-3 $R^7$ then $R^{24}$ is H, C(=O)$R^{33}$, nitro, $OR^{34}$, $S(O)_2R^{35}$ or $N(R^{36})R^{37}$, and $R^{25}$ is H or C(=O)$R^{33}$.

Embodiment 81. A compound of Formula I wherein when $R^1$ is phenyl optionally substituted with 1-3 $R^7$ then $R^{24}$ and $R^{25}$ are each H.

Embodiment 82. A compound of Formula I wherein $R^{24}$ is H, C(=O)$R^{33}$, nitro, $OR^{34}$, $S(O)_2R^{35}$ or $N(R^{36})R^{37}$, and $R^{25}$ is H or C(=O)$R^{33}$.

Embodiment 83. A compound of Formula I wherein $R^{24}$ and $R^{25}$ are each H.

Embodiment 84. A compound of Formula I wherein when $R^1$ is cyclopropyl or isopropyl optionally substituted with 1-5 $R^6$, then R is other than C(=$W^1$)N($R^{b1}$)$S(O)_2$—$R^{cd}$ wherein W comprises at least one atom; $R^{b1}$ comprises at least one atom and Rcd comprises at least one atom.

Embodiment 85. A compound of Formula I wherein when $R^1$ is cyclopropyl optionally substituted with 1-5 $R^5$ or isopropyl optionally substituted with 1-5 $R^6$, then R is other than C(=$W^1$)N($R^{b1}$)$S(O)_2$—$R^{cd}$ wherein W comprises at least one atom; $R^{b1}$ comprises at least one atom and Rcd comprises at least one atom.

Embodiment 86. A compound of Formula I wherein R is other than C(=$W^1$)N($R^{b1}$)$S(O)_2$—$R^{cd}$ wherein W comprises at least one atom; $R^{b1}$ comprises at least one atom and Rcd comprises at least one atom.

Embodiment 87. A compound of Embodiment 5 wherein $R^{18}$ is H, $C_1$-$C_4$ alkyl, hydroxy or $C_1$-$C_4$ alkoxy.

Embodiment 88. A compound of Embodiment 8 wherein $R^{18}$ is H, $C_1$-$C_4$ alkyl, hydroxy or $C_1$-$C_4$ alkoxy.

Embodiment 89. A compound of Formula I wherein each $R^5$ and $R^6$ is independently halogen, $C_1$-$C_2$ alkyl or $C_1$-$C_2$ haloalkyl.

Embodiment 90. A compound of Formula I wherein $R^{15}$ is H, halogen, $C_1$-$C_4$ alkyl, $C_1$-$C_4$ haloalkyl, hydroxy, $C_1$-$C_4$ alkoxy or $C_2$-$C_4$ alkylcarbonyloxy.

Embodiment 91. A compound of Formula I wherein $R^{16}$ is H, halogen, $C_1$-$C_4$ alkyl or $C_1$-$C_4$ haloalkyl.

Embodiment 92. A compound of Formula I wherein $R^{24}$ is H, $C_1$-$C_4$ alkyl optionally substituted with 1-2 $R^{30}$, $C_2$-$C_4$ alkenyl optionally substituted with 1-2 $R^{31}$, or $C_2$-$C_4$ alkynyl optionally substituted with 1-2 $R^{32}$; or $R^{24}$ is C(=O)$R^{33}$, nitro, $OR^{34}$, $S(O)^2R^{35}$ or $N(R^{36})R^{37}$.

Embodiment 93. A compound of Formula I wherein each $R^{33}$ is independently H, $C_1$-$C_4$ alkyl, $C_1$-$C_3$ haloalkyl, $C_1$-$C_4$ alkoxy, phenoxy or benzyloxy.

Embodiment 94. A compound of Formula I wherein $R^{34}$ is H, $C_1$-$C_4$ alkyl or $C_1$-$C_3$ haloalkyl.

Embodiment 95. A compound of Formula I wherein $R^{36}$ is H or $C_1$-$C_4$ alkyl.

Embodiment 96. A compound of Embodiment 5 wherein $R^{12}$ is H; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl and $C_2$-$C_{14}$ alkynyl, each radical optionally substituted with 1-3 $R^{27}$; or —N=C($R^{55}$)$R^{56}$.

Embodiment 97. A compound of Embodiment 5 wherein each $R^{27}$ is independently halogen, hydroxycarbonyl, $C_2$-$C_4$ alkoxycarbonyl, hydroxy, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ dialkylamino, —CH[O(CH$_2$)$_n$] or phenyl optionally substituted with 1-3 $R^{44}$; or two $R^{27}$ are taken together as —OC(O)O— or —O(C($R^{58}$)($R^{58}$))$_{1-2}$O—; or two $R^{27}$ are taken together as an oxygen atom to form, with the carbon atom to which they are attached, a carbonyl moiety.

Embodiment 98. A compound of Embodiment 5 wherein $R^{53}$ is H, $C_1$-$C_3$ alkyl, $C_1$-$C_3$ haloalkyl or $C_2$-$C_4$ alkoxyalkyl.

Combinations of Embodiments 1-98 are illustrated by:

Embodiment A. A compound of Formula I wherein
$R^2$ is $CO_2R^{12}$, $CH_2OR^{13}$, $CH(OR^{46})(OR^{47})$, CHO, C(=$NOR^{14}$)H, C(=$NNR^{48}R^{49}$)H, (O)$_jC(R^{15})(R^{16})$ $CO_2R^{17}$, C(=O)N($R^{18}$)$R^{19}$, C(=S)$OR^{50}$, C(=O) $SR^{51}$, C(=S)$SR^{52}$ or C(=$NR^{53}$)$YR^{54}$;
$R^{12}$ is H, —CH[C(O)O(CH$_2$)$_m$], —N=C($R^{55}$)$R^{56}$; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl, $C_2$-$C_{14}$ alkynyl and phenyl, each radical optionally substituted with 1-3 $R^{27}$; or
$R^{12}$ is a divalent radical linking the carboxylic ester function $CO_2R^{12}$ of each of two pyrimidine ring systems of Formula I, the divalent radical selected from —CH$_2$—, —(CH$_2$)$_2$—, —(CH$_2$)$_3$— and —CH(CH$_3$)CH$_2$—;
$R^{13}$ is H, $C_1$-$C_{10}$ alkyl optionally substituted with 1-3 $R^{28}$, or benzyl;
$R^{14}$ is H, $C_1$-$C_4$ alkyl, $C_1$-$C_4$ haloalkyl or benzyl;
$R^{17}$ is $C_1$-$C_{10}$ alkyl optionally substituted with 1-3 $R^{29}$, or benzyl;
$R^{18}$ is H, $C_1$-$C_4$ alkyl, hydroxy, $C_1$-$C_4$ alkoxy or $S(O)_2R^{57}$;
$R^{19}$ is H or $C_1$-$C_4$ alkyl;
each $R^{27}$ is independently halogen, cyano, hydroxycarbonyl, $C_2$-$C_4$ alkoxycarbonyl, hydroxy, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ dialkylamino, —CH$\{$—O(CH$_2$)$_n$—$\}$ or phenyl optionally substituted with 1-3 $R^{44}$; or two $R^{27}$ are taken together as —OC(O)O— or —O(C($R^{58}$)($R^{58}$))$_{1-2}$O—; or two $R^{27}$ are taken together as an oxygen atom to form, with the carbon atom to which they are attached, a carbonyl moiety;

each $R^{28}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino; or two $R^{28}$ are taken together as an oxygen atom to form, with the carbon atom to which they are attached, a carbonyl moiety;

each $R^{29}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino;

each $R^{44}$ is independently halogen, $C_1$-$C_4$ alkyl, $C_1$-$C_3$ haloalkyl, hydroxy, $C_1$-$C_4$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or nitro;

$R^{46}$ and $R^{47}$ are independently $C_1$-$C_4$ alkyl or $C_1$-$C_3$ haloalkyl; or $R^{46}$ and $R^{47}$ are taken together as —CH$_2$CH$_2$—, —CH$_2$CH(CH$_3$)— or —(CH$_2$)$_3$—;

$R^{48}$ is H, $C_1$-$C_4$ alkyl, $C_1$-$C_4$ haloalkyl, $C_2$-$C_4$ alkylcarbonyl, $C_2$-$C_4$ alkoxycarbonyl or benzyl;

$R^{49}$ is H, $C_1$-$C_4$ alkyl or $C_1$-$C_4$ haloalkyl;

$R^{50}$, $R^{51}$ and $R^{52}$ are H; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl and $C_2$-$C_{14}$ alkynyl, each radical optionally substituted with 1-3 $R^{27}$;

Y is O, S or NR$^{61}$;

$R^{53}$ is H, $C_1$-$C_3$ alkyl, $C_1$-$C_3$ haloalkyl, $C_2$-$C_4$ alkoxyalkyl, OH or $C_1$-$C_3$ alkoxy;

$R^{54}$ is $C_1$-$C_3$ alkyl, $C_1$-$C_3$ haloalkyl or $C_2$-$C_4$ alkoxyalkyl; or $R^{53}$ and $R^{54}$ are taken together as —(CH$_2$)$_2$—, —CH$_2$CH(CH$_3$)— or —(CH$_2$)$_3$—;

$R^{55}$ and $R^{56}$ are independently $C_1$-$C_4$ alkyl;

$R^{57}$ is $C_1$-$C_4$ alkyl, $C_1$-$C_3$ haloalkyl or NR$^{59}$R$^{60}$;

each $R^{58}$ is independently selected from H and $C_1$-$C_4$ alkyl;

$R^{59}$ and $R^{60}$ are independently H or $C_1$-$C_4$ alkyl;

$R^{61}$ is H, $C_1$-$C_3$ alkyl, $C_1$-$C_3$ haloalkyl or $C_2$-$C_4$ alkoxyalkyl;

m is an integer from 2 to 3; and n is an integer from 1 to 4.

Embodiment B. A compound of Embodiment A wherein $R^3$ is halogen.

Embodiment C. A compound of Embodiment B wherein $R^1$ is cyclopropyl or phenyl substituted with a halogen, methyl or methoxy radical in the para position and optionally with 1-2 radicals selected from halogen and methyl in other positions; and $R^4$ is —N(R$^{24}$)R$^{25}$.

Embodiment D. A compound of Embodiment C wherein $R^2$ is CO$_2$R$^{12}$, CH$_2$OR$^{13}$, CHO or CH$_2$CO$_2$R$^{17}$.

Embodiment E. A compound of Embodiment D wherein $R^{24}$ is H, C(O)R$^{33}$ or $C_1$-$C_4$ alkyl optionally substituted with $R^{30}$; $R^{25}$ is H or $C_1$-$C_2$ alkyl; or $R^{24}$ and $R^{25}$ are taken together as =C(R$^{39}$)N(R$^{40}$)R$^{41}$.

Embodiment F. A compound of Embodiment E wherein $R^2$ is CO$_2$R$^{12}$; and $R^{24}$ and $R^{25}$ are H.

Embodiment G. A compound of Embodiment F wherein $R^{12}$ is H, $C_1$-$C_4$ alkyl or benzyl.

Specific embodiments include compounds of Formula I selected from the group consisting of:

methyl 6-amino-5-bromo-2-cyclopropyl-4-pyrimidinecarboxylate, ethyl 6-amino-5-bromo-2-cyclopropyl-4-pyrimidinecarboxylate, phenylmethyl 6-amino-5-bromo-2-cyclopropyl-4-pyrimidinecarboxylate, 6-amino-5-bromo-2-cyclopropyl-4-pyrimidinecarboxylic acid monosodium salt, methyl 6-amino-5-chloro-2-cyclopropyl-4-pyrimidinecarboxylate, phenylmethyl 6-amino-5-chloro-2-cyclopropyl-4-pyrimidinecarboxylate, 6-amino-5-chloro-2-cyclopropyl-4-pyrimidinecarboxylic acid monosodium salt, ethyl 6-amino-5-chloro-2-cyclopropyl-4-pyrimidinecarboxylate, methyl 6-amino-5-chloro-2-(4-chlorophenyl)-4-pyrimidinecarboxylate, ethyl 6-amino-5-chloro-2-(4-chlorophenyl)-4-pyrimidinecarboxylate, 6-amino-5-chloro-2-(4-chlorophenyl)-4-pyrimidinecarboxylic acid, ethyl 6-amino-2-(4-bromophenyl)-5-chloro-4-pyrimidinecarboxylate, methyl 6-amino-2-(4-bromophenyl)-5-chloro-4-pyrimidinecarboxylate, and 6-amino-2-(4-bromophenyl)-5-chloro-4-pyrimidinecarboxylic acid.

Also noteworthy as embodiments are herbicidal compositions of the present invention comprising the compounds of embodiments described above.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above.

Of note is a compound of Formula I, including all geometric and stereoisomers, N-oxides or agriculturally suitable salts thereof, agricultural compositions containing them and their use as herbicides wherein $R^2$ is CO$_2$R$^{12}$, CH$_2$OR$^{13}$, CHO, C(=NOR$^{14}$)H, C(R$^{15}$)(R$^{16}$)CO$_2$R$^{17}$ or C(=O)N(R$^{18}$)R$^{19}$; each $R^7$ is independently halogen, $C_1$-$C_4$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio; $R^{12}$ is H; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl and $C_2$-$C_{14}$ alkynyl, each radical optionally substituted with 1-3 $R^{27}$; $R^{13}$ is H, $C_1$-$C_{10}$ alkyl optionally substituted with 1-3 $R^{28}$ or benzyl; $R^{14}$ is H, $C_1$-$C_4$ alkyl or $C_1$-$C_4$ haloalkyl; $R^{15}$ and $R^{16}$ are independently H, halogen, $C_1$-$C_4$ alkyl, $C_1$-$C_4$ haloalkyl, hydroxy or $C_1$-$C_4$ alkoxy; $R^{17}$ is $C_1$-$C_{10}$ alkyl optionally substituted with 1-3 $R^{29}$ or benzyl; $R^{18}$ and $R^{19}$ are independently H or $C_1$-$C_4$ alkyl; each $R^{27}$ is independently halogen, hydroxycarbonyl, $C_2$-$C_4$ alkoxycarbonyl, hydroxy, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ dialkylamino, —CH$\{$—O(CH$_2$)$_n$—$\}$ or phenyl optionally substituted with 1-3 $R^{44}$; or two $R^{27}$ are taken together with the carbon atom to which they are attached to form a carbonyl moiety; each $R^{28}$ and $R^{29}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino; each $R^{30}$, $R^{31}$ and $R^{32}$ is independently halogen, hydroxy, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ dialkylamino or $C_2$-$C_4$ alkoxycarbonyl; each $R^{38}$ is independently halogen, $C_1$-$C_3$ alkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl; each $R^{44}$ is independently halogen, $C_1$-$C_4$ alkyl, $C_1$-$C_3$ haloalkyl, hydroxy, $C_1$-$C_4$ alkoxy, $C_1$-$C_3$ haloalkoxy, $C_1$-$C_4$ alkylthio, $C_1$-$C_3$ haloalkylthio, amino, $C_1$-$C_3$ alkylamino, $C_2$-$C_4$ dialkylamino or nitro; m is an integer from 2 to 5; and n is an integer from 1 to 4. Also of note is a compound of Formula I, including all geometric and stereoisomers, N-oxides or agriculturally suitable salts thereof, agricultural compositions containing them and their use as herbicides wherein each $R^5$ and $R^6$ is independently halogen, $C_1$-$C_2$ alkyl or $C_1$-$C_2$ haloalkyl; $R^{15}$ is H, halogen, $C_1$-$C_4$ alkyl, $C_1$-$C_4$ haloalkyl, hydroxy, $C_1$-$C_4$ alkoxy or $C_2$-$C_4$ alkylcarbonyloxy; $R^{16}$ is H, halogen, $C_1$-$C_4$ alkyl or $C_1$-$C_4$ haloalkyl; $R^{24}$ is H, $C_1$-$C_4$ alkyl optionally substituted with 1-2 $R^{30}$, $C_2$-$C_4$ alkenyl optionally substituted with 1-2 $R^{31}$, or $C_2$-$C_4$ alkynyl optionally substituted with 1-2 $R^{32}$; or $R^{24}$ is C(=O)$R^{33}$, nitro, O$R^{34}$, S(O)$_2R^{35}$ or N($R^{36}$)$R^{37}$; each $R^{33}$ is independently H, $C_1$-$C_4$ alkyl, $C_1$-$C_3$ haloalkyl, $C_1$-$C_4$ alkoxy, phenoxy or benzyloxy; $R^{34}$ is H, $C_1$-$C_4$ alkyl, $C_1$-$C_3$ haloalkyl; and $R^{36}$ is H or $C_1$-$C_4$ alkyl.

The compounds of Formula I can be prepared by one or more of the following methods and variations as described in Schemes 1 through 7 and accompanying text. The definitions of R, $R^1$, $R^2$, $R^3$, $R^4$, $R^5$, $R^6$, $R^7$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, Y, j, k and n in the compounds of Formulae I through 12 below are as defined above in the Summary of the Invention and description of embodiments unless otherwise indicated.

Compounds of Formula I can be prepared from chlorides of Formula 2 by reaction with amines of Formula 3, optionally in the presence of a base such as triethylamine or potassium carbonate as outlined in Scheme 1. The reaction can be run in a variety of solvents including tetrahydrofuran, p-dioxane, ethanol and methanol with optimum temperatures ranging from room temperature to 200° C. The method of Scheme 1 is illustrated in Step C of Example 1, Steps D1 and D2 of Example 2, and Step B of Example 4.

Scheme 1

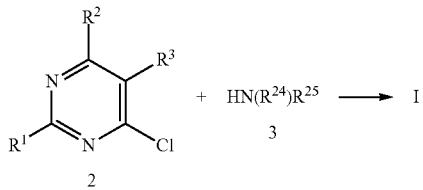

Compounds of Formula 2 can be prepared from hydroxy compounds of Formula 4 (which may exist in the keto form) by reaction with a chlorination reagent such as phosphorous oxychloride or thionyl chloride, optionally in the presence of a base such as N,N-dimethylaniline as shown in Scheme 2. The reaction can be run neat or in the presence of a solvent such as N,N-dimethylformamide at temperatures ranging from room temperature to 120° C. The method of Scheme 2 is illustrated in Step C of Example 1, Steps C1 and C2 of Example 2, and Step B of Example 4.

Scheme 2

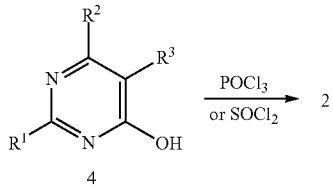

Compounds of Formula 4 can be prepared by the condensation of amidines of Formula 5 with keto esters of Formula 6 in solvents such as methanol or ethanol at temperatures ranging from room temperature to the reflux temperature of the solvent as shown in Scheme 3. Optionally a base such as a metal alkoxide or 1,1,3,3-tetramethylguanidine may be employed. The method of Scheme 3 is illustrated in Step A of Examples 1 and 4, and Steps A1 and A2 of Example 2.

Scheme 3

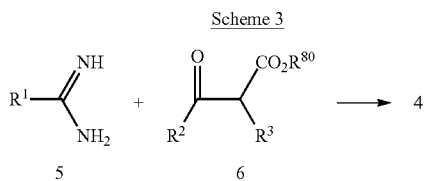

wherein $R^{80}$ is a carbon moiety such as alkyl, preferably $C_1$-$C_2$ alkyl.

Compounds of Formula 4 wherein $R^3$ is a halogen can be prepared from compounds of Formula 4 wherein $R^3$ is hydrogen by reaction with a halogen such as bromine or a halogenating reagent such as an N-halosuccinimide or a sulfuryl halide in a variety of solvents including acetic acid, N,N-dimethylformamide, dichloromethane and carbon tetrachloride at temperatures ranging from 0-100° C. as shown in Scheme 4. The method of Scheme 4 is illustrated in Step B of Example 1, and Steps B1 and B2 of Example 2.

Scheme 4

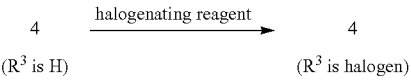

Also, compounds of Formula I wherein $R^3$ is a halogen can be prepared from compounds of Formula I wherein $R^3$ is hydrogen by reaction with a halogenating reagent analogous to the method of Scheme 4. This alternative method is illustrated in Step C of Example 4.

A particularly useful preparation of compounds of Formula 4 wherein $R^3$ is a halogen and $R^2$ is CO$_2R^{12}$ is the reaction of compounds of Formula 4 where $R^3$ is hydrogen and $R^2$ is CH(O$R^{12}$)$_2$ with a halogenating reagent and oxidizing reagent such as an N-halosuccinimide or bromine (when $R^3$ is bromine) in a solvent such as dichloromethane, trichloromethane or tetrachloromethane at temperatures ranging from room temperature to the reflux temperature of the solvent as shown in Scheme 5.

Scheme 5

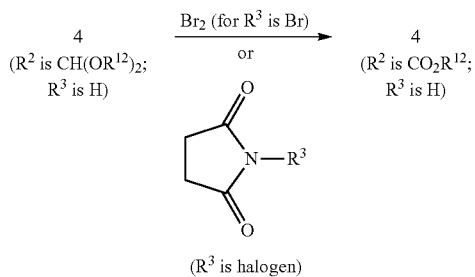

Compounds of Formula 5 and 6 are either commercially available or can be prepared by known methods. (For example see: P. J. Dunn in *Comprehensive Organic Functional Group Transformations*, A. R. Katritzky, O. Meth-Cohn, C. W. Rees Eds, Pergamon Press; Oxford, 1995; vol. 5, pp. 741-782; T. L. Gillchrist in *Comprehensive Organic Functional Group Transformations*, A. R. Katritzky, O. Meth-Cohn, C. W. Rees Eds., Pergamon Press; Oxford, 1995; vol. 6, pp. 601-637 and B. R. Davis, P. J. Garratt in *Comprehensive Organic Synthesis*, B. M. Trost Ed., Pergamom Press; Oxford, 1991; vol. 2, pp. 795-803.)

Alternatively compounds of Formula I can be prepared from corresponding compounds of Formula 7 wherein $X^1$ is a leaving group, such as a halogen or alkylsulfonyl group (e.g., methanesulfonyl, trifluoromethanesulfonyl, benzenesulfonyl), as shown in Scheme 6.

Scheme 6

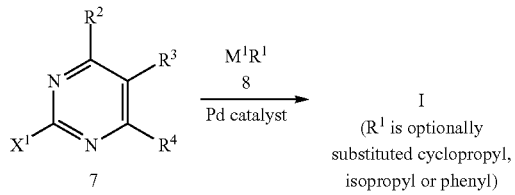

wherein $M^1$ is $B(OH)_2$, $Sn(n-Bu)_3$, $MgX^1$ or $ZnX^1$; $R^1$ is optionally substituted cyclopropyl, optionally substituted isopropyl or optionally substituted phenyl; and $X^1$ is a leaving group.

This method involves palladium-catalyzed reaction of a compound of Formula 7 with a compound of Formula 8 in the form of a boronic acid (e.g., $M^1$ is $B(OH)_2$), an organotin reagent (e.g., $M^1$ is $Sn(n-Bu)_3$), a Grignard reagent (e.g., $M^1$ is $MgX^1$) or an organozinc reagent (e.g., $M^1$ is $ZnX^1$). (For example see: N. Ali, A. McKillop, M. Mitchell, R. Rebelo, A. Ricardo, P. Wallbank, *Tetrahedron*, 1992, 48, 8117-8126; J. Solberg, K. Undheim, *Acta Chem. Scand.*, 1989, 43, 62-68, V. Bonnet, F. Mongin, F. Trécourt, G. Quéguiner and P. Knochel, *Tetrahedron*, 2002, 58, 4429-4438.)

Compounds of Formula 7 wherein $X^1$ is a halogen can be prepared from dihalo compounds of Formula 12 with an amine of Formula 3 optionally catalyzed by a base such as triethylamine or potassium carbonate in a variety of solvents including tetrahydrofuran and dichloromethane at temperatures ranging from 0° C. to the reflux temperature of the solvent as shown in Scheme 7.

Scheme 7

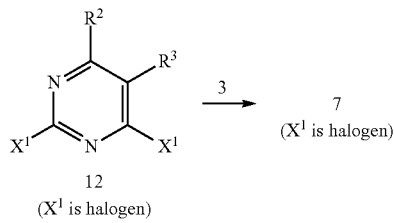

Compounds of Formula 12 can be prepared by known methods. (For example, see H. Gershon, *J. Org. Chem.*, 1962, 27, 3507-3510.)

As shown in Scheme 8, compounds of Formula I wherein $R^2$ is $CO_2R^{12}$ can also be prepared from compounds of Formula 13 by means of a carbonylation reaction. Typical conditions are 1-10 atmospheres of carbon monoxide in the presence of a palladium catalyst in a mixture of an alcohol and another solvent such as N,N-dimethylformamide, N-methylpyrrolidinone or tetrahydrofuran at temperatures ranging from room temperature to 150° C.

Scheme 8

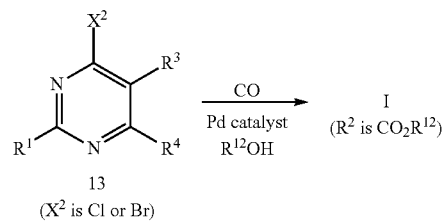

As shown in Scheme 9, compounds of Formula 13 can be prepared from compounds of Formula 14 by reaction with amines of Formula 3 in a reaction analogous to the method of Scheme 1.

Scheme 9

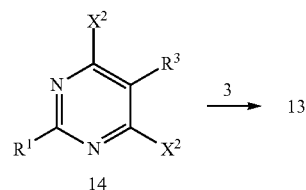

As shown in Scheme 10, compounds of Formula 14 can be prepared from diols of Formula 15 by reaction with a halogenating agent such as phosphorous oxychloride or phosphorous oxybromide in a reaction analogous to the method of Scheme 2. (See H. Gershon, R. Braun, A. Scala and R. Rodin, *J. Med. Chem.* 1964, 7, 808-811 and M. H. Norman, N. Chen, Z. Chen, C. Fotsch, N. Han, R. Hurt, T. Jenkins J. Kincaid, L. Liu, Y. Lu, O. Moreno, V. J. Santora, J. D. Sonnenberg and W. Karbon, *J. Med. Chem.*, 2000, 43, 4288-4312 for examples of this method and for examples of preparation of compounds of Formula 15.)

Scheme 10

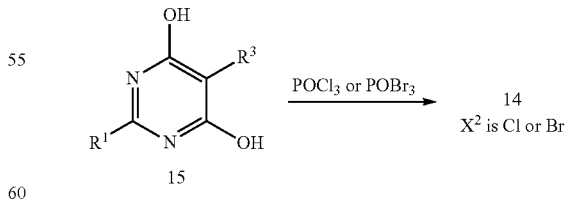

Compounds of Formula I wherein $R^2$ comprises an ester function (e.g., $CO_2R^{12}$ wherein $R^{12}$ is other than H) can be prepared from corresponding carboxylic acid compounds of Formula I (e.g., wherein $R^{12}$ is H) by a wide variety of esterification methods known in the art. One method is illustrated in Example 3. Conversely, carboxylic acid compounds of Formula I can be prepared from the corresponding ester compounds by a wide variety of hydrolysis methods known in the art, such as saponification.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene, P. G. M. Wuts, *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "ddd" means doublet of doublets of doublets, "dt" means doublet of triplets, "dq" means doublet of quartets, "br s" means broad singlet, "br d" means broad doublet.

EXAMPLE 1

Preparation of ethyl 6-amino-5-bromo-2-cyclopropyl-4-pyrimidinecarboxylate (Compound 1) and methyl 6-amino-5-bromo-2-cyclopropyl-4-pyrimidinecarboxylate (Compound 2)

Step A: Preparation of 2-cyclopropyl-6-(diethoxymethyl)-4(1H)-pyrimidinone

To a mixture of ethyl 4,4-diethoxy-3-oxobutanoate (prepared according to the method of E. Graf, R. Troschutz, *Synthesis*, 1999, 7, 1216; 10.0 g, 46 mmol) and cyclopropanecarboximidamide monohydrochloride (Lancaster Synthesis, 5.0 g, 41 mmol) in methanol (100 mL) was added a methanol solution of sodium methoxide (5.4 M, 8.4 mL, 46 mmol). The reaction mixture was stirred overnight. The solvent was removed with a rotary evaporator. Dichloromethane was added and the mixture was filtered. The solvent from the filtrate was removed with a rotary evaporator. The residue was purified by medium pressure liquid chromatography (MPLC) (35→100% ethyl acetate in hexanes as eluant) to afford the title compound as a white solid (4.67 g).

$^1$H NMR (CDCl$_3$) δ 6.55 (s, 1H), 5.10 (s, 1H), 3.61 (m, 4H), 1.91 (m, 1H), 1.23 (m, 8H), 1.09 (m, 2H).

Additionally 3.24 g of an undehydrated product was obtained. This material could be converted to the title compound by refluxing it in methanol with a catalytic amount of pyridinium p-toluenesulfonate.

Step B: Preparation of ethyl 5-bromo-2-cyclopropyl-1,6-dihydro-6-oxo-4-pyrimidinecarboxylate To a solution of 2-cyclopropyl-6-(diethoxymethyl)-4(1H)-pyrimidinone (i.e. the title product of Step A) (2.9 g, 12.1 mmol) in dichloromethane (75 mL) was added N-bromosuccinimide (4.76 g, 26.8 mmol). The reaction mixture was stirred overnight. The solvent was removed with a rotary evaporator. The residue was purified by MPLC (1→4% methanol in dichloromethane as eluant) to afford the title compound as a white solid (2.68 g).

$^1$H NMR (CDCl$_3$) δ 4.43 (q, 2H), 1.90 (m, 1H), 1.41 (t, 3H), 1.30 (m, 2H), 1.20 (m, 2H).

Step C: Preparation of ethyl 6-amino-5-bromo-2-cyclopropyl-4-pyrimidinecarboxylate and methyl 6-amino-5-bromo-2-cyclopropyl-4-pyrimidinecarboxylate To a solution of ethyl 5-bromo-2-cyclopropyl-1,6-dihydro-6-oxo-4-pyrimidinecarboxylate (i.e. the product of Step B) (1.07 g, 3.7 mmol) in N,N-dimethylformamide (15 mL) was added thionyl chloride (0.54 mL, 7.5 mmol). The reaction mixture was stirred for 2 h. The solvent was removed with a rotary evaporator. The residue was dissolved in dichloromethane, washed with saturated aqueous sodium bicarbonate and dried (Na$_2$SO$_4$). The solvent was removed with a rotary evaporator. The residue was dissolved in tetrahydrofuran (2 mL), and a methanolic solution of ammonia (7 N, 2 mL) was added. The reaction mixture was placed in a sealed vial and heated in a microwave reactor at 125° C. for 2 h. The reaction mixture was allowed to stand over the weekend. Dichloromethane was added and the reaction mixture was filtered. The solvent was removed with a rotary evaporator. The residue was purified by MPLC (10→30% ethyl acetate in hexanes as eluant) to afford the title product, a compound of the present invention, as a white solid (0.52 g).

$^1$H NMR (CDCl$_3$) δ 5.40 (br s, 2H), 4.44 (q, 2H), 2.05 (m, 1H), 1.01 (t, 3H), 1.05 (m, 2H), 0.99 (m, 2H).

Also isolated from the MPLC purification was the corresponding methyl ester, i.e. methyl 6-amino-5-bromo-2-cyclopropyl-4-pyrimidinecarboxylate, a further compound of the present invention, as a white solid (0.06 g).

$^1$H NMR (CDCl$_3$) δ 5.40 (br s, 2H), 3.97 (s, 3H) 2.05 (m, 1H), 1.05 (m, 2H), 0.99 (m, 2H).

EXAMPLE 2

Preparation of 6-amino-5-chloro-2-cyclopropyl-4-pyrimidinecarboxylic acid (Compound 135)

Step A1: Preparation of 2-cyclopropyl-1,6-dihydro-6-oxo-4-pyrimidinecarboxylic acid To a mixture of diethyl oxalacetate sodium salt (150 g, 714 mmol) in methanol (300 mL) and water (150 mL) warmed to 30° C. was added 50% aqueous sodium hydroxide (56 g, 700 mmol) in water (60 mL) over 30 minutes, over which time the temperature remained at 25-30° C. and the pH at 11-12. Then the stirred mixture was heated for an additional 30 min at 35° C. To this mixture was added cyclopropanecarboximidamide monohydrochloride (64 g, 530 mol) in portions over 15 minutes. The orange solution was heated to 50° C. over 30 minutes and held at that temperature for 3 h. The reaction mixture was cooled to 35° C., and concentrated hydrochloric acid (ca. 70 g, 0.7 mol) was added gradually (resulting in foaming) over 30 minutes at 30-40° C. until the pH was about 1.5-2.5. The mixture was concentrated with a rotary evaporator at 35-40° C. to remove alcohols, stirred for 3-4 h at 25° C. to complete crystallization of the product. After the mixture was cooled to 0° C. the solid was collected by filtration. The solid was washed with water (2×60 mL), suction-dried, and then dried in a vacuum-oven at 60° C. to afford the title compound as a beige solid (ca. 60 g).

$^1$H NMR (DMSO-$d_6$) δ 6.58 (s, 1H), 1.95 (m, 1H), 1.0 (m, 4H).

Step A2: Another preparation of 2-cyclopropyl-1,6-dihydro-6-oxo-4-pyrimidine-carboxylic acid To a mixture of diethyl oxalacetate sodium salt (210 g, 950 mmol) in methanol (500 mL) and water (400 mL) was added 50% aqueous sodium hydroxide (80 g, 1.0 mol) in water (60 mL) over 30 minutes, over which time the temperature remained at 25-30° C. and the pH at 11-12. Then the stirred mixture was heated for an additional 30 min at 30° C. To this mixture was added cyclopropanecarboximidamide monohydrochloride (110 g, 910 mol). The orange solution was heated to 50° C. over 30 minutes and held at that temperature for 5 h. The reaction mixture was cooled to 30° C. and concentrated to half volume at reduced pressure at 35-40° C. and concentrated hydrochloric acid (140 g, 1.4 mol) was added gradually (resulting in foaming) over 30 minutes at 25-30° C. until the pH was about 1-2. The mixture was stirred at 5° C. for 1 h to complete crystallization of the product. After the mixture was cooled to 0° C. the solid was collected by filtration. The solid was washed with water (3×60 mL), suction-dried, and then dried in a vacuum-oven at 70° C. to afford the title compound as a beige solid (100 g); m.p. 235-236° C. (dec.).

$^1$H NMR (DMSO-$d_6$) δ 6.58 (s, 1H), 1.95 (m, 1H), 1.0 (m, 4H).

Step B1: Preparation of 5-chloro-2-cyclopropyl-1,6-dihydro-6-oxo-4-pyrimidine-carboxylic acid To a mixture of 2-cyclopropyl-1,6-dihydro-6-oxo-4-pyrimidinecarboxylic acid (i.e. the product of Step A1 or A2) (9.2 g, 52 mmol) in water (30 mL) and concentrated hydrochloric acid (22 g, 220 mmol) at 15° C. was added dropwise aqueous sodium hypochlorite solution (11%, 40 g, 59 mmol) over 15 minutes so that with cooling the reaction mixture was maintained at 15-20° C. The mixture was then held at 20-25° C. for 1 h. Solid sodium bisulfite (ca. 2 g) was added, and then aqueous sodium hydroxide solution (50%, 8 g, 0.10 mol) was added dropwise so that with cooling the reaction mixture was maintained at about 25° C. The mixture was cooled to 10° C., and the suspended product was isolated by filtration and washed with a minimum amount of cold water. The product was then dried to constant weight in vacuum-oven at 50° C. to afford the title compound (7.5 g).

$^1$H NMR (DMSO-$d_6$) δ 13.4 (br s, 1H), 1.95 (m, 1H), 1.0 (m, 4H).

Step B2: Another preparation of 5-chloro-2-cyclopropyl-1,6-dihydro-6-oxo-4-pyrimidinecarboxylic acid To a mixture of 2-cyclopropyl-1,6-dihydro-6-oxo-4-pyrimidinecarboxylic acid (i.e. the product of Step A1 or A2) (184 g, 1.02 mol) in water (45 mL) and concentrated hydrochloric acid (292 g, 3 mol) at 8-12° C. was added dropwise aqueous sodium hypochlorite solution (8.4%, 1.02 kg, 1.15 mol) over 2 h so that with cooling the reaction mixture was maintained at 8-10° C. The mixture was then held at 10-12° C. for 1 h and the conversion was monitored by HPLC. When less than 5% of the starting material remained solid sodium bisulfite was added until a negative KI starch paper test was obtained. The mixture was cooled to 5° C., and the suspended product was isolated by filtration and washed with a minimum amount of cold water. The product was then dried to constant weight in vacuum-oven at 50° C. to afford the title compound (194 g); m.p. 189-190° C.

$^1$H NMR (DMSO-$d_6$) δ 13.4 (br s, 1H), 1.95 (m, 1H), 1.0 (m, 4H).

Step C1: Preparation of 5,6-dichloro-2-cyclopropyl-4-pyrimidinecarboxylic acid Phosphorus oxychloride (14 mL, 23 g, 0.15 mol) and 5-chloro-2-cyclopropyl-1,6-dihydro-6-oxo-4-pyrimidinecarboxylic acid (i.e. the product of Step B1 or B2) (75 g, 300 mmol) were combined and heated at 85° C. for 3 h. The reaction mixture was cooled to 30° C. and added over 30 minutes to a mixture of acetonitrile (50 mL) and ice water (80 mL), with the temperature maintained at 5-10° C. and the pH maintained in the range 1-3 by co-feeding aqueous ammonia (28%). The pH was adjusted to about 2, the mixture was concentrated at 25° C. with a rotary evaporator to remove acetonitrile, and the precipitated product was isolated by filtration and washed with water (2×25 mL). The solid was dried in a vacuum oven to afford the title compound (ca. 7.0 g).

$^1$H NMR (DMSO-$d_6$) δ 2.23 (m, 1H), 1.2 (m, 2H), 1.0 (m, 2H).

Step C2: Another preparation of 5,6-dichloro-2-cyclopropyl-4-pyrimidinecarboxylic acid Phosphorus oxychloride (200 mL, 328 g, 2.14 mol) and 5-chloro-2-cyclopropyl-1,6-dihydro-6-oxo-4-pyrimidinecarboxylic acid (i.e. the product of Step B1 or B2) (96.8 g, 451 mmol) were combined and heated at 90° C. for 5 h. The reaction mixture was cooled to 50-60° C. and concentrated at reduced pressure to half volume. After cooling to 30° C. the reaction mixture was added over 60 minutes to a mixture of t-butanol (200 mL) and water (300 mL), with the temperature maintained at 8-10° C. The mixture was seeded, water (300 mL) was added gradually at 10-15° C. and the mixture was stirred for 1 h. After cooling to 5° C. the precipitated product was isolated by filtration and washed with water (3×50 mL). The solid was dried in a vacuum oven to afford the title compound (93 g).

$^1$H NMR (DMSO-$d_6$) δ 2.23 (m, 1H), 1.2 (m, 2H), 1.0 (m, 2H).

Step D1: Preparation of 6-amino-5-chloro-2-cyclopropyl-4-pyrimidinecarboxylic acid A mixture of 5,6-dichloro-2-cyclopropyl-4-pyrimidinecarboxylic acid (i.e. the product of Step C1 or C2) (5.1 g, 22 mmol), water (30 mL) and aqueous ammonia (28%, 8 g, 130 mmol) was heated at 80° C. for 3 h. The solution was concentrated at 50° C. and 70 torr (9.3 kPa) pressure to about half volume to remove most of the excess ammonia. The resulting slurry was stirred at 20° C., acidified to pH 2 with aqueous hydrochloric acid, cooled to 5° C. and filtered. The isolated solid was dried in a vacuum oven to afford the title product (4.2 g), a compound of the present invention.

$^1$H NMR (DMSO-$d_6$) δ 13.4 (br s, 1H), 1.95 (m, 1H), 1.0 (m, 4H).

Step D2: Another preparation of 6-amino-5-chloro-2-cyclopropyl-4-pyrimidinecarboxylic acid A mixture of 5,6-dichloro-2-cyclopropyl-4-pyrimidinecarboxylic acid (i.e. the product of Step C1 or C2) (280 g, 1.2 mol), water (1.26 L) and aqueous ammonia (28%, 350 g, 5.76 mol) was heated at 80° C. for 5 h. The solution was concentrated at 50° C. and 70 torr (9.3 kPa) pressure to about half volume to remove most of the excess ammonia. The resulting slurry was stirred at 20° C., acidified to pH 1-2 with aqueous hydrochloric acid, cooled to 5° C. and filtered. The isolated solid was dried in a vacuum oven to afford the title product (270 g), a compound of the present invention.

$^1$H NMR (DMSO-$d_6$) δ 13.4 (br s, 1H), 1.95 (m, 1H), 1.0 (m, 4H).

EXAMPLE 3

Preparation of methyl 6-amino-5-chloro-2-cyclopropyl-4-pyrimidinecarboxylate (Compound 9)

To a solution of 6-amino-5-chloro-2-cyclopropyl-4-pyrimidinecarboxylic acid (i.e. the product of Step D1 or D2 of Example 2) (2.0 g, 8.5 mmol) in methanol (20 mL) was added dropwise thionyl chloride (4 mL, 70 mmol). The mixture was heated at reflux for 24 h. Concentrated sulfuric acid (5 drops) was added, and the reaction mixture was heated at reflux for 16 h. After the mixture was cooled, water (30 mL) was added, and aqueous ammonia (28%, 10 mL) was added dropwise. The mixture was cooled to 5° C., and the solid was isolated by filtration, washed with water and dried in a vacuum oven at 40° C. to afford the title product (2.3 g), a compound of the present invention.

$^1$H NMR (CDCl$_3$) δ 5.41 (br s, 2H), 3.98 (s, 3H), 2.06 (m, 1H), 1.04 (m, 2H), 1.00 (m, 2H).

Another preparation of methyl 6-amino-5-chloro-2-cyclopropyl-4-pyrimidinecarboxylate To a solution of 6-amino-5-chloro-2-cyclopropyl-4-pyrimidinecarboxylic acid (i.e. the product of Step D1 or D2 of Example 2) (8.5 g, 40 mmol) in methanol (120 mL) was added dropwise with cooling thionyl chloride (15 mL, 200 mmol). The mixture was heated at 60° C. for 24 h. The mixture was concentrated to 25% of the original volume and diluted with water (100 mL). Phenolphthalein pH indicator was added, and 10% aqueous sodium hydroxide was added dropwise with cooling at 10-20° C. to bring the pH to 8-10. The solid was isolated by filtration, washed with water and dried in a vacuum oven at 50-60° C. to afford the title product (7.3 g), a compound of the present invention.

$^1$H NMR (CDCl$_3$) δ 5.41 (br s, 2H), 3.98 (s, 3H), 2.06 (m, 1H), 1.04 (m, 2H), 1.00 (m, 2H).

EXAMPLE 4

Preparation of 6-amino-5-chloro-2-(4-chlorophenyl)-4-pyrimidinecarboxylic acid (Compound 65)

Step A: Preparation of 2-(4-chlorophenyl)-1,6-dihydro-6-oxo-4-pyrimidinecarboxylic acid To a mixture of diethyl oxalacetate sodium salt (123.2 g, 586 mmol) in water (750 mL) was slowly added aqueous sodium hydroxide (50%, 47 g, 586 mmol). After 1 h the solids had dissolved. 4-Chlorobenzenecarboximidamide monohydrochloride (111.95 g, 586 mmol) was then added, and the mixture was heated at 70° C. overnight. After cooling to room temperature concentrated hydrochloric acid was slowly added (causing foaming) until the pH was lowered to 1.5. The solid was isolated by filtration and washed with water and methanol. The solid was then triturated twice with hot methanol, washed repeatedly with 1 N hydrochloric acid, then once with methanol and dried to afford the title compound (66.07 g).

$^1$H NMR (DMSO-$d_6$) δ 8.23 (d, 2H), 7.65 (d, 2H), 6.90 (s, 1H).

Step B: Preparation of 6-amino-2-(4-chlorophenyl)-4-pyrimidinecarboxylic acid

To phosphorus oxychloride (180 mL) was added 2-(4-chlorophenyl)-1,6-dihydro-6-oxo-4-pyrimidinecarboxylic acid (i.e. the product of Step A) (81.81 g, 326 mmol). The mixture was heated to 90° C. for 2.5 h. After cooling to room temperature the reaction mixture was slowly added to 1:2 acetonitrile:water (1.5 L) while keeping the temperature between 35 and 45° C. After the reaction mixture was stirred at room temperature for 30 minutes the resulting solid was isolated by filtration and washed with water. The solid was then combined with aqueous ammonia (5%, 2.1 L) and heated to 80° C. for 18 h. After 2 days at room temperature the solid was isolated by filtration and washed with water. A second crop was obtained by cooling the filtrate and refiltering. The combined solids were dried to afford the title compound (58.8 g).

$^1$H NMR (DMSO-$d_6$) δ 8.33 (d, 2H), 7.51 (d, 2H), 6.89 (s, 2H), 6.81 (s, 1H).

Step C: Preparation of 6-amino-5-chloro-2-(4-chlorophenyl)-4-pyrimidinecarboxylic acid To a solution of 6-amino-2-(4-chlorophenyl)-4-pyrimidinecarboxylic acid (i.e. the product of Step B) (75 g, 300 mmol) in N,N-dimethylformamide (300 mL) at 50° C. was added portionwise N-chlorosuccinimide (44.1 g, 330 mmol). The temperature of the reaction mixture increased exothermically to 65° C. Then the reaction mixture was heated at 55° C. for 3 h. Additional N-chlorosuccinimide (14 g, 90 mmol) was added portionwise, and the reaction mixture was maintained at 55° C. for 30 minutes. After the reaction mixture was cooled water was added. The resulting solid was isolated by filtration, washed with water, dissolved in ethyl acetate, washed with water and dried. The solvent was removed using a rotary evaporator to afford the title product, a compound of the present invention, as a tan solid (73.68 g).

$^1$H NMR (DMSO-$d_6$) δ 8.28 (d, 2H), 7.70 (br s, 2H), 7.58 (d, 2H).

EXAMPLE 5

Preparation of ethyl 6-amino-5-chloro-2-(4-chlorophenyl)-4-pyrimidinecarboxylate (Compound 64)

To a solution of 6-amino-5-chloro-2-(4-chlorophenyl)-4-pyrimidinecarboxylic acid (i.e. the product of Example 4, Step C) (20.0 g, 70.4 mmol) in ethanol (70 mL) was added thionyl chloride (5.14 mL, 70.4 mmol) while maintaining the temperature below 15° C. using an ice bath. The reaction mixture was then heated at reflux overnight. Water was added. Then with external cooling aqueous sodium hydroxide (50%) was added to adjust the pH to 7. The resulting solid was isolated by filtration and dried to afford the title product, a compound of the present invention, as a light beige solid (20.1 g).

$^1$H NMR (CDCl$_3$) δ 8.31 (d, 2H), 7.42 (d, 2H), 5.50 (br s, 2H), 4.50 (q, 2H), 1.47 (t, 3H).

By the procedures described herein together with methods known in the art, the following compounds of Tables 1 to 4 can be prepared. The following abbreviations are used in the Tables which follow: t means tertiary, i means iso, Me means methyl, Et means ethyl, Pr means propyl, i-Pr means isopropyl, Bu means butyl, t-Bu means tert-butyl, CN means cyano, and S(O)$_2$Me means methylsulfonyl. "⁻" means negative formal charge, and "⁺" means positive formal charge.

TABLE 1

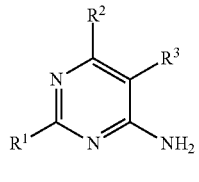

R$^1$ is cyclopropyl; R$^3$ is Cl.

| R$^2$ |
|---|
| CO$_2$H |
| CO$_2$Me |
| CO$_2$Et |
| CO$_2$Pr |
| CO$_2$iPr |
| CO$_2$t-Bu |
| CO$_2$cyclohexyl |
| CO$_2$hexyl |
| CO$_2$CH$_2$cyclohexyl |
| CO$_2$CH$_2$Ph |
| CO$_2$CH(Me)Ph |
| CO$_2$CH$_2$(4-Cl—Ph) |
| CO$_2$CH$_2$(3-F—Ph) |
| CO$_2$CH$_2$CH$_2$NMe$_2$ |
| CO$_2$CH$_2$CH$_2$OMe |
| CO$_2$CH$_2$CH$_2$OH |
| CO$_2$CH$_2$(3-oxetanyl) |
| CH$_2$OH |
| CH$_2$OMe |
| CH$_2$CO$_2$Me |
| CH(OH)CO$_2$Me |
| CH(OC(=O)Me)CO$_2$Me |
| CHO |
| C(=NOH)H |
| C(=NOMe)H |
| C(=O)NH$_2$ |
| C(=O)NHMe |
| C(=O)NMe$_2$ |
| CO$_2$Ph |
| C(O)O⁻, H$_3$N⁺Me |
| C(O)O⁻, H$_3$N⁺i-Pr |
| C(O)O⁻, H$_3$N⁺Pr |
| C(O)O⁻, H$_3$N⁺butyl |

TABLE 1-continued

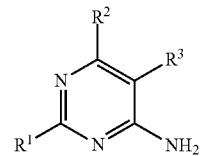

| R$^2$ |
|---|
| C(O)O⁻, H$_3$N⁺hexyl |
| C(O)O⁻, H$_3$N⁺octyl |
| C(O)O⁻, H$_3$N⁺hexadecyl |
| C(O)O⁻, H$_3$N⁺octadecyl |
| C(O)O⁻, H$_3$N⁺cyclohexyl |
| C(O)O⁻, H$_3$N⁺(Et)$_2$ |
| C(O)O⁻, H$_2$N⁺—(CH$_2$)$_2$O(CH$_2$)$_2$— |
| C(O)O⁻, H$_2$N⁺—CH$_2$(CH$_2$)$_2$CH$_2$— |
| C(O)O⁻, HN⁺(Et)$_3$ |
| C(O)O⁻, N⁺(Me)$_4$ |
| C(O)O⁻, N⁺(Me)$_3$CH$_2$Ph |
| C(O)O⁻, S⁺(Me)$_3$ |
| C(O)O⁻, K⁺ |

R$^1$ is cyclopropyl; R$^3$ is F.

| |
|---|
| CO$_2$H |
| CO$_2$Me |
| CO$_2$Et |
| CO$_2$Pr |
| CO$_2$iPr |
| CO$_2$t-Bu |
| CO$_2$cyclohexyl |
| CO$_2$hexyl |
| CO$_2$CH$_2$cyclohexyl |
| CO$_2$CH$_2$Ph |
| CO$_2$CH(Me)Ph |
| CO$_2$CH$_2$(4-Cl—Ph) |
| CO$_2$CH$_2$(3-F—Ph) |
| CO$_2$CH$_2$CH$_2$NMe$_2$ |
| CO$_2$CH$_2$CH$_2$OMe |
| CO$_2$CH$_2$CH$_2$OH |
| CO$_2$CH$_2$(3-oxetanyl) |
| CH$_2$OH |
| CH$_2$OMe |
| CH$_2$CO$_2$Me |
| CH(OH)CO$_2$Me |
| CH(OC(=O)Me)CO$_2$Me |
| CHO |
| C(=NOH)H |
| C(=NOMe)H |
| C(=O)NH$_2$ |
| C(=O)NHMe |
| C(=O)NMe$_2$ |
| CO$_2$Ph |
| C(O)O⁻, H$_3$N⁺Me |
| C(O)O⁻, H$_3$N⁺i-Pr |
| C(O)O⁻, H$_3$N⁺Pr |
| C(O)O⁻, H$_3$N⁺butyl |
| C(O)O⁻, H$_3$N⁺hexyl |
| C(O)O⁻, H$_3$N⁺octyl |
| C(O)O⁻, H$_3$N⁺hexadecyl |
| C(O)O⁻, H$_3$N⁺octadecyl |
| C(O)O⁻, H$_3$N⁺cyclohexyl |
| C(O)O⁻, H$_3$N⁺(Et)$_2$ |
| C(O)O⁻, H$_2$N⁺—(CH$_2$)$_2$O(CH$_2$)$_2$— |
| C(O)O⁻, H$_2$N⁺—CH$_2$(CH$_2$)$_2$CH$_2$— |
| C(O)O⁻, HN⁺(Et)$_3$ |
| C(O)O⁻, N⁺(Me)$_4$ |
| C(O)O⁻, N⁺(Me)$_3$CH$_2$Ph |
| C(O)O⁻, S⁺(Me)$_3$ |
| C(O)O⁻, K⁺ |

R$^1$ is cyclopropyl; R$^3$ is Br.

| |
|---|
| CO$_2$H |
| CO$_2$Me |
| CO$_2$Et |

TABLE 1-continued

[Structure: pyrimidine with R² at 6-position, R³ at 5-position, R¹ at 2-position, NH₂ at 4-position]

R²

| |
|---|
| CO₂Pr |
| CO₂iPr |
| CO₂t-Bu |
| CO₂cyclohexyl |
| CO₂hexyl |
| CO₂CH₂cyclohexyl |
| CO₂CH₂Ph |
| CO₂CH(Me)Ph |
| CO₂CH₂(4-Cl—Ph) |
| CO₂CH₂(3-F—Ph) |
| CO₂CH₂CH₂NMe₂ |
| CO₂CH₂CH₂OMe |
| CO₂CH₂CH₂OH |
| CO₂CH₂(3-oxetanyl) |
| CH₂OH |
| CH₂OMe |
| CH₂CO₂Me |
| CH(OH)CO₂Me |
| CH(OC(=O)Me)CO₂Me |
| CHO |
| C(=NOH)H |
| C(=NOMe)H |
| C(=O)NH₂ |
| C(=O)NHMe |
| C(=O)NMe₂ |
| CO₂Ph |
| C(O)O, H₃N⁺Me |
| C(O)O, H₃N⁺i-Pr |
| C(O)O, H₃N⁺Pr |
| C(O)O, H₃N⁺butyl |
| C(O)O, H₃N⁺hexyl |
| C(O)O, H₃N⁺octyl |
| C(O)O, H₃N⁺hexadecyl |
| C(O)O, H₃N⁺octadecyl |
| C(O)O, H₃N⁺cyclohexyl |
| C(O)O, H₃N⁺(Et)₂ |
| C(O)O, H₂N⁺﹢(CH₂)₂O(CH₂)₂﹢ |
| C(O)O, H₂N⁺﹢CH₂(CH₂)₂CH₂﹢ |
| C(O)O, HN⁺(Et)₃ |
| C(O)O, N⁺(Me)₄ |
| C(O)O, N⁺(Me)₃CH₂Ph |
| C(O)O, S⁺(Me)₃ |
| C(O)O, K⁺ |

R¹ is cyclopropyl; R³ is I.

| |
|---|
| CO₂H |
| CO₂Me |
| CO₂Et |
| CO₂Pr |
| CO₂iPr |
| CO₂t-Bu |
| CO₂cyclohexyl |
| CO₂hexyl |
| CO₂CH₂cyclohexyl |
| CO₂CH₂Ph |
| CO₂CH(Me)Ph |
| CO₂CH₂(4-Cl—Ph) |
| CO₂CH₂(3-F—Ph) |
| CO₂CH₂CH₂NMe₂ |
| CO₂CH₂CH₂OMe |
| CO₂CH₂CH₂OH |
| CO₂CH₂(3-oxetanyl) |
| CH₂OH |
| CH₂OMe |
| CH₂CO₂Me |
| CH(OH)CO₂Me |

TABLE 1-continued

[Structure: pyrimidine with R² at 6-position, R³ at 5-position, R¹ at 2-position, NH₂ at 4-position]

R²

| |
|---|
| CH(OC(=O)Me)CO₂Me |
| CHO |
| C(=NOH)H |
| C(=NOMe)H |
| C(=O)NH₂ |
| C(=O)NHMe |
| C(=O)NMe₂ |
| CO₂Ph |
| C(O)O, H₃N⁺Me |
| C(O)O, H₃N⁺i-Pr |
| C(O)O, H₃N⁺Pr |
| C(O)O, H₃N⁺butyl |
| C(O)O, H₃N⁺hexyl |
| C(O)O, H₃N⁺octyl |
| C(O)O, H₃N⁺hexadecyl |
| C(O)O, H₃N⁺octadecyl |
| C(O)O, H₃N⁺cyclohexyl |
| C(O)O, H₃N⁺(Et)₂ |
| C(O)O, H₂N⁺﹢(CH₂)₂O(CH₂)₂﹢ |
| C(O)O, H₂N⁺﹢CH₂(CH₂)₂CH₂﹢ |
| C(O)O, HN⁺(Et)₃ |
| C(O)O, N⁺(Me)₄ |
| C(O)O, N⁺(Me)₃CH₂Ph |
| C(O)O, S⁺(Me)₃ |
| C(O)O, K⁺ |

R¹ is 4-Cl—Ph; R³ is Cl.

| |
|---|
| CO₂H |
| CO₂Me |
| CO₂Et |
| CO₂Pr |
| CO₂iPr |
| CO₂t-Bu |
| CO₂cyclohexyl |
| CO₂hexyl |
| CO₂CH₂cyclohexyl |
| CO₂CH₂Ph |
| CO₂CH(Me)Ph |
| CO₂CH₂(4-Cl—Ph) |
| CO₂CH₂(3-F—Ph) |
| CO₂CH₂CH₂NMe₂ |
| CO₂CH₂CH₂OMe |
| CO₂CH₂CH₂OH |
| CO₂CH₂(3-oxetanyl) |
| CH₂OH |
| CH₂OMe |
| CH₂CO₂Me |
| CH(OH)CO₂Me |
| CHO |
| CH(OC(=O)Me)CO₂Me |
| C(=NOH)H |
| C(=NOMe)H |
| C(=O)NH₂ |
| C(=O)NHMe |
| C(=O)NMe₂ |
| CO₂Ph |
| C(O)O, H₃N⁺Me |
| C(O)O, H₃N⁺i-Pr |
| C(O)O, H₃N⁺Pr |
| C(O)O, H₃N⁺butyl |
| C(O)O, H₃N⁺hexyl |
| C(O)O, H₃N⁺octyl |
| C(O)O, H₃N⁺hexadecyl |
| C(O)O, H₃N⁺octadecyl |
| C(O)O, H₃N⁺cyclohexyl |
| C(O)O, H₂N⁺(Et)₂ |
| C(O)O, |

TABLE 1-continued

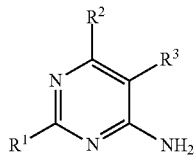

R²

| |
|---|
| H₂N⁺⎡(CH₂)₂O(CH₂)₂⎤ |
| C(O)O, |
| H₂N⁺⎡CH₂(CH₂)₂CH₂⎤ |
| C(O)O, HN⁺(Et)₃ |
| C(O)O, N⁺(Me)₄ |
| C(O)O, N⁺(Me)₃CH₂Ph |
| C(O)O, S⁺(Me)₃ |
| C(O)O, K⁺ |
| R¹ is 4-Cl—Ph; R³ is F. |

| |
|---|
| CO₂H |
| CO₂Me |
| CO₂Et |
| CO₂Pr |
| CO₂iPr |
| CO₂t-Bu |
| CO₂cyclohexyl |
| CO₂hexyl |
| CO₂CH₂cyclohexyl |
| CO₂CH₂Ph |
| CO₂CH(Me)Ph |
| CO₂CH₂(4-Cl—Ph) |
| CO₂CH₂(3-F—Ph) |
| CO₂CH₂CH₂NMe₂ |
| CO₂CH₂CH₂OMe |
| CO₂CH₂CH₂OH |
| CO₂CH₂(3-oxetanyl) |
| CH₂OH |
| CH₂OMe |
| CH₂CO₂Me |
| CH(OH)CO₂Me |
| CHO |
| CH(OC(=O)Me)CO₂Me |
| C(=NOH)H |
| C(=NOMe)H |
| C(=O)NH₂ |
| C(=O)NHMe |
| C(=O)NMe₂ |
| CO₂Ph |
| C(O)O, H₃N⁺Me |
| C(O)O, H₃N⁺i-Pr |
| C(O)O, H₃N⁺Pr |
| C(O)O, H₃N⁺butyl |
| C(O)O, H₃N⁺hexyl |
| C(O)O, H₃N⁺octyl |
| C(O)O, H₃N⁺hexadecyl |
| C(O)O, H₃N⁺octadecyl |
| C(O)O, H₃N⁺cyclohexyl |
| C(O)O, H₂N⁺(Et)₂ |
| C(O)O, |
| H₂N⁺⎡(CH₂)₂O(CH₂)₂⎤ |
| C(O)O, |
| H₂N⁺⎡CH₂(CH₂)₂CH₂⎤ |
| C(O)O, HN⁺(Et)₃ |
| C(O)O, N⁺(Me)₄ |
| C(O)O, N⁺(Me)₃CH₂Ph |
| C(O)O, S⁺(Me)₃ |
| C(O)O, K⁺ |
| R¹ is 4-Cl—Ph; R³ is Br. |

| |
|---|
| CO₂H |
| CO₂Me |
| CO₂Et |
| CO₂Pr |
| CO₂iPr |
| CO₂t-Bu |
| CO₂cyclohexyl |
| CO₂hexyl |

TABLE 1-continued

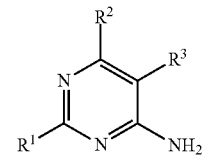

R²

| |
|---|
| CO₂CH₂cyclohexyl |
| CO₂CH₂Ph |
| CO₂CH(Me)Ph |
| CO₂CH₂(4-Cl—Ph) |
| CO₂CH₂(3-F—Ph) |
| CO₂CH₂CH₂NMe₂ |
| CO₂CH₂CH₂OMe |
| CO₂CH₂CH₂OH |
| CO₂CH₂(3-oxetanyl) |
| CH₂OH |
| CH₂OMe |
| CH₂CO₂Me |
| CH(OH)CO₂Me |
| CHO |
| CH(OC(=O)Me)CO₂Me |
| C(=NOH)H |
| C(=NOMe)H |
| C(=O)NH₂ |
| C(=O)NHMe |
| C(=O)NMe₂ |
| CO₂Ph |
| C(O)O, H₃N⁺Me |
| C(O)O, H₃N⁺i-Pr |
| C(O)O, H₃N⁺Pr |
| C(O)O, H₃N⁺butyl |
| C(O)O, H₃N⁺hexyl |
| C(O)O, H₃N⁺octyl |
| C(O)O, H₃N⁺hexadecyl |
| C(O)O, H₃N⁺octadecyl |
| C(O)O, H₃N⁺cyclohexyl |
| C(O)O, H₂N⁺(Et)₂ |
| C(O)O, |
| H₂N⁺⎡(CH₂)₂O(CH₂)₂⎤ |
| C(O)O, |
| H₂N⁺⎡CH₂(CH₂)₂CH₂⎤ |
| C(O)O, HN⁺(Et)₃ |
| C(O)O, N⁺(Me)₄ |
| C(O)O, N⁺(Me)₃CH₂Ph |
| C(O)O, S⁺(Me)₃ |
| C(O)O, K⁺ |
| R¹ is 4-Cl—Ph; R³ is I. |

| |
|---|
| CO₂H |
| CO₂Me |
| CO₂Et |
| CO₂Pr |
| CO₂iPr |
| CO₂t-Bu |
| CO₂cyclohexyl |
| CO₂hexyl |
| CO₂CH₂cyclohexyl |
| CO₂CH₂Ph |
| CO₂CH(Me)Ph |
| CO₂CH₂(4-Cl—Ph) |
| CO₂CH₂(3-F—Ph) |
| CO₂CH₂CH₂NMe₂ |
| CO₂CH₂CH₂OMe |
| CO₂CH₂CH₂OH |
| CO₂CH₂(3-oxetanyl) |
| CH₂OH |
| CH₂OMe |
| CH₂CO₂Me |
| CH(OH)CO₂Me |
| CHO |
| CH(OC(=O)Me)CO₂Me |
| C(=NOH)H |
| C(=NOMe)H |
| C(=O)NH₂ |
| C(=O)NHMe |

TABLE 1-continued $$\text{[pyrimidine structure with } R^1, R^2, R^3, NH_2 \text{]}$$

| $R^2$ |
|---|
| C(=O)NMe$_2$ |
| CO$_2$Ph |
| C(O)O, H$_3$N$^+$Me |
| C(O)O, H$_3$N$^+$i-Pr |
| C(O)O, H$_3$N$^+$Pr |
| C(O)O, H$_3$N$^+$butyl |
| C(O)O, H$_3$N$^+$hexyl |
| C(O)O, H$_3$N$^+$octyl |
| C(O)O, H$_3$N$^+$hexadecyl |
| C(O)O, H$_3$N$^+$octadecyl |
| C(O)O, H$_3$N$^+$cyclohexyl |
| C(O)O, H$_3$N$^+$(Et)$_2$ |
| C(O)O, H$_2$N$^+$-[-(CH$_2$)$_2$O(CH$_2$)$_2$-]- |
| C(O)O, H$_2$N$^+$-[-CH$_2$(CH$_2$)$_2$CH$_2$-]- |
| C(O)O, HN$^+$(Et)$_3$ |
| C(O)O, N$^+$(Me)$_4$ |
| C(O)O, N$^+$(Me)$_3$CH$_2$Ph |
| C(O)O, S$^+$(Me)$_3$ |
| C(O)O, K$^+$ |

TABLE 2

$$\text{[pyrimidine structure with } R^1, R^2, R^3, NH_2 \text{]}$$

| $R^1$ |
|---|
| $R^2$ is CO$_2$H; $R^3$ is Cl. |
| i-Pr |
| 1-Me-cyclopropyl |
| 2-Me-cyclopropyl |
| 2-F-cyclopropyl |
| 2-Cl-cyclopropyl |
| 2,2-di-F-cyclopropyl |
| 2,2-di-Cl-cyclopropyl |
| 1,2-di-F-cyclopropyl |
| 2,2,3,3-tetra-F-cyclopropyl |
| 1,2,2,3,3-penta-F-cyclopropyl |
| Ph |
| 4-Cl—Ph |
| 4-F—Ph |
| 3-OMe—Ph |
| 4-Br—Ph |
| 4-I—Ph |
| 4-CF$_3$—Ph |
| 4-OCHF$_2$—Ph |
| 4-OCF$_3$—Ph |
| 4-SCF$_3$—Ph |
| 4-SCHF$_2$—Ph |
| 4-CN—Ph |
| 4-CO$_2$Me—Ph |
| 2,4-di-Cl—Ph |
| 2-F-4-Cl—Ph |
| 3,4-di-Cl—Ph |
| 2-MeO-cyclopropyl |
| 2-MeS-cyclopropyl |

TABLE 2-continued $$\text{[pyrimidine structure with } R^1, R^2, R^3, NH_2 \text{]}$$

| $R^1$ |
|---|
| CH(Me)CH$_2$OMe |
| $R^2$ is CO$_2$Me; $R^3$ is Cl. |
| i-Pr |
| 1-Me-cyclopropyl |
| 2-Me-cyclopropyl |
| 2-F-cyclopropyl |
| 2-Cl-cyclopropyl |
| 2,2-di-F-cyclopropyl |
| 2,2-di-Cl-cyclopropyl |
| 1,2-di-F-cyclopropyl |
| 2,2,3,3-tetra-F-cyclopropyl |
| 1,2,2,3,3-penta-F-cyclopropyl |
| Ph |
| 4-Cl—Ph |
| 4-F—Ph |
| 3-OMe—Ph |
| 4-Br—Ph |
| 4-I—Ph |
| 4-CF$_3$—Ph |
| 4-OCHF$_2$—Ph |
| 4-OCF$_3$—Ph |
| 4-SCF$_3$—Ph |
| 4-SCHF$_2$—Ph |
| 4-CN—Ph |
| 4-CO$_2$Me—Ph |
| 2,4-di-Cl—Ph |
| 2-F-4-Cl—Ph |
| 3,4-di-Cl—Ph |
| 2-MeO-cyclopropyl |
| 2-MeS-cyclopropyl |
| CH(Me)CH$_2$OMe |
| $R^2$ is CO$_2$Et; $R^3$ is Cl. |
| i-Pr |
| 1-Me-cyclopropyl |
| 2-Me-cyclopropyl |
| 2-F-cyclopropyl |
| 2-Cl-cyclopropyl |
| 2,2-di-F-cyclopropyl |
| 2,2-di-Cl-cyclopropyl |
| 1,2-di-F-cyclopropyl |
| 2,2,3,3-tetra-F-cyclopropyl |
| 1,2,2,3,3-penta-F-cyclopropyl |
| Ph |
| 4-Cl—Ph |
| 4-F—Ph |
| 3-OMe—Ph |
| 4-Br—Ph |
| 4-I—Ph |
| 4-CF$_3$—Ph |
| 4-OCHF$_2$—Ph |
| 4-OCF$_3$—Ph |
| 4-SCF$_3$—Ph |
| 4-SCHF$_2$—Ph |
| 4-CN—Ph |
| 4-CO$_2$Me—Ph |
| 2,4-di-Cl—Ph |
| 2-F-4-Cl—Ph |
| 3,4-di-Cl—Ph |
| 2-MeO-cyclopropyl |
| 2-MeS-cyclopropyl |
| CH(Me)CH$_2$OMe |
| $R^2$ is CO$_2$H; $R^3$ is Br. |
| i-Pr |
| 1-Me-cyclopropyl |
| 2-Me-cyclopropyl |
| 2-F-cyclopropyl |

TABLE 2-continued

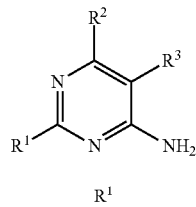

| R¹ |
|---|
| 2-Cl-cyclopropyl |
| 2,2-di-F-cyclopropyl |
| 2,2-di-Cl-cyclopropyl |
| 1,2-di-F-cyclopropyl |
| 2,2,3,3-tetra-F-cyclopropyl |
| 1,2,2,3,3-penta-F-cyclopropyl |
| Ph |
| 4-Cl—Ph |
| 4-F—Ph |
| 3-OMe—Ph |
| 4-Br—Ph |
| 4-I—Ph |
| 4-CF₃—Ph |
| 4-OCHF₂—Ph |
| 4-OCF₃—Ph |
| 4-SCF₃—Ph |
| 4-SCHF₂—Ph |
| 4-CN—Ph |
| 4-CO₂Me—Ph |
| 2,4-di-Cl—Ph |
| 2-F-4-Cl—Ph |
| 3,4-di-Cl—Ph |
| 2-MeO-cyclopropyl |
| 2-MeS-cyclopropyl |
| CH(Me)CH₂OMe |
| R² is CO₂Me; R³ is Br. |
| i-Pr |
| 1-Me-cyclopropyl |
| 2-Me-cyclopropyl |
| 2-F-cyclopropyl |
| 2-Cl-cyclopropyl |
| 2,2-di-F-cyclopropyl |
| 2,2-di-Cl-cyclopropyl |
| 1,2-di-F-cyclopropyl |
| 2,2,3,3-tetra-F-cyclopropyl |
| 1,2,2,3,3-penta-F-cyclopropyl |
| Ph |
| 4-Cl—Ph |
| 4-F—Ph |
| 3-OMe—Ph |
| 4-Br—Ph |
| 4-I—Ph |
| 4-CF₃—Ph |
| 4-OCHF₂—Ph |
| 4-OCF₃—Ph |
| 4-SCF₃—Ph |
| 4-SCHF₂—Ph |
| 4-CN—Ph |
| 4-CO₂Me—Ph |
| 2,4-di-Cl—Ph |
| 2-F-4-Cl—Ph |
| 3,4-di-Cl—Ph |
| 2-MeO-cyclopropyl |
| 2-MeS-cyclopropyl |
| CH(Me)CH₂OMe |
| R² is CO₂Et; R³ is Br. |
| i-Pr |
| 1-Me-cyclopropyl |
| 2-Me-cyclopropyl |
| 2-F-cyclopropyl |
| 2-Cl-cyclopropyl |
| 2,2-di-F-cyclopropyl |
| 2,2-di-Cl-cyclopropyl |
| 1,2-di-F-cyclopropyl |

TABLE 2-continued

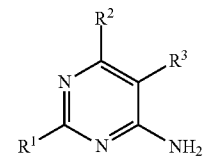

| R¹ |
|---|
| 2,2,3,3-tetra-F-cyclopropyl |
| 1,2,2,3,3-penta-F-cyclopropyl |
| Ph |
| 4-Cl—Ph |
| 4-F—Ph |
| 3-OMe—Ph |
| 4-Br—Ph |
| 4-I—Ph |
| 4-CF₃—Ph |
| 4-OCHF₂—Ph |
| 4-OCF₃—Ph |
| 4-SCF₃—Ph |
| 4-SCHF₂—Ph |
| 4-CN—Ph |
| 4-CO₂Me—Ph |
| 2,4-di-Cl—Ph |
| 2-F-4-Cl—Ph |
| 3,4-di-Cl—Ph |
| 2-MeO-cyclopropyl |
| 2-MeS-cyclopropyl |
| CH(Me)CH₂OMe |

TABLE 3

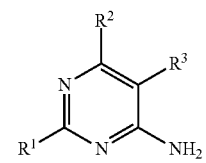

| R³ |
|---|
| R¹ is cyclopropyl; R² is CO₂Me. |
| CN |
| NO₂ |
| OMe |
| SMe |
| NH₂ |
| NHMe |
| NMe₂ |
| R¹ is cyclopropyl; R² is CO₂Et. |
| CN |
| NO₂ |
| OMe |
| SMe |
| NH₂ |
| NHMe |
| NMe₂ |

TABLE 4

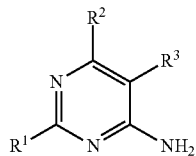

R⁴

R¹ is cyclopropyl; R² is CO₂Me; R³ is Cl.

NO₂
NHMe
NMe₂
N─[CH₂CH₂OCH₂CH₂]─
NHC(═O)Me
NHC(═O)OMe
NHS(O)₂Me
NHNH₂
NHNO₂
N═CHNMe₂
NHOH
NHOMe
NHCH₂CO₂Me
NHCH₂CO₂Et
NHCH₂CH₂OH
NHCH₂CH₂OMe
NHCH₂CH₂NMe₂

R¹ is cyclopropyl; R² is CO₂Me; R³ is Br.

NO₂
NHMe
NMe₂
N─[CH₂CH₂OCH₂CH₂]─
NHC(═O)Me
NHC(═O)OMe
NHS(O)₂Me
NHNH₂
NHNO₂
N═CHNMe₂
NHOH
NHOMe
NHCH₂CO₂Me
NHCH₂CO₂Et
NHCH₂CH₂OH
NHCH₂CH₂OMe
NHCH₂CH₂NMe₂

R¹ is cyclopropyl; R² is CO₂Et; R³ is Cl.

NO₂
NHMe
NMe₂
N─[CH₂CH₂OCH₂CH₂]─
NHC(═O)Me
NHC(═O)OMe
NHS(O)₂Me
NHNH₂
NHNO₂
N═CHNMe₂
NHOH
NHOMe
NHCH₂CO₂Me
NHCH₂CO₂Et
NHCH₂CH₂OH
NHCH₂CH₂OMe
NHCH₂CH₂NMe₂

R¹ is cyclopropyl; R² is CO₂Et; R³ is Br.

NO₂
NHMe
NMe₂
N─[CH₂CH₂OCH₂CH₂]─
NHC(═O)Me
NHC(═O)OMe
NHS(O)₂Me
NHNH₂
NHNO₂

TABLE 4-continued

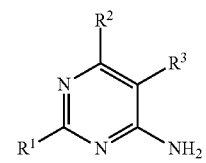

R⁴

N═CHNMe₂
NHOH
NHOMe
NHCH₂CO₂Me
NHCH₂CO₂Et
NHCH₂CH₂OH
NHCH₂CH₂OMe
NHCH₂CH₂NMe₂

R¹ is 4-Cl—Ph; R² is CO₂Me; R³ is Cl.

NO₂
NHMe
NMe₂
N─[CH₂CH₂OCH₂CH₂]─
NHC(═O)Me
NHC(═O)OMe
NHS(O)₂Me
NHNH₂
NHNO₂
N═CHNMe₂
NHOH
NHOMe
NHCH₂CO₂Me
NHCH₂CO₂Et
NHCH₂CH₂OH
NHCH₂CH₂OMe
NHCH₂CH₂NMe₂

R¹ is 4-Cl—Ph; R² is CO₂Me; R³ is Br.

NO₂
NHMe
NMe₂
N─[CH₂CH₂OCH₂CH₂]─
NHC(═O)Me
NHC(═O)OMe
NHS(O)₂Me
NHNH₂
NHNO₂
N═CHNMe₂
NHOH
NHOMe
NHCH₂CO₂Me
NHCH₂CO₂Et
NHCH₂CH₂OH
NHCH₂CH₂OMe
NHCH₂CH₂NMe₂

R¹ is 4-Cl—Ph; R² is CO₂Et; R³ is Cl.

NO₂
NHMe
NMe₂
N─[CH₂CH₂OCH₂CH₂]─
NHC(═O)Me
NHC(═O)OMe
NHS(O)₂Me
NHNH₂
NHNO₂
N═CHNMe₂
NHOH
NHOMe
NHCH₂CO₂Me
NHCH₂CO₂Et
NHCH₂CH₂OH

TABLE 4-continued $$\underset{R^4}{\underset{R^1}{\overset{R^2}{\longrightarrow}}} \underset{NH_2}{\overset{R^3}{\longrightarrow}}$$

NHCH$_2$CH$_2$OMe
NHCH$_2$CH$_2$NMe$_2$
R$^1$ is 4-Cl—Ph; R$^2$ is CO$_2$Et; R$^3$ is Br.

NO$_2$
NHMe
NMe$_2$
N—[—CH$_2$CH$_2$OCH$_2$CH$_2$—]—
NHC(=O)Me
NHC(=O)OMe
NHS(O)$_2$Me
NHNH$_2$
NHNO$_2$
N=CHNMe$_2$
NHOH
NHOMe
NHCH$_2$CO$_2$Me
NHCH$_2$CO$_2$Et
NHCH$_2$CH$_2$OH
NHCH$_2$CH$_2$OMe
NHCH$_2$CH$_2$NMe$_2$

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films (including seed coatings), and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, glycerol esters, poly-oxyethylene/polyoxypropylene block copolymers, and alkylpolyglycosides where the number of glucose units, referred to as degree of polymerization (D.P.), can range from 1 to 3 and the alkyl units can range from $C_6$ to $C_{14}$ (see *Pure and Applied Chemistry* 72, 1255-1264). Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, propylene glycol, propylene carbonate, dibasic esters, paraffins, alkylbenzenes, alkylnaphthalenes, glycerine, triacetine, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, acetates such as hexyl acetate, heptyl acetate and octyl acetate, and alcohols such as methanol, cyclohexanol, decanol, benzyl and tetrahydrofurfuryl alcohol.

Useful formulations of this invention may also contain materials well known to those skilled in the art as formulation aids such as antifoams, film formers and dyes. Antifoams can include water dispersible liquids comprising polyorganosiloxanes like Rhodorsil® 416. The film formers can include polyvinyl acetates, polyvinyl acetate copolymers, polyvinylpyrrolidone-vinyl acetate copolymer, polyvinyl alcohols, polyvinyl alcohol copolymers and waxes. Dyes can include water dispersible liquid colorant compositions like Pro-Ized® Colorant Red. One skilled in the art will appreciate that this is a non-exhaustive list of formulation aids. Suitable examples of formulation aids include those listed herein and those listed in *McCutcheon's* 2001, *Volume* 2: *Functional Materials* published by MC Publishing Company and PCT Publication WO 03/024222.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, Perry's Chemical Engineer's Handbook, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-D.

EXAMPLE A

High Strength Concentrate

| | |
|---|---|
| Compound 1 | 98.5% |
| silica aerogel | 0.5% |
| synthetic amorphous fine silica | 1.0%. |

EXAMPLE B

Wettable Powder

| | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE C

Granule

| | |
|---|---|
| Compound 4 | 10.0% |
| attapulgite granules (low volatile matter, 0.71/0.30 mm; U.S.S. No. 25-50 sieves) | 90.0%. |

EXAMPLE D

Aqueous Suspension

| | |
|---|---|
| Compound 9 | 25.0% |
| hydrated attapulgite | 3.0% |
| crude calcium ligninsulfonate | 10.0% |
| sodium dihydrogen phosphate | 0.5% |
| water | 61.5%. |

EXAMPLE E

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE F

Microemulsion

| | |
|---|---|
| Compound 2 | 1.0% |
| triacetine | 30.0% |
| $C_8$-$C_{10}$ alkylpolyglycoside | 30.0% |
| glyceryl monooleate | 19.0% |
| water | 20.0%. |

Example G

Wettable Powder

| | |
|---|---|
| Compound 9 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Test results indicate that the compounds of the present invention are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.0001 to 20 kg/ha with a preferred range of about 0.001 to 5 kg/ha and a more preferred range of about 0.004 to 3 kg/ha. One skilled in the art can easily determine the herbicidally effective amount necessary for the desired level of weed control.

Compounds of this invention can be used alone or in combination with other herbicides, insecticides and fungicides, and other agricultural chemicals such as fertilizers. Mixtures of the compounds of the invention with other herbicides can broaden the spectrum of activity against additional weed species, and suppress the proliferation of any resistant biotypes. A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clefoxydim, clethodim, clodinafop-propargyl, clomazone, clomeprop, clopyralid, clopyralid-olamine, cloransulam-methyl, copper sulfate, CUH-35 (2-methoxyethyl 2-[[[4-chloro-2-fluoro-5-[(1-methyl-2-propynyl)oxy]phenyl] (3-fluoro-benzoyl)amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, epoprodan, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, fluorochloridone, fluoroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)-methyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, isoxadifen, KUH-021 (N-[2-[(4,6-dimethoxy-2-pyrimidinyl)hydroxymethyl]-6-(methoxymethyl)phenyl]-1, 1-difluoro-methanesulfonamide), lactofen, lenacil, linuron, maleic hydrazide, MCPA and its salts (e.g., MCPA-dimethylammonium, MCPA-potassium and MCPA-sodium), esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen-ethyl, pyrazogyl, pyrazolate, pyrazolynate, pyrazoxyfen, pyrazosulfuron-ethyl, pyribenzoxim, pyributicarb, pyridate, pyriftalid, pyriminobac-methyl, pyrithiobac, pyrithiobac-sodium, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tepraloxydim, terbacil, terbumeton, terbuthylazine, terbutryn, thenylchlor, thiazopyr, thifensulfuron-methyl, thiobencarb, tiocarbazil, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butyl.) Butyl. and *Puccinia thlaspeos* Schub. Combinations of compounds of the invention with other herbicides can result in a greater-than-additive (i.e. synergistic) effect on weeds and/or a less-than-additive effect (i.e. safening) on crops or other desirable plants. In certain instances, combinations with other herbicides having a similar spectrum of control but a different mode of action will be particularly advantageous for preventing the development of resistant weeds. Herbicidally effective amounts of compounds of the invention as well as herbicidally effective amounts of other herbicides can be easily determined by one skilled in the art through simple experimentation.

Preferred for better control of undesired vegetation (e.g., lower use rate, broader spectrum of weeds controlled, or enhanced crop safety) or for preventing the development of resistant weeds are mixtures of a compound of this invention with a herbicide selected from the group consisting of diuron, hexazinone, terbacil, bromacil, glyphosate (particularly glyphosate-isopropylammonium, glyphosate-sodium, glyphosate-potassium, glyphosate-trimesium), glufosinate (particularly glufosinate-ammonium), azimsulfuron, chlorsulfuron, ethametsulfuron-methyl, chlorimuron-ethyl, bensulfuron-methyl, rimsulfuron, sulfometuron-methyl, metsulfuron-methyl, nicosulfuron, tribenuron-methyl, thifensulfuron-methyl, flupyrsulfuron-methyl, flupyrsulfuron-methyl-sodium, halosulfuron-methyl, primisulfuron-methyl, trifloxysulfuron, foramsulfuron, mesosulfuron-methyl, iodosulfuron-methyl, isoproturon, ametryn, amitrole, paraquat dichloride, diquat dibromide, atrazine, metribuzin, acetochlor, metolachlor, S-metolachlor, alachlor, pretilachlor, sethoxydim, tralkoxydim, clethodim, cyhalofop-butyl, quizalofop-ethyl, diclofop-methyl, clodinafop-propargyl, fenoxaprop-ethyl, dimethenamid, flufenacet, picloram, prodiamine, fosamine-ammonium, 2,4-D, 2,4-DB, dicamba, penoxsulam, flumetsulam, naptalam, pendimethalin, oryzalin, MCPA (and its dimethylammonium, potassium and sodium salts), MCPA-isoctyl, MCPA-thioethyl mecoprop, clopyralid, aminopyralid, triclopyr, fluoroxypyr, diflufenzopyr, imazapyr, imazethapyr, imazamox, picolinafen, oxyfluorfen, oxadiazon, carfentrazone-ethyl, sulfentrazone, flumioxazin, diflufenican, bromoxynil, propanil, thiobencarb, molinate, fluridone, mesotrione, sulcotrione, isoxaflutole, isoxaben, clomazone, anilofos, beflubutamid, benfuresate, bentazone, benzobicyclon, benzofenap, bromobutide, butachlor, butamifos, cafenstrole, clomeprop, dimepiperate, dimethametryn, daimuron, esprocarb, etobenzanide, fentrazamid, indanofan, cumylron, menfenacet, oxaziclomefone, oxadiargyl, pentoxazone, pyraclonil, pyrazolate, pyributicarb, pyriftalid, pyriminobac-methyl, thenylchlor, bispyribac-sodium, clefoxydim, copper sulfate, cinosulfuron, cyclosulfamuron, ethoxysulfuron, epoprodan, flucetosulfuron, imazosulfuron, metamifop, pyrazosulfuron-ethyl, quinclorac, flucarbazone-sodium, propoxycarbazone-sodium, amicarbazone, florasulam, triasulfuron, triaziflam, pinoxaden, tritosulfuron, amidosulfuron, metosulam, sulfosulfuron, pyraflufen-ethyl, HOK-201, KUH-021 and CUH-35. Specifically preferred mixtures (compound numbers refer to compounds in Index Tables A-D) are selected from the group: compound 4 and diuron; compound 9 and diuron; compound 58 and diuron; compound 64 and diuron; compound 65 (and salts thereof) and diuron; compound 94 and diuron; compound 95 (and salts thereof) and diuron; compound 96 and diuron; compound 135 (and salts thereof) and diuron; compound 4 and hexazinone; compound 9 and hexazinone; compound 58 and hexazinone; compound 64 and hexazinone; compound 65 (and salts thereof) and hexazinone; compound 94 and hexazinone; compound 95 (and salts thereof) and hexazinone; compound 96 and hexazinone; compound 135 (and salts thereof) and hexazinone; compound 4 and terbacil; compound 9 and terbacil; compound 58 and terbacil; compound 64 and terbacil; compound 65 (and salts thereof) and terbacil; compound 94 and terbacil; compound 95 (and salts thereof) and terbacil; compound 96 and terbacil; compound 135 (and salts thereof) and terbacil; compound 4 and bromacil; compound 9 and bromacil; compound 58 and bromacil; compound 64 and bromacil; compound 65 (and salts thereof) and bromacil; compound 94 and bromacil; compound 95 (and salts thereof) and bromacil; compound 96 and bromacil; compound 135 (and salts thereof) and bromacil; compound 4 and glyphosate; compound 9 and glyphosate; compound 58 and glyphosate; compound 64 and glyphosate; compound 65 (and salts thereof) and glyphosate; compound 94 and glyphosate; compound 95 (and salts thereof) and glyphosate; compound 96 and glyphosate; compound 135 (and salts thereof) and glyphosate; compound 4 and glufosinate; compound 9 and glufosinate; compound 58 and glufosinate; compound 64 and glufosinate; compound 65 (and salts thereof) and glufosinate; compound 94 and glufosinate; compound 95 (and salts thereof) and glufosinate; compound 96 and glufosinate; compound 135 (and salts thereof) and glufosinate; compound 4 and azimsulfuron; compound 9 and azimsulfuron; compound 58 and azimsulfuron; compound 64 and azimsulfuron; compound 65 (and salts thereof) and azimsulfuron; compound 94 and azimsulfuron; compound 95 (and salts thereof) and azimsulfuron; compound 96 and azimsulfuron; compound 135 (and salts thereof) and azimsulfuron; compound 4 and chlorsulfuron; compound 9 and chlorsulfuron; compound 58 and chlorsulfuron; compound 64 and chlorsulfuron; compound 65 (and salts thereof) and chlorsulfuron; compound 94 and chlorsulfuron; compound 95 (and salts thereof) and chlorsulfuron; compound 96 and chlorsulfuron; compound 135 (and salts thereof) and chlorsulfuron; compound 4 and ethametsufuron-methyl; compound 9 and ethametsufuron-methyl; compound 58 and ethametsufuron-methyl; compound 64 and ethametsufuron-methyl; compound 65 (and salts thereof) and ethametsufuron-methyl; compound 94 and ethametsufuron-methyl; compound 95 (and salts thereof) and ethametsufuron-methyl; compound 96 and ethametsufuron-methyl; compound 135 (and salts thereof) and ethametsufuron-methyl; compound 4 and chlorimuron-ethyl; compound 9 and chlorimuron-ethyl; compound 58 and chlorimuron-ethyl; compound 64 and chlorimuron-ethyl; compound 65 (and salts thereof) and chlorimuron-ethyl; compound 94 and chlorimuron-ethyl; compound 95 (and salts thereof) and chlorimuron-ethyl; compound 96 and chlorimuron-ethyl; compound 135

(and salts thereof) and chlorimuron-ethyl; compound 4 and bensulfuron-methyl; compound 9 and bensulfuron-methyl; compound 58 and bensulfuron-methyl; compound 64 and bensulfuron-methyl; compound 65 (and salts thereof) and bensulfuron-methyl; compound 94 and bensulfuron-methyl; compound 95 (and salts thereof) and bensulfuron-methyl; compound 96 and bensulfuron-methyl; compound 135 (and salts thereof) and bensulfuron-methyl; compound 4 and rimsulfuron; compound 9 and rimsulfuron; compound 58 and rimsulfuron; compound 64 and rimsulfuron; compound 65 (and salts thereof) and rimsulfuron; compound 94 and rimsulfuron; compound 95 (and salts thereof) and rimsulfuron; compound 96 and rimsulfuron; compound 135 (and salts thereof) and rimsulfuron; compound 4 and sulfometuron-methyl; compound 9 and sulfometuron-methyl; compound 58 and sulfometuron-methyl; compound 64 and sulfometuron-methyl; compound 65 (and salts thereof) and sulfometuron-methyl; compound 94 and sulfometuron-methyl; compound 95 (and salts thereof) and sulfometuron-methyl; compound 96 and sulfometuron-methyl; compound 135 (and salts thereof) and sulfometuron-methyl; compound 4 and metsulfuron-methyl; compound 9 and metsulfuron-methyl; compound 58 and metsulfuron-methyl; compound 64 and metsulfuron-methyl; compound 65 (and salts thereof) and metsulfuron-methyl; compound 94 and metsulfuron-methyl; compound 95 (and salts thereof) and metsulfuron-methyl; compound 96 and metsulfuron-methyl; compound 135 (and salts thereof) and metsulfuron-methyl; compound 4 and nicosulfuron; compound 9 and nicosulfuron; compound 58 and nicosulfuron; compound 64 and nicosulfuron; compound 65 (and salts thereof) and nicosulfuron; compound 94 and nicosulfuron; compound 95 (and salts thereof) and nicosulfuron; compound 96 and nicosulfuron; compound 135 (and salts thereof) and nicosulfuron; compound 4 and tribenuron-methyl; compound 9 and tribenuron-methyl; compound 58 and tribenuron-methyl; compound 64 and tribenuron-methyl; compound 65 (and salts thereof) and tribenuron-methyl; compound 94 and tribenuron-methyl; compound 95 (and salts thereof) and tribenuron-methyl; compound 96 and tribenuron-methyl; compound 135 (and salts thereof) and tribenuron-methyl; compound 4 and thifensulfuron-methyl; compound 9 and thifensulfuron-methyl; compound 58 and thifensulfuron-methyl; compound 64 and thifensulfuron-methyl; compound 65 (and salts thereof) and thifensulfuron-methyl; compound 94 and thifensulfuron-methyl; compound 95 (and salts thereof) and thifensulfuron-methyl; compound 96 and thifensulfuron-methyl; compound 135 (and salts thereof) and thifensulfuron-methyl; compound 4 and flupyrsulfuron-methyl; compound 9 and flupyrsulfuron-methyl; compound 58 and flupyrsulfuron-methyl; compound 64 and flupyrsulfuron-methyl; compound 65 (and salts thereof) and flupyrsulfuron-methyl; compound 94 and flupyrsulfuron-methyl; compound 95 (and salts thereof) and flupyrsulfuron-methyl; compound 96 and flupyrsulfuron-methyl; compound 135 (and salts thereof) and flupyrsulfuron-methyl; compound 4 and flupyrsulfuron-methyl-sodium; compound 9 and flupyrsulfuron-methyl-sodium; compound 58 and flupyrsulfuron-methyl-sodium; compound 64 and flupyrsulfuron-methyl-sodium; compound 65 (and salts thereof) and flupyrsulfuron-methyl-sodium; compound 94 and flupyrsulfuron-methyl-sodium; compound 95 (and salts thereof) and flupyrsulfuron-methyl-sodium; compound 96 and flupyrsulfuron-methyl-sodium; compound 135 (and salts thereof) and flupyrsulfuron-methyl-sodium; compound 4 and halosulfuron-methyl; compound 9 and halosulfuron-methyl; compound 58 and halosulfuron-methyl; compound 64 and halosulfuron-methyl; compound 65 (and salts thereof) and halosulfuron-methyl; compound 94 and halosulfuron-methyl; compound 95 (and salts thereof) and halosulfuron-methyl; compound 96 and halosulfuron-methyl; compound 135 (and salts thereof) and halosulfuron-methyl; compound 4 and primisulfuron-methyl; compound 9 and primisulfuron-methyl; compound 58 and primisulfuron-methyl; compound 64 and primisulfuron-methyl; compound 65 (and salts thereof) and primisulfuron-methyl; compound 94 and primisulfuron-methyl; compound 95 (and salts thereof) and primisulfuron-methyl; compound 96 and primisulfuron-methyl; compound 135 (and salts thereof) and primisulfuron-methyl; compound 4 and trifloxysulfuron; compound 9 and trifloxysulfuron; compound 58 and trifloxysulfuron; compound 64 and trifloxysulfuron; compound 65 (and salts thereof) and trifloxysulfuron; compound 94 and trifloxysulfuron; compound 95 (and salts thereof) and trifloxysulfuron; compound 96 and trifloxysulfuron; compound 135 (and salts thereof) and trifloxysulfuron; compound 4 and foramsulfuron; compound 9 and foramsulfuron; compound 58 and foramsulfuron; compound 64 and foramsulfuron; compound 65 (and salts thereof) and foramsulfuron; compound 94 and foramsulfuron; compound 95 (and salts thereof) and foramsulfuron; compound 96 and foramsulfuron; compound 135 (and salts thereof) and foramsulfuron; compound 4 and mesosulfuron-methyl; compound 9 and mesosulfuron-methyl; compound 58 and mesosulfuron-methyl; compound 64 and mesosulfuron-methyl; compound 65 (and salts thereof) and mesosulfuron-methyl; compound 94 and mesosulfuron-methyl; compound 95 (and salts thereof) and mesosulfuron-methyl; compound 96 and mesosulfuron-methyl; compound 135 (and salts thereof) and mesosulfuron-methyl; compound 4 and iodosulfuron-methyl; compound 9 and iodosulfuron-methyl; compound 58 and iodosulfuron-methyl; compound 64 and iodosulfuron-methyl; compound 65 (and salts thereof) and iodosulfuron-methyl; compound 94 and iodosulfuron-methyl; compound 95 (and salts thereof) and iodosulfuron-methyl; compound 96 and iodosulfuron-methyl; compound 135 (and salts thereof) and iodosulfuron-methyl; compound 4 and isoproturon; compound 9 and isoproturon; compound 58 and isoproturon; compound 64 and isoproturon; compound 65 (and salts thereof) and isoproturon; compound 94 and isoproturon; compound 95 (and salts thereof) and isoproturon; compound 96 and isoproturon; compound 135 (and salts thereof) and isoproturon; compound 4 and ametryn; compound 9 and ametryn; compound 58 and ametryn; compound 64 and ametryn; compound 65 (and salts thereof) and ametryn; compound 94 and ametryn; compound 95 (and salts thereof) and ametryn; compound 96 and ametryn; compound 135 (and salts thereof) and ametryn; compound 4 and amitrole; compound 9 and amitrole; compound 58 and amitrole; compound 64 and amitrole; compound 65 (and salts thereof) and amitrole; compound 94 and amitrole; compound 95 (and salts thereof) and amitrole; compound 96 and amitrole; compound 135 (and salts thereof) and amitrole; compound 4 and paraquat dichloride; compound 9 and paraquat dichloride; compound 58 and paraquat dichloride; compound 64 and paraquat dichloride; compound 65 (and salts thereof) and paraquat dichloride; compound 94 and paraquat dichloride; compound 95 (and salts thereof) and paraquat dichloride; compound 96 and paraquat dichloride; compound 135 (and salts thereof) and paraquat dichloride; compound 4 and diquat dibromide; compound 9 and diquat dibromide; compound 58 and diquat dibromide; compound 64 and diquat dibromide; compound 65 (and salts thereof) and diquat dibromide; compound 94 and diquat dibromide; compound 95 (and salts thereof) and diquat dibromide; compound 96 and diquat dibromide; compound 135 (and salts thereof) and diquat dibromide; compound 4 and atrazine; compound 9 and atrazine; compound 58 and atrazine; compound 64 and atrazine; compound 65 (and salts thereof) and atrazine; compound 94 and atrazine; compound 95 (and salts thereof) and atrazine; compound 96 and atrazine; compound 135 (and salts thereof) and atrazine; compound 4 and metribuzin; compound 9 and metribuzin; compound 58 and metribuzin; compound 64 and metribuzin; compound 65 (and salts thereof) and metribuzin; compound 94 and metribuzin; compound 95 (and salts thereof) and metribuzin; compound 96 and metribuzin; compound 135 (and salts thereof) and metribuzin; compound 4 and acetochlor; compound 9 and acetochlor; compound 58 and acetochlor; compound 64 and acetochlor; compound 65 (and salts thereof) and acetochlor; compound 94 and acetochlor; compound 95 (and salts thereof) and acetochlor; compound 96 and acetochlor; compound 135 (and salts thereof) and acetochlor; compound 4 and metolachlor; compound 9 and metolachlor; compound 58 and metolachlor; compound 64 and metolachlor; compound 65 (and salts thereof) and metolachlor; compound 94 and metolachlor; compound 95 (and salts thereof) and metolachlor; compound 96 and metolachlor; compound 135 (and salts thereof) and metolachlor; compound 4 and S-metolachlor; compound 9 and S-metolachlor; compound 58 and S-metolachlor; compound 64 and S-metolachlor; compound 65 (and salts thereof) and S-metolachlor; compound 94 and S-metolachlor; compound 95 (and salts thereof) and S-metolachlor; compound 96 and S-metolachlor; compound 135 (and salts thereof) and S-metolachlor; compound 4 and alachlor; compound 9 and alachlor; compound 58 and alachlor; compound 64 and alachlor; compound 65 (and salts thereof) and alachlor; compound 94 and alachlor; compound 95 (and salts thereof) and alachlor; compound 96 and alachlor; compound 135 (and salts thereof) and alachlor; compound 4 and pretilachlor; compound 9 and pretilachlor; compound 58 and pretilachlor; compound 64 and pretilachlor; compound 65 (and salts thereof) and pretilachlor; compound 94 and pretilachlor; compound 95 (and salts thereof) and pretilachlor; compound 96 and pretilachlor; compound 135 (and salts thereof) and pretilachlor; compound 4 and sethoxydim; compound 9 and sethoxydim; compound 58 and sethoxydim; compound 64 and sethoxydim; compound 65 (and salts thereof) and sethoxydim; compound 94 and sethoxydim; compound 95 (and salts thereof) and sethoxydim; compound 96 and sethoxydim; compound 135 (and salts thereof) and sethoxydim; compound 4 and tralkoxydim; compound 9 and tralkoxydim; compound 58 and tralkoxydim; compound 64 and tralkoxydim; compound 65 (and salts thereof) and tralkoxydim; compound 94 and tralkoxydim; compound 95 (and salts thereof) and tralkoxydim; compound 96 and tralkoxydim; compound 135 (and salts thereof) and tralkoxydim; compound 4 and clethodim; compound 9 and clethodim; compound 58 and clethodim; compound 64 and clethodim; compound 65 (and salts thereof) and clethodim; compound 94 and clethodim; compound 95 (and salts thereof) and clethodim; compound 96 and clethodim; compound 135 (and salts thereof) and clethodim; compound 4 and cyhalofop-butyl; compound 9 and cyhalofop-butyl; compound 58 and cyhalofop-butyl; compound 64 and cyhalofop-butyl; compound 65 (and salts thereof) and cyhalofop-butyl; compound 94 and cyhalofop-butyl; compound 95 (and salts thereof) and cyhalofop-butyl; compound 96 and cyhalofop-butyl; compound 135 (and salts thereof) and cyhalofop-butyl; compound 4 and quizalofop-ethyl; compound 9 and quizalofop-ethyl; compound 58 and quizalofop-ethyl; compound 64 and quizalofop-ethyl; compound 65 (and salts thereof) and quizalofop-ethyl; compound 94 and quizalofop-ethyl; compound 95 (and salts thereof) and quizalofop-ethyl; compound 96 and quizalofop-ethyl; compound 135 (and salts thereof) and quizalofop-ethyl; compound 4 and diclofop-methyl; compound 9 and diclofop-methyl; compound 58 and diclofop-methyl; compound 64 and diclofop-methyl; compound 65 (and salts thereof) and diclofop-methyl; compound 94 and diclofop-methyl; compound 95 (and salts thereof) and diclofop-methyl; compound 96 and diclofop-methyl; compound 135 (and salts thereof) and diclofop-methyl; compound 4 and clodinafop-propargyl; compound 9 and clodinafop-propargyl; compound 58 and clodinafop-propargyl; compound 64 and clodinafop-propargyl; compound 65 (and salts thereof) and clodinafop-propargyl; compound 94 and clodinafop-propargyl; compound 95 (and salts thereof) and clodinafop-propargyl; compound 96 and clodinafop-propargyl; compound 135 (and salts thereof) and clodinafop-propargyl; compound 4 and fenoxaprop-ethyl; compound 9 and fenoxaprop-ethyl; compound 58 and fenoxaprop-ethyl; compound 64 and fenoxaprop-ethyl; compound 65 (and salts thereof) and fenoxaprop-ethyl; compound 94 and fenoxaprop-ethyl; compound 95 (and salts thereof) and fenoxaprop-ethyl; compound 96 and fenoxaprop-ethyl; compound 135 (and salts thereof) and fenoxaprop-ethyl; compound 4 and dimethenamid; compound 9 and dimethenamid; compound 58 and dimethenamid; compound 64 and dimethenamid; compound 65 (and salts thereof) and dimethenamid; compound 94 and dimethenamid; compound 95 (and salts thereof) and dimethenamid; compound 96 and dimethenamid; compound 135 (and salts thereof) and dimethenamid; compound 4 and flufenacet; compound 9 and flufenacet; compound 58 and flufenacet; compound 64 and flufenacet; compound 65 (and salts thereof) and flufenacet; compound 94 and flufenacet; compound 95 (and salts thereof) and flufenacet; compound 96 and flufenacet; compound 135 (and salts thereof) and flufenacet; compound 4 and picloram; compound 9 and picloram; compound 58 and picloram; compound 64 and picloram; compound 65 (and salts thereof) and picloram; compound 94 and picloram; compound 95 (and salts thereof) and picloram; compound 96 and picloram; compound 135 (and salts thereof) and picloram; compound 4 and prodiamine; compound 9 and prodiamine; compound 58 and prodiamine; compound 64 and prodiamine; compound 65 (and salts thereof) and prodiamine; compound 94 and prodiamine; compound 95 (and salts thereof) and prodiamine; compound 96 and prodiamine; compound 135 (and salts thereof) and prodiamine; compound 4 and fosamine-ammonium; compound 9 and fosamine-ammonium; compound 58 and fosamine-ammonium; compound 64 and fosamine-ammonium; compound 65 (and salts thereof) and fosamine-ammonium; compound 94 and fosamine-ammonium; compound 95 (and salts thereof) and fosamine-ammonium; compound 96 and fosamine-ammonium; compound 135 (and salts thereof) and fosamine-ammonium; compound 4 and 2,4-D; compound 9 and 2,4-D; compound 58 and 2,4-D; compound 64 and 2,4-D; compound 65 (and salts thereof) and 2,4-D; compound 94 and 2,4-D; compound 95 (and salts thereof) and 2,4-D; compound 96 and 2,4-D; compound 135 (and salts thereof) and 2,4-D; compound 4 and 2,4-DB; compound 9 and 2,4-DB; compound 58 and 2,4-DB; compound 64 and 2,4-DB; compound 65 (and salts thereof) and 2,4-DB; compound 94 and 2,4-DB; compound 95 (and salts thereof) and 2,4-DB; compound 96 and 2,4-DB; compound 135 (and salts thereof) and 2,4-DB; compound 4 and dicamba; compound 9 and dicamba; compound 58 and dicamba; compound 64 and dicamba; compound 65 (and salts thereof) and dicamba; compound 94 and dicamba; compound 95 (and salts thereof) and dicamba; compound 96 and dicamba; compound 135 (and salts thereof) and dicamba; compound 4 and penoxsulam; compound 9 and penoxsulam; compound 58 and penoxsulam; compound 64 and penoxsulam; compound 65 (and salts thereof) and penoxsulam; compound 94 and penoxsulam; compound 95 (and salts thereof) and penoxsulam; compound 96 and penoxsulam; compound 135 (and salts thereof) and penoxsulam; compound 4 and flumetsulam; compound 9 and flumetsulam; compound 58 and flumetsulam; compound 64 and flumetsulam; compound 65 (and salts thereof) and flumetsulam; compound 94 and flumetsulam; compound 95 (and salts thereof) and flumetsulam; compound 96 and flumetsulam; compound 135 (and salts thereof) and flumetsulam; compound 4 and naptalam; compound 9 and naptalam; compound 58 and naptalam; compound 64 and naptalam; compound 65 (and salts thereof) and naptalam; compound 94 and naptalam; compound 95 (and salts thereof) and naptalam; compound 96 and naptalam; compound 135 (and salts thereof) and naptalam; compound 4 and pendimethalin; compound 9 and pendimethalin; compound 58 and pendimethalin; compound 64 and pendimethalin; compound 65 (and salts thereof) and pendimethalin; compound 94 and pendimethalin; compound 95 (and salts thereof) and pendimethalin; compound 96 and pendimethalin; compound 135 (and salts thereof) and pendimethalin; compound 4 and oryzalin; compound 9 and oryzalin; compound 58 and oryzalin; compound 64 and oryzalin; compound 65 (and salts thereof) and oryzalin; compound 94 and oryzalin; compound 95 (and salts thereof) and oryzalin; compound 96 and oryzalin; compound 135 (and salts thereof) and oryzalin; compound 4 and MCPA (and salts and (thio)esters thereof); compound 9 and MCPA (and salts and (thio)esters thereof); compound 58 and MCPA (and salts and (thio)esters thereof); compound 64 and MCPA (and salts and (thio)esters thereof); compound 65 (and salts thereof) and MCPA (and salts and (thio)esters thereof); compound 94 and MCPA (and salts and (thio)esters thereof); compound 95 (and salts thereof) and MCPA (and salts and (thio)esters thereof); compound 96 and MCPA (and salts and (thio)esters thereof); compound 135 (and salts thereof) and MCPA (and salts and (thio)esters thereof); compound 4 and mecoprop; compound 9 and mecoprop; compound 58 and mecoprop; compound 64 and mecoprop; compound 65 (and salts thereof) and mecoprop; compound 94 and mecoprop; compound 95 (and salts thereof) and mecoprop; compound 96 and mecoprop; compound 135 (and salts thereof) and mecoprop; compound 4 and clopyralid; compound 9 and clopyralid; compound 58 and clopyralid; compound 64 and clopyralid; compound 65 (and salts thereof) and clopyralid; compound 94 and clopyralid; compound 95 (and salts thereof) and clopyralid; compound 96 and clopyralid; compound 135 (and salts thereof) and clopyralid; compound 4 and aminopyralid; compound 9 and aminopyralid; compound 58 and aminopyralid; compound 64 and aminopyralid; compound 65 (and salts thereof) and aminopyralid; compound 94 and aminopyralid; compound 95 (and salts thereof) and aminopyralid; compound 96 and aminopyralid; compound 135 (and salts thereof) and aminopyralid; compound 4 and triclopyr; compound 9 and triclopyr; compound 58 and triclopyr; compound 64 and triclopyr; compound 65 (and salts thereof) and triclopyr; compound 94 and triclopyr; compound 95 (and salts thereof) and triclopyr; compound 96 and triclopyr; compound 135 (and salts thereof) and triclopyr; compound 4 and fluoroxypyr; compound 9 and fluoroxypyr; compound 58 and fluoroxypyr; compound 64 and fluoroxypyr; compound 65 (and salts thereof) and fluoroxypyr; compound 94 and fluoroxypyr; compound 95 (and salts thereof) and fluoroxypyr; compound 96 and fluoroxypyr; compound 135 (and salts thereof) and fluoroxypyr; compound 4 and diflufenzopyr; compound 9 and diflufenzopyr; compound 58 and diflufenzopyr; compound 64 and diflufenzopyr; compound 65 (and salts thereof) and diflufenzopyr; compound 94 and diflufenzopyr; compound 95 (and salts thereof) and diflufenzopyr; compound 96 and diflufenzopyr; compound 135 (and salts thereof) and diflufenzopyr; compound 4 and imazapyr; compound 9 and imazapyr; compound 58 and imazapyr; compound 64 and imazapyr; compound 65 (and salts thereof) and imazapyr; compound 94 and imazapyr; compound 95 (and salts thereof) and imazapyr; compound 96 and imazapyr; compound 135 (and salts thereof) and imazapyr; compound 4 and imazethapyr; compound 9 and imazethapyr; compound 58 and imazethapyr; compound 64 and imazethapyr; compound 65 (and salts thereof) and imazethapyr; compound 94 and imazethapyr; compound 95 (and salts thereof) and imazethapyr; compound 96 and imazethapyr; compound 135 (and salts thereof) and imazethapyr; compound 4 and imazamox; compound 9 and imazamox; compound 58 and imazamox; compound 64 and imazamox; compound 65 (and salts thereof) and imazamox; compound 94 and imazamox; compound 95 (and salts thereof) and imazamox; compound 96 and imazamox; compound 135 (and salts thereof) and imazamox; compound 4 and picolinafen; compound 9 and picolinafen; compound 58 and picolinafen; compound 64 and picolinafen; compound 65 (and salts thereof) and picolinafen; compound 94 and picolinafen; compound 95 (and salts thereof) and picolinafen; compound 96 and picolinafen; compound 135 (and salts thereof) and picolinafen; compound 4 and oxyfluorfen; compound 9 and oxyfluorfen; compound 58 and oxyfluorfen; compound 64 and oxyfluorfen; compound 65 (and salts thereof) and oxyfluorfen; compound 94 and oxyfluorfen; compound 95 (and salts thereof) and oxyfluorfen; compound 96 and oxyfluorfen; compound 135 (and salts thereof) and oxyfluorfen; compound 4 and oxadiazon; compound 9 and oxadiazon; compound 58 and oxadiazon; compound 64 and oxadiazon; compound 65 (and salts thereof) and oxadiazon; compound 94 and oxadiazon; compound 95 (and salts thereof) and oxadiazon; compound 96 and oxadiazon; compound 135 (and salts thereof) and oxadiazon; compound 4 and carfentrazone-ethyl; compound 9 and carfentrazone-ethyl; compound 58 and carfentrazone-ethyl; compound 64 and carfentrazone-ethyl; compound 65 (and salts thereof) and carfentrazone-ethyl; compound 94 and carfentrazone-ethyl; compound 95 (and salts thereof) and carfentrazone-ethyl; compound 96 and carfentrazone-ethyl; compound 135 (and salts thereof) and carfentrazone-ethyl; compound 4 and sulfentrazone; compound 9 and sulfentrazone; compound 58 and sulfentrazone; compound 64 and sulfentrazone; compound 65 (and salts thereof) and sulfentrazone; compound 94 and sulfentrazone; compound 95 (and salts thereof) and sulfentrazone; compound 96 and sulfentrazone; compound 135 (and salts thereof) and sulfentrazone; compound 4 and flumioxazin; compound 9 and flumioxazin; compound 58 and flumioxazin; compound 64 and flumioxazin; compound 65 (and salts thereof) and flumioxazin; compound 94 and flumioxazin; compound 95 (and salts thereof) and flumioxazin; compound 96 and flumioxazin; compound 135 (and salts thereof) and flumioxazin; compound 4 and diflufenican; compound 9 and diflufenican; compound 58 and diflufenican; compound 64 and diflufenican; compound 65 (and salts thereof) and diflufenican; compound 94 and diflufenican; compound 95 (and salts thereof) and diflufenican; compound 96 and diflufenican; compound 135 (and salts thereof) and diflufenican; compound 4 and bromoxynil; compound 9 and bromoxynil; compound 58 and bromoxynil; compound 64 and bromoxynil; compound 65 (and salts thereof) and bromoxynil; compound 94 and bromoxynil; compound 95 (and salts thereof) and bromoxynil; compound 96 and bromoxynil; compound 135 (and salts thereof) and bromoxynil; compound 4 and propanil; compound 9 and propanil; compound 58 and propanil; compound 64 and propanil; compound 65 (and salts thereof) and propanil; compound 94 and propanil; compound 95 (and salts thereof) and propanil; compound 96 and propanil; compound 135 (and salts thereof) and propanil; compound 4 and thiobencarb; compound 9 and thiobencarb; compound 58 and thiobencarb; compound 64 and thiobencarb; compound 65 (and salts thereof) and thiobencarb; compound 94 and thiobencarb; compound 95 (and salts thereof) and thiobencarb; compound 96 and thiobencarb; compound 135 (and salts thereof) and thiobencarb; compound 4 and fluridone; compound 9 and fluridone; compound 58 and fluridone; compound 64 and fluridone; compound 65 (and salts thereof) and fluridone; compound 94 and fluridone; compound 95 (and salts thereof) and fluridone; compound 96 and fluridone; compound 135 (and salts thereof) and fluridone; compound 4 and mesotrione; compound 9 and mesotrione; compound 58 and mesotrione; compound 64 and mesotrione; compound 65 (and salts thereof) and mesotrione; compound 94 and mesotrione; compound 95 (and salts thereof) and mesotrione; compound 96 and mesotrione; compound 135 (and salts thereof) and mesotrione; compound 4 and sulcotrione; compound 9 and sulcotrione; compound 58 and sulcotrione; compound 64 and sulcotrione; compound 65 (and salts thereof) and sulcotrione; compound 94 and sulcotrione; compound 95 (and salts thereof) and sulcotrione; compound 96 and sulcotrione; compound 135 (and salts thereof) and sulcotrione; compound 4 and isoxaflutole; compound 9 and isoxaflutole; compound 58 and isoxaflutole; compound 64 and isoxaflutole; compound 65 (and salts thereof) and isoxaflutole; compound 94 and isoxaflutole; compound 95 (and salts thereof) and isoxaflutole; compound 96 and isoxaflutole; compound 135 (and salts thereof) and isoxaflutole; compound 4 and isoxaben; compound 9 and isoxaben; compound 58 and isoxaben; compound 64 and isoxaben; compound 65 (and salts thereof) and isoxaben; compound 94 and isoxaben; compound 95 (and salts thereof) and isoxaben; compound 96 and isoxaben; compound 135 (and salts thereof) and isoxaben; compound 4 and clomazone; compound 9 and clomazone; compound 58 and clomazone; compound 64 and clomazone; compound 65 (and salts thereof) and clomazone; compound 94 and clomazone; compound 95 (and salts thereof) and clomazone; compound 96 and clomazone; compound 135 (and salts thereof) and clomazone; compound 4 and beflubutamid; compound 9 and beflubutamid; compound 58 and beflubutamid; compound 64 and beflubutamid; compound 65 (and salts thereof) and beflubutamid; compound 94 and beflubutamid; compound 95 (and salts thereof) and beflubutamid; compound 96 and beflubutamid; compound 135 (and salts thereof) and beflubutamid; compound 4 and benfuresate; compound 9 and benfuresate; compound 58 and benfuresate; compound 64 and benfuresate; compound 65 (and salts thereof) and benfuresate; compound 94 and benfuresate; compound 95 (and salts thereof) and benfuresate; compound 96 and benfuresate; compound 135 (and salts thereof) and benfuresate; compound 4 and bentazone; compound 9 and bentazone; compound 58 and bentazone; compound 64 and bentazone; compound 65 (and salts thereof) and bentazone; compound 94 and bentazone; compound 95 (and salts thereof) and bentazone; compound 96 and bentazone; compound 135 (and salts thereof) and bentazone; compound 4 and benzobicyclon; compound 9 and benzobicyclon; compound 58 and benzobicyclon; compound 64 and benzobicyclon; compound 65 (and salts thereof) and benzobicyclon; compound 94 and benzobicyclon; compound 95 (and salts thereof) and benzobicyclon; compound 96 and benzobicyclon; compound 135 (and salts thereof) and benzobicyclon; compound 4 and benzofenap; compound 9 and benzofenap; compound 58 and benzofenap; compound 64 and benzofenap; compound 65 (and salts thereof) and benzofenap; compound 94 and benzofenap; compound 95 (and salts thereof) and benzofenap; compound 96 and benzofenap; compound 135 (and salts thereof) and benzofenap; compound 4 and bromobutide; compound 9 and bromobutide; compound 58 and bromobutide; compound 64 and bromobutide; compound 65 (and salts thereof) and bromobutide; compound 94 and bromobutide; compound 95 (and salts thereof) and bromobutide; compound 96 and bromobutide; compound 135 (and salts thereof) and bromobutide; compound 4 and butachlor; compound 9 and butachlor; compound 58 and butachlor; compound 64 and butachlor; compound 65 (and salts thereof) and butachlor; compound 94 and butachlor; compound 95 (and salts thereof) and butachlor; compound 96 and butachlor; compound 135 (and salts thereof) and butachlor; compound 4 and cafenstrole; compound 9 and cafenstrole; compound 58 and cafenstrole; compound 64 and cafenstrole; compound 65 (and salts thereof) and cafenstrole; compound 94 and cafenstrole; compound 95 (and salts thereof) and cafenstrole; compound 96 and cafenstrole; compound 135 (and salts thereof) and cafenstrole; compound 4 and clomeprop; compound 9 and clomeprop; compound 58 and clomeprop; compound 64 and clomeprop; compound 65 (and salts thereof) and clomeprop; compound 94 and clomeprop; compound 95 (and salts thereof) and clomeprop; compound 96 and clomeprop; compound 135 (and salts thereof) and clomeprop; compound 4 and dimepiperate; compound 9 and dimepiperate; compound 58 and dimepiperate; compound 64 and dimepiperate; compound 65 (and salts thereof) and dimepiperate; compound 94 and dimepiperate; compound 95 (and salts thereof) and dimepiperate; compound 96 and dimepiperate; compound 135 (and salts thereof) and dimepiperate; compound 4 and dimethametryn; compound 9 and dimethametryn; compound 58 and dimethametryn; compound 64 and dimethametryn; compound 65 (and salts thereof) and dimethametryn; compound 94 and dimethametryn; compound 95 (and salts thereof) and dimethametryn; compound 96 and dimethametryn; compound 135 (and salts thereof) and dimethametryn; compound 4 and diamuron; compound 9 and diamuron; compound 58 and diamuron; compound 64 and diamuron; compound 65 (and salts thereof) and diamuron; compound 94 and diamuron; compound 95 (and salts thereof) and diamuron; compound 96 and diamuron; compound 135 (and salts thereof) and diamuron; compound 4 and esprocarb; compound 9 and esprocarb; compound 58 and esprocarb; compound 64 and esprocarb; compound 65 (and salts thereof) and esprocarb; compound 94 and esprocarb; compound 95 (and salts thereof) and esprocarb; compound 96 and esprocarb; compound 135 (and salts thereof) and esprocarb; compound 4 and etobenzanide; compound 9 and etobenzanide; compound 58 and etobenzanide; compound 64 and etobenzanide; compound 65 (and salts thereof) and etobenzanide; compound 94 and etobenzanide; compound 95 (and salts thereof) and etobenzanide; compound 96 and etobenzanide; compound 135 (and salts thereof) and etobenzanide; compound 4 and fentrazamid; compound 9 and fentrazamid; compound 58 and fentrazamid; compound 64 and fentrazamid; compound 65 (and salts thereof) and fentrazamid; compound 94 and fentrazamid; compound 95 (and salts thereof) and fentrazamid; compound 96 and fentrazamid; compound 135 (and salts thereof) and fentrazamid; compound 4 and indanofan;

compound 9 and indanofan; compound 58 and indanofan; compound 64 and indanofan; compound 65 (and salts thereof) and indanofan; compound 94 and indanofan; compound 95 (and salts thereof) and indanofan; compound 96 and indanofan; compound 135 (and salts thereof) and indanofan; compound 4 and cumylron; compound 9 and cumylron; compound 58 and cumylron; compound 64 and cumylron; compound 65 (and salts thereof) and cumylron; compound 94 and cumylron; compound 95 (and salts thereof) and cumylron; compound 96 and cumylron; compound 135 (and salts thereof) and cumylron; compound 4 and menfenacet; compound 9 and menfenacet; compound 58 and menfenacet; compound 64 and menfenacet; compound 65 (and salts thereof) and menfenacet; compound 94 and menfenacet; compound 95 (and salts thereof) and menfenacet; compound 96 and menfenacet; compound 135 (and salts thereof) and menfenacet; compound 4 and oxaziclomefone; compound 9 and oxaziclomefone; compound 58 and oxaziclomefone; compound 64 and oxaziclomefone; compound 65 (and salts thereof) and oxaziclomefone; compound 94 and oxaziclomefone; compound 95 (and salts thereof) and oxaziclomefone; compound 96 and oxaziclomefone; compound 135 (and salts thereof) and oxaziclomefone; compound 4 and oxadiargyl; compound 9 and oxadiargyl; compound 58 and oxadiargyl; compound 64 and oxadiargyl; compound 65 (and salts thereof) and oxadiargyl; compound 94 and oxadiargyl; compound 95 (and salts thereof) and oxadiargyl; compound 96 and oxadiargyl; compound 135 (and salts thereof) and oxadiargyl; compound 4 and pentoxazone; compound 9 and pentoxazone; compound 58 and pentoxazone; compound 64 and pentoxazone; compound 65 (and salts thereof) and pentoxazone; compound 94 and pentoxazone; compound 95 (and salts thereof) and pentoxazone; compound 96 and pentoxazone; compound 135 (and salts thereof) and pentoxazone; compound 4 and pyraclonil; compound 9 and pyraclonil; compound 58 and pyraclonil; compound 64 and pyraclonil; compound 65 (and salts thereof) and pyraclonil; compound 94 and pyraclonil; compound 95 (and salts thereof) and pyraclonil; compound 96 and pyraclonil; compound 135 (and salts thereof) and pyraclonil; compound 4 and pyrazolate; compound 9 and pyrazolate; compound 58 and pyrazolate; compound 64 and pyrazolate; compound 65 (and salts thereof) and pyrazolate; compound 94 and pyrazolate; compound 95 (and salts thereof) and pyrazolate; compound 96 and pyrazolate; compound 135 (and salts thereof) and pyrazolate; compound 4 and pyributicarb; compound 9 and pyributicarb; compound 58 and pyributicarb; compound 64 and pyributicarb; compound 65 (and salts thereof) and pyributicarb; compound 94 and pyributicarb; compound 95 (and salts thereof) and pyributicarb; compound 96 and pyributicarb; compound 135 (and salts thereof) and pyributicarb; compound 4 and pyriftalid; compound 9 and pyriftalid; compound 58 and pyriftalid; compound 64 and pyriftalid; compound 65 (and salts thereof) and pyriftalid; compound 94 and pyriftalid; compound 95 (and salts thereof) and pyriftalid; compound 96 and pyriftalid; compound 135 (and salts thereof) and pyriftalid; compound 4 and pyriminobac-methyl; compound 9 and pyriminobac-methyl; compound 58 and pyriminobac-methyl; compound 64 and pyriminobac-methyl; compound 65 (and salts thereof) and pyriminobac-methyl; compound 94 and pyriminobac-methyl; compound 95 (and salts thereof) and pyriminobac-methyl; compound 96 and pyriminobac-methyl; compound 135 (and salts thereof) and pyriminobac-methyl; compound 4 and thenylchlor; compound 9 and thenylchlor; compound 58 and thenylchlor; compound 64 and thenylchlor; compound 65 (and salts thereof) and thenylchlor; compound 94 and thenylchlor; compound 95 (and salts thereof) and thenylchlor; compound 96 and thenylchlor; compound 135 (and salts thereof) and thenylchlor; compound 4 and bispyribac-sodium; compound 9 and bispyribac-sodium; compound 58 and bispyribac-sodium; compound 64 and bispyribac-sodium; compound 65 (and salts thereof) and bispyribac-sodium; compound 94 and bispyribac-sodium; compound 95 (and salts thereof) and bispyribac-sodium; compound 96 and bispyribac-sodium; compound 135 (and salts thereof) and bispyribac-sodium; compound 4 and clefoxydim; compound 9 and clefoxydim; compound 58 and clefoxydim; compound 64 and clefoxydim; compound 65 (and salts thereof) and clefoxydim; compound 94 and clefoxydim; compound 95 (and salts thereof) and clefoxydim; compound 96 and clefoxydim; compound 135 (and salts thereof) and clefoxydim; compound 4 and cinosulfuron; compound 9 and cinosulfuron; compound 58 and cinosulfuron; compound 64 and cinosulfuron; compound 65 (and salts thereof) and cinosulfuron; compound 94 and cinosulfuron; compound 95 (and salts thereof) and cinosulfuron; compound 96 and cinosulfuron; compound 135 (and salts thereof) and cinosulfuron; compound 4 and cyclosulfamuron; compound 9 and cyclosulfamuron; compound 58 and cyclosulfamuron; compound 64 and cyclosulfamuron; compound 65 (and salts thereof) and cyclosulfamuron; compound 94 and cyclosulfamuron; compound 95 (and salts thereof) and cyclosulfamuron; compound 96 and cyclosulfamuron; compound 135 (and salts thereof) and cyclosulfamuron; compound 4 and ethoxysulfuron; compound 9 and ethoxysulfuron; compound 58 and ethoxysulfuron; compound 64 and ethoxysulfuron; compound 65 (and salts thereof) and ethoxysulfuron; compound 94 and ethoxysulfuron; compound 95 (and salts thereof) and ethoxysulfuron; compound 96 and ethoxysulfuron; compound 135 (and salts thereof) and ethoxysulfuron; compound 4 and epoprodan; compound 9 and epoprodan; compound 58 and epoprodan; compound 64 and epoprodan; compound 65 (and salts thereof) and epoprodan; compound 94 and epoprodan; compound 95 (and salts thereof) and epoprodan; compound 96 and epoprodan; compound 135 (and salts thereof) and epoprodan; compound 4 and flucetosulfuron; compound 9 and flucetosulfuron; compound 58 and flucetosulfuron; compound 64 and flucetosulfuron; compound 65 (and salts thereof) and flucetosulfuron; compound 94 and flucetosulfuron; compound 95 (and salts thereof) and flucetosulfuron; compound 96 and flucetosulfuron; compound 135 (and salts thereof) and flucetosulfuron; compound 4 and imazosulfuron; compound 9 and imazosulfuron; compound 58 and imazosulfuron; compound 64 and imazosulfuron; compound 65 (and salts thereof) and imazosulfuron; compound 94 and imazosulfuron; compound 95 (and salts thereof) and imazosulfuron; compound 96 and imazosulfuron; compound 135 (and salts thereof) and imazosulfuron; compound 4 and metamifop; compound 9 and metamifop; compound 58 and metamifop; compound 64 and metamifop; compound 65 (and salts thereof) and metamifop; compound 94 and metamifop; compound 95 (and salts thereof) and metamifop; compound 96 and metamifop; compound 135 (and salts thereof) and metamifop; compound 4 and pyrazosulfuron-ethyl; compound 9 and pyrazosulfuron-ethyl; compound 58 and pyrazosulfuron-ethyl; compound 64 and pyrazosulfuron-ethyl; compound 65 (and salts thereof) and pyrazosulfuron-ethyl; compound 94 and pyrazosulfuron-ethyl; compound 95 (and salts thereof) and pyrazosulfuron-ethyl; compound 96 and pyrazosulfuron-ethyl; compound 135 (and salts thereof) and pyrazosulfuron-ethyl; compound 4 and quinclorac; compound 9 and quinclorac; compound 58 and quinclorac; compound 64 and quinclorac; compound 65 (and salts thereof) and quinclorac; compound 94 and quinclorac; compound 95 (and salts thereof) and quinclorac; compound 96 and quinclorac; compound 135 (and salts thereof) and quinclorac; compound 4 and flucarbazone-sodium; compound 9 and flucarbazone-sodium; compound 58 and flucarbazone-sodium; compound 64 and flucarbazone-sodium; compound 65 (and salts thereof) and flucarbazone-sodium; compound 94 and flucarbazone-sodium; compound 95 (and salts thereof) and flucarbazone-sodium; compound 96 and flucarbazone-sodium; compound 135 (and salts thereof) and flucarbazone-sodium; compound 4 and propoxycarbazone-sodium; compound 9 and propoxycarbazone-sodium; compound 58 and propoxycarbazone-sodium; compound 64 and propoxycarbazone-sodium; compound 65 (and salts thereof) and propoxycarbazone-sodium; compound 94 and propoxycarbazone-sodium; compound 95 (and salts thereof) and propoxycarbazone-sodium; compound 96 and propoxycarbazone-sodium; compound 135 (and salts thereof) and propoxycarbazone-sodium; compound 4 and amicarbazone; compound 9 and amicarbazone; compound 58 and amicarbazone; compound 64 and amicarbazone; compound 65 (and salts thereof) and amicarbazone; compound 94 and amicarbazone; compound 95 (and salts thereof) and amicarbazone; compound 96 and amicarbazone; compound 135 (and salts thereof) and amicarbazone; compound 4 and florasulam; compound 9 and florasulam; compound 58 and florasulam; compound 64 and florasulam; compound 65 (and salts thereof) and florasulam; compound 94 and florasulam; compound 95 (and salts thereof) and florasulam; compound 96 and florasulam; compound 135 (and salts thereof) and florasulam; compound 4 and triasulfuron; compound 9 and triasulfuron; compound 58 and triasulfuron; compound 64 and triasulfuron; compound 65 (and salts thereof) and triasulfuron; compound 94 and triasulfuron; compound 95 (and salts thereof) and triasulfuron; compound 96 and triasulfuron; compound 135 (and salts thereof) and triasulfuron; compound 4 and triaziflam; compound 9 and triaziflam; compound 58 and triaziflam; compound 64 and triaziflam; compound 65 (and salts thereof) and triaziflam; compound 94 and triaziflam; compound 95 (and salts thereof) and triaziflam; compound 96 and triaziflam; compound 135 (and salts thereof) and triaziflam; compound 4 and pinoxaden; compound 9 and pinoxaden; compound 58 and pinoxaden; compound 64 and pinoxaden; compound 65 (and salts thereof) and pinoxaden; compound 94 and pinoxaden; compound 95 (and salts thereof) and pinoxaden; compound 96 and pinoxaden; compound 135 (and salts thereof) and pinoxaden; compound 4 and tritosulfuron; compound 9 and tritosulfuron; compound 58 and tritosulfuron; compound 64 and tritosulfuron; compound 65 (and salts thereof) and tritosulfuron; compound 94 and tritosulfuron; compound 95 (and salts thereof) and tritosulfuron; compound 96 and tritosulfuron; compound 135 (and salts thereof) and tritosulfuron; compound 4 and amidosulfuron; compound 9 and amidosulfuron; compound 58 and amidosulfuron; compound 64 and amidosulfuron; compound 65 (and salts thereof) and amidosulfuron; compound 94 and amidosulfuron; compound 95 (and salts thereof) and amidosulfuron; compound 96 and amidosulfuron; compound 135 (and salts thereof) and amidosulfuron; compound 4 and metosulam; compound 9 and metosulam; compound 58 and metosulam; compound 64 and metosulam; compound 65 (and salts thereof) and metosulam; compound 94 and metosulam; compound 95 (and salts thereof) and metosulam; compound 96 and metosulam; compound 135 (and salts thereof) and metosulam; compound 4 and sulfosulfuron; compound 9 and sulfosulfuron; compound 58 and sulfosulfuron; compound 64 and sulfosulfuron; compound 65 (and salts thereof) and sulfosulfuron; compound 94 and sulfosulfuron; compound 95 (and salts thereof) and sulfosulfuron; compound 96 and sulfosulfuron; compound 135 (and salts thereof) and sulfosulfuron; compound 4 and pyraflufen-ethyl; compound 9 and pyraflufen-ethyl; compound 58 and pyraflufen-ethyl; compound 64 and pyraflufen-ethyl; compound 65 (and salts thereof) and pyraflufen-ethyl; compound 94 and pyraflufen-ethyl; compound 95 (and salts thereof) and pyraflufen-ethyl; compound 96 and pyraflufen-ethyl; compound 135 (and salts thereof) and pyraflufen-ethyl; compound 4 and HOK-201; compound 9 and HOK-201; compound 58 and HOK-201; compound 64 and HOK-201; compound 65 (and salts thereof) and HOK-201; compound 94 and HOK-201; compound 95 (and salts thereof) and HOK-201; compound 96 and HOK-201; compound 135 (and salts thereof) and HOK-201; compound 4 and KUH-021; compound 9 and KUH-021; compound 58 and KUH-021; compound 64 and KUH-021; compound 65 (and salts thereof) and KUH-021; compound 94 and KUH-021; compound 95 (and salts thereof) and KUH-021; compound 96 and KUH-021; compound 135 (and salts thereof) and KUH-021; compound 4 and CUH-35; compound 9 and CUH-35; compound 58 and CUH-35; compound 64 and CUH-35; compound 65 (and salts thereof) and CUH-35; compound 94 and CUH-35; compound 95 (and salts thereof) and CUH-35; compound 96 and CUH-35; compound 135 (and salts thereof) and CUH-35. The proportions of the compounds of the invention with other herbicidal active ingredients in herbicidal compositions are generally in the ratio of 100:1 to 1:100, more commonly 10:1 to 1:10 and most commonly 5:1 to 1:5 by weight. The optimum ratios can be easily determined by those skilled in the art based on the weed control spectrum desired.

Particularly noteworthy because of greater than additive (i.e. synergistic) efficacy on certain weeds are mixtures of compounds of the invention with auxin transport inhibitors (phytotropins), an example being the combination of compound 1 (ethyl 6-amino-5-bromo-2-cyclopropyl-4-pyrimidinecarboxylate) with diflufenzopyr. Auxin transport inhibitors are chemical substances that inhibit auxin transport in plants, such as by binding with an auxin-carrier protein. Other examples of auxin transport inhibitors include naptalam (also known as N-(1-naphthyl)phthalamic acid and 2-[(1-naphthalenylamino)carbonyl]benzoic acid), 9-hydroxyfluorene-9-carboxylic acid and 2,3,5-triiodobenzoic acid. Therefore an aspect of the present invention relates to a herbicidal mixture comprising synergistically effective amounts of a compound of Claim 1 and an auxin transport inhibitor. Synergistically effective amounts of auxin transport inhibitors with the compounds of the invention can be easily determined.

Compounds of this invention can also be used in combination with herbicide safeners such as benoxacor, BCS (1-bromo-4-[(chloromethyl)sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-ethyl, methoxyphenone ((4-methoxy-3-methylphenyl)(3-methylphenyl)methanone), naphthalic anhydride (1,8-naphthalic anhydride) and oxabetrinil to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

The following Tests demonstrate the control efficacy of the compounds of this invention against specific weeds. The weed control afforded by the compounds is not limited, however, to these species. See Index Tables A-D for compound descriptions. The following abbreviations are used in the Index Tables which follow: t means tertiary, s means secondary, n means normal, i means iso, c means cyclo, Me means methyl, Et means ethyl, Pr means propyl, i-Pr means isopropyl, Bu means butyl, Ph means phenyl, MeO means methoxy, EtO means ethoxy, and CN means cyano. "⁻" means negative formal charge, and "⁺" means positive formal charge. The abbreviation "dec." indicates that the compound appeared to decompose on melting. The abbreviation "Ex." stands for "Example" and is followed by a number indicating in which example the compound is prepared.

INDEX TABLE A

[Structure: pyrimidine ring with $R^1$ at 2-position, $R^2$ at 4-position, $R^3$ at 5-position, $R^4$ at 6-position]

| Compound | $R^1$ | $R^2$ | $R^3$ | $R^4$ | m.p. (° C.) |
|---|---|---|---|---|---|
| 1 (Ex. 1) | c-Pr | $CO_2CH_2CH_3$ | Br | $NH_2$ | 107-108 |
| 2 (Ex. 1) | c-Pr | $CO_2CH_3$ | Br | $NH_2$ | 148-150 |
| 3 | i-Pr | $CO_2CH_3$ | Br | $NH_2$ | 107-109 |
| 4 | c-Pr | $CO_2CH_2CH_3$ | Cl | $NH_2$ | 87-89 |
| 5 | c-Pr | $CO_2CH_3$ | Br | $NHCH_3$ | * |
| 7 | c-Pr | $CO_2CH_3$ | I | $NH_2$ | 145-146 |
| 8 | c-Pr | $CO_2H$ | Br | $NH_2$ | 160-162 |
| 9 (Ex. 3) | c-Pr | $CO_2CH_3$ | Cl | $NH_2$ | 143-145 |
| 10 | c-Pr | $CO_2CH_3$ | Br | $NHCH_2CO_2CH_3$ | 95-96 |
| 11 | c-Pr | $CH_2OCH_3$ | Br | $NH_2$ | * |
| 12 | c-Pr | $CH_2CO_2CH_2CH_3$ | Br | $NH_2$ | * |
| 13 | c-Pr | $CH_2CO_2CH_3$ | Br | $NH_2$ | * |
| 14 | c-Pr | $CO_2(i\text{-Pr})$ | Br | $NH_2$ | 141-142 |
| 15 | c-Pr | $CO_2CH_2CH_2CH_3$ | Br | $NH_2$ | 86-90 |
| 16 | c-Pr | $CO_2CH_2CH_2CH_2CH_3$ | Br | $NH_2$ | 87-90 |
| 17 | c-Pr | $CO_2(i\text{-Bu})$ | Br | $NH_2$ | 121-123 |
| 18 | Ph | $CO_2CH_2CH_3$ | Br | $NH_2$ | 110-111 |
| 19 | c-Pr | $CO_2CH_3$ | Br | $N=CHN(CH_3)_2$ | * |
| 20 | c-Pr | $C(O)NH_2$ | Br | $NH_2$ | * |
| 21 | c-Pr | $CH_2OH$ | Br | $NH_2$ | 182-185 |
| 22 | c-Pr | $CO_2CH_2Ph$ | Br | $NH_2$ | 129-131 |
| 23 | Ph | $CO_2CH_3$ | Br | $NH_2$ | * |
| 24 | c-Pr | CHO | F | $NH_2$ | * |
| 25 | c-Pr | $CO_2CH_3$ | F | $NH_2$ | * |
| 26 | c-Pr | CHO | Br | $NH_2$ | * |
| 27 | c-Pr | CH=NOH | Br | $NH_2$ | * |
| 28 | 2-Me—c-Pr | $CO_2CH_3$ | Br | $NH_2$ | 132-133 |
| 30 | c-Pr | $CO_2CH_2CH_3$ | F | $NH_2$ | * |
| 31 | c-Pr | $CH(Cl)CO_2CH_2CH_3$ | Br | $NH_2$ | * |
| 32 | c-Pr | $CH(CH_3)CO_2CH_2CH_3$ | Br | $NH_2$ | * |
| 33 | c-Pr | $CH_2CO_2CH_2CH_3$ | Br | $N=CHN(CH_3)_2$ | * |
| 34 | c-Pr | $CCl_2CO_2CH_2CH_3$ | Br | $NH_2$ | * |
| 35 | c-Pr | $CO_2CH_3$ | Br | NHOH | * |
| 36 | t-Bu | $CO_2CH_2CH_3$ | Br | $NH_2$ | 69-70 |
| 37 | 4-Cl—Ph | $CO_2CH_2CH_3$ | Br | $NH_2$ | 120-121 |
| 38 | c-Pr | $CO_2CH_2CH_3$ | Br | $NH(CH_2)_2N(CH_3)_2$ | * |
| 39 | c-Pr | $CO_2CH_2CH_3$ | Br | $NHCH_2CH_2OCH_3$ | * |
| 40 | c-Pr | $CO_2CH_2CH_3$ | Br | $N=CHN(CH_3)_2$ | * |
| 41 | 4-Cl—Ph | $CH_2CO_2CH_2CH_3$ | Br | $NH_2$ | * |
| 42 | c-Pr | $CO_2CH_2CH_3$ | Br | $NHNH_2$ | * |
| 43 | 4-F—Ph | $CO_2CH_3$ | Cl | $NH_2$ | * |
| 44 | 4-$CF_3$—Ph | $CO_2CH_3$ | Cl | $NH_2$ | * |
| 45 | c-Pr | $CH(OCH_2CH_3)_2$ | Br | $NH_2$ | * |
| 46 | c-Pr | $CH(OCH_3)_2$ | F | $NH_2$ | * |
| 47 | c-Pr | $CH(CO_2CH_2CH_3)OC(O)CH_3$ | Br | $NH_2$ | * |
| 48 | c-Pr | $CH=NOCH_3$ | Br | $NH_2$ | * |
| 49 | c-Pr | $CH=NNHCH_3$ | Br | $NH_2$ | * |
| 50 | c-Pr | $CH=NN(CH_3)_2$ | Br | $NH_2$ | * |

INDEX TABLE A-continued

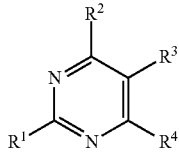

| Compound | R[1] | R[2] | R[3] | R[4] | m.p. (° C.) |
|---|---|---|---|---|---|
| 51 | c-Pr | CH=NNHC(O)CH$_3$ | Br | NH$_2$ | * |
| 52 | c-Pr | CO$_2$CH$_2$CH$_3$ | Br | NHOCH$_3$ | * |
| 53 | c-Pr | CO$_2$CH$_2$CH$_3$ | Br | NHC(O)CH$_3$ | * |
| 54 | c-Pr | CO$_2$CH$_2$CH$_3$ | Br | NHOCH$_2$Ph | * |
| 55 | c-Pr | CO$_2$CH$_2$CH$_3$ | Br | NHO(t-Bu) | * |
| 56 | c-Pr | CO$_2$CH$_2$CH$_3$ | Br | N⎯CH$_2$(CH$_2$)$_2$CH$_2$⎯ | * |
| 57 | c-Pr | C(OH)CO$_2$CH$_2$CH$_3$ | Br | NH$_2$ | * |
| 58 | 4-Cl—Ph | CO$_2$CH$_3$ | Cl | NH$_2$ | 215-218 |
| 59 | c-Pr | CO$_2$CH$_3$ | OMe | NH$_2$ | * |
| 60 | 4-CF$_3$—Ph | CO$_2$CH$_2$CH$_3$ | Br | NH$_2$ | * |
| 61 | 4-CH$_3$—Ph | CO$_2$CH$_2$CH$_3$ | Br | NH$_2$ | * |
| 62 | 4-CH$_3$—Ph | CO$_2$CH$_2$CH$_3$ | Cl | NH$_2$ | * |
| 63 | 4-F—Ph | CO$_2$CH$_2$CH$_3$ | Br | NH$_2$ | * |
| 64 (Ex. 5) | 4-Cl—Ph | CO$_2$CH$_2$CH$_3$ | Cl | NH$_2$ | 132-133 |
| 65 (Ex. 4) | 4-Cl—Ph | CO$_2$H | Cl | NH$_2$ | 158-160 dec. |
| 66 | 3,4-di-Cl—Ph | CO$_2$CH$_2$CH$_3$ | Br | NH$_2$ | * |
| 67 | 2,4-di-Cl—Ph | CO$_2$CH$_2$CH$_3$ | Br | NH$_2$ | * |
| 68 | 1,3-benzodioxol-5-yl | CO$_2$CH$_2$CH$_3$ | Br | NH$_2$ | * |
| 69 | 2-F-4-Cl—Ph | CO$_2$CH$_2$CH$_3$ | Br | NH$_2$ | * |
| 70 | 3,4-di-Me—Ph | CO$_2$CH$_2$CH$_3$ | Br | NH$_2$ | * |
| 71 | 3,4-di-Me—Ph | CO$_2$CH$_2$CH$_3$ | Cl | NH$_2$ | * |
| 72 | 2,4-di-Cl—Ph | CO$_2$CH$_2$CH$_3$ | Cl | NH$_2$ | * |
| 73 | 3,4-di-Cl—Ph | CO$_2$CH$_2$CH$_3$ | Cl | NH$_2$ | * |
| 74 | 1,3-benzodioxol-5-yl | CO$_2$CH$_2$CH$_3$ | Cl | NH$_2$ | * |
| 75 | c-Pr | CO$_2$CH$_2$CH$_2$CH$_3$ | Cl | NH$_2$ | 87-90 |
| 76 | c-Pr | CO$_2$CH$_2$CH$_2$CH$_2$CH$_3$ | Cl | NH$_2$ | 97-99 |
| 77 | c-Pr | C(O)O$^-$ Na$^+$ | Cl | NH$_2$ | 297 dec. |
| 78 | c-Pr | CO$_2$CH$_2$Ph | Cl | NH$_2$ | 126-128 |
| 79 | c-Pr | CO$_2$CH$_3$ | Cl | NHCH$_3$ | * |
| 80 | c-Pr | CO$_2$CH$_2$(4-Cl—Ph) | Cl | NH$_2$ | 123-125 |
| 81 | c-Pr | C(O)NHCH$_3$ | Cl | NH$_2$ | * |
| 82 | 4-Me—Ph | CO$_2$CH$_3$ | Br | NH$_2$ | * |
| 83 | 4-Cl—Ph | CO$_2$CH$_3$ | Br | NH$_2$ | * |
| 84 | 4-Me—Ph | CO$_2$CH$_3$ | Cl | NH$_2$ | * |
| 85 | c-Pr | C(O)NH$_2$ | Cl | NH$_2$ | 232-236 |
| 86 | 3-F-4-Me—Ph | CO$_2$CH$_3$ | Cl | NH$_2$ | 185-186 |
| 87 | 3-F-4-Me—Ph | CO$_2$H | Cl | NH$_2$ | 150 dec. |
| 88 | 4-Cl—Ph | CO$_2$H | Br | NH$_2$ | * |
| 89 | 4-Me—Ph | CO$_2$H | Br | NH$_2$ | * |
| 90 | 4-F—Ph | CO$_2$H | Cl | NH$_2$ | * |
| 91 | 4-Me—Ph | CO$_2$H | Cl | NH$_2$ | * |
| 92 | 4-F—Ph | CO$_2$CH$_3$ | Br | NH$_2$ | * |
| 93 | 4-F—Ph | CO$_2$H | Br | NH$_2$ | * |
| 94 | 4-Br—Ph | CO$_2$CH$_2$CH$_3$ | Cl | NH$_2$ | 136-137 |
| 95 | 4-Br—Ph | CO$_2$H | Cl | NH$_2$ | 157-158 dec. |
| 96 | 4-Br—Ph | CO$_2$CH$_3$ | Cl | NH$_2$ | 223-224 |
| 97 | 3-Me—Ph | CO$_2$CH$_3$ | Cl | NH$_2$ | * |
| 98 | 4-MeO—Ph | CO$_2$CH$_2$CH$_3$ | Cl | NH$_2$ | * |
| 99 | 4-Et—Ph | CO$_2$CH$_2$CH$_3$ | Cl | NH$_2$ | * |
| 100 | 3-Cl—Ph | CO$_2$CH$_2$CH$_3$ | Cl | NH$_2$ | * |
| 101 | 3-Br-5-MeO—Ph | CO$_2$CH$_2$CH$_3$ | Cl | NH$_2$ | 110-112 |
| 102 | 4-Cl—Ph | CO$_2$(i-Pr) | Cl | NH$_2$ | 153-156 |
| 103 | 4-CF$_3$O—Ph | CO$_2$CH$_2$CH$_3$ | Cl | NH$_2$ | * |
| 104 | 4-CF$_3$—Ph | CO$_2$CH$_2$CH$_3$ | Cl | NH$_2$ | 138-140 |
| 105 | 4-Cl—Ph | CO$_2$CH$_2$CH$_2$CH$_3$ | Cl | NH$_2$ | 80-81 |
| 106 | 2-F—Ph | CO$_2$CH$_2$CH$_3$ | Cl | NH$_2$ | 120-124 |
| 107 | 3-CF$_3$—Ph | CO$_2$CH$_2$CH$_3$ | Cl | NH$_2$ | 121-122 |
| 108 | i-Pr | CO$_2$CH$_2$CH$_3$ | Cl | NH$_2$ | 102-103 |
| 109 | i-Pr | C(O)O$^-$ Na$^+$ | Cl | NH$_2$ | 190-192 dec. |
| 110 | i-Pr | CO$_2$CH$_3$ | Cl | NH$_2$ | 100-104 dec. |
| 111 | 4-Cl—Ph | CO$_2$CH$_3$ | Cl | NHCH$_3$ | 124-126 |
| 112 | c-Pr | OCH$_2$CO$_2$CH$_3$ | Cl | NH$_2$ | 148-150 |
| 113 | c-Pr | C(O)O$^-$ Na$^+$ | Br | NH$_2$ | >300 |
| 114 | 4-Cl—Ph | OCH$_2$CO$_2$CH$_2$CH$_3$ | Cl | NH$_2$ | * |

INDEX TABLE A-continued

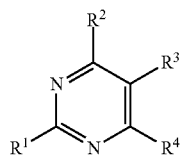

| Compound | R¹ | R² | R³ | R⁴ | m.p. (° C.) |
|---|---|---|---|---|---|
| 115 | c-Pr | OCH$_2$CO$_2$CH$_2$CH$_3$ | Cl | NH$_2$ | 164-168 |
| 116 | c-Pr | OCH$_2$C(O)O, Na⁺ | Cl | NH$_2$ | 264-267 dec. |
| 117 | 4-Cl—Ph | C(O)O, Na⁺ | Cl | NH$_2$ | >300 |
| 118 | 4-Cl—Ph | CO$_2$CH$_2$Ph | Cl | NH$_2$ | 150-153 |
| 119 | 4-Cl—Ph | OCH$_2$CO$_2$CH$_3$ | Cl | NH$_2$ | 129-132 |
| 120 | 4-Cl—Ph | CH$_2$CO$_2$CH$_2$CH$_3$ | Cl | NH$_2$ | * |
| 121 | 4-MeS—Ph | CO$_2$CH$_3$ | Cl | NH$_2$ | 169-173 |
| 122 | 4-MeS(O)$_2$—Ph | CO$_2$CH$_3$ | Cl | NH$_2$ | 173-175 |
| 123 | 4-MeS(O)—Ph | CO$_2$CH$_3$ | Cl | NH$_2$ | 173-175 |
| 124 | c-Pr | CO$_2$CH$_3$ | Br | NHN=CHCH$_3$ | * |
| 125 | c-Pr | CO$_2$CH$_2$CH$_3$ | Br | NHOCH$_2$CO$_2$H | * |
| 126 | c-Pr | CO$_2$CH$_2$CH$_3$ | Br | NHNHC(O)CH$_3$ | * |
| 127 | 2-naphthalenyl | CO$_2$CH$_2$CH$_3$ | Cl | NH$_2$ | * |
| 128 | 4-I—Ph | CO$_2$CH$_3$ | Br | NH$_2$ | 192-195 |
| 129 | 4-Br—Ph | CO$_2$CH$_3$ | Br | NH$_2$ | 204-206 |
| 130 | 4-Br—Ph | C(O)NH$_2$ | Br | NH$_2$ | 234-236 |
| 131 | 4-Cl—Ph | C(O)NHSO$_2$CH$_3$ | Cl | NH$_2$ | 243-245 |
| 132 | c-Pr | C(O)NHSO$_2$CH$_3$ | Cl | NH$_2$ | 227-233 |
| 133 | 4-I—Ph | CO$_2$CH$_2$CH$_3$ | Cl | NH$_2$ | 140-142 |
| 134 | 4-I—Ph | CH(OCH$_3$)$_2$ | Cl | NH$_2$ | 176-179 |
| 135 (Ex. 2) | c-Pr | CO$_2$H | Cl | NH$_2$ | 144-146 |
| 136 | 4-Br—Ph | CO$_2$H | Br | NH$_2$ | 167-170 |
| 137 | 4-Cl—Ph | CO$_2$CH$_2$CH$_3$ | I | NH$_2$ | 116-119 |
| 138 | 4-I—Ph | CH(OCH$_2$CH$_3$)$_2$ | Cl | NH$_2$ | * |
| 139 | c-Pr | CO$_2$CH$_2$CH$_2$O(n-Bu) | Cl | NH$_2$ | 64-66 |
| 141 | c-Pr | CO$_2$CH$_2$CH$_2$OCH$_2$CH$_2$OCH$_3$ | Cl | NH$_2$ | 79-80 |
| 143 | c-Pr | CO$_2$CH$_2$CH$_2$CH$_2$OH | Cl | NH$_2$ | 91-94 |
| 144 | c-Pr | C(O)O, (i-Pr)NH$_3$⁺ | Cl | NH$_2$ | 170 dec. |
| 145 | c-Pr | CO$_2$(4-Cl—Ph) | Cl | NH$_2$ | 145-147 |
| 146 | c-Pr | CO$_2$N=C(CH$_3$)$_2$ | Cl | NH$_2$ | 101-103 |
| 148 | c-Pr | CO$_2$CH$_2$CO$_2$CH$_3$ | Cl | NH$_2$ | 107-108 |
| 151 | c-Pr | C(O)O, (c-hexyl)NH$_3$⁺ | Cl | NH$_2$ | 170 dec. |
| 152 | c-Pr | C(O)O, +(CH$_2$)$_2$O(CH$_2$)$_2$+NH$_2$⁺ | Cl | NH$_2$ | 189-190 dec. |
| 153 | c-Pr | C(O)O, (HOCH$_2$CH$_2$)$_2$NH$_2$⁺ | Cl | NH$_2$ | 118-124 |
| 154 | c-Pr | C(O)O, (CH$_3$CH$_2$)$_3$NH⁺ | Cl | NH$_2$ | 138-141 dec. |
| 155 | c-Pr | C(O)O, pyridine-H⁺ | Cl | NH$_2$ | 144-147 dec. |
| 156 | c-Pr | C(O)O, Li⁺ | Cl | NH$_2$ | 280 dec. |
| 157 | c-Pr | C(O)O, K⁺ | Cl | NH$_2$ | 273 dec. |
| 158 | c-Pr | C(O)O, Cs⁺ | Cl | NH$_2$ | 300 dec. |
| 159 | c-Pr | C(O)O, (CH$_3$)$_4$N⁺ | Cl | NH$_2$ | 263 dec. |
| 160 | c-Pr | C(O)O, (CH$_3$)$_3$S⁺ | Cl | NH$_2$ | 157 dec. |
| 161 | c-Pr | C(O)O, HOCH$_2$CH$_2$NH$_3$⁺ | Cl | NH$_2$ | 168 dec. |
| 162 | c-Pr | C(O)O, (HOCH$_2$CH$_2$)$_3$NH⁺ | Cl | NH$_2$ | 125-128 |
| 163 | c-Pr | C(O)O, (CH$_3$)$_2$NH$_2$⁺ | Cl | NH$_2$ | 170 dec. |
| 164 | c-Pr | CO$_2$(CH$_2$)$_7$CH$_3$ | Cl | NH$_2$ | 73-74 |
| 165 | c-Pr | CO$_2$(i-Pr) | Cl | NH$_2$ | 143-144 |
| 166 | c-Pr | CO$_2$CH(CH$_3$)(CH$_2$)$_5$CH$_3$ | Cl | NH$_2$ | 82-85 |
| 167 | c-Pr | CO$_2$CH$_2$CH(C$_2$H$_5$)(CH$_2$)$_3$CH$_3$ | Cl | NH$_2$ | 60-62 |

* See Index Table D for ¹H NMR data.

INDEX TABLE B

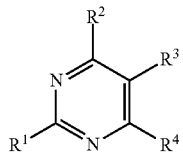

| Compound | $R^1$ | $R^2$ | $R^3$ | $R^4$ | m.p. (° C.) |
|---|---|---|---|---|---|
| 140 | c-Pr | CO$_2$CH$_2$(2-oxiranyl) | Cl | NH$_2$ | * |
| 147 | c-Pr | CO$_2$CH$_2$(2,2-di-Me-1,3-dioxlan-4-yl) | Cl | NH$_2$ | 104-105 |
| 149 | c-Pr | CO$_2$CH$_2$(2-oxo-1,3 dioxlan-4-yl) | Cl | NH$_2$ | 142-150 |
| 150 | c-Pr | CO$_2$CH$_2$(tetrahydro-2-furanyl) | Cl | NH$_2$ | 114-116 |

* See Index Table D for $^1$H NMR data.

INDEX TABLE C

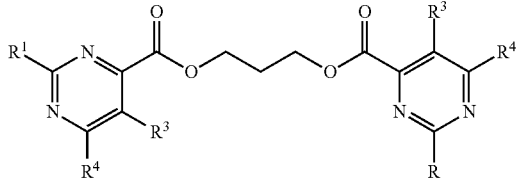

| Compound | $R^1$ | $R^3$ | $R^4$ | m.p. (° C.) |
|---|---|---|---|---|
| 142 | c-Pr | Cl | NH$_2$ | 107-108 |

* See Index Table D for $^1$H NMR data.

INDEX TABLE D

| Compound | $^1$H NMR Data (CDCl$_3$ solution unless indicated otherwise)$^a$ |
|---|---|
| 5 | δ 5.60 (br s, 1H), 3.96 (s, 3H), 3.02 (d, 3H), 2.10 (m, 1H), 1.10 (m, 2H), 0.98 (m, 2H). |
| 11 | δ 5.20 (br s, 2H), 4.97 (s, 2H), 3.49 (s, 3H), 2.07 (m, 1H), 1.02 (m, 2H), 0.95 (m, 2H). |
| 12 | δ 5.20 (br s, 2H), 4.18 (q, 2H), 3.80 (s, 2H), 1.90 (m, 1H), 1.25 (t, 3H), 1.01-0.93 (m, 4H). |
| 13 | δ 5.26 (br s, 2H), 3.82 (s, 3H), 3.73 (s, 3H), 1.90 (m, 1H), 1.02-0.92 (m, 4H). |
| 19 | δ 8.60 (s, 1H), 3.97 (s, 3H), 3.20 (s, 3H), 3.19 (s, 3H), 2.10 (m, 1H), 1.08 (m, 2H), 0.99 (m, 2H). |
| 20 | δ 7.65 (br s, 1H), 5.94 (br s, 2H), 5.8 (br s, 1H), 2.01 (m, 1H), 1.03 (m, 4H). |
| 23 | δ 8.35 (m, 2H), 7.46 (m, 3H), 5.61 (br s, 2H), 4.02 (s, 3H). |
| 24 | δ 10.01 (s, 1H), 5.31 (br s, 2H), 2.10 (m, 1H), 1.10-0.95 (m, 4H). |
| 25 | δ 5.15 (br s, 2H), 3.98 (s, 3H), 2.03 (m, 1H), 1.04-0.92 (m, 4H). |
| 26 | δ 9.98 (s, 1H), 5.60 (br s, 2H), 2.10 (m, 1H), 1.10-1.02 (m, 4H). |
| 27 | δ 8.19 (s, 1H), 1.89 (m, 1H), 0.92-0.87 (m, 4H). |
| 30 | δ 5.12 (br s, 2H), 4.45 (q, 2H), 2.13 (m, 1H), 1.41 (t, 3H), 1.04-0.92 (m, 4H). |
| 31 | δ 5.66 (s, 1H), 5.34 (br s, 2H), 4.30 (q, 2H), 1.98 (m, 1H), 1.30 (t, 3H), 1.13-0.92 (m, 4H). |
| 32 | δ 5.26 (br s, 2H), 4.21-4.07 (m, 3H), 1.94 (m, 1H), 1.45 (d, 2H), 1.22 (t, 3H), 1.08-0.90 (m, 4H). |
| 33 | δ 8.57 (s, 1H), 4.18 (q, 2H), 3.88 (s, 2H), 3.18 (s, 3H), 3.16 (s, 3H), 2.00 (m, 1H), 1.24 (t, 3H), 1.05-0.96 (m, 4H). |
| 34 | δ 5.48 (br s, 2H), 4.38 (q, 2H), 2.02 (m, 1H), 1.36 (t, 3H), 1.11-0.97 (m, 4H). |
| 35 | δ 3.97 (s, 3H), 2.07 (m, 1H), 1.20-1.13 (m, 2H), 1.12-1.04 (m, 2H). |
| 38 | δ 6.20 (br s, 1H), 4.43 (q, 2H), 3.48 (m, 2H), 2.50 (m, 2H), 2.27 (s, 6H), 2.07 (m, 1H), 1.41 (t, 3H), 1.07 (m, 2H), 0.96 (m, 2H). |
| 39 | δ 5.90 (br s, 1H), 4.43 (q, 2H), 3.65 (m, 2H), 3.54 (m, 2H), 3.39 (s, 3H), 2.08 (m, 1H), 1.41 (t, 3H), 1.04 (m, 2H), 0.98 (m, 2H). |
| 40 | δ 8.59 (s, 1H), 4.44 (q, 2H), 3.20 (s, 3H), 3.18 (s, 3H), 2.10 (m, 1H), 1.41 (t, 3H), 1.11-1.05 (m, 2H), 1.01-0.94 (m, 2H). |
| 41 | δ 8.27 (m, 2H), 7.39 (m, 2H), 5.39 (br s, 2H), 4.23 (q, 2H), 3.93 (s, 2H), 1.29 (t, 3H). |
| 42 | δ 6.70 (br s, 1H), 4.43 (q, 2H), 4.0 (br s, 2H), 2.10 (m, 1H), 1.41 (t, 3H), 1.11 (m, 2H), 1.01 (m, 2H). |
| 43 | δ 8.35 (m, 2H), 7.10 (dd, 2H), 5.54 (br s, 2H), 4.02 (s, 3H). |
| 44 | δ 8.47 (d, 2H), 7.69 (d, 2H), 5.61 (br s, 2H), 4.04 (s, 3H). |
| 45 | δ 5.56 (s, 1H), 5.29 (br s, 2H), 3.86-3.74 (m, 2H), 3.71-3.58 (m, 2H), 2.14-2.03 (m, 1H), 1.30-1.23 (m, 6H), 1.07-0.89 (m, 4H). |
| 46 | δ 5.39 (s, 1H), 4.96 (br s, 2H), 3.49 (s, 6H), 2.15-2.04 (m, 1H), 1.02-0.87 (m, 4H). |
| 47 | δ 6.32 (s, 1H), 5.34 (br s, 2H), 4.28 (q, 2H), 2.21 (s, 3H), 2.03-1.93 (m, 1H), 1.28 (t, 3H), 1.11-0.91 (m, 4H). |
| 48 | δ 8.41 (s, 1H), 5.34 (br s, 2H), 4.12 (s, 3H), 2.19-2.10 (m, 1H), 0.90-0.80 (m, 4H). |
| 49 | (DMSO-d$_6$) δ 8.45 (q, 1H), 7.34 (s, 1H), 6.82 (br s), 2.86 (d, 3H), 1.91-1.81 (m, 1H), 1.07-0.92 (m, 4H). |
| 50 | δ 7.23 (s, 1H), 5.18 (br s, 2H), 3.21 (s, 6H), 2.19-2.08 (m, 1H), 1.05-0.88 (m, 4H). |
| 51 | (DMSO-d$_6$) δ 11.68 + 11.55 (2 × s, 1H), 8.39 + 8.09 (2 × s, 1H), 2.20 + 1.97 (2 × s, 3H), 1.97-1.86 (m, 1H), 0.90 (d, 4H). |
| 52 | δ 8.76 + 8.07 (2 × s, 1H), 4.50-4.32 (br s, 2H), 3.94 + 3.89 (2 × s, 3H), 2.26-2.11 (br m, 1H), 1.40 (br s, 3H), 1.20-1.12 (m, 2H), 1.09-1.00 (m, 2H). |
| 53 | δ 4.49 (q, 2H), 2.30 (s, 3H), 2.3-2.2 (m, 1H), 1.43 (t, 3H), 1.27-1.09 (m, 4H). |
| 54 | δ 7.47-7.34 (m, 5H), 5.06 (s, 2H), 4.43 (q, 2H), 1.90-1.84 (m, 1H), 1.41 (t, 3H), 1.23-1.03 (m, 4H). |
| 55 | δ 8.64 + 7.64 (2 × s, 1H), 4.45 + 4.36 (2 × q, 2H), 2.20-2.10 (m, 1H), 1.42 + 1.37 (2 × t, 3H), 1.34 + 1.32 (2 × s, 9H), 1.18-0.98 (m, 4H). |
| 56 | δ 4.42 (q, 2H), 3.77 (m, 4H), 2.07-1.97 (m, 1H), 1.91 (m, 4H), 1.40 (t, 3H), 1.07-0.89 (m, 4H). |
| 57 | δ 5.37-5.30 (m, 3H), 4.51 (d, 1H), 4.28-4.16 (m, 2H), 2.06-1.96 (m, 1H), 1.27 (t, 3H), 1.09-0.94 (m, 4H). |
| 59 | δ 5.14 (br s, 2H), 3.97 (s, 3H), 3.84 (s, 3H), 2.09 (m, 1H), 1.00 (m, 2H), 0.94 (m, 2H). |
| 60 | δ 8.46 (d, 2H), 7.69 (d, 2H), 5.65 (br s, 2H), 4.50 (m, 2H), 1.46 (t, 3H). |
| 61 | δ 8.23 (d, 2H), 7.24 (d, 2H), 5.57 + 5.53 (2 × br s, 2H), 4.49 (m, 2H), 2.40 (s, 3H), 1.45 (t, 3H). |
| 62 | δ 8.23 (d, 2H), 7.24 (d, 2H), 5.53 (br s, 2H), 4.49 (m, 2H), 2.40 (s, 3H), 1.45 (t, 3H). |
| 63 | δ 8.35 (m, 2H), 7.11 (t, 2H), 5.57 (br s, 2H), 4.49 (m, 2H), 1.45 (t, 3H). |
| 66 | δ 8.46 (d, 1H), 8.20 (dd, 1H), 7.50 (d, 1H), 5.62 (br s, 2H), 4.50 (m, 2H), 1.46 (t, 3H). |
| 67 | δ 7.67 (d, 1H), 7.48 (d, 1H), 7.32 (dd, 1H), 5.69 (br s, 2H), 4.47 (m, 2H), 1.43 (t, 3H). |
| 68 | δ 7.96 (dd, 1H), 7.83 (d, 1H), 6.85 (d, 1H), 6.02 (s, 2H), 5.53 (br s, 2H), 4.48 (m, 2H), 1.45 (t, 3H). |
| 69 | δ 8.97 (t, 1H), 7.23-7.15 (m, 2H), 5.67 (br s, 2H), 4.48 (m, 2H), 1.44 (t, 3H). |
| 70 | δ 8.11 (m, 1H), 8.06 (m, 1H), 7.19 (d, 1H), 5.57 (br s, 2H), 4.49 (m, 2H), 2.32 (t, 3H), 2.30 (t, 3H), 1.45 (t, 3H). |
| 71 | δ 8.11 (m, 1H), 8.06 (m, 1H), 7.20 (d, 1H), 5.50 (br s, 2H), 4.49 (m, 2H), 2.33 (t, 3H), 2.31 (t, 3H), 1.45 (t, 3H). |
| 72 | δ 7.67 (d, 1H), 7.48 (d, 1H), 7.32 (dd, 1H), 5.63 (br s, 2H), 4.48 (m, 2H), 1.43 (t, 3H). |
| 73 | δ 8.46 (d, 1H), 8.20 (dd, 1H), 7.50 (d, 1H), 5.56 (br s, 2H), 4.50 (m, 2H), 1.46 (t, 3H). |
| 74 | δ 7.95 (dd, 1H), 7.83 (d, 1H), 6.86 (d, 1H), 6.02 (s, 2H), 5.48 (br s, 2H), 4.48 (m, 2H), 1.45 (t, 3H). |
| 79 | δ 5.56 (br s, 1H), 3.97 (s, 3H), 3.04 (d, 3H), 2.11 (m, 1H), 1.10 (m, 2H), 0.98 (m, 2H). |
| 81 | δ 7.82 (br s, 1H), 5.48 (br s, 2H), 2.97 (d, 3H), 2.01 (m, 1H), 1.04 (m, 2H), 0.99 (m, 2H). |
| 82 | δ 8.22 (d, 2H), 7.24 (d, 2H), 5.57 + 5.52 (2 × br s, 2H), 4.02 (s, 3H), 2.40 (s, 3H). |
| 83 | δ 8.29 (d, 2H), 7.40 (d, 2H), 5.60 (br s, 2H), 4.02 (s, 3H). |
| 84 | δ 8.22 (d, 2H), 7.24 (d, 2H), 5.53 (br s, 2H), 4.02 (s, 3H), 2.40 (s, 3H). |
| 88 | (DMSO-d$_6$) δ 14.1-13.9 (br s), 8.25 (d, 2H), 7.56 (d, 2H). |
| 89 | (DMSO-d$_6$) δ 8.15 (d, 2H), 7.29 (d, 2H), 2.36 (s, 3H). |
| 90 | (DMSO-d$_6$) δ 14.2-13.9 (br s), 8.29 (d, 2H), 7.31 (t, 2H). |
| 91 | δ 8.18 (d, 2H), 7.30 (d, 2H), 5.84 (br s, 2H), 2.43 (s, 3H). |
| 92 | δ 8.35 (m, 2H), 7.11 (t, 2H), 5.59 (br s, 2H), 4.02 (s, 3H). |
| 93 | δ 8.32 (m, 2H), 7.17 (t, 2H), 5.96 (br s, 2H). |

INDEX TABLE D-continued

| Compound | ¹H NMR Data (CDCl₃ solution unless indicated otherwise)$^a$ |
|---|---|
| 97 | δ 8.11 (m, 2H), 7.31 (m, 2H), 5.57 (br s, 2H), 4.02 (s, 3H), 2.42 (s, 3H). |
| 98 | δ 8.30 (d, 2H), 6.94 (d, 2H), 5.48 (br s, 2H), 4.49 (q, 2H), 3.86 (s, 3H), 1.45 (t, 3H). |
| 99 | δ 8.24 (d, 2H), 7.26 (d, 2H), 5.51 (br s, 2H), 4.49 (q, 2H), 2.70 (q, 2H) 1.45 (t, 3H), 1.26 (t, 3H). |
| 100 | δ 8.35 (s, 1H), 8.24 (d, 1H), 7.46-7.34 (m, 2H), 5.56 (br s, 2H), 4.50 (q, 2H), 1.46 (t, 3H). |
| 103 | δ 8.39 (d, 2H), 7.27 (d, 2H), 5.47 (br s, 2H), 4.50 (q, 2H), 1.45 (t, 3H). |
| 114 | δ 8.19 (d, 2H), 7.38 (d, 2H), 5.26 (br s, 2H), 4.98 (s, 2H), 4.24 (q, 2H), 1.26 (t, 3H). |
| 120 | δ 8.27 (d, 2H), 7.39 (d, 2H), 5.34 (br s, 2H), 4.23 (q, 2H), 3.91 (s, 2H), 1.29 (t, 3H). |
| 124 | δ 8.61 + 8.48 (2 × s, 1H), 7.48 + 7.12 (2 × q, 1H), 3.98 + 3.96 (2 × s, 3H), 2.30-2.15 (m, 1H), 2.14 + 2.00 (2 × d, 3H), 1.19-1.12 (2 × m, 2H), 1.06-0.97 (2 × m, 2H). |
| 125 | δ 4.61 + 4.54 (2 × br s, 2H), 4.47-4.36 (m, 2H), 2.18-1.98 (br m, 1H), 1.44-1.34 (m, 3H), 1.32-1.00 (br m, 4H). |
| 126 | δ 7.83 (d, 1H), 7.69 (d, 1H), 4.45 (q, 2H), 2.14 (s, 3H), 1.41 (t, 3H), 1.08-1.00 (m, 4H). |
| 127 | δ 8.89 (s, 1H), 8.43 (d, 1H), 7.97 (d, 1H), 7.92-7.83 (m, 2H), 7.57-7.46 (m, 2H), 5.57 (br s, 2H), 4.53 (q, 2H), 1.48 (t, 3H). |
| 138 | δ 8.11 (d, 2H), 7.76 (d, 2H), 5.65 (s, 1H), 5.39 (br s, 2H), 3.88 (m, 2H), 3.70 (m, 2H), 1.30 (t, 6H). |
| 140 | 5.38 (br s, 2H), 4.44 (dd, 1H), 4.28 (dd, 1H), 3.35 (m, 1H), 2.88 (dd, 1H), 2.76 (dd, 1H), 2.07 (m, 1H), 1.05 (m, 2H), 1.00 (m, 2H). |

$^a$¹H NMR data are in ppm downfield from tetramethylsilane. Couplings are designated by (s)—singlet, (d)—doublet, (t)—triplet, (q)—quartet, (m)—multiplet, (dd)—doublet of doublets, (dt)—doublet of triplets, (dq)—doublet of quartets, (br s)—broad singlet, (br d)—broad d, (br m)—broad multiplet.

Biological Examples of the Invention

Test A

Seeds of barnyardgrass (*Echinochloa crus-galli*), crabgrass (*Digitaria sanguinalis*), giant foxtail (*Setaria faberi*), morningglory (*Ipomoea* spp.), redroot pigweed (*Amaranthus retroflexus*) and velvetleaf (*Abutilon theophrasti*) were planted into a blend of loam soil and sand and treated preemergence with a directed soil spray using test chemicals formulated in a non-phytotoxic solvent mixture which included a surfactant. At the same time these species were also treated with postemergence applications of test chemicals formulated in the same manner.

Plants ranged in height from 2 to 10 cm and were in the 1- to 2-leaf stage for the postemergence treatment. Treated plants and untreated controls were maintained in a greenhouse for approximately ten days, after which time all treated plants were compared to untreated controls and visually evaluated for injury. Plant response ratings, summarized in Table A, are based on a 0 to 100 scale where 0 is no effect and 100 is complete control. A dash (-) response means no test results.

TABLE A

| 2000 g ai/ha | Compounds | |
|---|---|---|
| | 1 | 57 |
| Postemergence | | |
| Barnyardgrass | 75 | 75 |
| Crabgrass | 80 | 30 |
| Foxtail, Giant | 75 | 80 |
| Morningglory | 100 | 80 |
| Pigweed | 100 | 95 |
| Velvetleaf | 85 | 80 |

| 1000 g ai/ha | Compound 43 |
|---|---|
| Postemergence | |
| Barnyardgrass | 20 |
| Crabgrass | 30 |
| Foxtail, Giant | 10 |
| Morningglory | 45 |
| Pigweed | 85 |
| Velvetleaf | 50 |

| 500 g ai/ha | Compounds | | | | | | | | | | | | | |
|---|---|---|---|---|---|---|---|---|---|---|---|---|---|---|
| | 1 | 20 | 57 | 58 | 59 | 60 | 61 | 62 | 63 | 64 | 65 | 66 | 67 | 68 |
| Postemergence | | | | | | | | | | | | | | |
| Barnyardgrass | 75 | 0 | 25 | 10 | 30 | 0 | 60 | 80 | 0 | 70 | 85 | 0 | 0 | 0 |
| Crabgrass | 65 | 0 | 10 | 10 | 10 | 0 | 5 | 35 | 0 | 70 | 80 | 0 | 5 | 0 |

TABLE A-continued

| | | | | | | | | | | | | | | |
|---|---|---|---|---|---|---|---|---|---|---|---|---|---|---|
| Foxtail, Giant | 70 | 0 | 60 | 50 | 35 | 0 | 25 | 80 | 0 | 80 | 95 | 0 | 0 | 0 |
| Morningglory | 95 | 40 | 70 | 80 | 100 | 20 | 30 | 35 | 25 | 95 | 95 | 30 | 60 | 35 |
| Pigweed | 100 | 60 | 75 | 80 | 80 | 40 | 50 | 60 | 65 | 100 | 100 | 65 | 90 | 55 |
| Velvetleaf | 95 | 55 | 50 | 85 | 85 | 40 | 100 | 95 | 70 | 100 | 100 | 75 | 75 | 60 |

Compounds

| 500 g ai/ha | 69 | 70 | 71 | 72 | 73 | 74 | 75 | 76 | 77 | 78 | 79 | 80 | 81 | 82 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 5 | 0 | 0 | 0 | 5 | 70 | 90 | 90 | 90 | 90 | 90 | 90 | 30 | 50 |
| Crabgrass | 40 | 20 | 5 | 30 | 35 | 60 | 90 | 70 | 90 | 80 | 75 | 70 | 10 | 0 |
| Foxtail, Giant | 55 | 0 | 0 | 0 | 45 | 70 | 90 | 90 | 90 | 80 | 90 | 90 | 30 | 0 |
| Morningglory | 90 | 10 | 0 | 70 | 65 | 30 | 90 | 95 | 100 | 90 | 95 | 95 | 80 | 40 |
| Pigweed | 90 | 20 | 30 | 95 | 80 | 70 | 100 | 95 | 95 | 95 | 100 | 95 | 75 | 75 |
| Velvetleaf | 90 | 60 | 55 | 85 | 75 | 80 | 100 | 100 | 100 | 90 | 95 | 90 | 75 | 90 |

Compounds

| 500 g ai/ha | 83 | 84 | 85 | 86 | 87 | 88 | 89 | 90 | 91 | 92 | 93 | 94 | 95 | 96 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 10 | 80 | 0 | 30 | 90 | 85 | 85 | 10 | 90 | 0 | 0 | 60 | 90 | 25 |
| Crabgrass | 10 | 10 | 0 | 0 | 10 | 85 | 10 | 20 | 15 | 5 | 0 | 50 | 80 | 20 |
| Foxtail, Giant | 10 | 20 | 0 | 0 | 30 | 90 | 45 | 30 | 75 | 0 | 0 | 65 | 85 | 35 |
| Morningglory | 75 | 20 | 75 | 20 | 15 | 85 | 30 | 65 | 30 | 75 | 55 | 75 | 80 | 65 |
| Pigweed | 85 | 65 | 90 | 50 | 90 | 95 | 100 | 90 | 100 | 70 | 70 | 85 | 95 | 85 |
| Velvetleaf | 90 | 90 | 60 | 85 | 95 | 95 | 95 | 85 | 95 | 70 | 80 | 90 | 95 | 85 |

Compounds

| 500 g ai/ha | 97 | 98 | 99 | 100 | 101 | 102 | 103 | 104 | 105 | 106 | 107 | 108 | 109 | 110 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 10 | 20 | 0 | 10 | 0 | 0 | 0 | 10 | 25 | 5 | 0 | 5 | 10 | 10 |
| Crabgrass | 0 | 10 | 0 | 0 | 0 | 10 | 0 | 30 | 45 | 0 | 5 | 0 | 10 | 10 |
| Foxtail, Giant | 0 | 15 | 0 | 0 | 0 | 0 | 0 | 5 | 10 | 0 | 35 | 10 | 10 | 5 |
| Morningglory | 50 | 0 | 0 | 55 | 0 | 15 | 0 | 40 | 70 | 35 | 0 | 90 | 80 | 85 |
| Pigweed | 30 | 15 | 10 | 25 | 5 | 65 | 20 | 45 | 90 | 70 | 10 | 85 | 85 | 85 |
| Velvetleaf | 70 | 45 | 35 | 70 | 15 | 70 | 70 | 80 | 95 | 55 | 65 | 65 | 80 | 65 |

Compounds

| 500 g ai/ha | 111 | 112 | 113 | 114 | 115 | 116 | 117 | 118 | 119 | 120 | 121 | 122 | 123 | 127 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 10 | 0 | 90 | 0 | 0 | 0 | 90 | 0 | 5 | 40 | 5 | 0 | 10 | 0 |
| Crabgrass | 30 | 0 | 55 | 0 | 0 | 0 | 90 | 20 | 0 | 5 | 0 | 0 | 0 | 0 |
| Foxtail, Giant | 0 | 0 | 85 | 0 | 0 | 0 | 90 | 15 | 0 | 0 | 0 | 0 | 10 | 0 |
| Morningglory | 50 | 50 | 90 | 55 | 60 | 60 | 90 | 70 | 35 | 55 | 10 | 0 | 20 | 0 |
| Pigweed | 85 | 40 | 90 | 55 | 45 | 35 | 100 | 75 | 45 | 35 | 0 | 0 | 0 | 10 |
| Velvetleaf | 85 | 35 | 95 | 5 | 40 | 40 | 100 | 95 | 10 | 65 | 0 | 0 | 0 | 80 |

Compounds

| 500 g ai/ha | 128 | 129 | 130 | 131 | 132 | 133 | 134 | 135 | 136 | 137 | 138 | 139 | 140 | 141 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 0 | 0 | 0 | 20 | 10 | 40 | 0 | 90 | 80 | 0 | 0 | 90 | 90 | 90 |
| Crabgrass | 0 | 0 | 0 | 30 | 10 | 55 | 0 | 65 | 70 | 0 | 0 | 70 | 80 | 80 |
| Foxtail, Giant | 0 | 0 | 0 | 30 | 5 | 60 | 0 | 80 | 80 | 0 | 0 | 80 | 90 | 85 |
| Morningglory | 80 | 70 | 0 | 20 | 50 | 85 | 0 | 100 | 90 | 30 | 20 | 90 | 90 | 90 |
| Pigweed | 75 | 85 | 15 | 70 | 65 | 90 | 30 | 95 | 100 | 45 | 35 | 100 | 100 | 100 |
| Velvetleaf | 80 | 90 | 30 | 60 | 60 | 85 | 55 | 100 | 95 | 60 | 70 | 90 | 90 | 100 |

Compounds

| 500 g ai/ha | 142 | 143 | 144 | 145 | 146 | 147 | 148 | 149 | 150 |
|---|---|---|---|---|---|---|---|---|---|

Postemergence

| | | | | | | | | | |
|---|---|---|---|---|---|---|---|---|---|
| Barnyardgrass | 75 | 75 | 90 | 60 | 90 | 90 | 90 | 90 | 95 |
| Crabgrass | 25 | 60 | 80 | 30 | 80 | 75 | 85 | 75 | 80 |
| Foxtail, Giant | 45 | 80 | 80 | 70 | 85 | 90 | 80 | 80 | 85 |
| Morningglory | 90 | 90 | 95 | 95 | 100 | 100 | 100 | 95 | 100 |

TABLE A-continued

|  |  |  |  |  |  |  |  |  |  |  |  |  |  |
|---|---|---|---|---|---|---|---|---|---|---|---|---|---|
| Pigweed | 90 | 90 | 100 | 90 | 95 | 95 | 95 | 90 | 90 |
| Velvetleaf | 90 | 95 | 100 | 95 | 100 | 100 | 95 | 100 | 100 |

| 250 g ai/ha | Compound 43 |
|---|---|

Postemergence

|  |  |
|---|---|
| Barnyardgrass | 10 |
| Crabgrass | 10 |
| Foxtail, Giant | 10 |
| Morningglory | 20 |
| Pigweed | 60 |
| Velvetleaf | 50 |

Compounds

| 125 g ai/ha | 20 | 58 | 59 | 60 | 61 | 62 | 63 | 64 | 65 | 66 | 67 | 68 | 69 | 70 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 0 | 5 | 0 | 0 | 35 | 15 | 0 | 25 | 85 | 0 | 0 | 0 | 0 | 0 |
| Crabgrass | 0 | 5 | 0 | 0 | 0 | 0 | 0 | 50 | 55 | 0 | 5 | 0 | 20 | 0 |
| Foxtail, Giant | 0 | 0 | 0 | 0 | 0 | 0 | 0 | 70 | 85 | 0 | 0 | 0 | 0 | 0 |
| Morningglory | 20 | 55 | 90 | 0 | 10 | 10 | 20 | 80 | 75 | 20 | 50 | 15 | 75 | 0 |
| Pigweed | 40 | 70 | 60 | 10 | 25 | 30 | 40 | 90 | 100 | 50 | 90 | 50 | 90 | 15 |
| Velvetleaf | 10 | 70 | 60 | 30 | 70 | 90 | 55 | 95 | 95 | 50 | 65 | 60 | 85 | 35 |

Compounds

| 125 g ai/ha | 71 | 72 | 73 | 74 | 75 | 76 | 77 | 78 | 79 | 80 | 81 | 82 | 83 | 84 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 0 | 0 | 0 | 30 | 85 | 90 | 90 | 80 | 85 | 55 | 0 | 40 | 0 | 55 |
| Crabgrass | 0 | 10 | 15 | 30 | 80 | 45 | 70 | 70 | 40 | 30 | 0 | 0 | 0 | 0 |
| Foxtail, Giant | 0 | 0 | 15 | 60 | 90 | 90 | 85 | 70 | 80 | 70 | 0 | 0 | 0 | 0 |
| Morningglory | 0 | 55 | 50 | 40 | 90 | 90 | 95 | 80 | 90 | 90 | 50 | 20 | 55 | 5 |
| Pigweed | 5 | 95 | 75 | 60 | 90 | 85 | 95 | 85 | 90 | 65 | 55 | 45 | 70 | 60 |
| Velvetleaf | 40 | 85 | 70 | 70 | 85 | 80 | 95 | 75 | 90 | 65 | 50 | 90 | 90 | 75 |

Compounds

| 125 g ai/ha | 85 | 86 | 87 | 88 | 89 | 90 | 91 | 92 | 93 | 94 | 95 | 96 | 97 | 98 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 0 | 10 | 50 | 50 | 60 | 0 | 75 | 0 | 0 | 30 | 75 | 20 | 30 | 0 |
| Crabgrass | 0 | 0 | 0 | 60 | 0 | 0 | 5 | 0 | 0 | 35 | 70 | 5 | 0 | 0 |
| Foxtail, Giant | 0 | 0 | 0 | 80 | 10 | 0 | 5 | 0 | 0 | 45 | 85 | 25 | 0 | 0 |
| Morningglory | 20 | 0 | 0 | 60 | 0 | 20 | 5 | 45 | 40 | 70 | 75 | 60 | 45 | 0 |
| Pigweed | 75 | 20 | 55 | 90 | 50 | 35 | 55 | 35 | 45 | 80 | 85 | 70 | 10 | 5 |
| Velvetleaf | 25 | 70 | 90 | 90 | 70 | 65 | 75 | 45 | 65 | 90 | 90 | 80 | 60 | 35 |

Compounds

| 125 g ai/ha | 99 | 100 | 101 | 102 | 103 | 104 | 105 | 106 | 107 | 108 | 109 | 110 | 111 | 112 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 0 | 0 | 0 | 0 | 0 | 0 | 10 | 0 | 0 | 0 | 0 | 0 | 0 | 0 |
| Crabgrass | 0 | 0 | 0 | 10 | 0 | 15 | 20 | 0 | 0 | 0 | 0 | 0 | 5 | 0 |
| Foxtail, Giant | 0 | 0 | 0 | 0 | 0 | 0 | 10 | 0 | 0 | 0 | 0 | 0 | 0 | 0 |
| Morningglory | 0 | 40 | 0 | 0 | 0 | 25 | 50 | 20 | 0 | 70 | 70 | 70 | 20 | 55 |
| Pigweed | 5 | 10 | 0 | 50 | 0 | 30 | 65 | 15 | 10 | 50 | 60 | 55 | 55 | 20 |
| Velvetleaf | 0 | 50 | 0 | 45 | 45 | 70 | 85 | 25 | 35 | 35 | 25 | 40 | 75 | 20 |

Compounds

| 125 g ai/ha | 113 | 114 | 115 | 116 | 117 | 118 | 119 | 120 | 121 | 122 | 123 | 127 | 128 | 129 |
|---|---|---|---|---|---|---|---|---|---|---|---|---|---|---|

Postemergence

| | | | | | | | | | | | | | | |
|---|---|---|---|---|---|---|---|---|---|---|---|---|---|---|
| Barnyardgrass | 55 | 0 | 0 | 0 | 85 | 0 | 0 | 10 | 0 | 0 | 0 | 0 | 0 | 0 |
| Crabgrass | 25 | 0 | 0 | 0 | 75 | 10 | 0 | 0 | 0 | 0 | 0 | 0 | 0 | 0 |
| Foxtail, Giant | 65 | 0 | 0 | 0 | 80 | 0 | 0 | 0 | 0 | 0 | 0 | 0 | 0 | 0 |
| Morningglory | 90 | 40 | 35 | 40 | 90 | 65 | 40 | 25 | 0 | 0 | 0 | 0 | 55 | 60 |

TABLE A-continued

| | | | | | | | | | | | | | | |
|---|---|---|---|---|---|---|---|---|---|---|---|---|---|---|
| Pigweed | 80 | 45 | 10 | 20 | 100 | 60 | 25 | 20 | 0 | 0 | 0 | 0 | 55 | 80 |
| Velvetleaf | 80 | 0 | 30 | 15 | 100 | 90 | 0 | 50 | 0 | 0 | 0 | 60 | 65 | 80 |

| | Compounds | | | | | | | | | | | | | |
|---|---|---|---|---|---|---|---|---|---|---|---|---|---|---|
| 125 g ai/ha | 130 | 131 | 132 | 133 | 134 | 135 | 136 | 137 | 138 | 139 | 140 | 141 | 142 | 143 |

| | Postemergence | | | | | | | | | | | | | |
|---|---|---|---|---|---|---|---|---|---|---|---|---|---|---|
| Barnyardgrass | 0 | 10 | 0 | 10 | 0 | 75 | 50 | 0 | 0 | 80 | 70 | 80 | 45 | 55 |
| Crabgrass | 0 | 10 | 5 | 30 | 0 | 65 | 35 | 0 | 0 | 60 | 65 | 25 | 15 | 5 |
| Foxtail, Giant | 0 | 15 | 0 | 15 | 0 | 75 | 75 | 0 | 0 | 80 | 85 | 40 | 30 | 25 |
| Morningglory | 0 | 0 | 45 | 70 | 0 | 90 | 70 | 5 | 0 | 80 | 85 | 90 | 90 | 90 |
| Pigweed | 0 | 50 | 50 | 80 | 15 | 90 | 85 | 25 | 20 | 90 | 90 | 90 | 85 | 70 |
| Velvetleaf | 0 | 35 | 50 | 80 | 50 | 85 | 85 | 45 | 60 | 85 | 90 | 85 | 80 | 75 |

| | Compounds | | | | | | |
|---|---|---|---|---|---|---|---|
| 125 g ai/ha | 144 | 145 | 146 | 147 | 148 | 149 | 150 |

| | Postemergence | | | | | | |
|---|---|---|---|---|---|---|---|
| Barnyardgrass | 60 | 30 | 70 | 80 | 68 | 65 | 80 |
| Crabgrass | 40 | 5 | 20 | 25 | 10 | 25 | 65 |
| Foxtail, Giant | 70 | 20 | 80 | 60 | 45 | 60 | 80 |
| Morningglory | 85 | 80 | 85 | 85 | 90 | 80 | 80 |
| Pigweed | 85 | 80 | 90 | 85 | 75 | 75 | 90 |
| Velvetleaf | 95 | 75 | 85 | 80 | 75 | 85 | 90 |

| | Compounds | |
|---|---|---|
| 2000 g ai/ha | 1 | 57 |

| | Preemergence | |
|---|---|---|
| Barnyardgrass | 80 | 80 |
| Crabgrass | 75 | 70 |
| Foxtail, Giant | 85 | 70 |
| Morningglory | 100 | 100 |
| Pigweed | 100 | 100 |
| Velvetleaf | 80 | 95 |

| | Compound |
|---|---|
| 1000 g ai/ha | 43 |

| | Preemergence |
|---|---|
| Barnyardgrass | 10 |
| Crabgrass | 10 |
| Foxtail, Giant | 10 |
| Morningglory | 45 |
| Pigweed | 75 |
| Velvetleaf | 20 |

| | Compounds | | | | | | | | | | | | | |
|---|---|---|---|---|---|---|---|---|---|---|---|---|---|---|
| 500 g ai/ha | 1 | 20 | 57 | 58 | 59 | 60 | 61 | 62 | 63 | 64 | 65 | 66 | 67 | 68 |

| | Preemergence | | | | | | | | | | | | | |
|---|---|---|---|---|---|---|---|---|---|---|---|---|---|---|
| Barnyardgrass | 60 | 0 | 25 | 0 | 15 | 0 | 10 | 45 | 40 | 60 | 90 | 0 | 0 | 0 |
| Crabgrass | 25 | 0 | 10 | 0 | 0 | 0 | 30 | 60 | 75 | 90 | 90 | 15 | 30 | 0 |
| Foxtail, Giant | 40 | 0 | 10 | 10 | 0 | 0 | 10 | 0 | 35 | 70 | 80 | 0 | 30 | 0 |
| Morningglory | 85 | 60 | 100 | 25 | 100 | 0 | 15 | 35 | 0 | 70 | 90 | 0 | 0 | 0 |
| Pigweed | 85 | 70 | 90 | 60 | 70 | 0 | 30 | 75 | 80 | 100 | 100 | 10 | 75 | 15 |
| Velvetleaf | 60 | 70 | 80 | 40 | 45 | 0 | 50 | 75 | 15 | 95 | 95 | 35 | 40 | 10 |

| | Compounds | | | | | | | | | | | | | |
|---|---|---|---|---|---|---|---|---|---|---|---|---|---|---|
| 500 g ai/ha | 69 | 70 | 71 | 72 | 73 | 74 | 75 | 76 | 77 | 78 | 79 | 80 | 81 | 82 |

| | Preemergence | | | | | | | | | | | | | |
|---|---|---|---|---|---|---|---|---|---|---|---|---|---|---|
| Barnyardgrass | 15 | 0 | 0 | 0 | 30 | 50 | 95 | 90 | 100 | 75 | 80 | 80 | 20 | 15 |
| Crabgrass | 75 | 20 | 0 | 0 | 35 | 50 | 90 | 75 | 80 | 70 | 80 | 85 | 10 | 0 |
| Foxtail, Giant | 50 | 5 | 0 | 0 | 15 | 40 | 90 | 85 | 95 | 65 | 95 | 70 | 10 | 0 |
| Morningglory | 0 | 0 | 0 | 0 | 0 | 30 | 100 | 100 | 100 | 100 | 100 | 100 | 50 | 0 |

TABLE A-continued

| | | | | | | | | | | | | | | |
|---|---|---|---|---|---|---|---|---|---|---|---|---|---|---|
| Pigweed | 85 | 10 | 15 | 100 | 60 | 40 | 95 | 90 | 95 | 90 | 100 | 90 | 70 | 70 |
| Velvetleaf | 65 | 35 | 50 | 55 | 40 | 50 | 95 | 100 | 100 | 85 | 90 | 90 | 40 | 35 |

| | Compounds | | | | | | | | | | | | | |
|---|---|---|---|---|---|---|---|---|---|---|---|---|---|---|
| 500 g ai/ha | 83 | 84 | 85 | 86 | 87 | 88 | 89 | 90 | 91 | 92 | 93 | 94 | 95 | 96 |

| Preemergence | | | | | | | | | | | | | | |
|---|---|---|---|---|---|---|---|---|---|---|---|---|---|---|
| Barnyardgrass | 5 | 25 | 0 | 0 | 20 | 55 | 50 | 35 | 80 | 0 | 30 | 40 | 80 | 10 |
| Crabgrass | 5 | 15 | 5 | 0 | 75 | 85 | 60 | 50 | 75 | 0 | 45 | 55 | 85 | 65 |
| Foxtail, Giant | 0 | 20 | 0 | 0 | 0 | 50 | 10 | 15 | 25 | 0 | 35 | 40 | 90 | 10 |
| Morningglory | 10 | 0 | 20 | 0 | 20 | 90 | 0 | 25 | 50 | 0 | 5 | 35 | 85 | 80 |
| Pigweed | 50 | 80 | 60 | 5 | 100 | 100 | 100 | 80 | 100 | 45 | 90 | 95 | 100 | 80 |
| Velvetleaf | 30 | 70 | 10 | 10 | 95 | 70 | 75 | 45 | 100 | 45 | 85 | 90 | 95 | 80 |

| | Compounds | | | | | | | | | | | | | |
|---|---|---|---|---|---|---|---|---|---|---|---|---|---|---|
| 500 g ai/ha | 97 | 98 | 99 | 100 | 101 | 102 | 103 | 104 | 105 | 106 | 107 | 108 | 109 | 110 |

| Preemergence | | | | | | | | | | | | | | |
|---|---|---|---|---|---|---|---|---|---|---|---|---|---|---|
| Barnyardgrass | 0 | 0 | 0 | 0 | 0 | 0 | 0 | 5 | 0 | 5 | 0 | 15 | 25 | 15 |
| Crabgrass | 25 | 15 | 0 | 0 | 0 | 0 | 0 | 10 | 0 | 0 | 5 | 20 | 25 | 15 |
| Foxtail, Giant | 5 | 0 | 0 | 0 | 0 | 0 | 0 | 5 | 0 | 0 | 0 | 0 | 5 | 0 |
| Morningglory | 0 | 0 | 0 | 0 | 0 | 0 | 0 | 0 | 0 | 0 | 0 | 90 | 95 | 90 |
| Pigweed | 70 | 0 | 0 | 0 | 0 | 15 | 10 | 10 | 0 | 30 | 0 | 75 | 80 | 65 |
| Velvetleaf | 50 | 5 | 0 | 0 | 0 | 20 | 10 | 10 | 0 | 30 | 10 | 50 | 50 | 35 |

| | Compounds | | | | | | | | | | | | | |
|---|---|---|---|---|---|---|---|---|---|---|---|---|---|---|
| 500 g ai/ha | 111 | 112 | 113 | 114 | 115 | 116 | 117 | 118 | 119 | 120 | 121 | 122 | 123 | 127 |

| Preemergence | | | | | | | | | | | | | | |
|---|---|---|---|---|---|---|---|---|---|---|---|---|---|---|
| Barnyardgrass | 0 | 10 | 80 | 0 | 20 | 20 | 85 | 10 | 10 | 15 | 0 | 0 | 0 | 0 |
| Crabgrass | 0 | 10 | 70 | 0 | 10 | 10 | 75 | 25 | 0 | 0 | 0 | 0 | 0 | 0 |
| Foxtail, Giant | 0 | 0 | 80 | 0 | 0 | 0 | 85 | 15 | 0 | 0 | 0 | 0 | 0 | 0 |
| Morningglory | 0 | 10 | 100 | 0 | 35 | 50 | 85 | 0 | 0 | 0 | 0 | 0 | 0 | 0 |
| Pigweed | 0 | 30 | 90 | 0 | 40 | 50 | 100 | 55 | 0 | 0 | 0 | 0 | 0 | 0 |
| Velvetleaf | 0 | 10 | 95 | 0 | 10 | 15 | 100 | 15 | 0 | 0 | 0 | 0 | 0 | 0 |

| | Compounds | | | | | | | | | | | | | |
|---|---|---|---|---|---|---|---|---|---|---|---|---|---|---|
| 500 g ai/ha | 128 | 129 | 130 | 131 | 132 | 133 | 134 | 135 | 136 | 137 | 138 | 139 | 140 | 141 |

| Preemergence | | | | | | | | | | | | | | |
|---|---|---|---|---|---|---|---|---|---|---|---|---|---|---|
| Barnyardgrass | 0 | 0 | 0 | 0 | 0 | 15 | 0 | 90 | 40 | 0 | 0 | 90 | 90 | 75 |
| Crabgrass | 0 | 0 | 0 | 0 | 0 | 45 | 0 | 95 | 60 | 0 | 0 | 90 | 90 | 85 |
| Foxtail, Giant | 0 | 0 | 0 | 0 | 0 | 30 | 0 | 85 | 60 | 0 | 0 | 90 | 85 | 85 |
| Morningglory | 0 | 0 | 0 | 0 | 0 | 35 | 0 | 100 | 20 | 0 | 0 | 100 | 95 | 95 |
| Pigweed | 0 | 15 | 0 | 0 | 65 | 65 | 0 | 100 | 100 | 0 | 0 | 100 | 95 | 85 |
| Velvetleaf | 0 | 5 | 0 | 0 | 5 | 30 | 0 | 100 | 75 | 0 | 0 | 90 | 95 | 85 |

| | Compounds | | | | | | | | |
|---|---|---|---|---|---|---|---|---|---|
| 500 g ai/ha | 142 | 143 | 144 | 145 | 146 | 147 | 148 | 149 | 150 |

| Preemergence | | | | | | | | | |
|---|---|---|---|---|---|---|---|---|---|
| Barnyardgrass | 75 | 85 | 80 | 75 | 90 | 85 | 85 | 85 | 80 |
| Crabgrass | 85 | 95 | 95 | 80 | 75 | 80 | 90 | 75 | 80 |
| Foxtail, Giant | 65 | 75 | 80 | 60 | 90 | 85 | 80 | 90 | 80 |
| Morningglory | 95 | 100 | 95 | 100 | 100 | 100 | 100 | 100 | 100 |

TABLE A-continued

| | | | | | | | | | | |
|---|---|---|---|---|---|---|---|---|---|---|
| Pigweed | 90 | 95 | 85 | 85 | 95 | 90 | 90 | 90 | 95 | |
| Velvetleaf | 85 | 95 | 85 | 85 | 100 | 95 | 100 | 85 | 95 | |

| | Compound 43 |
|---|---|
| 250 g ai/ha | |

Preemergence

| | |
|---|---|
| Barnyardgrass | 0 |
| Crabgrass | 0 |
| Foxtail, Giant | 0 |
| Morningglory | 0 |
| Pigweed | 0 |
| Velvetleaf | 0 |

Compounds

| 125 g ai/ha | 20 | 58 | 59 | 60 | 61 | 62 | 63 | 64 | 65 | 66 | 67 | 68 | 69 | 70 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 50 | 0 | 0 | 0 | 0 | 0 |
| Crabgrass | 0 | 0 | 0 | 0 | 0 | 0 | 0 | 25 | 60 | 0 | 0 | 0 | 50 | 5 |
| Foxtail, Giant | 0 | 0 | 0 | 0 | 0 | 0 | 0 | 15 | 40 | 0 | 0 | 0 | 10 | 5 |
| Morningglory | 10 | 10 | 80 | 0 | 0 | 0 | 0 | 40 | 25 | 0 | 0 | 0 | 0 | 0 |
| Pigweed | 40 | 0 | 20 | 0 | 0 | 0 | 0 | 20 | 100 | 0 | 10 | 0 | 65 | 0 |
| Velvetleaf | 0 | 0 | 10 | 0 | 0 | 0 | 0 | 25 | 55 | 0 | 10 | 5 | 35 | 20 |

Compounds

| 125 g ai/ha | 71 | 72 | 73 | 74 | 75 | 76 | 77 | 78 | 79 | 80 | 81 | 82 | 83 | 84 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 0 | 0 | 5 | 0 | 70 | 75 | 90 | 45 | 30 | 10 | 10 | 0 | 0 | 0 |
| Crabgrass | 0 | 0 | 5 | 20 | 85 | 30 | 70 | 55 | 30 | 45 | 0 | 0 | 0 | 0 |
| Foxtail, Giant | 0 | 0 | 0 | 0 | 75 | 70 | 75 | 10 | 40 | 15 | 0 | 0 | 0 | 0 |
| Morningglory | 0 | 0 | 0 | 0 | 95 | 100 | 100 | 90 | 55 | 90 | 0 | 0 | 0 | 0 |
| Pigweed | 0 | 75 | 15 | 0 | 90 | 80 | 85 | 75 | 90 | 80 | 60 | 0 | 20 | 0 |
| Velvetleaf | 30 | 40 | 35 | 30 | 80 | 90 | 100 | 80 | 60 | 75 | 20 | 5 | 15 | 15 |

Compounds

| 125 g ai/ha | 85 | 86 | 87 | 88 | 89 | 90 | 91 | 92 | 93 | 94 | 95 | 96 | 97 | 98 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 0 | 0 | 0 | 10 | 0 | 0 | 5 | 0 | 5 | 5 | 20 | 5 | 0 | 0 |
| Crabgrass | 0 | 0 | 10 | 35 | 0 | 10 | 25 | 0 | 25 | 45 | 65 | 50 | 15 | 0 |
| Foxtail, Giant | 0 | 0 | 0 | 10 | 0 | 0 | 0 | 0 | 5 | 20 | 65 | 5 | 5 | 0 |
| Morningglory | 0 | 0 | 0 | 10 | 0 | 0 | 5 | 0 | 0 | 30 | 80 | 15 | 0 | 0 |
| Pigweed | 50 | 0 | 85 | 80 | 80 | 70 | 100 | 15 | 80 | 90 | 95 | 80 | 25 | 0 |
| Velvetleaf | 0 | 0 | 25 | 10 | 20 | 10 | 80 | 10 | 55 | 75 | 55 | 65 | 45 | 0 |

Compounds

| 125 g ai/ha | 99 | 100 | 101 | 102 | 103 | 104 | 105 | 106 | 107 | 108 | 109 | 110 | 111 | 112 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 0 | 5 | 0 | 0 | 0 | 0 | 0 | 0 | 0 | 10 | 0 | 0 | 0 | 0 |
| Crabgrass | 0 | 10 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 30 | 0 | 0 | 0 |
| Pigweed | 0 | 20 | 0 | 10 | 0 | 0 | 0 | 0 | 0 | 55 | 50 | 40 | 0 | 10 |
| Velvetleaf | 0 | 0 | 0 | 10 | 0 | 0 | 0 | 5 | 0 | 10 | 15 | 25 | 0 | 0 |

Compounds

| 125 g ai/ha | 113 | 114 | 115 | 116 | 117 | 118 | 119 | 120 | 121 | 122 | 123 | 127 | 128 | 129 |
|---|---|---|---|---|---|---|---|---|---|---|---|---|---|---|

Preemergence

| | | | | | | | | | | | | | | |
|---|---|---|---|---|---|---|---|---|---|---|---|---|---|---|
| Barnyardgrass | 25 | 0 | 0 | 10 | 25 | 0 | 0 | 5 | 0 | 0 | 0 | 0 | 0 | 0 |
| Crabgrass | 15 | 0 | 0 | 0 | 45 | 10 | 0 | 0 | 0 | 0 | 0 | 0 | 0 | 0 |
| Foxtail, Giant | 15 | 0 | 0 | 0 | 50 | 0 | 0 | 0 | 0 | 0 | 0 | 0 | 0 | 0 |
| Morningglory | 90 | 0 | 25 | 30 | 10 | 0 | 0 | 0 | 0 | 0 | 0 | 0 | 0 | 0 |

TABLE A-continued

| | | | | | | | | | | | | | | |
|---|---|---|---|---|---|---|---|---|---|---|---|---|---|---|
| Pigweed | 80 | 0 | 30 | 30 | 65 | 10 | 0 | 0 | 0 | 0 | 0 | 0 | 0 | 0 |
| Velvetleaf | 65 | 0 | 5 | 0 | 55 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 130 | 131 | 132 | 133 | 134 | 135 | 136 | 137 | 138 | 139 | 140 | 141 | 142 | 143 |
| | Preemergence | | | | | | | | | | | | | |
| Barnyardgrass | 0 | 0 | 0 | 0 | 0 | 65 | 5 | 0 | 0 | 75 | 70 | 35 | 50 | 65 |
| Crabgrass | 0 | 0 | 0 | 0 | 0 | 75 | 20 | 0 | 0 | 75 | 70 | 60 | 45 | 70 |
| Foxtail, Giant | 0 | 0 | 0 | 0 | 0 | 30 | 10 | 0 | 0 | 80 | 40 | 5 | 25 | 35 |
| Morningglory | 0 | 0 | 0 | 0 | 0 | 95 | 10 | 0 | 0 | 90 | 90 | 85 | 85 | 90 |
| Pigweed | 0 | 0 | 15 | 10 | 0 | 85 | 45 | 0 | 0 | 90 | 90 | 80 | 70 | 65 |
| Velvetleaf | 0 | 0 | 0 | 10 | 0 | 80 | 30 | 0 | 0 | 90 | 90 | 80 | 85 | 90 |

| | Compounds | | | | | | |
|---|---|---|---|---|---|---|---|
| 125 g ai/ha | 144 | 145 | 146 | 147 | 148 | 149 | 150 |
| | Preemergence | | | | | | |
| Barnyardgrass | 65 | 30 | 65 | 70 | 65 | 70 | 65 |
| Crabgrass | 75 | 65 | 35 | 70 | 45 | 20 | 50 |
| Foxtail, Giant | 35 | 0 | 60 | 40 | 40 | 35 | 50 |
| Morningglory | 85 | 75 | 95 | 95 | 90 | 85 | 90 |
| Pigweed | 75 | 65 | 75 | 80 | 80 | 70 | 70 |
| Velvetleaf | 75 | 70 | 85 | 75 | 80 | 70 | 75 |

Test B

Seeds selected from barnyardgrass (*Echinochloa crus-galli*), Surinam grass (*Brachiaria decumbens*), cocklebur (*Xanthium strumarium*), corn (*Zea mays*), crabgrass (*Digitaria sanguinalis*), giant foxtail (*Setaria faberii*), lambsquarters (*Chenopodium album*), morningglory (*Ipomoea coccinea*), pigweed (*Amaranthus retroflexus*), velvetleaf (*Abutilon theophrasti*), and wheat (*Triticum aestivum*) were planted and treated preemergence with test chemicals formulated in a non-phytotoxic solvent mixture which included a surfactant.

At the same time, plants selected from these crop and weed species and also blackgrass (*Alopecurus myosuroides*) and wild oat (*Avena fatua*) were treated with postemergence applications of test chemicals formulated in the same manner. Plants ranged in height from 2 to 18 cm (1- to 4-leaf stage) for postemergence treatments. Plant species in the flooded paddy test consisted of rice (*Oryza sativa*), umbrella sedge (*Cyperus difformis*), duck salad (*Heteranthera limosa*) and barnyardgrass (*Echinochloa crus-galli*) grown to the 2-leaf stage for testing. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| | Compounds | | | | | | | | | | | | | |
|---|---|---|---|---|---|---|---|---|---|---|---|---|---|---|
| 1000 g ai/ha | 1 | 2 | 3 | 4 | 5 | 7 | 8 | 9 | 10 | 11 | 12 | 13 | 14 | 15 |
| | Flood | | | | | | | | | | | | | |
| Barnyardgrass | 80 | 90 | 0 | 90 | 50 | 20 | 70 | 90 | 0 | 0 | 0 | 0 | 80 | 90 |
| Ducksalad | 80 | 90 | 0 | 100 | 90 | 0 | 90 | 100 | 0 | 70 | 20 | 0 | 80 | 80 |
| Rice | 70 | 60 | 0 | 80 | 0 | 0 | 60 | 80 | 0 | 0 | 20 | 0 | 20 | 70 |
| Sedge, Umbrella | 20 | 90 | 0 | 80 | 90 | 0 | 40 | 90 | 0 | 20 | 0 | 0 | 50 | 70 |

| | Compounds | | | | | | | | | | | | | |
|---|---|---|---|---|---|---|---|---|---|---|---|---|---|---|
| 1000 g ai/ha | 16 | 17 | 18 | 19 | 21 | 22 | 23 | 24 | 25 | 26 | 27 | 28 | 30 | 31 |
| | Flood | | | | | | | | | | | | | |
| Barnyardgrass | 90 | 80 | 0 | 80 | 60 | 80 | 0 | 0 | 30 | 60 | 0 | 0 | 0 | 30 |
| Ducksalad | 90 | 90 | 80 | 80 | 80 | 90 | 30 | 0 | 40 | 90 | 60 | 30 | 0 | 60 |
| Rice | 70 | 50 | 0 | 60 | 40 | 60 | 0 | 10 | 30 | 70 | 20 | 0 | 0 | 20 |
| Sedge, Umbrella | 60 | 50 | 0 | 70 | 0 | 50 | 0 | 20 | 40 | 80 | 60 | 0 | 0 | 0 |

| | Compounds | | | | | | | | | | | | | |
|---|---|---|---|---|---|---|---|---|---|---|---|---|---|---|
| 1000 g ai/ha | 32 | 33 | 34 | 35 | 36 | 37 | 38 | 39 | 40 | 41 | 42 | 44 | 45 | 46 |
| | Flood | | | | | | | | | | | | | |
| Barnyardgrass | 0 | 0 | 0 | 0 | 0 | 20 | 0 | 0 | 70 | 0 | 0 | 0 | 0 | 0 |
| Ducksalad | 0 | 0 | 0 | 0 | 0 | 100 | 0 | 0 | 80 | 90 | 0 | 90 | 0 | 60 |

TABLE B-continued

| | | | | | | | | | | | | | | |
|---|---|---|---|---|---|---|---|---|---|---|---|---|---|---|
| Rice | 0 | 0 | 0 | 0 | 0 | 0 | 0 | 0 | 60 | 0 | 0 | 0 | 0 | 0 |
| Sedge, Umbrella | 0 | 0 | 0 | 0 | 0 | 90 | 0 | 0 | 70 | 80 | 0 | 80 | 0 | 30 |

| | Compounds | | | | | |
|---|---|---|---|---|---|---|
| 1000 g ai/ha | 47 | 48 | 49 | 50 | 51 | 124 |

Flood

| | | | | | | |
|---|---|---|---|---|---|---|
| Barnyardgrass | 0 | 20 | 50 | 30 | 0 | 0 |
| Ducksalad | 80 | 20 | 60 | 40 | 0 | 0 |
| Rice | 0 | 0 | 30 | 30 | 0 | 0 |
| Sedge, Umbrella | 70 | 0 | 70 | 0 | 0 | 0 |

| | Compounds | | | | | | | | | | | | |
|---|---|---|---|---|---|---|---|---|---|---|---|---|---|
| 500 g ai/ha | 58 | 59 | 60 | 64 | 75 | 76 | 77 | 78 | 79 | 80 | 83 | 88 | 91 | 92 |

Flood

| | | | | | | | | | | | | | | |
|---|---|---|---|---|---|---|---|---|---|---|---|---|---|---|
| Barnyardgrass | 0 | 0 | 20 | 0 | 70 | 70 | 60 | 40 | 0 | 50 | 0 | 0 | 20 | 0 |
| Ducksalad | 100 | 0 | 90 | 100 | 70 | 70 | 80 | 70 | 70 | 70 | 100 | 90 | 100 | 90 |
| Rice | 0 | 0 | 0 | 0 | 70 | 50 | 50 | 40 | 20 | 50 | 0 | 0 | 0 | 0 |
| Sedge, Umbrella | 100 | 0 | 30 | 90 | 10 | 70 | 40 | 50 | 0 | 70 | 100 | 90 | 90 | 90 |

| | Compounds | | | | | | | | |
|---|---|---|---|---|---|---|---|---|---|
| 500 g ai/ha | 94 | 95 | 96 | 113 | 117 | 128 | 129 | 133 | 135 | 136 |

Flood

| | | | | | | | | | | |
|---|---|---|---|---|---|---|---|---|---|---|
| Barnyardgrass | 0 | 30 | 10 | 0 | 70 | 30 | 20 | 0 | 80 | 20 |
| Ducksalad | 100 | 100 | 100 | 0 | 100 | 100 | 100 | 90 | 90 | 90 |
| Rice | 0 | 40 | 0 | 0 | 50 | 0 | 0 | 0 | 60 | 40 |
| Sedge, Umbrella | 90 | 90 | 90 | 0 | 90 | 100 | 100 | 90 | 80 | 90 |

| | Compound |
|---|---|
| 250 g ai/ha | 64 |

Flood

| | |
|---|---|
| Barnyardgrass | 0 |
| Ducksalad | 100 |
| Rice | 0 |
| Sedge, Umbrella | 70 |

| | Compounds | | | | | | | | | | | | |
|---|---|---|---|---|---|---|---|---|---|---|---|---|---|
| 125 g ai/ha | 58 | 59 | 60 | 64 | 75 | 76 | 77 | 78 | 79 | 80 | 83 | 88 | 91 | 92 |

Flood

| | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 | 0 |
| Ducksalad | 100 | 0 | 80 | 90 | 0 | 0 | 40 | 20 | 10 | 50 | 100 | 90 | 100 | 80 |
| Rice | 0 | 0 | 0 | 0 | 0 | 0 | 0 | 20 | 0 | 0 | 0 | 0 | 0 | 0 |
| Sedge, Umbrella | 90 | 0 | 0 | 0 | 0 | 30 | 0 | 10 | 0 | 20 | 90 | 60 | 80 | 80 |

| | Compounds | | | | | | | | |
|---|---|---|---|---|---|---|---|---|---|
| 125 g ai/ha | 94 | 95 | 96 | 113 | 117 | 128 | 129 | 133 | 135 | 136 |

Flood

| | | | | | | | | | | |
|---|---|---|---|---|---|---|---|---|---|---|
| Barnyardgrass | 0 | 0 | 0 | 0 | 20 | 0 | 0 | 0 | 30 | 0 |
| Ducksalad | 100 | 90 | 100 | 0 | 100 | 90 | 100 | 90 | 60 | 90 |

TABLE B-continued

| | | | | | | | | | | | |
|---|---|---|---|---|---|---|---|---|---|---|---|
| Rice | 0 | 0 | 0 | 0 | 20 | 0 | 0 | 0 | 20 | 0 | |
| Sedge, Umbrella | 90 | 90 | 90 | 0 | 80 | 90 | 90 | 90 | 70 | 90 | |

| 62 g ai/ha | Compound 64 |
|---|---|

| Flood | |
|---|---|
| Barnyardgrass | 0 |
| Ducksalad | 80 |
| Rice | 0 |
| Sedge, Umbrella | 0 |

Compounds

| 500 g ai/ha | 2 | 3 | 5 | 7 | 8 | 9 | 10 | 11 | 12 | 13 | 14 | 15 | 16 | 17 |
|---|---|---|---|---|---|---|---|---|---|---|---|---|---|---|
| Postemergence | | | | | | | | | | | | | | |
| Barnyardgrass | 90 | 10 | 90 | 30 | 90 | 90 | 10 | 90 | 40 | 10 | 90 | 90 | 90 | 90 |
| Blackgrass | 80 | 50 | 80 | 80 | 0 | 80 | 0 | 60 | 0 | 20 | 60 | 80 | 70 | 70 |
| Cocklebur | 100 | 100 | 100 | 100 | 100 | 100 | 70 | 90 | 70 | 40 | 70 | 100 | 100 | 100 |
| Corn | 80 | 0 | 90 | 30 | 90 | 90 | 0 | 0 | 0 | 0 | 70 | 80 | 80 | 80 |
| Crabgrass | 90 | 40 | 90 | 30 | 90 | 90 | 40 | 70 | 30 | 30 | 30 | 60 | 80 | 50 |
| Foxtail, Giant | 80 | 40 | 50 | 40 | 90 | 90 | 10 | 50 | 30 | 20 | 50 | 70 | 80 | 70 |
| Lambsquarters | 100 | 100 | 100 | 100 | 100 | 100 | 90 | 100 | 80 | 70 | 100 | 100 | 100 | 100 |
| Morningglory | 100 | 100 | 100 | 90 | 100 | 100 | 80 | 100 | 80 | 70 | 100 | 100 | 100 | 100 |
| Oat, Wild | 70 | 30 | 60 | 70 | 0 | 70 | 10 | 10 | 0 | 0 | 70 | 70 | 60 | 50 |
| Pigweed | 100 | 90 | 100 | 90 | 100 | 100 | 90 | 90 | 80 | 70 | 90 | 100 | 100 | 90 |
| Surinam Grass | 90 | 30 | 80 | 20 | 90 | 90 | 10 | 50 | 0 | 0 | 50 | 90 | 90 | 80 |
| Velvetleaf | 100 | 80 | 90 | 90 | 100 | 100 | 80 | 80 | 60 | 50 | 70 | 90 | 90 | 100 |
| Wheat | 70 | 20 | 60 | 80 | 0 | 70 | 0 | 40 | 0 | 0 | 50 | 70 | 60 | 60 |

Compounds

| 500 g ai/ha | 18 | 19 | 21 | 22 | 23 | 24 | 25 | 26 | 27 | 28 | 30 | 31 | 32 | 33 |
|---|---|---|---|---|---|---|---|---|---|---|---|---|---|---|
| Postemergence | | | | | | | | | | | | | | |
| Barnyardgrass | 0 | 90 | 0 | 90 | 0 | 10 | 80 | 60 | 0 | 50 | 80 | 0 | 70 | 20 |
| Blackgrass | 0 | 80 | 20 | 80 | 10 | 10 | 60 | 70 | 30 | 30 | 70 | 0 | 40 | 40 |
| Cocklebur | 70 | 100 | 10 | 100 | 90 | 70 | 90 | 90 | 100 | 100 | 100 | 80 | 90 | 80 |
| Corn | 0 | 70 | 0 | 80 | 0 | 10 | 30 | 20 | 20 | 0 | 30 | 0 | 10 | 0 |
| Crabgrass | 0 | 80 | 0 | 90 | 0 | 40 | 80 | 70 | 10 | 50 | 90 | 30 | 20 | 20 |
| Foxtail, Giant | 0 | 80 | 0 | 80 | 10 | 30 | 80 | 40 | 30 | 40 | 90 | 0 | 20 | 40 |
| Lambsquarters | 90 | 100 | 20 | 100 | 80 | 80 | 90 | 80 | 90 | 90 | 100 | 70 | 80 | 70 |
| Morningglory | 70 | 100 | 30 | 100 | 70 | 90 | 90 | 80 | 90 | 90 | 100 | 70 | 90 | 70 |
| Oat, Wild | 0 | 70 | 0 | 60 | 10 | 0 | 20 | 40 | 30 | 10 | 70 | 0 | 30 | 20 |
| Pigweed | 70 | 100 | 30 | 100 | 70 | 80 | 100 | 80 | 70 | 90 | 100 | 50 | 80 | 80 |
| Surinam Grass | 0 | 90 | 0 | 90 | 10 | 10 | 70 | 60 | 0 | 50 | 80 | 0 | 10 | 0 |
| Velvetleaf | 50 | 100 | 30 | 100 | 70 | 50 | 70 | 70 | 70 | 90 | 90 | 60 | 50 | 50 |
| Wheat | 0 | 60 | 20 | 70 | 20 | 0 | 30 | 30 | 30 | 10 | 60 | 0 | 30 | 20 |

Compounds

| 500 g ai/ha | 34 | 35 | 36 | 37 | 38 | 39 | 40 | 41 | 42 | 44 | 46 | 47 | 48 | 49 |
|---|---|---|---|---|---|---|---|---|---|---|---|---|---|---|
| Postemergence | | | | | | | | | | | | | | |
| Barnyardgrass | 60 | 90 | 0 | 90 | 0 | 70 | 90 | 70 | 30 | 50 | 30 | 60 | 20 | 70 |
| Blackgrass | 70 | 70 | 40 | 60 | 0 | 0 | 60 | 60 | 60 | 40 | 10 | 0 | 20 | 50 |
| Cocklebur | 80 | 100 | 70 | 100 | 0 | 50 | 90 | — | 90 | 100 | 0 | 100 | 80 | 100 |
| Corn | 0 | 60 | 0 | 70 | 0 | 50 | 60 | 80 | 0 | 70 | 0 | 0 | 0 | 30 |
| Crabgrass | 30 | 50 | 0 | 80 | 20 | 40 | 80 | 20 | 30 | 80 | 30 | 60 | 20 | 80 |
| Foxtail, Giant | 50 | 60 | 10 | 60 | 0 | 30 | 60 | 30 | 0 | — | 10 | 50 | 10 | 70 |
| Lambsquarters | 90 | 100 | 50 | 100 | 60 | 90 | 100 | 90 | 90 | 90 | 30 | 90 | 80 | 90 |
| Morningglory | 70 | 100 | 70 | 100 | 40 | 100 | 100 | 90 | 90 | 100 | 90 | 90 | 80 | 100 |
| Oat, Wild | 40 | 60 | 40 | 0 | 0 | 0 | 60 | 0 | 0 | 0 | 0 | 0 | 20 | 60 |
| Pigweed | 80 | 100 | 30 | 100 | 30 | 70 | 100 | 90 | 90 | 90 | 80 | 80 | 80 | 90 |
| Surinam Grass | 50 | 80 | 0 | 70 | 20 | 30 | 70 | 10 | 10 | 50 | 10 | 20 | 10 | 60 |

TABLE B-continued

| | | | | | | | | | | | | | | |
|---|---|---|---|---|---|---|---|---|---|---|---|---|---|---|
| Velvetleaf | 60 | 90 | 40 | 100 | 50 | 70 | 90 | 70 | 80 | 90 | 0 | 40 | 60 | 80 |
| Wheat | 40 | 60 | 40 | 60 | 0 | 0 | 60 | 40 | 50 | 30 | 0 | 0 | 20 | 40 |

| | Compounds | | | | | | | | |
|---|---|---|---|---|---|---|---|---|---|
| 500 g ai/ha | 50 | 51 | 52 | 54 | 55 | 56 | 124 | 125 | 126 |
| | Postemergence | | | | | | | | |
| Barnyardgrass | 50 | 60 | 80 | 70 | 50 | 30 | 40 | 70 | 0 |
| Blackgrass | 50 | 30 | 50 | 40 | 40 | 20 | 40 | 20 | 0 |
| Cocklebur | 90 | 90 | 60 | 80 | 80 | 20 | 80 | 60 | 0 |
| Corn | 40 | 0 | 60 | 20 | 20 | 0 | 0 | 0 | 10 |
| Crabgrass | 80 | 60 | 60 | 30 | 30 | 0 | 40 | 30 | 20 |
| Foxtail, Giant | 70 | 30 | 60 | 30 | 20 | 0 | 20 | 40 | 0 |
| Lambsquarters | 90 | 90 | 90 | 90 | 90 | 30 | 90 | 70 | 40 |
| Morningglory | 90 | 90 | 90 | 90 | 90 | 50 | 100 | 90 | 60 |
| Oat, Wild | 60 | 30 | 20 | 40 | 20 | 20 | 30 | 20 | 20 |
| Pigweed | 90 | 90 | 90 | 90 | 80 | 70 | 90 | 60 | 30 |
| Surinam Grass | 60 | 40 | 30 | 0 | 0 | 0 | 0 | 10 | 70 |
| Velvetleaf | 90 | 80 | 50 | 60 | 30 | 0 | 50 | 50 | 20 |
| Wheat | 60 | 40 | 20 | 20 | 0 | 0 | 30 | 0 | 0 |

| | Compounds | | | |
|---|---|---|---|---|
| 250 g ai/ha | 1 | 4 | 45 | 53 |
| | Postemergence | | | |
| Barnyardgrass | 90 | 90 | 0 | 90 |
| Blackgrass | 70 | 90 | 0 | 60 |
| Cocklebur | 90 | 100 | 10 | 90 |
| Corn | 70 | 90 | 0 | 70 |
| Crabgrass | 90 | 90 | 20 | 30 |
| Foxtail, Giant | 80 | 90 | 0 | 70 |
| Lambsquarters | 100 | 100 | 30 | 100 |
| Morningglory | 100 | 100 | 60 | 90 |
| Oat, Wild | 60 | 80 | 0 | 60 |
| Pigweed | 100 | 100 | 50 | 100 |
| Surinam Grass | 90 | 90 | 0 | 50 |
| Velvetleaf | 90 | 100 | 20 | 80 |
| Wheat | 70 | 80 | 0 | 60 |

| | Compounds | | | | | | | | | | | | | | |
|---|---|---|---|---|---|---|---|---|---|---|---|---|---|---|---|
| 125 g ai/ha | 2 | 3 | 5 | 7 | 8 | 9 | 10 | 11 | 12 | 13 | 14 | 15 | 16 | 17 | |
| | Postemergence | | | | | | | | | | | | | | |
| Barnyardgrass | 90 | 0 | 50 | 0 | 90 | 90 | 0 | 20 | 0 | 0 | 30 | 90 | 70 | 20 | |
| Blackgrass | 50 | 20 | 70 | 60 | 0 | 60 | 0 | 20 | 0 | 10 | 30 | 70 | 10 | 0 | |
| Cocklebur | 100 | 70 | 80 | 90 | 100 | 100 | 60 | 80 | 40 | 10 | 50 | 100 | 90 | 100 | |
| Corn | 20 | 0 | 30 | 0 | 70 | 70 | 0 | 0 | 0 | 0 | 30 | 50 | 30 | 0 | |
| Crabgrass | 90 | 30 | 50 | 10 | 80 | 90 | 30 | 30 | 10 | 20 | 10 | 30 | 30 | 20 | |
| Foxtail, Giant | 70 | 20 | 40 | 20 | 80 | 90 | 0 | 10 | 0 | 10 | 20 | 40 | 30 | 10 | |
| Lambsquarters | 100 | 100 | 100 | 80 | 100 | 90 | 80 | 90 | 60 | 60 | 100 | 100 | 100 | 100 | |
| Morningglory | 100 | 80 | 100 | 80 | 100 | 100 | 80 | 80 | 60 | 50 | 100 | 100 | 100 | 100 | |
| Oat, Wild | 40 | 10 | 40 | 40 | 0 | 20 | 0 | 0 | 0 | 0 | 20 | 10 | 10 | 0 | |
| Pigweed | 100 | 80 | 90 | 0 | 100 | 100 | 80 | 80 | 50 | 50 | 80 | 80 | 90 | 70 | |
| Surinam Grass | 90 | 10 | 50 | 0 | 80 | 90 | 10 | 20 | 0 | 0 | 10 | 60 | 60 | 30 | |
| Velvetleaf | 60 | 50 | 70 | 50 | 80 | 100 | 50 | 60 | 20 | 40 | 50 | 80 | 80 | 60 | |
| Wheat | 40 | 10 | 50 | 50 | 0 | 40 | 0 | 0 | 0 | 0 | 20 | 40 | 30 | 0 | |

| | Compounds | | | | | | | | | | | | | |
|---|---|---|---|---|---|---|---|---|---|---|---|---|---|---|
| 125 g ai/ha | 18 | 19 | 21 | 22 | 23 | 24 | 25 | 26 | 27 | 28 | 30 | 32 | 33 | 34 |
| | Postemergence | | | | | | | | | | | | | |
| Barnyardgrass | 0 | 80 | 0 | 70 | 0 | 0 | 40 | 20 | 0 | 20 | 0 | 20 | 0 | 0 |
| Blackgrass | 0 | 60 | 10 | 60 | 0 | 0 | 10 | 40 | 30 | 10 | 60 | 30 | 40 | 60 |
| Cocklebur | 70 | 90 | 0 | 100 | 30 | 50 | 90 | 80 | 100 | 90 | 100 | 40 | 60 | 80 |
| Corn | 0 | 30 | 0 | 20 | 0 | 0 | 0 | 0 | 0 | 0 | 0 | 0 | 0 | 0 |
| Crabgrass | 0 | 40 | 0 | 50 | 0 | 20 | 60 | 40 | 10 | 30 | 30 | 10 | 10 | 0 |
| Foxtail, Giant | 0 | 20 | 0 | 70 | 0 | 20 | 50 | 30 | 20 | 20 | 0 | 10 | 10 | 20 |
| Lambsquarters | 70 | 100 | 10 | 100 | 70 | 70 | 90 | 70 | 80 | 90 | 90 | 70 | 60 | 70 |
| Morningglory | 20 | 100 | 10 | 90 | 40 | 60 | 90 | 70 | 70 | 90 | 90 | 40 | 40 | 60 |
| Oat, Wild | 0 | 40 | 0 | 10 | 10 | 0 | 10 | 30 | 20 | 0 | 60 | 20 | 20 | 30 |
| Pigweed | 20 | 90 | 0 | 100 | 30 | 70 | 90 | 70 | 60 | 80 | 90 | 80 | 60 | 50 |
| Surinam Grass | 0 | 40 | 0 | 80 | 0 | 0 | 50 | 30 | 0 | 10 | 10 | 0 | 0 | 10 |

TABLE B-continued

| | | | | | | | | | | | | | | |
|---|---|---|---|---|---|---|---|---|---|---|---|---|---|---|
| Velvetleaf | 20 | 70 | 10 | 100 | 40 | 40 | 60 | 40 | 60 | 70 | 50 | 10 | 40 | 30 |
| Wheat | 0 | 20 | 10 | 0 | 0 | 0 | 20 | 30 | 20 | 0 | 50 | 20 | 20 | 30 |

| | Compounds | | | | | | | | | | | | | |
|---|---|---|---|---|---|---|---|---|---|---|---|---|---|---|
| 125 g ai/ha | 35 | 36 | 37 | 38 | 39 | 40 | 41 | 42 | 44 | 46 | 47 | 48 | 49 | 50 |
| | Postemergence | | | | | | | | | | | | | |
| Barnyardgrass | 40 | 0 | 0 | 0 | 0 | 0 | 20 | 10 | 40 | 0 | 20 | 10 | 30 | 10 |
| Blackgrass | 60 | 0 | 40 | 0 | 0 | 50 | 20 | 30 | 30 | 0 | 0 | 0 | 20 | 30 |
| Cocklebur | 30 | 20 | 100 | 0 | 30 | 0 | 70 | 80 | 90 | 0 | 90 | 20 | 90 | 90 |
| Corn | 0 | 0 | 0 | 0 | 0 | 0 | 20 | 0 | 30 | 0 | 0 | 0 | 0 | 0 |
| Crabgrass | 20 | 0 | 60 | 0 | 0 | 0 | 10 | 0 | 70 | 10 | 10 | 10 | 30 | 40 |
| Foxtail, Giant | 10 | 0 | 10 | 0 | 0 | 0 | 20 | 0 | — | 0 | 10 | 10 | 10 | 20 |
| Lambsquarters | 90 | 40 | 100 | 20 | 70 | 0 | 80 | 80 | 90 | 10 | 80 | 60 | 80 | 80 |
| Morningglory | 70 | 10 | 90 | 10 | 80 | 0 | 70 | 80 | 80 | 80 | 80 | 30 | 90 | 90 |
| Oat, Wild | 60 | 0 | 0 | 0 | 0 | 40 | 0 | 0 | 0 | 0 | 0 | 0 | 30 | 30 |
| Pigweed | 70 | 20 | 100 | 30 | 50 | 0 | 70 | 80 | 80 | 70 | 70 | 60 | 90 | 80 |
| Surinam Grass | 20 | 0 | 20 | 0 | 0 | 0 | 0 | 0 | — | 0 | 0 | 0 | 10 | 20 |
| Velvetleaf | 50 | 20 | 80 | 0 | 40 | 0 | 50 | 50 | 80 | 0 | 20 | 10 | 50 | 70 |
| Wheat | 20 | 0 | 0 | 0 | 0 | 50 | 30 | 50 | 0 | 0 | 0 | 0 | 30 | 30 |

| | Compounds | | | | | | | | | | | | | |
|---|---|---|---|---|---|---|---|---|---|---|---|---|---|---|
| 125 g ai/ha | 51 | 52 | 54 | 55 | 56 | 75 | 76 | 77 | 78 | 79 | 83 | 88 | 92 | 94 |
| | Postemergence | | | | | | | | | | | | | |
| Barnyardgrass | 20 | 30 | 0 | 0 | 0 | 90 | 90 | 90 | 90 | 80 | 80 | 90 | 10 | 90 |
| Blackgrass | 20 | 0 | 40 | 30 | 0 | 60 | 60 | 60 | 40 | 50 | 60 | 60 | 20 | 60 |
| Cocklebur | 80 | 40 | 20 | 20 | 0 | 100 | 90 | 100 | 100 | 60 | 100 | 100 | 80 | 100 |
| Corn | 0 | 0 | 0 | 0 | 0 | 70 | 70 | 80 | 80 | 60 | 10 | 80 | 0 | 90 |
| Crabgrass | 30 | 0 | 20 | 0 | 0 | 80 | 90 | 80 | 70 | 60 | 60 | 80 | 20 | 80 |
| Foxtail, Giant | 0 | 40 | 20 | 20 | 0 | 80 | 80 | 80 | 70 | 70 | 50 | 70 | 30 | 60 |
| Lambsquarters | 80 | 80 | 80 | 70 | 20 | 100 | 100 | 100 | 100 | 100 | 100 | 100 | 90 | 90 |
| Morningglory | 80 | 90 | 80 | 80 | 0 | 100 | 100 | 100 | 100 | 100 | 100 | 90 | 60 | 90 |
| Oat, Wild | 20 | 0 | 0 | 0 | 0 | 60 | 60 | 60 | 70 | 40 | 40 | 50 | 0 | 30 |
| Pigweed | 80 | 60 | 80 | 70 | 50 | 90 | 100 | 100 | 100 | 100 | 100 | 100 | 80 | 90 |
| Surinam Grass | 0 | 0 | 0 | 0 | 0 | 80 | 80 | 80 | 80 | 60 | 60 | 80 | 10 | 80 |
| Velvetleaf | 70 | 40 | 50 | 10 | 0 | 100 | 90 | 90 | 80 | 80 | 90 | 100 | 60 | 100 |
| Wheat | 30 | 0 | 0 | 0 | 0 | 70 | 70 | 60 | 70 | 40 | 30 | 60 | 0 | 60 |

| | Compounds | | | | | | | | | | |
|---|---|---|---|---|---|---|---|---|---|---|---|
| 125 g ai/ha | 95 | 113 | 117 | 124 | 125 | 126 | 128 | 129 | 133 | 135 | 136 |
| | Postemergence | | | | | | | | | | |
| Barnyardgrass | 90 | 80 | 90 | 0 | 0 | 0 | 60 | 70 | 70 | 90 | 90 |
| Blackgrass | — | 40 | 70 | 0 | 0 | 0 | 50 | 70 | 70 | 70 | 70 |
| Cocklebur | 90 | 90 | 100 | 30 | 40 | 0 | 90 | 100 | 100 | 100 | 100 |
| Corn | 90 | 40 | 90 | 0 | 0 | 0 | 70 | 80 | 80 | 80 | 70 |
| Crabgrass | 80 | 40 | 80 | 10 | 20 | 0 | 40 | 70 | 70 | 70 | 80 |
| Foxtail, Giant | 80 | 50 | 80 | 10 | 0 | 0 | 50 | 50 | 70 | 80 | 70 |
| Lambsquarters | 100 | 90 | 100 | 40 | 60 | 30 | 90 | 100 | 100 | 100 | 100 |
| Morningglory | 100 | 90 | 100 | 50 | 70 | 30 | 90 | 100 | 100 | 100 | 100 |
| Oat, Wild | 60 | 50 | 50 | 0 | 0 | 0 | 40 | 40 | 60 | 60 | 50 |
| Pigweed | 100 | 90 | 100 | 50 | 60 | 0 | 90 | 100 | 100 | 100 | 100 |
| Surinam Grass | 90 | 80 | 70 | 0 | 0 | 0 | 40 | 70 | 70 | 80 | 80 |
| Velvetleaf | 100 | 80 | 100 | 20 | 0 | 10 | 80 | 90 | 100 | 100 | 90 |
| Wheat | 50 | 50 | 70 | 0 | 0 | 0 | 20 | 20 | 50 | 60 | 60 |

| | Compounds | | | | | | | | | | | | | |
|---|---|---|---|---|---|---|---|---|---|---|---|---|---|---|
| 62 g ai/ha | 1 | 4 | 31 | 45 | 53 | 65 | 75 | 76 | 77 | 78 | 79 | 83 | 88 | 92 |
| | Postemergence | | | | | | | | | | | | | |
| Barnyardgrass | 50 | 70 | 0 | 0 | 80 | 70 | 80 | 90 | 60 | 80 | 50 | 50 | 90 | 10 |
| Blackgrass | 40 | 70 | 0 | 0 | 20 | 70 | 50 | 50 | 50 | 20 | 20 | 50 | 40 | 20 |
| Cocklebur | 90 | 90 | 70 | 0 | 50 | 100 | 70 | 60 | 70 | 100 | — | 90 | 100 | 60 |
| Corn | 30 | 50 | 0 | 0 | 0 | 80 | 60 | 50 | 30 | 40 | 20 | 10 | 70 | 0 |
| Crabgrass | 70 | 80 | 0 | 0 | 0 | 80 | 70 | 70 | 70 | 60 | 30 | 50 | 70 | 0 |
| Foxtail, Giant | 50 | 80 | 0 | 0 | 30 | 70 | 60 | 70 | 60 | 70 | 60 | 40 | 40 | 20 |
| Lambsquarters | 100 | 100 | 40 | 10 | 90 | 100 | 90 | 100 | 100 | 100 | 90 | 100 | 100 | 90 |
| Morningglory | 90 | 90 | 50 | 40 | 90 | 80 | 100 | 100 | 100 | 100 | 90 | 60 | 60 | 50 |
| Oat, Wild | 20 | 50 | 0 | 0 | 30 | 40 | 50 | 50 | 50 | 50 | 30 | 0 | 40 | 0 |
| Pigweed | 90 | 100 | 20 | 30 | 80 | 100 | 80 | 90 | 90 | 80 | 80 | 100 | 100 | 70 |
| Surinam Grass | 60 | 90 | 0 | 0 | 10 | 80 | 70 | 70 | 70 | 60 | 20 | 50 | 80 | 0 |

TABLE B-continued

| | | | | | | | | | | | | | | |
|---|---|---|---|---|---|---|---|---|---|---|---|---|---|---|
| Velvetleaf | 90 | 70 | 10 | 0 | 40 | 90 | 70 | 90 | 80 | 70 | 50 | 80 | 90 | 50 |
| Wheat | 30 | 40 | 0 | 0 | 30 | 50 | 50 | 60 | 50 | 50 | 0 | 0 | 50 | 0 |

| | Compounds | | | | | | | | |
|---|---|---|---|---|---|---|---|---|---|
| 62 g ai/ha | 94 | 95 | 113 | 117 | 128 | 129 | 133 | 135 | 136 |
| | Postemergence | | | | | | | | |
| Barnyardgrass | 80 | 90 | 50 | 90 | 40 | 60 | 70 | 70 | 70 |
| Blackgrass | 40 | 60 | 30 | 60 | 40 | 70 | 60 | 60 | 70 |
| Cocklebur | 100 | 90 | 90 | 100 | 70 | 70 | 100 | 100 | 90 |
| Corn | 70 | 80 | 10 | 90 | 10 | 70 | 70 | 50 | 40 |
| Crabgrass | 70 | 80 | 20 | 60 | 20 | 50 | 60 | 60 | 70 |
| Foxtail, Giant | 50 | 80 | 20 | 80 | 30 | 40 | 60 | 80 | 60 |
| Lambsquarters | 90 | 100 | 80 | 90 | 90 | 100 | 100 | 100 | 100 |
| Morningglory | 80 | 90 | 90 | 80 | 40 | 50 | 70 | 100 | 40 |
| Oat, Wild | 30 | 30 | 40 | 30 | 0 | 0 | 40 | 60 | 20 |
| Pigweed | 90 | 100 | 70 | 100 | 90 | 100 | 90 | 100 | 90 |
| Surinam Grass | 80 | 80 | 30 | 70 | 30 | 50 | 60 | 80 | 70 |
| Velvetleaf | 90 | 100 | 60 | 90 | 50 | 80 | 90 | 100 | 80 |
| Wheat | 40 | 40 | 30 | 50 | 0 | 0 | 0 | 40 | 20 |

| | Compound |
|---|---|
| 4 g ai/ha | 65 |
| | Postemergence |
| Barnyardgrass | 20 |
| Blackgrass | 20 |
| Cocklebur | 80 |
| Corn | 10 |
| Crabgrass | 20 |
| Foxtail, Giant | 40 |
| Lambsquarters | 80 |
| Morningglory | 70 |
| Oat, Wild | 0 |
| Pigweed | 70 |
| Surinam Grass | 20 |
| Velvetleaf | 50 |
| Wheat | 0 |

| | Compounds | | | | | | | | | | | | | |
|---|---|---|---|---|---|---|---|---|---|---|---|---|---|---|
| 500 g ai/ha | 2 | 3 | 5 | 7 | 8 | 9 | 10 | 11 | 12 | 13 | 14 | 15 | 16 | 17 |
| | Preemergence | | | | | | | | | | | | | |
| Barnyardgrass | 90 | 0 | 30 | 30 | 90 | 90 | 50 | 10 | 80 | 80 | 80 | 90 | 90 | 80 |
| Cocklebur | 100 | 80 | 80 | 80 | 100 | 100 | 90 | 90 | 90 | 100 | 80 | 100 | 100 | 90 |
| Corn | 80 | 0 | 70 | 0 | 90 | 80 | 0 | 0 | 30 | 30 | 70 | 80 | 70 | 60 |
| Crabgrass | 90 | 50 | 70 | 30 | 90 | 100 | 60 | 80 | 70 | 70 | 80 | 90 | 100 | 100 |
| Foxtail, Giant | 90 | 0 | 10 | 0 | 90 | 80 | 20 | 70 | 50 | 40 | 80 | 80 | 80 | 70 |
| Lambsquarters | 100 | 90 | 100 | 90 | 100 | 100 | 90 | 100 | 100 | 100 | 100 | 100 | 100 | 100 |
| Morningglory | 100 | 60 | 80 | 80 | 100 | 100 | 90 | 90 | 90 | 100 | 100 | 100 | 100 | 100 |
| Pigweed | 100 | 90 | 90 | 90 | 100 | 100 | 90 | 90 | 90 | 90 | 90 | 100 | 90 | 100 |
| Surinam Grass | 90 | 20 | 10 | 0 | 90 | 90 | 0 | 70 | — | — | 80 | 90 | 80 | 90 |
| Velvetleaf | 100 | 70 | 90 | 80 | 100 | 100 | 90 | 90 | 90 | 90 | 80 | 100 | 100 | 90 |
| Wheat | 70 | 0 | 50 | 30 | 80 | 80 | 0 | 50 | 60 | 60 | 50 | 60 | 60 | 60 |

| | Compounds | | | | | | | | | | | | | |
|---|---|---|---|---|---|---|---|---|---|---|---|---|---|---|
| 500 g ai/ha | 18 | 19 | 21 | 22 | 23 | 24 | 25 | 26 | 27 | 28 | 30 | 31 | 32 | 33 |
| | Preemergence | | | | | | | | | | | | | |
| Barnyardgrass | 0 | 90 | 10 | 20 | 0 | 20 | 60 | 90 | 60 | 30 | 40 | 70 | 10 | 50 |
| Cocklebur | 40 | 100 | 80 | 80 | 10 | 90 | 90 | 90 | 90 | 90 | 100 | 100 | 90 | 90 |
| Corn | 0 | 90 | — | — | 0 | 0 | 0 | 80 | 50 | 0 | 80 | 40 | 0 | 30 |
| Crabgrass | 0 | 90 | 60 | 100 | 0 | 80 | 70 | 90 | 70 | 80 | 90 | 80 | 40 | 50 |
| Foxtail, Giant | 0 | 80 | 10 | 20 | 0 | 60 | 80 | 80 | 40 | 50 | 80 | 80 | 0 | 40 |
| Lambsquarters | 60 | 100 | 80 | 100 | 30 | 90 | 90 | 100 | 100 | 100 | 90 | 100 | 90 | 100 |
| Morningglory | 0 | 100 | 90 | 100 | 10 | 90 | 90 | 100 | 90 | 90 | 100 | 100 | 80 | 90 |
| Pigweed | 70 | 100 | 70 | 80 | 20 | 90 | 90 | 100 | 100 | 90 | 90 | 100 | 90 | 90 |
| Surinam Grass | 0 | 90 | 20 | 20 | 0 | 50 | 70 | 80 | 70 | 60 | 80 | 60 | 0 | 40 |

TABLE B-continued

| | | | | | | | | | | | | | | |
|---|---|---|---|---|---|---|---|---|---|---|---|---|---|---|
| Velvetleaf | 40 | 100 | 80 | 100 | 20 | 80 | 80 | 100 | 90 | 90 | 80 | 90 | 80 | 80 |
| Wheat | 0 | 60 | 30 | 50 | 0 | 70 | 60 | 60 | 50 | 40 | 60 | 70 | 10 | 50 |

| | Compounds | | | | | | | | | | | | | |
|---|---|---|---|---|---|---|---|---|---|---|---|---|---|---|
| 500 g ai/ha | 34 | 35 | 36 | 37 | 38 | 39 | 40 | 41 | 42 | 44 | 46 | 47 | 48 | 49 |

Preemergence

| | | | | | | | | | | | | | | |
|---|---|---|---|---|---|---|---|---|---|---|---|---|---|---|
| Barnyardgrass | 0 | 80 | 0 | 40 | 0 | 20 | 90 | 10 | 0 | 10 | 0 | 40 | 10 | 60 |
| Cocklebur | 60 | 90 | 60 | 80 | 0 | 30 | 100 | 10 | 70 | 80 | 40 | 90 | 20 | 90 |
| Corn | 0 | 50 | 0 | 10 | 10 | 50 | 50 | 0 | 0 | 0 | 0 | 30 | 0 | 40 |
| Crabgrass | 70 | 80 | 0 | 90 | 0 | 50 | 80 | 20 | 20 | 80 | 40 | 90 | — | 90 |
| Foxtail, Giant | 20 | 70 | 0 | 60 | 0 | 20 | 80 | 0 | 0 | 40 | 50 | 40 | 50 | 70 |
| Lambsquarters | 80 | 100 | 40 | 100 | 90 | 100 | 100 | 60 | 90 | 60 | 60 | 100 | 100 | 100 |
| Morningglory | 70 | 100 | 0 | 50 | 50 | 70 | 100 | 20 | 80 | 40 | 90 | 100 | 30 | 100 |
| Pigweed | 80 | 100 | 20 | 100 | 70 | 100 | 100 | 60 | 90 | 80 | 90 | 90 | 80 | 100 |
| Surinam Grass | 50 | 60 | 0 | 40 | 0 | 0 | 70 | 0 | 20 | 60 | 40 | 20 | 60 | 60 |
| Velvetleaf | 60 | 90 | 40 | 80 | 0 | 30 | 90 | 30 | 70 | 80 | 20 | 90 | 0 | 90 |
| Wheat | 10 | 50 | 0 | 60 | 0 | 10 | 70 | 20 | 10 | 60 | 20 | 50 | 30 | 70 |

| | Compounds | | | | | | | | |
|---|---|---|---|---|---|---|---|---|---|
| 500 g ai/ha | 50 | 51 | 52 | 54 | 55 | 56 | 124 | 125 | 126 |

Preemergence

| | | | | | | | | | |
|---|---|---|---|---|---|---|---|---|---|
| Barnyardgrass | 50 | 0 | 30 | 40 | 60 | 0 | 0 | — | 0 |
| Cocklebur | 90 | 20 | 60 | 90 | 90 | 30 | 60 | 90 | 90 |
| Corn | 20 | 0 | 0 | 0 | 0 | 0 | 0 | 0 | 0 |
| Crabgrass | 80 | 0 | 0 | 0 | 60 | 0 | 0 | 100 | 100 |
| Foxtail, Giant | 40 | 0 | 0 | 0 | 0 | 0 | 0 | 0 | 0 |
| Lambsquarters | 100 | 80 | — | — | — | — | 70 | — | — |
| Morningglory | 90 | 40 | 100 | — | 100 | 20 | 60 | 100 | 70 |
| Pigweed | 90 | 70 | 50 | 100 | 100 | 80 | 70 | 90 | 80 |
| Surinam Grass | 70 | 0 | 0 | 0 | 50 | 0 | 0 | 0 | 20 |
| Velvetleaf | 90 | 0 | 30 | 80 | 90 | 30 | 50 | 90 | 20 |
| Wheat | 40 | 0 | 0 | 0 | 70 | 0 | 0 | 0 | 0 |

| | Compounds | | | |
|---|---|---|---|---|
| 250 g ai/ha | 1 | 4 | 45 | 53 |

Preemergence

| | | | | |
|---|---|---|---|---|
| Barnyardgrass | 90 | 90 | 0 | 70 |
| Cocklebur | 100 | 100 | 0 | 100 |
| Corn | 80 | 80 | — | 0 |
| Crabgrass | 90 | 90 | 0 | 50 |
| Foxtail, Giant | 90 | 80 | 0 | 50 |
| Lambsquarters | 100 | 100 | 30 | — |
| Morningglory | 100 | 100 | 50 | 100 |
| Pigweed | 100 | 100 | 50 | 100 |
| Surinam Grass | 80 | 90 | 0 | 30 |
| Velvetleaf | 100 | 90 | 0 | 90 |
| Wheat | 60 | 70 | 0 | 40 |

| | Compounds | | | | | | | | | | | | |
|---|---|---|---|---|---|---|---|---|---|---|---|---|---|
| 125 g ai/ha | 2 | 3 | 5 | 7 | 8 | 9 | 10 | 11 | 12 | 13 | 14 | 15 | 16 | 17 |

Preemergence

| | | | | | | | | | | | | | | |
|---|---|---|---|---|---|---|---|---|---|---|---|---|---|---|
| Barnyardgrass | 70 | 0 | 10 | 0 | 70 | 50 | 20 | 0 | 50 | 40 | 10 | 40 | 30 | 20 |
| Cocklebur | 90 | 80 | 70 | 70 | 90 | 90 | 80 | 80 | 80 | 90 | 60 | 70 | 70 | 80 |
| Corn | 0 | 0 | 0 | 0 | 90 | 50 | 0 | 0 | 0 | — | 0 | 20 | 30 | 0 |
| Crabgrass | 90 | 10 | 20 | 0 | 80 | 90 | 20 | 30 | 20 | 50 | 10 | 70 | 70 | 70 |
| Foxtail, Giant | 30 | 0 | 0 | 0 | 50 | 70 | 0 | 10 | 20 | 20 | 30 | 40 | 30 | 20 |
| Lambsquarters | 100 | 70 | 90 | 80 | 90 | 90 | — | 100 | 90 | 90 | 90 | 90 | 100 | 90 |
| Morningglory | 100 | 50 | 70 | 70 | 100 | 100 | 80 | 80 | 70 | 90 | 70 | 70 | 90 | 100 |
| Pigweed | 90 | 80 | 90 | 90 | 100 | 90 | 80 | 80 | 80 | 80 | 80 | 90 | 90 | 80 |
| Surinam Grass | 40 | 0 | 0 | 0 | 60 | 70 | 0 | 10 | 0 | 0 | 40 | 30 | 40 | 30 |

TABLE B-continued

| | | | | | | | | | | | | | | |
|---|---|---|---|---|---|---|---|---|---|---|---|---|---|---|
| Velvetleaf | 90 | 40 | 70 | 50 | 80 | 90 | 80 | 80 | 80 | 80 | 60 | 70 | 80 | 70 |
| Wheat | 60 | 0 | — | 0 | 60 | 40 | 0 | 0 | 30 | 40 | 40 | 40 | 50 | 40 |

| | Compounds | | | | | | | | | | | | | |
|---|---|---|---|---|---|---|---|---|---|---|---|---|---|---|
| 125 g ai/ha | 18 | 19 | 21 | 22 | 23 | 24 | 25 | 26 | 27 | 28 | 30 | 32 | 33 | 34 |
| | Preemergence | | | | | | | | | | | | | |
| Barnyardgrass | 0 | 40 | 0 | 0 | 0 | 0 | 20 | 50 | 30 | 10 | 10 | 0 | 20 | 0 |
| Cocklebur | 10 | 90 | 30 | 50 | 0 | 80 | 80 | 80 | 80 | 80 | 60 | 80 | 80 | 30 |
| Corn | 0 | 70 | 0 | 10 | 0 | — | 0 | 30 | 10 | 0 | 10 | 0 | 10 | 0 |
| Crabgrass | 0 | 80 | 0 | 20 | 0 | 60 | 60 | 30 | 30 | 70 | 50 | 0 | 0 | 0 |
| Foxtail, Giant | 0 | 20 | 0 | 0 | 0 | 10 | 40 | 10 | 0 | 30 | 10 | 0 | 0 | 0 |
| Lambsquarters | 10 | 100 | 70 | 70 | 0 | 70 | 90 | 100 | 90 | 80 | 80 | 40 | 90 | 50 |
| Morningglory | 0 | 90 | 50 | 100 | 0 | 50 | 80 | 90 | 80 | 80 | 90 | 40 | 0 | 20 |
| Pigweed | 0 | 90 | 50 | 60 | 0 | 80 | 80 | 90 | 90 | 80 | 50 | 40 | 80 | 40 |
| Surinam Grass | 0 | 60 | 0 | 0 | 0 | 10 | 20 | 10 | 0 | — | 0 | 0 | 0 | 10 |
| Velvetleaf | 0 | 90 | 10 | 30 | 0 | 50 | 70 | 90 | 80 | 80 | 10 | 50 | 70 | 30 |
| Wheat | 0 | 50 | 0 | 10 | 0 | 30 | 50 | 30 | 10 | 10 | 30 | 0 | 0 | 0 |

| | Compounds | | | | | | | | | | | | | |
|---|---|---|---|---|---|---|---|---|---|---|---|---|---|---|
| 125 g ai/ha | 35 | 36 | 37 | 38 | 39 | 40 | 41 | 42 | 44 | 46 | 47 | 48 | 49 | 50 |
| | Preemergence | | | | | | | | | | | | | |
| Barnyardgrass | 10 | 0 | 10 | 0 | 0 | 50 | 0 | 0 | 0 | 0 | 0 | 0 | 30 | 30 |
| Cocklebur | 60 | 10 | 20 | 0 | 10 | 90 | 0 | 40 | 10 | 0 | 80 | 0 | 80 | 80 |
| Corn | 0 | 0 | 0 | 0 | 30 | 0 | 0 | 0 | 0 | 0 | 0 | 0 | 10 | 20 |
| Crabgrass | 30 | 0 | 50 | 0 | 0 | 60 | 0 | 0 | 40 | 0 | 20 | 10 | 80 | 50 |
| Foxtail, Giant | 0 | 0 | 10 | 0 | 0 | 20 | 0 | 0 | 20 | 0 | 20 | 30 | 40 | 10 |
| Lambsquarters | 90 | 0 | 100 | 20 | 50 | 100 | 30 | 40 | — | 10 | 90 | 70 | 90 | 90 |
| Morningglory | 70 | 0 | 10 | 0 | 30 | 90 | 0 | 20 | 10 | 50 | 80 | 0 | 80 | 80 |
| Pigweed | 80 | 0 | 100 | 10 | 70 | 90 | 0 | 50 | 70 | 80 | 80 | 60 | 90 | 70 |
| Surinam Grass | 10 | 0 | — | 0 | 0 | 50 | — | 0 | 40 | 0 | 0 | 30 | 40 | 20 |
| Velvetleaf | 70 | 10 | 40 | 0 | 0 | 90 | 10 | 10 | 30 | 0 | 60 | 0 | 80 | 80 |
| Wheat | 20 | 0 | 30 | 0 | 0 | 40 | 0 | 10 | 30 | 0 | 20 | 0 | 30 | 20 |

| | Compounds | | | | | | | | | | | | |
|---|---|---|---|---|---|---|---|---|---|---|---|---|---|
| 125 g ai/ha | 51 | 52 | 54 | 55 | 56 | 75 | 76 | 77 | 78 | 79 | 83 | 88 | 92 | 94 |
| | Preemergence | | | | | | | | | | | | | |
| Barnyardgrass | 0 | 0 | 0 | 0 | 0 | 80 | 90 | 90 | 70 | 70 | 30 | — | 30 | — |
| Cocklebur | 0 | 10 | 50 | 70 | 0 | 90 | 100 | 100 | 100 | 80 | 50 | 90 | 50 | 50 |
| Corn | 0 | — | 0 | 0 | 0 | 80 | 80 | 80 | 70 | 60 | 0 | 10 | 0 | 0 |
| Crabgrass | 0 | 0 | 0 | 50 | 0 | 90 | 90 | 90 | 90 | 70 | 60 | 70 | 10 | 70 |
| Foxtail, Giant | 0 | 0 | 0 | 0 | 0 | 90 | 80 | 90 | 70 | 20 | 10 | 30 | 10 | 20 |
| Lambsquarters | — | — | — | — | — | 100 | 100 | 100 | 100 | 90 | 90 | — | 80 | — |
| Morningglory | 0 | 10 | 0 | 80 | — | 100 | 100 | 100 | 100 | 90 | 10 | 10 | 0 | 0 |
| Pigweed | 10 | — | 100 | 80 | — | 100 | 100 | 100 | 100 | 100 | 100 | — | 80 | — |
| Surinam Grass | 0 | 0 | 0 | 0 | 0 | 80 | 90 | 90 | 90 | 0 | 10 | 50 | 0 | 30 |
| Velvetleaf | 0 | 0 | 10 | 50 | 0 | 100 | 90 | 100 | 90 | 80 | 60 | 90 | 70 | 70 |
| Wheat | 0 | 0 | 0 | 0 | 0 | 70 | 70 | 70 | 70 | 60 | 50 | 70 | 30 | 60 |

| | Compounds | | | | | | | | | | |
|---|---|---|---|---|---|---|---|---|---|---|---|
| 125 g ai/ha | 95 | 113 | 117 | 124 | 125 | 126 | 128 | 129 | 133 | 135 | 136 |
| | Preemergence | | | | | | | | | | |
| Barnyardgrass | — | 20 | 30 | 0 | 0 | 0 | 10 | 30 | 30 | 90 | 180 |
| Cocklebur | 100 | 80 | 90 | 10 | 30 | 0 | 10 | 30 | 50 | 100 | 70 |
| Corn | 80 | 20 | 10 | 0 | 0 | 0 | 0 | 0 | 0 | 80 | 0 |
| Crabgrass | 100 | 70 | 90 | 0 | 0 | 80 | 0 | 30 | 70 | 90 | 80 |
| Foxtail, Giant | 90 | 10 | 90 | 0 | 0 | 0 | 0 | 0 | 20 | 90 | 50 |
| Lambsquarters | — | 80 | 100 | 0 | — | — | 50 | 80 | 70 | 100 | 100 |
| Morningglory | 60 | 60 | 20 | 10 | 30 | 0 | 0 | 0 | 0 | 100 | 40 |
| Pigweed | — | 90 | 100 | 20 | 30 | 20 | 50 | 90 | 80 | 100 | 100 |
| Surinam Grass | 100 | 60 | 100 | 0 | 0 | 0 | 0 | 10 | 10 | 90 | 50 |

TABLE B-continued

| | | | | | | | | | | | |
|---|---|---|---|---|---|---|---|---|---|---|---|
| Velvetleaf | 100 | 90 | 90 | 20 | 10 | 10 | 40 | 60 | 60 | 100 | 80 |
| Wheat | 80 | 60 | 80 | 0 | 0 | 0 | 0 | 20 | 60 | 90 | 70 |

| | Compounds | | | | | | | | | | | | | |
|---|---|---|---|---|---|---|---|---|---|---|---|---|---|---|
| 62 g ai/ha | 1 | 4 | 31 | 45 | 53 | 65 | 75 | 76 | 77 | 78 | 79 | 83 | 88 | 92 |
| Preemergence | | | | | | | | | | | | | | |
| Barnyardgrass | 60 | 30 | 20 | 0 | 0 | 40 | 60 | 40 | 70 | 60 | 0 | 20 | — | 10 |
| Cocklebur | 90 | 80 | 90 | — | 60 | 80 | 90 | 80 | 80 | 80 | 50 | 10 | 60 | 40 |
| Corn | 20 | 0 | 0 | 0 | 0 | 0 | 50 | 70 | 70 | 30 | 30 | 0 | 0 | 0 |
| Crabgrass | 90 | 70 | 10 | 0 | 0 | 70 | 80 | 80 | 80 | 80 | 0 | 30 | 50 | 0 |
| Foxtail, Giant | 30 | 10 | 10 | 0 | 0 | 30 | 30 | 40 | 70 | 20 | 0 | 0 | 10 | 0 |
| Lambsquarters | 100 | 90 | 90 | 0 | — | 90 | 100 | 90 | 100 | 90 | 90 | 70 | — | 50 |
| Morningglory | 90 | 60 | 90 | 30 | 90 | 30 | 80 | 100 | 100 | 80 | 70 | 0 | 0 | 0 |
| Pigweed | 90 | 90 | 90 | 0 | 60 | 100 | 100 | 100 | 100 | 100 | 80 | 80 | — | 40 |
| Surinam Grass | 50 | 40 | 20 | 0 | 0 | 40 | 70 | 70 | 60 | 60 | 0 | 0 | 20 | 0 |
| Velvetleaf | 90 | 80 | 80 | 0 | 20 | 70 | 80 | 80 | 80 | 70 | 50 | 50 | 70 | 50 |
| Wheat | 30 | 50 | 40 | 0 | 0 | 80 | 30 | 30 | 70 | 30 | 0 | 20 | 50 | 0 |

| | Compounds | | | | | | | | |
|---|---|---|---|---|---|---|---|---|---|
| 62 g ai/ha | 94 | 95 | 113 | 117 | 128 | 129 | 133 | 135 | 136 |
| Preemergence | | | | | | | | | |
| Barnyardgrass | — | — | 0 | 10 | 0 | 10 | 30 | 70 | 30 |
| Cocklebur | 30 | 90 | 70 | 50 | 0 | 10 | 20 | 100 | 40 |
| Corn | 0 | 40 | 0 | 0 | 0 | — | 0 | 50 | 0 |
| Crabgrass | 40 | 80 | 40 | 90 | 0 | 10 | 40 | 80 | 70 |
| Foxtail, Giant | 0 | 50 | 0 | 20 | 0 | 0 | 0 | 60 | 10 |
| Lambsquarters | — | — | 70 | 90 | 10 | — | — | 100 | 90 |
| Morningglory | 0 | 30 | 50 | 10 | 0 | 0 | 0 | 100 | 10 |
| Pigweed | — | — | 70 | 100 | 10 | 80 | 70 | 100 | 80 |
| Surinam Grass | 10 | 50 | 20 | 80 | 0 | 0 | 0 | 80 | 10 |
| Velvetleaf | 40 | 80 | 80 | 70 | 0 | 50 | 50 | 90 | 60 |
| Wheat | 30 | 70 | 10 | 50 | 0 | 0 | 50 | 70 | 50 |

| 4 g ai/ha | Compound 65 |
|---|---|
| Preemergence | |
| Barnyardgrass | 0 |
| Cocklebur | 10 |
| Corn | 0 |
| Crabgrass | 20 |
| Foxtail, Giant | 0 |
| Lambsquarters | 30 |
| Morningglory | 0 |
| Pigweed | 20 |
| Surinam Grass | 0 |
| Velvetleaf | 0 |
| Wheat | 20 |

Test C

Seeds or nutlets of plant species selected from bermudagrass (*Cynodon dactylon*), Surinam grass (*Brachiaria decumbens*), cocklebur (*Xanthium strumarium*), corn (*Zea mays*), crabgrass (*Digitaria sanguinalis*), woolly cupgrass (*Eriochloa villosa*), giant foxtail (*Setaria faberii*), goosegrass (*Eleusine indica*), johnsongrass (*Sorghum halepense*), kochia (*Kochia scoparia*), lambsquarters (*Chenopodium album*), morningglory (*Ipomoea coccinea*), eastern black nightshade (*Solanum ptycanthum*), yellow nutsedge (*Cyperus esculentus*), pigweed (*Amaranthus retroflexus*), common ragweed (*Ambrosia elatior*), soybean (*Glycine max*), common (oilseed) sunflower (*Helianthus annuus*), and velvetleaf (*Abutilon theophrasti*) were planted and treated preemergence with test chemicals formulated in a non-phytotoxic solvent mixture which included a surfactant.

At the same time, plants selected from these crop and weed species and also winter barley (*Hordeum vulgare*), blackgrass (*Alopecurus myosuroides*), canarygrass (*Phalaris minor*), chickweed (*Stellaria media*), downy brome (*Bromus tectorum*), green foxtail (*Setaria viridis*), Italian ryegrass (*Lolium multiflorum*), wheat (*Triticum aestivum*), wild oat (*Avena fatua*) and windgrass (*Apera spica-venti*) were treated with postemergence applications of some of the test chemicals formulated in the same manner. Plants ranged in height from 2 to 18 cm (1- to 4-leaf stage) for postemergence treatments. Plant species in the flooded paddy test consisted of rice (*Oryza sativa*), umbrella sedge (*Cyperus difformis*), duck salad (*Heteranthera limosa*) and barnyardgrass (*Echinochloa crus-galli*) grown to the 2-leaf stage for testing. Treated plants and controls were maintained in a greenhouse for 12 to 14 days, after which time all species were compared to controls and visually evaluated. Plant response ratings, summarized in Table C, are based on a scale of 0 to 100 where 0 is no effect and 100 is complete control. A dash (-) response means no test result.

TABLE C

| | Compounds | | | | | | | | | | | | |
|---|---|---|---|---|---|---|---|---|---|---|---|---|---|
| | 1 | 2 | 4 | 5 | 9 | 14 | 15 | 16 | 17 | 19 | 22 | 26 | 37 |
| | Flood | | | | | | | | | | | | |
| 500 g ai/ha | | | | | | | | | | | | | |
| Barnyardgrass | 25 | 75 | 85 | 20 | 85 | 45 | 75 | 50 | 50 | 60 | 70 | 0 | 0 |
| Ducksalad | 0 | 95 | 100 | 0 | 90 | 55 | 85 | 85 | 80 | 60 | 95 | 40 | 100 |
| Rice | 0 | 65 | 80 | 0 | 75 | 0 | 50 | 65 | 75 | 20 | 60 | 25 | 0 |
| Sedge, Umbrella | 0 | 25 | 75 | 0 | 85 | 30 | 25 | 55 | 25 | 50 | 95 | 20 | 95 |
| 250 g ai/ha | | | | | | | | | | | | | |
| Barnyardgrass | 15 | 45 | 65 | 0 | 55 | 0 | 25 | 15 | 0 | 0 | 40 | 0 | 0 |
| Ducksalad | 0 | 90 | 90 | 0 | 80 | 45 | 50 | 75 | 80 | 60 | 90 | 40 | 100 |
| Rice | 0 | 45 | 75 | 0 | 55 | 0 | 20 | 0 | 45 | 10 | 40 | 20 | 0 |
| Sedge, Umbrella | 0 | 0 | 65 | 0 | 15 | 0 | 10 | 50 | 20 | 50 | 75 | 20 | 90 |
| 125 g ai/ha | | | | | | | | | | | | | |
| Barnyardgrass | 0 | 20 | 60 | 0 | 15 | 0 | 0 | 0 | 0 | 0 | 0 | 0 | 0 |
| Ducksalad | — | 70 | 80 | 0 | 70 | 40 | 45 | 65 | 0 | 40 | 60 | 40 | 95 |
| Rice | 0 | 25 | 40 | 0 | 30 | 0 | 0 | 0 | 0 | 0 | 20 | 0 | 0 |
| Sedge, Umbrella | — | 0 | 30 | 0 | 15 | 0 | 0 | 0 | 0 | 50 | 30 | 0 | 85 |
| 62 g ai/ha | | | | | | | | | | | | | |
| Barnyardgrass | 0 | 0 | 0 | 0 | 0 | 0 | 0 | 0 | 0 | 0 | 0 | 0 | 0 |
| Ducksalad | 0 | 50 | 70 | 0 | 45 | 0 | 45 | 65 | 0 | 20 | 30 | 40 | 95 |
| Rice | 0 | 0 | 0 | 0 | 0 | 0 | 0 | 0 | 0 | 0 | 20 | 0 | 0 |
| Sedge, Umbrella | 0 | 0 | 0 | 0 | 0 | 0 | 0 | — | 0 | 20 | 0 | 0 | 85 |

| | Compounds | | | | | | | | | | | | |
|---|---|---|---|---|---|---|---|---|---|---|---|---|---|
| 500 g ai/ha | 1 | 4 | 5 | 7 | 8 | 10 | 15 | 22 | 27 | 28 | 35 | 37 | 49 | 50 |
| | Postemergence | | | | | | | | | | | | |
| Barley | — | 65 | — | — | — | — | — | — | — | — | 45 | — | 40 | — |
| Bermudagrass | 90 | 80 | 80 | 0 | 75 | 0 | 75 | 60 | 30 | 0 | — | 20 | 65 | 95 |
| Blackgrass | — | 70 | — | — | — | — | — | — | — | — | 65 | — | 60 | — |
| Bromegrass, Downy | — | 70 | — | — | — | — | — | — | — | — | 40 | — | 30 | — |
| Canarygrass | — | 60 | — | — | — | — | — | — | — | — | 55 | — | 40 | — |
| Chickweed | — | 100 | — | 0 | 100 | 70 | 85 | 90 | 0 | 20 | — | 0 | 45 | 20 |
| Cocklebur | 100 | 100 | 100 | 30 | 100 | 75 | 100 | 100 | 25 | 100 | — | 95 | 95 | 90 |
| Corn | 45 | 95 | 45 | 0 | 90 | 0 | 75 | 65 | 0 | 0 | — | 25 | 25 | 65 |
| Crabgrass | 90 | 80 | 80 | 25 | 75 | 0 | 80 | 85 | 30 | 20 | — | 60 | 95 | 80 |
| Cupgrass, Woolly | 90 | 95 | 70 | 20 | 85 | 0 | 75 | 65 | 0 | 0 | — | 45 | 65 | 30 |
| Foxtail, Giant | 90 | 95 | 60 | 10 | 75 | 0 | 70 | 60 | 0 | 15 | — | 45 | 0 | 20 |
| Foxtail, Green | — | 75 | — | — | — | — | — | — | — | — | 65 | — | 60 | — |
| Goosegrass | 70 | 75 | 50 | 0 | 60 | 0 | 55 | 50 | 0 | 15 | — | 0 | 25 | 0 |
| Johnsongrass | 70 | 95 | 45 | 0 | 85 | 0 | 80 | 100 | 0 | 0 | — | 55 | 70 | 60 |
| Kochia | 100 | 100 | 100 | 80 | 100 | 100 | 100 | 100 | 60 | 95 | — | 95 | 100 | 95 |
| Lambsquarters | 100 | 100 | 100 | 80 | 100 | 100 | 100 | 95 | 50 | 95 | — | 95 | 95 | 85 |
| Morningglory | 100 | 100 | 100 | 65 | 100 | 95 | 100 | 100 | 85 | 95 | — | 95 | 100 | 95 |
| Nutsedge, Yellow | 5 | 0 | 0 | 0 | 0 | 0 | 0 | 0 | 0 | 0 | — | 20 | 0 | 0 |
| Oat, Wild | — | 70 | — | — | — | — | — | — | — | — | 55 | — | 60 | — |
| Pigweed | 100 | 100 | 100 | 55 | 100 | 95 | 100 | 100 | 80 | 75 | — | 100 | 95 | 95 |
| Ragweed | 100 | 100 | 100 | 75 | 100 | 90 | 95 | 90 | 50 | 95 | — | 95 | 90 | 80 |
| Ryegrass, Italian | — | 65 | — | — | — | — | — | — | — | — | 40 | — | 50 | — |
| Soybean | 100 | 100 | 100 | 60 | 100 | 100 | 100 | 100 | 95 | 95 | — | 100 | 100 | 100 |
| Surinam Grass | 95 | 95 | 70 | 0 | 80 | 0 | 65 | 85 | 0 | 0 | — | 0 | 45 | 60 |
| Velvetleaf | 100 | 100 | 95 | 40 | 95 | 90 | 90 | 95 | 30 | 75 | — | 95 | 80 | 80 |
| Wheat | — | 65 | — | — | — | — | — | — | — | — | 45 | — | 60 | — |
| Windgrass | — | 75 | — | — | — | — | — | — | — | — | 65 | — | 60 | — |

| | Compound |
|---|---|
| 500 g ai/ha | 51 |
| | Postemergence |
| Bermudagrass | 0 |
| Chickweed | 45 |
| Cocklebur | 85 |
| Corn | 0 |
| Crabgrass | 45 |
| Cupgrass, Woolly | 0 |
| Foxtail, Giant | 0 |
| Goosegrass | 0 |
| Johnsongrass | 0 |
| Kochia | 95 |

TABLE C-continued

|  |  |  |
|---|---|---|
| Lambsquarters | | 90 |
| Morningglory | | 100 |
| Nutsedge, Yellow | | 0 |
| Pigweed | | 85 |
| Ragweed | | 85 |
| Soybean | | 95 |
| Surinam Grass | | 0 |
| Velvetleaf | | 65 |

| | Compounds | | | | | | | | | | | | |
|---|---|---|---|---|---|---|---|---|---|---|---|---|---|
| 250 g ai/ha | 1 | 2 | 3 | 4 | 5 | 7 | 8 | 9 | 10 | 15 | 16 | 17 | 22 | 27 |
| | Postemergence | | | | | | | | | | | | |
| Barley | — | 60 | 30 | 65 | — | — | — | — | — | — | — | — | — | — |
| Bermudagrass | 90 | 80 | 45 | 70 | 70 | 0 | 65 | 80 | 0 | 65 | 75 | 0 | 60 | 0 |
| Blackgrass | — | 75 | 0 | 70 | — | — | — | — | — | — | — | — | — | — |
| Bromegrass, Downy | — | 60 | 20 | 65 | — | — | — | — | — | — | — | — | — | — |
| Canarygrass | — | 40 | 10 | 60 | — | — | — | — | — | — | — | — | — | — |
| Chickweed | 90 | 95 | 40 | 100 | 20 | 0 | 95 | 100 | 20 | 65 | 35 | 85 | 85 | 0 |
| Cocklebur | 100 | 85 | 90 | 100 | 100 | 30 | 100 | 100 | 60 | 100 | 100 | 100 | 100 | 25 |
| Corn | 40 | 30 | 0 | 90 | 40 | 0 | 70 | 95 | 0 | 55 | 55 | 20 | 60 | 0 |
| Crabgrass | 85 | 70 | 0 | 75 | 70 | 5 | 70 | 80 | 0 | 65 | 75 | 65 | 85 | 5 |
| Cupgrass, Woolly | 90 | 75 | 0 | 85 | 50 | 0 | 75 | 85 | 0 | 65 | 65 | 20 | 60 | 0 |
| Foxtail, Giant | 80 | 70 | 0 | 85 | 50 | 0 | 70 | 80 | 0 | 65 | 65 | 35 | 50 | 0 |
| Foxtail, Green | — | 70 | 35 | 70 | — | — | — | — | — | — | — | — | — | — |
| Goosegrass | 40 | 45 | 0 | 65 | 40 | 0 | 45 | 45 | 0 | 40 | 20 | 0 | 20 | 0 |
| Johnsongrass | 70 | 60 | 0 | 95 | 45 | 0 | 45 | 85 | 0 | 70 | 70 | 60 | 80 | 0 |
| Kochia | 100 | 100 | 100 | 100 | 100 | 70 | 100 | 100 | 95 | 100 | 100 | 100 | 100 | 50 |
| Lambsquarters | 100 | 100 | 100 | 100 | 100 | 70 | 100 | 100 | 90 | 100 | 100 | 100 | 95 | 25 |
| Morningglory | 100 | 100 | 75 | 100 | 100 | 55 | 100 | 100 | 95 | 100 | 100 | 100 | 95 | 85 |
| Nutsedge, Yellow | 5 | 20 | 0 | 0 | 0 | 0 | 0 | 0 | 0 | 0 | 0 | 0 | 0 | 0 |
| Oat, Wild | — | 60 | 40 | 70 | — | — | — | — | — | — | — | — | — | — |
| Pigweed | 100 | 100 | 80 | 100 | 90 | 40 | 100 | 100 | 95 | 85 | 95 | 95 | 100 | 30 |
| Ragweed | 100 | 95 | 95 | 100 | 95 | 65 | 95 | 100 | 80 | 90 | 95 | 95 | 90 | 40 |
| Ryegrass, Italian | — | 60 | 35 | 65 | — | — | — | — | — | — | — | — | — | — |
| Soybean | 100 | 100 | 95 | 100 | 100 | 35 | 100 | 100 | 90 | 95 | 100 | 100 | 100 | 85 |
| Surinam Grass | 90 | 70 | 0 | 75 | 30 | 0 | 70 | 80 | 0 | 55 | 55 | 0 | 85 | 0 |
| Velvetleaf | 100 | 100 | 70 | 100 | 90 | 35 | 85 | 95 | 80 | 85 | 90 | 95 | 90 | 0 |
| Wheat | — | 65 | 10 | 65 | — | — | — | — | — | — | — | — | — | — |
| Windgrass | — | 70 | 30 | 70 | — | — | — | — | — | — | — | — | — | — |

| | Compounds | | | | | | | | | | |
|---|---|---|---|---|---|---|---|---|---|---|---|
| 250 g ai/ha | 28 | 30 | 34 | 35 | 37 | 42 | 49 | 50 | 51 | 64 | 78 | 88 |
| | Postemergence | | | | | | | | | | |
| Barley | — | — | 40 | 40 | — | — | 30 | — | — | 100 | 90 | — |
| Bermudagrass | 0 | 5 | — | — | 0 | 5 | 55 | 90 | 0 | 70 | 65 | 80 |
| Blackgrass | — | — | 45 | 60 | — | — | 50 | — | — | 50 | 50 | — |
| Bromegrass, Downy | — | — | 35 | 40 | — | — | 0 | — | — | 20 | 55 | — |
| Canarygrass | — | — | 45 | 45 | — | — | 30 | — | — | 10 | 0 | — |
| Chickweed | 15 | 85 | — | — | 0 | 10 | 40 | — | 0 | 55 | 70 | 100 |
| Cocklebur | 95 | 100 | — | — | 95 | 20 | 95 | 65 | 70 | — | 100 | 90 |
| Corn | 0 | 50 | — | — | 15 | 0 | 20 | 60 | 0 | — | 40 | 30 |
| Crabgrass | 0 | 50 | — | — | 40 | 0 | 75 | 75 | 0 | 90 | 90 | 85 |
| Cupgrass, Woolly | 0 | 40 | — | — | 0 | 5 | 60 | 15 | 0 | — | 90 | 85 |
| Foxtail, Giant | 0 | 40 | — | — | 40 | 0 | 0 | 0 | 0 | 50 | 70 | 85 |
| Foxtail, Green | — | — | 45 | 60 | — | — | 50 | — | — | 45 | 75 | — |
| Goosegrass | 0 | 0 | — | — | 0 | 0 | 20 | 0 | 0 | 70 | 50 | 80 |
| Johnsongrass | 0 | 40 | — | — | — | 10 | 35 | — | 0 | 85 | 40 | 85 |
| Kochia | 95 | 100 | — | — | 95 | 85 | 95 | 65 | 85 | 90 | 95 | 95 |
| Lambsquarters | 85 | 90 | — | — | 95 | 25 | 95 | 80 | 85 | 90 | 100 | 100 |
| Morningglory | 95 | 95 | — | — | 80 | 85 | 80 | 85 | 85 | 90 | 100 | 85 |
| Nutsedge, Yellow | 0 | 5 | — | — | 0 | 0 | 0 | 0 | 0 | 50 | 0 | 75 |
| Oat, Wild | — | — | 50 | 45 | — | — | 40 | — | — | 10 | 60 | — |
| Pigweed | 60 | 90 | — | — | 100 | 30 | 95 | 85 | 80 | 100 | 100 | 100 |
| Ragweed | 90 | 90 | — | — | 90 | 40 | 75 | 45 | 80 | 90 | 100 | 100 |
| Ryegrass, Italian | — | — | 60 | 40 | — | — | 50 | — | — | 45 | 25 | — |
| Soybean | 95 | 95 | — | — | 95 | 70 | 95 | 100 | 95 | 100 | 100 | 100 |
| Surinam Grass | 0 | 35 | — | — | 0 | 0 | 40 | 0 | 0 | — | 90 | 85 |
| Velvetleaf | 70 | 60 | — | — | 90 | 20 | 75 | 70 | 60 | 95 | 100 | 95 |

TABLE C-continued

| | | | | | | | | | | | | | |
|---|---|---|---|---|---|---|---|---|---|---|---|---|---|
| Wheat | — | — | 35 | 45 | — | — | 50 | — | — | 10 | 55 | — | |
| Windgrass | — | — | 60 | 65 | — | — | 60 | — | — | 60 | 40 | — | |

| | Compounds | | | | | | | | | | | | |
|---|---|---|---|---|---|---|---|---|---|---|---|---|---|
| 125 g ai/ha | 1 | 2 | 3 | 4 | 5 | 7 | 8 | 9 | 10 | 11 | 15 | 16 | 17 | 19 |

| Postemergence | | | | | | | | | | | | | | |
|---|---|---|---|---|---|---|---|---|---|---|---|---|---|---|
| Barley | — | 60 | 0 | 65 | — | — | — | — | — | — | — | — | — | 45 |
| Bermudagrass | 90 | 70 | 0 | 65 | 50 | 0 | 60 | 70 | 0 | 0 | 45 | 60 | 0 | 45 |
| Blackgrass | — | 70 | 0 | 65 | — | — | — | — | — | — | — | — | — | 65 |
| Bromegrass, Downy | — | 45 | 20 | 60 | — | — | — | — | — | — | — | — | — | 60 |
| Canarygrass | — | 40 | 10 | 45 | — | — | — | — | — | — | — | — | — | 65 |
| Chickweed | — | 75 | 0 | 85 | 10 | 0 | 75 | 100 | 0 | 0 | 50 | 20 | 55 | 5 |
| Cocklebur | 100 | 85 | 75 | 100 | 95 | 30 | 100 | 100 | 15 | 40 | 100 | 100 | 100 | 90 |
| Corn | 15 | 20 | 0 | 80 | 40 | 0 | 20 | 65 | 0 | 0 | 15 | 20 | 0 | 35 |
| Crabgrass | 85 | 60 | 0 | 75 | 50 | 0 | 65 | 75 | 0 | 20 | 45 | 45 | 20 | 70 |
| Cupgrass, Woolly | 80 | 70 | 0 | 70 | 50 | 0 | 60 | 70 | 0 | 0 | 50 | 0 | 0 | 65 |
| Foxtail, Giant | 65 | 65 | 0 | 75 | 30 | 0 | 60 | 75 | 0 | 0 | 60 | 55 | 0 | 55 |
| Foxtail, Green | — | 65 | 35 | 70 | — | — | — | — | — | — | — | — | — | 60 |
| Goosegrass | 0 | 0 | 0 | 20 | 5 | 0 | 0 | 40 | 0 | 0 | 0 | 0 | 0 | 0 |
| Johnsongrass | 30 | 25 | 0 | 80 | 40 | 0 | 35 | 80 | 0 | 0 | 55 | 60 | 40 | — |
| Kochia | 100 | 95 | 90 | 100 | 100 | 65 | 100 | 100 | 90 | 90 | 95 | 100 | 100 | 90 |
| Lambsquarters | 100 | 100 | 90 | 100 | 100 | 60 | 100 | 100 | 80 | 80 | 100 | 100 | 100 | 95 |
| Morningglory | 100 | 100 | 65 | 100 | 95 | 50 | 95 | 100 | 85 | 0 | 95 | 100 | 100 | 85 |
| Nutsedge, Yellow | 0 | 0 | 0 | 0 | 0 | 0 | 0 | 0 | 0 | 0 | 0 | 0 | 0 | 0 |
| Oat, Wild | — | 55 | 40 | 65 | — | — | — | — | — | — | — | — | — | 65 |
| Pigweed | 100 | 95 | 75 | 100 | 90 | 40 | 75 | 100 | 80 | 90 | 70 | 95 | 75 | 65 |
| Ragweed | 100 | 90 | 80 | 100 | 95 | 35 | 80 | 95 | 65 | 75 | 85 | 95 | 95 | 80 |
| Ryegrass, Italian | — | 60 | 35 | 60 | — | — | — | — | — | — | — | — | — | 70 |
| Soybean | 100 | 100 | 90 | 100 | 100 | 25 | 95 | 100 | 80 | 95 | 95 | 100 | 100 | 75 |
| Surinam Grass | 90 | 65 | 0 | 75 | 20 | 0 | 65 | 75 | 0 | 0 | 20 | 25 | 0 | — |
| Velvetleaf | 90 | 80 | 55 | 100 | 90 | 10 | 70 | 80 | 70 | 75 | 70 | 65 | 80 | 60 |
| Wheat | — | 65 | 0 | 60 | — | — | — | — | — | — | — | — | — | 45 |
| Windgrass | — | 70 | 30 | 65 | — | — | — | — | — | — | — | — | — | 60 |

| | Compounds | | | | | | | | | | | | |
|---|---|---|---|---|---|---|---|---|---|---|---|---|---|
| 125 g ai/ha | 22 | 25 | 27 | 28 | 30 | 34 | 35 | 37 | 42 | 47 | 49 | 50 | 51 | 64 |

| Postemergence | | | | | | | | | | | | | | |
|---|---|---|---|---|---|---|---|---|---|---|---|---|---|---|
| Barley | — | — | — | — | — | 30 | 35 | — | — | — | 20 | — | — | — |
| Bermudagrass | 60 | 0 | 0 | 0 | 5 | — | — | 0 | 0 | 15 | 55 | 75 | 0 | 65 |
| Blackgrass | — | — | — | — | — | 35 | 50 | — | — | — | 40 | — | — | 50 |
| Bromegrass, Downy | — | — | — | — | — | 30 | 30 | — | — | — | 0 | — | — | 20 |
| Canarygrass | — | — | — | — | — | 35 | 45 | — | — | — | 20 | — | — | 10 |
| Chickweed | 60 | 85 | 0 | 0 | 65 | — | — | 0 | 0 | 0 | 0 | 0 | 0 | 0 |
| Cocklebur | 90 | 90 | 25 | 95 | 100 | — | — | 95 | 5 | 65 | 95 | 40 | 65 | 100 |
| Corn | 40 | 0 | 0 | 0 | 0 | — | — | 10 | 0 | 0 | 0 | 0 | 0 | 50 |
| Crabgrass | 55 | 50 | 0 | 0 | 5 | — | — | 15 | 0 | 20 | 65 | 60 | 0 | 85 |
| Cupgrass, Woolly | 60 | 30 | 0 | 0 | 0 | — | — | 0 | 0 | 0 | 15 | 0 | 0 | 65 |
| Foxtail, Giant | 45 | 30 | 0 | 0 | 0 | — | — | 0 | 0 | 0 | 0 | 0 | 0 | 50 |
| Foxtail, Green | — | — | — | — | — | 45 | 50 | — | — | — | 20 | — | — | 40 |
| Goosegrass | 10 | 0 | 0 | 0 | 0 | — | — | 0 | 0 | 0 | 0 | 0 | 0 | 60 |
| Johnsongrass | 80 | 20 | 0 | 0 | 10 | — | — | 20 | 0 | 0 | 20 | — | — | 85 |
| Kochia | 100 | 85 | 20 | 85 | 100 | — | — | 90 | 50 | 100 | 45 | 55 | 60 | 90 |
| Lambsquarters | 95 | 90 | 20 | 75 | 80 | — | — | 95 | 20 | 80 | 90 | 75 | 75 | 90 |
| Morningglory | 90 | 90 | 85 | 95 | 95 | — | — | 65 | 80 | 65 | 70 | 80 | 80 | 90 |
| Nutsedge, Yellow | 0 | 0 | 0 | 0 | 0 | — | — | 0 | 0 | 0 | 0 | 0 | 0 | 50 |
| Oat, Wild | — | — | — | — | — | 45 | 45 | — | — | — | 40 | — | — | 10 |
| Pigweed | 100 | 100 | 20 | 35 | 80 | — | — | 95 | 20 | 70 | 80 | 80 | 70 | 100 |
| Ragweed | 85 | 70 | 20 | 80 | 85 | — | — | 80 | 40 | 80 | 65 | 45 | 80 | 85 |
| Ryegrass, Italian | — | — | — | — | — | 45 | 40 | — | — | — | 30 | — | — | 35 |
| Soybean | 100 | 90 | 45 | 85 | 90 | — | — | 85 | 40 | 75 | 95 | 95 | 95 | 100 |
| Surinam Grass | 60 | 5 | 0 | 0 | 0 | — | — | 0 | 0 | 20 | 0 | 0 | 0 | 60 |
| Velvetleaf | 60 | 45 | 0 | 50 | 60 | — | — | 85 | 0 | 0 | 70 | 55 | 20 | 90 |
| Wheat | — | — | — | — | — | 30 | 40 | — | — | — | 40 | — | — | 10 |
| Windgrass | — | — | — | — | — | 50 | 55 | — | — | — | 40 | — | — | 55 |

| | Compounds | | | | | | | | | | |
|---|---|---|---|---|---|---|---|---|---|---|---|
| 125 g ai/ha | 65 | 76 | 78 | 79 | 83 | 88 | 94 | 117 | 129 | 133 | 135 | 136 |

| Postemergence | | | | | | | | | | | | |
|---|---|---|---|---|---|---|---|---|---|---|---|---|
| Barley | 50 | — | 30 | 35 | — | — | — | — | 45 | — | — | 55 |
| Bermudagrass | 70 | 75 | 60 | — | 55 | 70 | 80 | 90 | — | 85 | 75 | 85 |
| Blackgrass | 65 | — | 5 | 60 | — | — | — | — | 50 | — | — | 65 |

TABLE C-continued

| | | | | | | | | | | | | |
|---|---|---|---|---|---|---|---|---|---|---|---|---|
| Bromegrass, Downy | 55 | — | 15 | 35 | — | — | — | — | 0 | — | — | 55 |
| Canarygrass | 45 | — | 0 | 35 | — | — | — | — | 30 | — | — | 65 |
| Chickweed | 70 | 95 | — | — | 30 | 100 | 95 | — | — | 45 | 85 | 50 |
| Cocklebur | 100 | 100 | 100 | — | 100 | 90 | 100 | 90 | — | 95 | 100 | 100 |
| Corn | 90 | 70 | 40 | — | 60 | — | 60 | — | — | 80 | 35 | 75 |
| Crabgrass | 90 | 90 | 90 | — | 75 | 80 | 85 | 90 | — | 80 | 75 | 75 |
| Cupgrass, Woolly | 85 | 95 | — | — | 60 | 85 | 90 | 85 | — | 70 | 80 | 70 |
| Foxtail, Giant | 70 | 85 | 65 | — | 40 | 80 | 80 | 80 | — | 75 | 75 | 85 |
| Foxtail, Green | 70 | — | 70 | 60 | — | — | — | — | 60 | — | — | 70 |
| Goosegrass | 70 | 50 | 40 | — | 45 | 75 | 80 | 80 | — | 70 | 55 | 80 |
| Johnsongrass | 85 | 95 | 20 | — | 70 | 75 | 90 | 50 | — | 95 | 70 | 95 |
| Kochia | 90 | 100 | 95 | — | 90 | 95 | 100 | 90 | — | 85 | 95 | 90 |
| Lambsquarters | 95 | 100 | 95 | — | 100 | 95 | 100 | 95 | — | 100 | 95 | 95 |
| Morningglory | 95 | 100 | 100 | — | 90 | 85 | 100 | 50 | — | 100 | 95 | 100 |
| Nutsedge, Yellow | 50 | 60 | 0 | — | 75 | 55 | 75 | 60 | — | 80 | 40 | 75 |
| Oat, Wild | 40 | — | 60 | 45 | — | — | — | — | 40 | — | — | 60 |
| Pigweed | 100 | 100 | 95 | — | 100 | 100 | 100 | 95 | — | 100 | 100 | 100 |
| Ragweed | 95 | 100 | 95 | — | 95 | 100 | 100 | 100 | — | 95 | 95 | 95 |
| Ryegrass, Italian | 60 | — | 20 | 45 | — | — | — | — | 60 | — | — | 65 |
| Soybean | 100 | 100 | 100 | — | 100 | 100 | 100 | 100 | — | 100 | 100 | 100 |
| Surinam Grass | 80 | — | 55 | — | 65 | 80 | 100 | 80 | — | 70 | 60 | 70 |
| Velvetleaf | 90 | 95 | 95 | — | 100 | 95 | 95 | 95 | — | 95 | 95 | 95 |
| Wheat | 45 | — | 30 | 40 | — | — | — | — | 35 | — | — | 55 |
| Windgrass | 70 | — | 30 | 50 | — | — | — | — | 60 | — | — | 65 |

| | Compounds | | | | | | | | | | | | |
|---|---|---|---|---|---|---|---|---|---|---|---|---|---|
| 62 g ai/ha | 1 | 2 | 3 | 4 | 5 | 7 | 8 | 9 | 10 | 11 | 15 | 16 | 17 | 19 |
| | Postemergence | | | | | | | | | | | | |
| Barley | — | 35 | 0 | 30 | — | — | — | — | — | — | — | — | — | 35 |
| Bermudagrass | 70 | 60 | 0 | 40 | 5 | 0 | 50 | 65 | 0 | 0 | 0 | 0 | 0 | 30 |
| Blackgrass | — | 65 | 0 | 65 | — | — | — | — | — | — | — | — | — | 65 |
| Bromegrass, Downy | — | 35 | 20 | 45 | — | — | — | — | — | — | — | — | — | 50 |
| Canarygrass | — | 40 | 10 | 35 | — | — | — | — | — | — | — | — | — | 60 |
| Chickweed | 80 | 65 | 0 | 30 | 0 | 0 | 20 | 85 | 0 | 0 | 20 | 0 | 0 | 5 |
| Cocklebur | 90 | 75 | 65 | 85 | 80 | 30 | 80 | 85 | 0 | 25 | 85 | 95 | 100 | 50 |
| Corn | 10 | 15 | 0 | 0 | 10 | 0 | 0 | 55 | 0 | 0 | 15 | 0 | 0 | 0 |
| Crabgrass | 30 | 55 | 0 | 70 | 40 | 0 | 60 | 70 | 0 | 0 | 15 | 15 | 0 | 70 |
| Cupgrass, Woolly | 65 | 60 | 0 | 60 | 5 | 0 | 30 | 60 | 0 | 0 | 0 | 0 | 0 | 65 |
| Foxtail, Giant | 40 | 35 | 0 | 60 | 20 | 0 | 40 | 65 | 0 | 0 | 45 | 20 | 0 | 40 |
| Foxtail, Green | — | 55 | 30 | 65 | — | — | — | — | — | — | — | — | — | 45 |
| Goosegrass | 0 | 0 | 0 | 0 | 0 | 0 | 0 | 0 | 0 | 0 | 0 | 0 | 0 | 0 |
| Johnsongrass | 30 | 0 | 0 | 70 | 0 | 0 | 30 | 65 | 0 | 0 | 20 | 0 | 0 | 0 |
| Kochia | 100 | 95 | 65 | 100 | 100 | 40 | 95 | 100 | 80 | 75 | 95 | 100 | 100 | 90 |
| Lambsquarters | 100 | 100 | 90 | 100 | 95 | 50 | 75 | 95 | 60 | 70 | 100 | 100 | 100 | 90 |
| Morningglory | 100 | 75 | 60 | 15 | 95 | — | 95 | 95 | 70 | 0 | 90 | 95 | 95 | 80 |
| Nutsedge, Yellow | 0 | 0 | 0 | 0 | 0 | 0 | 0 | 0 | 0 | 0 | 0 | 0 | 0 | 0 |
| Oat, Wild | — | 55 | 30 | 60 | — | — | — | — | — | — | — | — | — | 60 |
| Pigweed | 90 | 80 | 65 | 100 | 85 | 20 | 70 | 70 | 65 | 80 | 65 | 90 | 65 | 65 |
| Ragweed | 100 | 85 | 75 | 100 | 90 | 25 | 60 | 80 | 45 | 65 | 75 | 85 | 85 | 70 |
| Ryegrass, Italian | — | 45 | 35 | 45 | — | — | — | — | — | — | — | — | — | 65 |
| Soybean | 100 | 100 | 75 | 100 | 95 | 25 | 95 | 100 | 70 | 80 | 95 | 95 | 95 | 75 |
| Surinam Grass | 90 | 55 | 0 | 60 | 0 | 0 | 40 | 65 | 0 | 0 | 0 | 0 | 0 | 45 |
| Velvetleaf | 85 | 70 | 55 | 80 | 55 | 0 | 60 | 75 | 65 | 60 | 65 | 60 | 50 | 50 |
| Wheat | — | 60 | 0 | 50 | — | — | — | — | — | — | — | — | — | 40 |
| Windgrass | — | 65 | 30 | 60 | — | — | — | — | — | — | — | — | — | 60 |

| | Compounds | | | | | | | | | | | | |
|---|---|---|---|---|---|---|---|---|---|---|---|---|---|
| 62 g ai/ha | 22 | 25 | 27 | 28 | 30 | 34 | 35 | 37 | 42 | 47 | 49 | 50 | 51 | 64 |
| | Postemergence | | | | | | | | | | | | |
| Barley | — | — | — | — | — | 20 | 20 | — | — | — | 0 | — | — | 20 |
| Bermudagrass | 50 | 0 | 0 | 0 | 0 | — | — | 0 | 0 | 0 | 0 | 50 | 0 | 60 |
| Blackgrass | — | — | — | — | — | 35 | 50 | — | — | — | 40 | — | — | 45 |
| Bromegrass, Downy | — | — | — | — | — | 0 | 30 | — | — | — | 0 | — | — | 15 |
| Canarygrass | — | — | — | — | — | 30 | 35 | — | — | — | 0 | — | — | 5 |
| Chickweed | 30 | 40 | 0 | 0 | 50 | — | — | 0 | 0 | 0 | 0 | 0 | 0 | 0 |
| Cocklebur | 90 | 90 | 20 | 85 | 95 | — | — | 0 | 0 | 60 | 75 | 40 | 65 | 90 |
| Corn | 30 | 0 | 0 | 0 | 0 | — | — | 0 | 0 | 0 | 0 | 0 | 0 | 50 |
| Crabgrass | 50 | 30 | 0 | 0 | 0 | — | — | 0 | 0 | 0 | 0 | 60 | 0 | 80 |
| Cupgrass, Woolly | 60 | 0 | 0 | 0 | 0 | — | — | 0 | 0 | 0 | 0 | 0 | 0 | 40 |
| Foxtail, Giant | 40 | 5 | 0 | 0 | 0 | — | — | 0 | 0 | 0 | 0 | 0 | 0 | 20 |
| Foxtail, Green | — | — | — | — | — | 40 | 40 | — | — | — | 0 | — | — | 30 |
| Goosegrass | 10 | 0 | 0 | 0 | 0 | — | — | 0 | 0 | 0 | 0 | 0 | 0 | 35 |
| Johnsongrass | 40 | 10 | 0 | 0 | 5 | — | — | 0 | 0 | 0 | — | 0 | 0 | 80 |
| Kochia | 95 | 85 | 0 | 75 | 90 | — | — | 0 | 30 | 20 | 20 | 20 | 15 | 85 |

TABLE C-continued

| | | | | | | | | | | | | | | |
|---|---|---|---|---|---|---|---|---|---|---|---|---|---|---|
| Lambsquarters | 90 | 85 | 20 | 60 | 60 | — | — | 0 | 20 | 70 | 70 | 70 | 60 | 90 |
| Morningglory | 90 | 90 | 20 | 80 | 90 | — | — | 0 | 50 | 40 | 50 | 65 | 80 | 90 |
| Nutsedge, Yellow | 0 | 0 | 0 | 0 | 0 | — | — | 0 | 0 | 0 | 0 | 0 | 0 | 50 |
| Oat, Wild | — | — | — | — | — | 40 | 30 | — | — | — | 30 | — | — | 5 |
| Pigweed | 85 | 80 | 5 | 30 | 70 | — | — | 0 | 10 | 45 | 65 | 75 | 65 | 95 |
| Ragweed | 80 | 65 | 5 | 65 | 80 | — | — | 0 | 10 | 40 | 45 | 20 | 65 | 80 |
| Ryegrass, Italian | — | — | — | — | — | 40 | 40 | — | — | — | 30 | — | — | 30 |
| Soybean | 95 | 90 | 30 | 75 | 90 | — | — | 20 | 30 | 65 | 95 | 95 | 75 | 90 |
| Surinam Grass | 55 | 0 | 0 | 0 | 0 | — | — | 0 | 0 | 0 | 0 | 0 | 0 | 60 |
| Velvetleaf | 55 | 45 | 0 | 45 | 10 | — | — | 0 | 0 | 0 | 45 | 50 | 0 | 85 |
| Wheat | — | — | — | — | — | 20 | 35 | — | — | — | 20 | — | — | 0 |
| Windgrass | — | — | — | — | — | 40 | 40 | — | — | — | 40 | — | — | 55 |

| | Compounds | | | | | | | | | | | | | |
|---|---|---|---|---|---|---|---|---|---|---|---|---|---|---|
| 62 g ai/ha | 65 | 76 | 78 | 79 | 83 | 88 | 94 | 95 | 117 | 129 | 133 | 135 | 136 | |
| Postemergence | | | | | | | | | | | | | | |
| Barley | 50 | — | 5 | 35 | — | — | — | — | — | 45 | — | — | 50 | |
| Bermudagrass | 70 | 75 | 60 | — | 20 | 70 | 75 | 85 | 85 | — | 85 | 60 | 80 | |
| Blackgrass | 65 | — | 5 | 60 | — | — | — | — | — | 50 | — | — | 65 | |
| Bromegrass, Downy | 50 | — | 10 | 30 | — | — | — | — | — | 0 | — | — | 45 | |
| Canarygrass | 35 | — | 0 | 25 | — | — | — | — | — | 30 | — | — | 55 | |
| Chickweed | 60 | 70 | 0 | — | 10 | 100 | 50 | 95 | 40 | — | 20 | 25 | 50 | |
| Cocklebur | 100 | 100 | 100 | — | 70 | 90 | 90 | 100 | 90 | — | 95 | — | 100 | |
| Corn | 90 | 55 | 40 | — | 50 | 0 | 35 | 35 | — | — | 60 | 20 | 65 | |
| Crabgrass | 90 | 85 | 90 | — | 65 | 80 | 85 | 80 | 90 | — | 75 | 75 | 75 | |
| Cupgrass, Woolly | 85 | 80 | 55 | — | 45 | 75 | 90 | 80 | 80 | — | 60 | 60 | 70 | |
| Foxtail, Giant | 70 | 55 | 30 | — | 20 | 75 | 80 | 80 | 70 | — | 70 | 65 | 75 | |
| Foxtail, Green | 60 | — | 40 | 30 | — | — | — | — | — | 40 | — | — | 70 | |
| Goosegrass | 70 | 45 | 0 | — | 30 | 75 | 80 | 80 | 75 | — | 65 | 45 | 75 | |
| Johnsongrass | 85 | — | 10 | — | 55 | 45 | 75 | 90 | 50 | — | 90 | 65 | 85 | |
| Kochia | 85 | 95 | 90 | — | 75 | 95 | 95 | 95 | 90 | — | 85 | 90 | 90 | |
| Lambsquarters | 90 | 100 | 95 | — | 95 | 95 | 95 | 100 | 95 | — | 95 | 90 | 95 | |
| Morningglory | 90 | 95 | 90 | — | 90 | — | 90 | 95 | 50 | — | 100 | 95 | 90 | |
| Nutsedge, Yellow | 20 | 40 | 0 | — | 60 | 45 | 70 | 75 | 50 | — | 75 | 15 | 75 | |
| Oat, Wild | 20 | — | 10 | 25 | — | — | — | — | — | 40 | — | — | 55 | |
| Pigweed | 100 | 100 | 80 | — | 100 | 100 | 100 | 100 | 95 | — | 95 | 100 | 100 | |
| Ragweed | 95 | 95 | 85 | — | 75 | 100 | 95 | 95 | 100 | — | 85 | 85 | 90 | |
| Ryegrass, Italian | 55 | — | 10 | 40 | — | — | — | — | — | 55 | — | — | 60 | |
| Soybean | 100 | 95 | 100 | — | 100 | 100 | 100 | 100 | 100 | — | 100 | 100 | 100 | |
| Surinam Grass | 80 | 95 | 55 | — | 45 | 60 | 90 | 75 | 80 | — | 55 | 60 | 65 | |
| Velvetleaf | 80 | 95 | 80 | — | 85 | 90 | 95 | 100 | 95 | — | 85 | — | 90 | |
| Wheat | 45 | — | 20 | 30 | — | — | — | — | — | 35 | — | — | 45 | |
| Windgrass | 70 | — | 30 | 45 | — | — | — | — | — | 60 | — | — | 65 | |

| | Compounds | | | | | | | | | | | | | |
|---|---|---|---|---|---|---|---|---|---|---|---|---|---|---|
| 31 g ai/ha | 2 | 3 | 9 | 11 | 16 | 17 | 19 | 25 | 30 | 34 | 42 | 47 | 64 | 65 |
| Postemergence | | | | | | | | | | | | | | |
| Barley | 0 | 0 | — | — | — | — | 25 | — | — | 20 | — | — | 20 | 40 |
| Bermudagrass | 15 | 0 | 60 | 0 | 0 | 0 | 5 | 0 | 0 | — | 0 | 0 | 20 | 60 |
| Blackgrass | 60 | 0 | — | — | — | — | 60 | — | — | 0 | — | — | 40 | 60 |
| Bromegrass, Downy | 20 | 20 | — | — | — | — | 0 | — | — | 0 | — | — | 10 | 50 |
| Canarygrass | 30 | 10 | — | — | — | — | 60 | — | — | 20 | — | — | 5 | 30 |
| Chickweed | 60 | 0 | 15 | 0 | 0 | 0 | 0 | — | 40 | — | 0 | 0 | 0 | 60 |
| Cocklebur | 65 | 60 | 40 | 0 | 75 | 95 | 25 | 85 | 90 | — | 0 | 45 | 90 | 100 |
| Corn | 15 | 0 | 45 | 0 | 0 | 0 | 0 | 0 | 0 | — | 0 | 0 | 20 | 90 |
| Crabgrass | 40 | 0 | 60 | 0 | 0 | 0 | 40 | 0 | 0 | — | 0 | 0 | 70 | 80 |
| Cupgrass, Woolly | 40 | 0 | 40 | 0 | 0 | 0 | 25 | 0 | 0 | — | 0 | 0 | 30 | 80 |
| Foxtail, Giant | 0 | 0 | 60 | 0 | 0 | 0 | 5 | 0 | 0 | — | 0 | 0 | 0 | 60 |
| Foxtail, Green | 55 | 20 | — | — | — | — | 35 | — | — | 40 | — | — | 0 | 55 |
| Goosegrass | 0 | 0 | 0 | 0 | 0 | 0 | 0 | 0 | 0 | — | 0 | 0 | 35 | 50 |
| Johnsongrass | 0 | 0 | 55 | 0 | 0 | 0 | 0 | 10 | 0 | — | 0 | 0 | 60 | 60 |
| Kochia | 85 | 20 | 95 | 65 | 95 | 100 | 90 | 80 | 55 | — | 5 | 0 | 80 | 85 |
| Lambsquarters | 100 | 75 | 90 | 60 | 95 | 95 | 90 | 60 | 50 | — | 10 | 45 | 80 | 90 |
| Morningglory | 70 | 45 | 90 | 0 | 85 | 95 | 55 | 90 | 90 | — | 0 | 35 | 90 | 90 |
| Nutsedge, Yellow | 0 | 0 | 0 | 0 | 0 | 0 | 0 | 0 | 0 | — | 0 | 0 | 40 | 0 |
| Oat, Wild | 20 | 30 | — | — | — | — | 40 | — | — | 20 | — | — | 5 | 15 |
| Pigweed | 65 | 60 | 55 | 70 | 85 | 45 | 50 | 50 | 60 | — | 10 | 15 | 85 | 90 |
| Ragweed | 65 | 55 | 70 | 45 | 60 | 65 | 40 | 50 | 60 | — | 0 | 0 | 75 | 90 |
| Ryegrass, Italian | 35 | 35 | — | — | — | 65 | — | — | — | 40 | — | — | 5 | 50 |
| Soybean | 100 | 60 | 95 | 60 | 85 | 85 | 55 | 90 | 80 | — | 10 | 40 | 90 | 100 |
| Surinam Grass | 0 | 0 | 45 | 0 | 0 | 0 | 25 | 0 | 0 | — | 0 | 0 | 20 | 80 |
| Velvetleaf | 65 | 25 | 0 | 50 | 55 | 25 | 40 | 20 | 10 | — | 0 | 0 | 80 | 80 |

TABLE C-continued

| | | | | | | | | | | | | | |
|---|---|---|---|---|---|---|---|---|---|---|---|---|---|
| Wheat | 20 | 0 | — | — | — | — | 30 | — | — | 0 | — | — | 0 | 40 |
| Windgrass | 65 | 10 | — | — | — | — | 40 | — | — | 40 | — | — | 40 | 60 |

| | Compounds | | | | | | | | | | | |
|---|---|---|---|---|---|---|---|---|---|---|---|---|
| 31 g ai/ha | 76 | 78 | 79 | 83 | 88 | 94 | 95 | 117 | 129 | 133 | 135 | 136 |

Postemergence

| | 76 | 78 | 79 | 83 | 88 | 94 | 95 | 117 | 129 | 133 | 135 | 136 |
|---|---|---|---|---|---|---|---|---|---|---|---|---|
| Barley | — | 5 | 30 | — | — | — | — | — | 40 | — | — | 50 |
| Bermudagrass | 70 | 60 | — | 5 | 50 | 70 | 85 | 65 | — | 85 | — | 80 |
| Blackgrass | — | 0 | 40 | — | — | — | — | — | 45 | — | — | 55 |
| Bromegrass, Downy | — | 5 | 20 | — | — | — | — | — | 0 | — | — | — |
| Canarygrass | — | 0 | 20 | — | — | — | — | — | 30 | — | — | 45 |
| Chickweed | 45 | 0 | — | 0 | 80 | 45 | — | — | — | 10 | 15 | 50 |
| Cocklebur | 100 | 90 | — | 70 | 90 | 80 | 100 | — | — | 85 | 100 | 100 |
| Corn | 35 | 40 | — | 15 | 0 | 35 | — | 30 | — | 40 | 10 | 35 |
| Crabgrass | 75 | 55 | — | 45 | 75 | 80 | 80 | 90 | — | 75 | 75 | 75 |
| Cupgrass, Woolly | 60 | 50 | — | 15 | 70 | 80 | 75 | 80 | — | 50 | 60 | 65 |
| Foxtail, Giant | 25 | 0 | — | 0 | 55 | 65 | 75 | 55 | — | 60 | 60 | 75 |
| Foxtail, Green | — | 25 | 20 | — | — | — | — | — | 40 | — | — | 65 |
| Goosegrass | 45 | 0 | — | 10 | 50 | 60 | 75 | 40 | — | 55 | 35 | 65 |
| Johnsongrass | 65 | 10 | — | 55 | 30 | 60 | 75 | 50 | — | 85 | 35 | 85 |
| Kochia | 95 | 90 | — | 75 | 85 | 90 | 95 | 90 | — | 80 | 90 | 80 |
| Lambsquarters | 95 | 90 | — | 95 | 90 | 95 | 100 | 95 | — | 95 | 90 | 95 |
| Morningglory | 95 | 90 | — | 85 | 60 | 80 | 80 | 50 | — | 90 | 90 | 85 |
| Nutsedge, Yellow | 30 | 0 | — | 60 | 40 | 60 | 60 | 50 | — | 75 | 0 | 65 |
| Oat, Wild | — | 5 | 25 | — | — | — | — | — | 35 | — | — | 45 |
| Pigweed | 95 | 50 | — | 95 | 95 | 100 | 100 | 95 | — | 85 | 95 | 100 |
| Ragweed | 90 | 70 | — | 70 | 90 | 90 | 95 | 95 | — | 80 | 80 | 85 |
| Ryegrass, Italian | — | 0 | 35 | — | — | — | — | — | 55 | — | — | 50 |
| Soybean | 95 | 90 | — | 90 | 100 | 100 | 100 | 100 | — | 95 | — | 100 |
| Surinam Grass | 70 | 50 | — | 30 | 45 | 60 | 70 | 50 | — | 45 | 50 | 65 |
| Velvetleaf | 80 | 50 | — | 85 | 85 | 90 | 100 | 70 | — | 85 | 90 | 85 |
| Wheat | — | 20 | 20 | — | — | — | — | — | 35 | — | — | 40 |
| Windgrass | — | 5 | 40 | — | — | — | — | — | 45 | — | — | 60 |

| | Compounds | | | | | | | | | | | | |
|---|---|---|---|---|---|---|---|---|---|---|---|---|---|
| 16 g ai/ha | 11 | 19 | 25 | 47 | 65 | 76 | 79 | 83 | 94 | 95 | 117 | 129 | 133 | 135 |

Postemergence

| | 11 | 19 | 25 | 47 | 65 | 76 | 79 | 83 | 94 | 95 | 117 | 129 | 133 | 135 |
|---|---|---|---|---|---|---|---|---|---|---|---|---|---|---|
| Barley | — | 25 | — | — | 40 | — | 0 | — | — | — | — | 35 | — | — |
| Bermudagrass | 0 | 0 | 0 | 0 | 60 | 15 | — | 0 | 60 | 70 | 60 | — | 50 | 40 |
| Blackgrass | — | 55 | — | — | 50 | — | 20 | — | — | — | — | 35 | — | — |
| Bromegrass, Downy | — | 0 | — | — | 40 | — | 0 | — | — | — | — | 0 | — | — |
| Canarygrass | — | 45 | — | — | 30 | — | 0 | — | — | — | — | 0 | — | — |
| Chickweed | 0 | 0 | 0 | 0 | 60 | 35 | — | 0 | — | — | 30 | — | 0 | 0 |
| Cocklebur | 0 | 25 | 70 | 35 | 90 | 100 | — | 60 | 75 | 100 | 90 | — | 75 | 90 |
| Corn | 0 | 0 | 0 | 0 | 5 | 10 | — | 5 | 10 | 20 | 30 | — | 35 | 5 |
| Crabgrass | 0 | 20 | 0 | 0 | 80 | 55 | — | 25 | 70 | 75 | 85 | — | 50 | 65 |
| Cupgrass, Woolly | 0 | 0 | 0 | 0 | 60 | 55 | — | 15 | 60 | 75 | 60 | — | 35 | 30 |
| Foxtail, Giant | 0 | 0 | 0 | 0 | 50 | 15 | — | 0 | 30 | 50 | 50 | — | 15 | 10 |
| Foxtail, Green | — | 30 | — | — | 50 | — | 20 | — | — | — | — | 40 | — | — |
| Goosegrass | 0 | 0 | 0 | 0 | 50 | 30 | — | 10 | 35 | 65 | 40 | — | 15 | 5 |
| Johnsongrass | 0 | 0 | 0 | — | 45 | 25 | — | 10 | 55 | 70 | 10 | — | 70 | 15 |
| Kochia | 40 | 80 | 10 | 0 | 85 | 90 | — | 65 | 75 | 95 | 90 | — | 75 | 75 |
| Lambsquarters | 50 | 70 | 30 | 0 | 85 | 90 | — | 90 | 95 | 100 | 95 | — | 95 | 60 |
| Morningglory | 0 | — | 90 | 20 | 90 | 95 | — | 70 | 60 | — | 20 | — | 80 | 80 |
| Nutsedge, Yellow | 0 | 0 | 0 | 0 | 0 | 10 | — | 60 | 55 | 60 | 5 | — | 60 | 0 |
| Oat, Wild | — | 40 | — | — | 5 | — | 0 | — | — | — | — | 30 | — | — |
| Pigweed | 60 | 50 | 50 | 0 | 90 | 85 | — | 95 | 95 | 95 | 90 | — | 85 | 85 |
| Ragweed | 15 | 35 | 40 | 0 | 80 | 80 | — | 65 | 90 | 95 | 95 | — | 80 | 75 |
| Ryegrass, Italian | — | 65 | — | — | 10 | — | 35 | — | — | — | — | 45 | — | — |
| Soybean | 45 | 45 | 40 | 20 | 100 | 95 | — | 85 | 100 | 100 | 100 | — | 95 | 100 |
| Surinam Grass | 0 | 0 | 0 | 0 | 60 | 60 | — | 20 | 50 | 65 | 45 | — | 35 | 45 |
| Velvetleaf | 20 | 30 | 5 | 0 | 65 | 45 | — | 70 | 75 | 95 | 60 | — | 80 | 55 |

TABLE C-continued

| | | | | | | | | | | | | | | |
|---|---|---|---|---|---|---|---|---|---|---|---|---|---|---|
| Wheat | — | 10 | — | — | 40 | — | 0 | — | — | — | — | 0 | — | — |
| Windgrass | — | 40 | — | — | 50 | — | 40 | — | — | — | — | 40 | — | — |

| 16 g ai/ha | Compound 136 |
|---|---|
| Postemergence | |
| Barley | 40 |
| Bermudagrass | 75 |
| Blackgrass | 40 |
| Bromegrass, Downy | 30 |
| Canarygrass | 40 |
| Chickweed | 45 |
| Cocklebur | 95 |
| Corn | 35 |
| Crabgrass | 60 |
| Cupgrass, Woolly | 55 |
| Foxtail, Giant | 65 |
| Foxtail, Green | 45 |
| Goosegrass | 50 |
| Johnsongrass | 60 |
| Kochia | 75 |
| Lambsquarters | 95 |
| Morningglory | 65 |
| Nutsedge, Yellow | 60 |
| Oat, Wild | 40 |
| Pigweed | 90 |
| Ragweed | 75 |
| Ryegrass, Italian | 45 |
| Soybean | 95 |
| Surinam Grass | 55 |
| Velvetleaf | 85 |
| Wheat | 20 |
| Windgrass | 45 |

| 8 g ai/ha | Compound 95 |
|---|---|
| Postemergence | |
| Bermudagrass | 70 |
| Chickweed | 95 |
| Cocklebur | 100 |
| Corn | 20 |
| Crabgrass | 75 |
| Cupgrass, Woolly | 75 |
| Foxtail, Giant | 70 |
| Goosegrass | 50 |
| Johnsongrass | 55 |
| Kochia | 90 |
| Lambsquarters | 75 |
| Morningglory | 60 |
| Nutsedge, Yellow | 55 |
| Pigweed | 90 |
| Ragweed | 90 |
| Soybean | 100 |
| Surinam Grass | 55 |
| Velvetleaf | 95 |

| 500 g ai/ha | Compounds | | | | | | | | | | | | |
|---|---|---|---|---|---|---|---|---|---|---|---|---|---|
| | 1 | 4 | 5 | 8 | 10 | 15 | 22 | 26 | 27 | 28 | 33 | 40 | 49 | 50 |
| Preemergence | | | | | | | | | | | | | | |
| Bermudagrass | 90 | 95 | 70 | 100 | 0 | 70 | 90 | 0 | 0 | 35 | 0 | 70 | 95 | 95 |
| Cocklebur | 100 | 100 | 100 | 100 | 100 | 100 | 100 | 95 | 95 | 100 | 95 | 100 | 100 | 95 |
| Corn | 70 | 90 | 50 | 75 | 0 | 60 | 65 | 20 | 25 | 0 | 40 | 40 | 65 | 45 |
| Crabgrass | 95 | 95 | 60 | 0 | 0 | 100 | 100 | — | 85 | — | 100 | 100 | 100 | 95 |
| Cupgrass, Woolly | 95 | 95 | 0 | 100 | 0 | 95 | 95 | 0 | 15 | 0 | 0 | 95 | 25 | 40 |
| Foxtail, Giant | 90 | 85 | 60 | 0 | 0 | 80 | 60 | 10 | 20 | 0 | 50 | 35 | 65 | 70 |
| Goosegrass | 70 | 65 | 40 | 45 | 0 | 0 | 100 | 0 | 20 | 20 | 0 | 40 | 15 | 0 |
| Johnsongrass | 90 | 95 | 70 | 20 | 0 | 95 | 100 | 100 | 65 | — | 40 | 95 | 85 | 85 |
| Kochia | 100 | 100 | 100 | 100 | 65 | 100 | — | 50 | 45 | 100 | 50 | — | 100 | 90 |
| Lambsquarters | 100 | 100 | 100 | 100 | 95 | 100 | 100 | 90 | 100 | 100 | — | 100 | 100 | 100 |
| Morningglory | 100 | 100 | 100 | 100 | 100 | 100 | 100 | 90 | 100 | 100 | 95 | 100 | 100 | 100 |
| Nightshade | 100 | 100 | 100 | — | 95 | 100 | 100 | 100 | 100 | 100 | 100 | 100 | 100 | 100 |
| Nutsedge, Yellow | 50 | 80 | 0 | 100 | — | 20 | 95 | 0 | 20 | 0 | 0 | 0 | 0 | 0 |
| Pigweed | 100 | 100 | 100 | 95 | 85 | 100 | 100 | 100 | 100 | 100 | 90 | 100 | 100 | 100 |

TABLE C-continued

| | | | | | | | | | | | | | | |
|---|---|---|---|---|---|---|---|---|---|---|---|---|---|---|
| Ragweed | 100 | 100 | 100 | 100 | 85 | 100 | 100 | 90 | 95 | 100 | 90 | 100 | 100 | 100 |
| Soybean | 100 | 100 | 100 | 100 | — | 100 | 100 | 20 | 75 | 90 | 90 | 95 | 90 | 90 |
| Sunflower | 100 | 100 | 100 | 100 | 0 | 100 | 100 | 90 | 95 | 100 | 90 | 95 | 100 | 100 |
| Surinam Grass | 90 | 100 | 0 | 100 | 0 | 95 | 100 | 10 | 30 | 0 | 10 | 90 | 65 | 85 |
| Velvetleaf | 100 | 100 | 90 | 100 | 60 | 100 | 100 | 90 | 70 | 100 | 85 | 100 | 100 | 100 |

| | Compounds | | | | | | | | | | | | | |
|---|---|---|---|---|---|---|---|---|---|---|---|---|---|---|
| 250 g ai/ha | 1 | 2 | 3 | 4 | 5 | 8 | 9 | 10 | 12 | 13 | 15 | 16 | 17 | 22 |
| | Preemergence | | | | | | | | | | | | | |
| Bermudagrass | 70 | 0 | 0 | 45 | 30 | 100 | 100 | 0 | 20 | 0 | 0 | 0 | 0 | 50 |
| Cocklebur | 100 | 100 | 70 | 100 | 100 | 100 | 100 | 0 | 90 | 95 | 100 | 100 | 100 | 100 |
| Corn | 50 | 0 | 0 | 75 | 20 | 10 | 75 | 0 | — | 30 | 45 | 75 | 75 | 65 |
| Crabgrass | 90 | 50 | 0 | 85 | 20 | 0 | 100 | 0 | 0 | 0 | 95 | 95 | 80 | 95 |
| Cupgrass, Woolly | 90 | 45 | 0 | 95 | 0 | 100 | 100 | 0 | 100 | 0 | 85 | 65 | 85 | 95 |
| Foxtail, Giant | 90 | 30 | 0 | 75 | 10 | 0 | 80 | 0 | 0 | 5 | 65 | 75 | 75 | 20 |
| Goosegrass | 10 | 60 | 0 | 55 | 0 | 35 | 50 | 0 | 0 | 0 | 0 | 0 | 0 | 80 |
| Johnsongrass | 80 | 40 | 0 | 90 | 60 | 0 | 90 | 0 | 5 | 45 | 75 | 80 | 75 | 100 |
| Kochia | 100 | 100 | 30 | 100 | 100 | 100 | 100 | 45 | 85 | 85 | 100 | 100 | 85 | — |
| Lambsquarters | 100 | 100 | 80 | 100 | 100 | 90 | 100 | 65 | 70 | 90 | 100 | 100 | 100 | 100 |
| Morningglory | 100 | 100 | 35 | 100 | 90 | 100 | 100 | 0 | 90 | 90 | 100 | 100 | 100 | 100 |
| Nightshade | 100 | 100 | 20 | 100 | 100 | — | — | 20 | 80 | 90 | 100 | 100 | 100 | 100 |
| Nutsedge, Yellow | 50 | 0 | 0 | 15 | 0 | 100 | 100 | — | 0 | 0 | 0 | 0 | 0 | 95 |
| Pigweed | 100 | 100 | 80 | 100 | 100 | 90 | 100 | 0 | 70 | 85 | 90 | 100 | 100 | 100 |
| Ragweed | 100 | 0 | 45 | 100 | 100 | 100 | 100 | 55 | 85 | 85 | 100 | 100 | 100 | 100 |
| Soybean | 100 | 100 | 20 | 100 | 98 | 100 | 100 | — | 70 | 90 | 95 | 100 | 100 | 100 |
| Sunflower | 100 | 100 | 0 | 100 | 100 | 100 | 100 | 0 | 85 | 90 | 100 | 100 | 100 | 100 |
| Surinam Grass | 90 | 0 | 0 | 85 | 0 | 100 | 100 | 0 | 0 | 10 | 75 | 80 | 0 | 100 |
| Velvetleaf | 95 | 90 | 35 | 95 | 90 | 100 | 100 | 0 | 70 | 90 | 100 | 100 | 100 | 100 |

| | Compounds | | | | | | | | | |
|---|---|---|---|---|---|---|---|---|---|---|
| 250 g ai/ha | 26 | 27 | 28 | 30 | 31 | 33 | 40 | 49 | 50 | 64 |
| | Preemergence | | | | | | | | | |
| Bermudagrass | 0 | 0 | 30 | 0 | 0 | 0 | 0 | 85 | 0 | 20 |
| Cocklebur | 90 | 70 | 95 | 90 | 85 | 90 | 90 | 95 | 95 | 30 |
| Corn | 0 | 15 | 0 | 0 | 0 | 30 | 20 | 15 | 20 | 30 |
| Crabgrass | — | 0 | — | 85 | 0 | 100 | — | 95 | 95 | 90 |
| Cupgrass, Woolly | 0 | 10 | 0 | 50 | 0 | 0 | 70 | 20 | 0 | 40 |
| Foxtail, Giant | 0 | 0 | 0 | 60 | 0 | 50 | 30 | 0 | 0 | 0 |
| Goosegrass | 0 | 0 | 0 | 50 | 20 | 0 | 5 | 0 | 0 | 75 |
| Johnsongrass | 0 | 45 | 0 | 5 | 5 | 10 | 80 | 80 | 65 | 60 |
| Kochia | — | 30 | 90 | 90 | 70 | 50 | — | 100 | 20 | 70 |
| Lambsquarters | — | 90 | 100 | 90 | 80 | 85 | 100 | 100 | 100 | 100 |
| Morningglory | 85 | 95 | 100 | 100 | 50 | 90 | 90 | 100 | 95 | 10 |
| Nightshade | 100 | 100 | 100 | 100 | — | 95 | 100 | 100 | 100 | 95 |
| Nutsedge, Yellow | 0 | 0 | 0 | 0 | 0 | 0 | 0 | 0 | 0 | 10 |
| Pigweed | 100 | 90 | 100 | 90 | 40 | 90 | 100 | 100 | 95 | 100 |
| Ragweed | 85 | 85 | 100 | 100 | 60 | 70 | 100 | 100 | 95 | 100 |
| Soybean | 10 | 20 | 65 | 70 | 80 | 80 | 90 | 90 | 75 | 85 |
| Sunflower | 70 | 90 | 100 | 90 | 70 | 80 | 90 | 100 | 95 | 85 |
| Surinam Grass | 10 | 20 | 0 | 20 | 0 | 0 | 10 | 40 | 65 | 90 |
| Velvetleaf | 90 | 50 | 95 | 50 | 60 | 60 | 90 | 90 | 85 | 0 |

| | Compounds | | | | | | | | | | | | | |
|---|---|---|---|---|---|---|---|---|---|---|---|---|---|---|
| 125 g ai/ha | 1 | 2 | 3 | 4 | 5 | 8 | 9 | 10 | 11 | 12 | 13 | 15 | 16 | 17 |
| | Preemergence | | | | | | | | | | | | | |
| Bermudagrass | 50 | 0 | 0 | 20 | 0 | 100 | 100 | 0 | 0 | 0 | 0 | 0 | 0 | 0 |
| Cocklebur | 100 | 80 | 55 | 95 | 90 | 85 | 100 | 0 | 0 | 85 | 90 | 90 | 95 | 95 |
| Corn | 0 | — | 0 | 0 | 5 | 0 | 60 | 0 | 0 | 60 | 10 | 15 | 20 | 35 |
| Crabgrass | 60 | 0 | 0 | 65 | 0 | 0 | 95 | 0 | 60 | 0 | 0 | 95 | 65 | 20 |
| Cupgrass, Woolly | 60 | 0 | 0 | 80 | 0 | 65 | 95 | 0 | 0 | 10 | 0 | 20 | 15 | 20 |
| Foxtail, Giant | 30 | 0 | 0 | 40 | 0 | 0 | 75 | 0 | 20 | 0 | 0 | 0 | 0 | 20 |
| Goosegrass | 0 | 0 | 0 | 25 | 0 | 0 | 20 | 0 | 0 | 0 | 0 | 0 | 0 | 0 |
| Johnsongrass | 30 | 0 | 0 | 70 | 20 | 0 | 65 | 0 | 75 | 5 | 5 | 65 | 65 | 55 |
| Kochia | 100 | 95 | 20 | 100 | 95 | 85 | 100 | 0 | 60 | 50 | 80 | 100 | 100 | 25 |
| Lambsquarters | 100 | 100 | 0 | 100 | 95 | 20 | 100 | 50 | 85 | 40 | 90 | 100 | 100 | 100 |
| Morningglory | 100 | 100 | 20 | 100 | 80 | 100 | 100 | 0 | 0 | 60 | 85 | 100 | 100 | 100 |
| Nightshade | 100 | 100 | 0 | 100 | 100 | — | — | — | — | 60 | 90 | 100 | 95 | 95 |
| Nutsedge, Yellow | 0 | 0 | 0 | 0 | 0 | 0 | 100 | 0 | — | 0 | 0 | 0 | 0 | 0 |
| Pigweed | 100 | 95 | 65 | 100 | 90 | 85 | 100 | 55 | 90 | 50 | 85 | 100 | 100 | 100 |
| Ragweed | 100 | 0 | 0 | 100 | 90 | 100 | 100 | 0 | 45 | 20 | 70 | 95 | 95 | 95 |
| Soybean | 100 | 90 | 15 | 100 | 90 | 100 | 100 | — | 55 | — | 90 | 90 | 100 | 95 |

TABLE C-continued

| | | | | | | | | | | | | | | |
|---|---|---|---|---|---|---|---|---|---|---|---|---|---|---|
| Sunflower | 100 | 100 | 0 | 100 | 90 | 40 | 100 | 0 | 0 | 0 | 60 | 100 | 100 | 100 |
| Surinam Grass | 35 | 0 | 0 | 65 | 0 | 100 | 100 | 0 | 100 | 0 | 0 | 65 | 15 | 0 |
| Velvetleaf | 90 | 75 | 20 | 95 | 85 | 75 | 100 | 0 | 0 | 50 | 80 | 95 | 95 | 100 |

| | Compounds | | | | | | | | | | | | | |
|---|---|---|---|---|---|---|---|---|---|---|---|---|---|---|
| 125 g ai/ha | 19 | 22 | 25 | 26 | 27 | 28 | 30 | 31 | 33 | 40 | 47 | 49 | 50 | 64 |

| | Preemergence | | | | | | | | | | | | | |
|---|---|---|---|---|---|---|---|---|---|---|---|---|---|---|
| Bermudagrass | 0 | 50 | 10 | 0 | 0 | 20 | 0 | 0 | 0 | 0 | 95 | 0 | 0 | 20 |
| Cocklebur | 80 | 95 | 85 | 70 | 50 | 95 | 85 | 75 | 0 | 70 | 75 | 95 | 85 | 5 |
| Corn | 0 | 50 | 0 | 0 | 10 | 0 | 0 | 0 | 0 | 20 | 0 | 15 | 10 | 20 |
| Crabgrass | 0 | 95 | 0 | — | 0 | — | 70 | 0 | 20 | — | 100 | 95 | 90 | 70 |
| Cupgrass, Woolly | 0 | 95 | 50 | 0 | 0 | 0 | 45 | 0 | 0 | 5 | 0 | 0 | 0 | 0 |
| Foxtail, Giant | 0 | 15 | 0 | 0 | 0 | 0 | 20 | 0 | 10 | 0 | 20 | 0 | 0 | 0 |
| Goosegrass | 0 | 0 | 0 | 0 | 0 | 0 | 35 | 0 | 0 | 0 | 90 | 0 | 0 | 0 |
| Johnsongrass | 55 | 100 | 0 | — | 20 | — | 5 | 0 | 5 | 80 | 0 | 65 | 55 | 50 |
| Kochia | 90 | — | 70 | — | 0 | 80 | 70 | 50 | — | — | 100 | 100 | 0 | 25 |
| Lambsquarters | 100 | 100 | 50 | — | 40 | 100 | 85 | 40 | — | 100 | 95 | 100 | 100 | 95 |
| Morningglory | 90 | 100 | 90 | 5 | 70 | 100 | 90 | 10 | 85 | 90 | 100 | 95 | 95 | 0 |
| Nightshade | 100 | 100 | 75 | 100 | 70 | 100 | 100 | 0 | 50 | 100 | 100 | 100 | 100 | 85 |
| Nutsedge, Yellow | 0 | 0 | 0 | 0 | 0 | 0 | 0 | 0 | 0 | 0 | 0 | 0 | 0 | 0 |
| Pigweed | 95 | 100 | 85 | 100 | 80 | 95 | 80 | 35 | 90 | 100 | 85 | 90 | 90 | 100 |
| Ragweed | 80 | 100 | 85 | 10 | 65 | 95 | 90 | 60 | 20 | 90 | 65 | 100 | 85 | 95 |
| Soybean | 90 | 95 | 65 | 10 | 0 | 45 | 5 | 15 | 30 | 40 | 0 | 70 | 60 | 85 |
| Sunflower | 90 | 95 | 90 | 20 | 20 | 50 | 90 | 5 | 70 | 90 | 100 | 75 | 55 | 30 |
| Surinam Grass | 10 | 90 | 40 | 0 | 0 | 0 | 0 | 0 | 0 | 0 | 0 | 15 | 15 | 50 |
| Velvetleaf | 65 | 95 | 40 | 10 | 0 | 55 | 15 | 0 | 20 | 70 | 50 | 70 | 75 | 0 |

| | Compounds | | | | | | |
|---|---|---|---|---|---|---|---|
| 125 g ai/ha | 65 | 75 | 76 | 77 | 78 | 117 | 135 |

| | Preemergence | | | | | | |
|---|---|---|---|---|---|---|---|
| Bermudagrass | 80 | 20 | 0 | 0 | 20 | 65 | 0 |
| Cocklebur | 90 | 100 | 90 | 95 | 90 | 90 | 100 |
| Corn | 30 | 65 | 45 | 35 | 40 | 25 | 70 |
| Crabgrass | 80 | 60 | 60 | 0 | 45 | 60 | 5 |
| Cupgrass, Woolly | 70 | 60 | 50 | 0 | 10 | 50 | 0 |
| Foxtail, Giant | 60 | 10 | 10 | 0 | 0 | 50 | 0 |
| Goosegrass | 50 | 30 | 0 | 0 | 0 | 30 | 40 |
| Johnsongrass | 70 | 55 | 50 | 0 | 50 | 70 | 40 |
| Kochia | 70 | 100 | 100 | 80 | 100 | 60 | 100 |
| Lambsquarters | 100 | 100 | 80 | 40 | 80 | 100 | 90 |
| Morningglory | 100 | 100 | 100 | 75 | 100 | 50 | 100 |
| Nightshade | 80 | 100 | 100 | 0 | 70 | 45 | 50 |
| Nutsedge, Yellow | 70 | 0 | 0 | 0 | — | 50 | 0 |
| Pigweed | 100 | 90 | 90 | 65 | 95 | 100 | 100 |
| Ragweed | 100 | 90 | 100 | 55 | 80 | 98 | 70 |
| Soybean | 100 | 100 | 95 | 100 | 95 | 100 | 100 |
| Sunflower | 100 | 100 | 100 | 100 | 100 | 100 | 90 |
| Surinam Grass | 80 | 55 | 45 | 0 | 75 | 95 | 0 |
| Velvetleaf | 100 | 100 | 90 | 90 | 80 | 90 | 100 |

| | Compounds | | | | | | | | | | | | |
|---|---|---|---|---|---|---|---|---|---|---|---|---|---|
| 62 g ai/ha | 1 | 2 | 3 | 4 | 5 | 8 | 9 | 10 | 11 | 12 | 13 | 15 | 16 | 17 |

| | Preemergence | | | | | | | | | | | | |
|---|---|---|---|---|---|---|---|---|---|---|---|---|---|---|
| Bermudagrass | 0 | 0 | 0 | 0 | 0 | 100 | 100 | 0 | 0 | 0 | 0 | 0 | 0 | 0 |
| Cocklebur | 90 | — | 30 | 80 | 10 | — | 80 | — | 0 | 50 | 60 | 65 | 95 | 90 |
| Corn | 0 | 0 | 0 | — | 5 | 0 | 5 | 0 | 0 | 30 | 5 | 0 | 15 | 20 |
| Crabgrass | 10 | 0 | 0 | 40 | 0 | 0 | 95 | 0 | 0 | 0 | 0 | 0 | 0 | 0 |
| Cupgrass, Woolly | 0 | 0 | 0 | 0 | 0 | 0 | 90 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Goosegrass | 0 | 0 | 0 | 0 | 0 | 0 | 0 | 0 | 0 | 0 | 0 | 0 | 0 | 0 |
| Johnsongrass | 0 | 0 | 0 | 50 | 5 | 0 | 45 | 0 | 0 | 0 | 0 | 20 | 40 | 0 |
| Kochia | 95 | 90 | 0 | 95 | 80 | 50 | 95 | 0 | 0 | 50 | 60 | 95 | 95 | 0 |
| Lambsquarters | 95 | 100 | 0 | 95 | 95 | 0 | 100 | 0 | 40 | 10 | 85 | 95 | 95 | 95 |
| Morningglory | 90 | 100 | 0 | 100 | 50 | 20 | 100 | 0 | 0 | 60 | 65 | 95 | 95 | 95 |
| Nightshade | 100 | 20 | 0 | 100 | 100 | — | — | — | — | 50 | 0 | 95 | 90 | 80 |
| Nutsedge, Yellow | 0 | 0 | 0 | 0 | 0 | 0 | 100 | 0 | 0 | 0 | 0 | 0 | 0 | 0 |
| Pigweed | 90 | 95 | 50 | 95 | 60 | 65 | 95 | 20 | 65 | 50 | 60 | 90 | 95 | 100 |
| Ragweed | 95 | 0 | 0 | 100 | 85 | 100 | 100 | 0 | 20 | 10 | 60 | 90 | 90 | 80 |
| Soybean | 85 | 75 | 0 | 95 | 85 | 100 | 100 | 0 | — | 50 | 60 | 75 | 85 | 90 |
| Sunflower | 80 | 100 | 0 | 100 | 60 | 20 | 100 | 0 | 0 | 0 | 50 | 65 | 85 | 95 |

TABLE C-continued

| | | | | | | | | | | | | | | |
|---|---|---|---|---|---|---|---|---|---|---|---|---|---|---|
| Surinam Grass | 0 | 0 | 0 | 0 | 0 | 0 | 100 | — | 100 | — | 0 | 15 | 0 | 0 |
| Velvetleaf | 80 | 50 | 0 | 75 | 85 | 65 | 95 | 0 | 0 | 5 | 60 | 80 | 90 | 80 |

| | Compounds | | | | | | | | | | | | | |
|---|---|---|---|---|---|---|---|---|---|---|---|---|---|---|
| 62 g ai/ha | 19 | 22 | 25 | 26 | 27 | 28 | 30 | 31 | 33 | 40 | 47 | 49 | 50 | 64 |

| | Preemergence | | | | | | | | | | | | | |
|---|---|---|---|---|---|---|---|---|---|---|---|---|---|---|
| Bermudagrass | 0 | 0 | 0 | 0 | 0 | 0 | 0 | 0 | 0 | 0 | 0 | 0 | — | 0 |
| Cocklebur | 65 | 90 | 60 | 70 | 0 | 90 | 60 | 60 | 0 | 5 | 70 | 20 | 70 | 0 |
| Corn | 0 | 40 | 0 | 0 | 0 | 0 | 0 | 0 | 0 | 0 | 0 | — | 10 | 0 |
| Crabgrass | 0 | 90 | 0 | — | 0 | — | 0 | 0 | 0 | 5 | 100 | 95 | 90 | 0 |
| Cupgrass, Woolly | 0 | 40 | 0 | 0 | 0 | 0 | 5 | 0 | 0 | 5 | 0 | 0 | 0 | 0 |
| Foxtail, Giant | 0 | 10 | 0 | 0 | 0 | 0 | 0 | 0 | 0 | 0 | 0 | 0 | 0 | 0 |
| Goosegrass | 0 | 0 | 0 | 0 | 0 | 0 | 30 | 0 | 0 | 0 | 85 | 0 | 0 | 0 |
| Johnsongrass | 35 | 80 | 0 | 0 | 0 | — | 0 | 0 | 0 | 0 | 0 | 45 | 0 | 5 |
| Kochia | 85 | — | 5 | 0 | 0 | 0 | 70 | 0 | — | — | 0 | 100 | — | 20 |
| Lambsquarters | 100 | 100 | 30 | 10 | — | 95 | 80 | 40 | — | 100 | 85 | 100 | 95 | 95 |
| Morningglory | 90 | 100 | 50 | 0 | 0 | 100 | 85 | 0 | 0 | — | 70 | 90 | 80 | 0 |
| Nightshade | 100 | 100 | 30 | 10 | 0 | 100 | 80 | 0 | 0 | 100 | 95 | 95 | 95 | 85 |
| Nutsedge, Yellow | 0 | 0 | 0 | 0 | 0 | 0 | 0 | 0 | 0 | 0 | 0 | 0 | 0 | 0 |
| Pigweed | 70 | 90 | 35 | 30 | 20 | 80 | 30 | 30 | 85 | 20 | 85 | 85 | 75 | 30 |
| Ragweed | 70 | 90 | 70 | 0 | 20 | 65 | 85 | 10 | 0 | 90 | 45 | 70 | 70 | 85 |
| Soybean | 85 | 95 | 60 | 0 | 0 | 0 | 5 | 5 | 0 | 10 | 0 | 0 | 0 | 85 |
| Sunflower | 70 | 90 | 75 | 0 | 0 | 45 | 80 | 0 | 0 | 5 | 20 | 15 | 15 | 0 |
| Surinam Grass | 0 | — | 0 | 0 | 0 | 0 | 0 | 0 | 0 | — | 0 | 0 | 0 | 0 |
| Velvetleaf | 40 | 90 | 0 | 0 | 0 | 50 | 10 | 0 | 0 | 0 | 20 | 15 | 65 | 0 |

| | Compounds | | | | | | | |
|---|---|---|---|---|---|---|---|---|
| 62 g ai/ha | 65 | 75 | 76 | 77 | 78 | 95 | 117 | 135 |

| | Preemergence | | | | | | | |
|---|---|---|---|---|---|---|---|---|
| Bermudagrass | 70 | 0 | 0 | 0 | 0 | 55 | 30 | 0 |
| Cocklebur | 50 | 95 | 90 | 80 | 90 | 60 | 5 | 95 |
| Corn | 0 | 30 | 35 | 0 | 20 | 5 | 20 | 30 |
| Crabgrass | 70 | 20 | 5 | 0 | 40 | 35 | 0 | 0 |
| Cupgrass, Woolly | 5 | 60 | 20 | 0 | 0 | 5 | 15 | 0 |
| Foxtail, Giant | 50 | 0 | 0 | 0 | 0 | 35 | 5 | 0 |
| Goosegrass | 0 | 0 | 0 | 0 | 0 | 40 | 0 | 0 |
| Johnsongrass | 60 | 50 | 20 | 0 | 20 | 80 | 60 | 5 |
| Kochia | 50 | 100 | 95 | 50 | 100 | 45 | 20 | 75 |
| Lambsquarters | 80 | 80 | 80 | — | 80 | 100 | 100 | 70 |
| Morningglory | 20 | 95 | 100 | 50 | 85 | 60 | 5 | 90 |
| Nightshade | — | 70 | 60 | 0 | 60 | 75 | 40 | 35 |
| Nutsedge, Yellow | 30 | 0 | 0 | 0 | 0 | 60 | 50 | 0 |
| Pigweed | 80 | 80 | 80 | 65 | 70 | 100 | 90 | 80 |
| Ragweed | 90 | 80 | 80 | 50 | 80 | 100 | 90 | 35 |
| Soybean | 95 | 100 | 95 | 100 | 80 | 100 | 100 | 95 |
| Sunflower | 95 | 100 | 100 | 100 | 100 | 100 | 90 | 90 |
| Surinam Grass | 80 | 55 | 0 | 0 | 0 | 10 | 50 | 0 |
| Velvetleaf | 80 | 85 | 70 | 85 | 70 | 90 | 65 | 90 |

| | Compounds | | | | | | | | | | | | |
|---|---|---|---|---|---|---|---|---|---|---|---|---|---|
| 31 g ai/ha | 2 | 3 | 9 | 11 | 12 | 13 | 16 | 17 | 19 | 25 | 30 | 31 | 47 | 64 |

| | Preemergence | | | | | | | | | | | | | |
|---|---|---|---|---|---|---|---|---|---|---|---|---|---|---|
| Bermudagrass | 0 | 0 | 100 | 0 | 0 | 0 | 0 | 0 | 0 | 0 | 0 | 0 | 0 | 0 |
| Cocklebur | 60 | 0 | 75 | 0 | 50 | 40 | 45 | 75 | 30 | 20 | 0 | 0 | 0 | 0 |
| Corn | 0 | 0 | 0 | 0 | 0 | 0 | 0 | 0 | 0 | 0 | 0 | 0 | 0 | 0 |
| Crabgrass | 0 | 0 | 20 | 0 | 0 | 0 | 0 | 0 | 0 | 0 | 0 | 0 | 100 | 0 |
| Cupgrass, Woolly | 0 | 0 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 | 0 | 0 |
| Goosegrass | 0 | 0 | 0 | 0 | 0 | 0 | 0 | 0 | 0 | 0 | 0 | 0 | 45 | 0 |
| Johnsongrass | 0 | 0 | 15 | 0 | 0 | 0 | 0 | 0 | 0 | 0 | 0 | 0 | 0 | 5 |
| Kochia | 75 | 0 | 95 | 0 | 0 | 45 | 90 | 0 | — | 0 | 50 | 0 | — | 20 |
| Lambsquarters | 90 | 0 | 95 | 0 | 0 | 50 | 95 | 95 | 100 | 0 | 0 | 0 | — | 70 |
| Morningglory | 100 | 0 | 100 | 0 | 30 | 60 | 65 | 70 | 10 | 0 | 0 | 0 | 0 | 0 |
| Nightshade | 0 | 0 | — | — | — | 0 | 55 | 0 | 40 | 0 | 50 | 0 | 85 | 5 |
| Nutsedge, Yellow | 0 | 0 | 20 | 0 | 0 | 0 | 0 | 0 | 0 | 0 | 0 | 0 | 0 | 0 |
| Pigweed | 90 | 20 | 95 | 0 | 10 | 50 | 85 | 95 | 45 | 30 | 0 | 10 | 80 | 10 |
| Ragweed | 0 | 0 | 100 | 0 | — | 45 | 45 | 70 | 55 | 70 | 30 | 5 | — | 85 |
| Soybean | 15 | 0 | 100 | — | — | 0 | 75 | 70 | 25 | — | 0 | 0 | 0 | 0 |
| Sunflower | 20 | 0 | 100 | 0 | 0 | 5 | 20 | 60 | 25 | 60 | 20 | 0 | 0 | 0 |

TABLE C-continued

| | | | | | | | | | | | | | | |
|---|---|---|---|---|---|---|---|---|---|---|---|---|---|---|
| Surinam Grass | 0 | 0 | 95 | 0 | 0 | 0 | 0 | 0 | — | 0 | 0 | 0 | 0 | — |
| Velvetleaf | 20 | 0 | 70 | 0 | 0 | 60 | 25 | 20 | 35 | 0 | 0 | 0 | 20 | 0 |

| | Compounds | | | | | | | |
|---|---|---|---|---|---|---|---|---|
| 31 g ai/ha | 65 | 75 | 76 | 77 | 78 | 95 | 117 | 135 |
| Preemergence | | | | | | | | |
| Bermudagrass | 50 | 0 | 0 | 0 | 0 | 0 | 0 | 0 |
| Cocklebur | 30 | 90 | 90 | 70 | 70 | 0 | 0 | 95 |
| Corn | 0 | 0 | 0 | 0 | 0 | 0 | 5 | 30 |
| Crabgrass | 20 | 10 | 0 | 0 | 5 | 30 | 0 | 0 |
| Cupgrass, Woolly | 0 | 0 | 0 | 0 | 0 | 0 | 0 | 0 |
| Foxtail, Giant | 10 | 0 | 0 | 0 | 0 | 30 | 0 | 0 |
| Goosegrass | 0 | 0 | 0 | 0 | 0 | 10 | 0 | 0 |
| Johnsongrass | 50 | 10 | 0 | 0 | 10 | 60 | 35 | 0 |
| Kochia | 0 | 80 | 90 | — | 80 | 40 | 5 | 75 |
| Lambsquarters | 50 | 75 | 70 | 0 | 70 | 100 | 100 | 70 |
| Morningglory | 0 | 90 | 60 | 50 | 70 | 10 | 0 | 90 |
| Nightshade | 0 | 50 | 40 | 0 | 30 | 60 | 5 | 30 |
| Nutsedge, Yellow | 0 | 0 | 0 | 0 | 0 | 60 | 0 | 0 |
| Pigweed | 80 | 75 | 80 | 60 | 60 | 100 | 80 | 70 |
| Ragweed | 85 | 70 | 60 | 0 | 65 | 100 | 60 | — |
| Soybean | 95 | 60 | 70 | 100 | 70 | 100 | 100 | 95 |
| Sunflower | 70 | 70 | 85 | 50 | 70 | 95 | 50 | 70 |
| Surinam Grass | 40 | 0 | 0 | 0 | 0 | 5 | 40 | 0 |
| Velvetleaf | 40 | 60 | 40 | 30 | 55 | 60 | 50 | 85 |

| | Compounds | | | | | | | | | | | |
|---|---|---|---|---|---|---|---|---|---|---|---|---|
| 16 g ai/ha | 11 | 19 | 25 | 47 | 65 | 75 | 76 | 77 | 78 | 95 | 117 | 135 |
| Preemergence | | | | | | | | | | | | |
| Bermudagrass | 0 | 0 | 0 | 0 | 0 | 0 | 0 | 0 | 0 | 0 | 0 | 0 |
| Cocklebur | 0 | 15 | 0 | 0 | 0 | 55 | 65 | 55 | 55 | 0 | 0 | 85 |
| Corn | 0 | 0 | 0 | 0 | 0 | — | 0 | 0 | 0 | 0 | 0 | 5 |
| Crabgrass | 0 | 0 | 0 | 20 | 0 | 0 | 0 | 0 | 0 | 0 | 0 | 0 |
| Cupgrass, Woolly | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 0 | 0 | 0 |
| Goosegrass | 0 | 0 | 0 | 0 | 0 | 0 | 0 | 0 | 0 | 0 | 0 | 0 |
| Johnsongrass | 0 | 0 | 0 | 0 | 0 | 0 | 0 | 0 | 0 | 50 | 0 | 0 |
| Kochia | 0 | 35 | 0 | 0 | 0 | 70 | 70 | 20 | 70 | 0 | 0 | 60 |
| Lambsquarters | 0 | 75 | 0 | 0 | 0 | 70 | 70 | 0 | 0 | 100 | 20 | 0 |
| Morningglory | 0 | 10 | 0 | 0 | 0 | 50 | 40 | 5 | 0 | 0 | 0 | 85 |
| Nightshade | — | 0 | 0 | 80 | 0 | 0 | 30 | 0 | 0 | 0 | 0 | 0 |
| Nutsedge, Yellow | 0 | 0 | 0 | 0 | 0 | 0 | 0 | 0 | 0 | 40 | 0 | 0 |
| Pigweed | 0 | 35 | 0 | 0 | 40 | 70 | 60 | 60 | 55 | 90 | 50 | 70 |
| Ragweed | 0 | 55 | 0 | 0 | 85 | 20 | 50 | 0 | 10 | 90 | 60 | 5 |
| Soybean | — | 0 | 30 | 0 | 85 | 55 | 50 | 40 | 30 | 90 | 85 | 85 |
| Sunflower | 0 | 10 | 5 | 0 | 40 | 50 | 50 | 20 | 50 | 40 | 0 | 65 |
| Surinam Grass | 0 | 0 | 0 | 0 | 0 | 0 | 0 | 0 | 0 | 0 | 40 | 0 |
| Velvetleaf | 0 | 25 | 0 | 0 | 0 | 5 | 30 | 10 | 10 | 0 | 0 | 60 |

| | Compound |
|---|---|
| 8 g ai/ha | 95 |
| Preemergence | |
| Bermudagrass | 0 |
| Cocklebur | 0 |
| Corn | 0 |
| Crabgrass | 0 |
| Cupgrass, Woolly | 0 |
| Foxtail, Giant | 0 |
| Goosegrass | 0 |
| Johnsongrass | 0 |
| Kochia | 0 |
| Lambsquarters | 0 |
| Morningglory | 0 |
| Nightshade | 0 |
| Nutsedge, Yellow | 0 |
| Pigweed | 50 |
| Ragweed | 65 |
| Soybean | 90 |
| Sunflower | 5 |
| Surinam Grass | 0 |
| Velvetleaf | 0 |

Test D

Seeds of plant species selected from catchweed bedstraw (galium; *Galium aparine*), common chickweed (*Stellaria media*), kochia (*Kochia scoparia*), lambsquarters (*Chenopodium album*), pigweed (*Amaranthus retroflexus*), Russian thistle (*Salsola kali*), wild buckwheat (*Polygonum convolvulus*), wild mustard (*Sinapis arvensis*), winter barley (*Hordeum vulgare*), and wheat (*Triticum aestivum*) were planted and treated preemergence with test chemicals formulated in a non-phytotoxic solvent mixture which included a surfactant.

At the same time, plants selected from these crop and weed species were treated with postemergence applications of some of the test chemicals formulated in the same manner. Plants ranged in height from 2 to 18 cm (1- to 4-leaf stage) for postemergence treatments. Treated plants and controls were maintained in a controlled growth environment for 15 to 25 days after which time all species were compared to controls and visually evaluated. Plant response ratings, summarized in Table D, are based on a scale of 0 to 100 where 0 is no effect and 100 is complete control. A dash (-) response means no test result.

TABLE D

| 500 g ai/ha | Compound 58 |
|---|---|
| Postemergence | |
| Buckwheat, Wild | 100 |
| Galium | 100 |
| Kochia | 100 |
| Lambsquarters | 100 |
| Mustard, Wild | 100 |
| Pigweed | 100 |
| Russian Thistle | 80 |
| Wheat | 85 |

| 250 g ai/ha | Compounds | | | | | |
|---|---|---|---|---|---|---|
| | 26 | 28 | 33 | 35 | 47 | 58 |
| Postemergence | | | | | | |
| Barley | 50 | 40 | 45 | 70 | — | — |
| Buckwheat, Wild | 55 | 60 | 55 | 80 | 70 | 100 |
| Chickweed | 55 | 65 | 60 | 85 | 70 | — |
| Galium | 85 | 100 | 65 | 100 | 98 | 100 |
| Kochia | 55 | 75 | 50 | 85 | 75 | 100 |
| Lambsquarters | 50 | 75 | 45 | 100 | 45 | 100 |
| Mustard, Wild | 75 | 60 | 50 | 75 | 70 | 100 |
| Pigweed | 70 | 70 | 55 | 100 | 65 | 100 |
| Russian Thistle | 40 | 70 | 40 | 100 | 70 | 70 |
| Wheat | 20 | 35 | 45 | 70 | 45 | 70 |

| 125 g ai/ha | Compounds | | | | | | | | |
|---|---|---|---|---|---|---|---|---|---|
| | 1 | 2 | 4 | 9 | 26 | 28 | 33 | 35 | 47 | 58 |
| Postemergence | | | | | | | | | |
| Barley | — | — | — | — | 45 | 40 | 45 | 65 | — | — |
| Buckwheat, Wild | 80 | 95 | 100 | 100 | 35 | 55 | 50 | 70 | 65 | 90 |
| Chickweed | 85 | 85 | 100 | 100 | 45 | 65 | 50 | 80 | 65 | — |
| Galium | 100 | 100 | 100 | 100 | 70 | — | 60 | 100 | 80 | 100 |
| Kochia | 100 | 100 | 100 | 100 | 35 | 75 | 50 | 85 | 65 | 100 |
| Lambsquarters | 100 | 100 | 100 | 100 | 40 | 70 | 30 | 100 | 40 | 85 |
| Mustard, Wild | 75 | 80 | 90 | 95 | 60 | 60 | 50 | 75 | 65 | 100 |
| Pigweed | 100 | 100 | 100 | 100 | 60 | 60 | 55 | 100 | 55 | 100 |
| Russian Thistle | 100 | 100 | 100 | 100 | 40 | 70 | 40 | 100 | 65 | 70 |
| Wheat | 100 | 100 | 100 | 100 | 45 | 35 | 40 | 65 | 35 | 60 |

| 62 g ai/ha | Compounds | | | | | | | |
|---|---|---|---|---|---|---|---|---|
| | 1 | 2 | 4 | 9 | 28 | 33 | 35 | 47 | 58 |
| Postemergence | | | | | | | | |
| Barley | — | — | — | — | 20 | 45 | 65 | — | — |
| Buckwheat, Wild | 80 | 90 | 100 | 100 | 35 | 40 | 60 | 65 | 65 |
| Chickweed | 65 | 85 | 100 | 100 | 65 | 40 | 80 | 60 | — |
| Galium | 100 | 100 | 100 | 100 | 100 | 55 | 100 | 75 | 100 |
| Kochia | 100 | 100 | 100 | 100 | 70 | 50 | 80 | 50 | 70 |
| Lambsquarters | 100 | 100 | 100 | 100 | 65 | 30 | 100 | 35 | 80 |
| Mustard, Wild | 70 | 70 | 75 | 80 | 45 | 50 | 75 | 60 | 100 |
| Pigweed | 100 | 100 | 100 | 100 | 60 | 45 | 100 | 50 | 80 |

TABLE D-continued

| | | | | | | | | | |
|---|---|---|---|---|---|---|---|---|---|
| Russian Thistle | 85 | 95 | 100 | 100 | 65 | 30 | 100 | 55 | 70 |
| Wheat | 90 | 100 | 100 | 90 | 20 | 35 | 0 | 35 | 55 |

| | Compounds | | | | |
|---|---|---|---|---|---|
| 31 g ai/ha | 1 | 2 | 4 | 9 | 47 |

Postemergence

| | | | | | |
|---|---|---|---|---|---|
| Buckwheat, Wild | 80 | 65 | 85 | 80 | 60 |
| Chickweed | 65 | 60 | 100 | 100 | 35 |
| Galium | 100 | 100 | 100 | 100 | 65 |
| Kochia | 100 | 100 | 100 | 100 | 45 |
| Lambsquarters | 95 | 100 | 100 | 100 | 35 |
| Mustard, Wild | 70 | 65 | 65 | 80 | 55 |
| Pigweed | 100 | 85 | 100 | 100 | 35 |
| Russian Thistle | 65 | 85 | 90 | 90 | 45 |
| Wheat | 80 | 70 | 85 | 80 | 30 |

| | Compounds | | | |
|---|---|---|---|---|
| 16 g ai/ha | 1 | 2 | 4 | 9 |

Postemergence

| | | | | |
|---|---|---|---|---|
| Buckwheat, Wild | 50 | 45 | 80 | 65 |
| Chickweed | 65 | 60 | 65 | 60 |
| Galium | 95 | 75 | 100 | 100 |
| Kochia | 85 | 75 | 85 | 85 |
| Lambsquarters | 95 | 60 | 95 | 95 |
| Mustard, Wild | 60 | 65 | 65 | 65 |
| Pigweed | 60 | 65 | 85 | 65 |
| Russian Thistle | 45 | 65 | 80 | 65 |
| Wheat | 40 | 70 | 80 | 50 |

| | Compound |
|---|---|
| 500 g ai/ha | 58 |

Preemergence

| | |
|---|---|
| Buckwheat, Wild | 100 |
| Chickweed | 100 |
| Galium | 100 |
| Kochia | 100 |
| Lambsquarters | 100 |
| Mustard, Wild | 100 |
| Pigweed | 100 |
| Russian Thistle | 85 |
| Wheat | 70 |

| | Compounds | | | | |
|---|---|---|---|---|---|
| 250 g ai/ha | 26 | 28 | 33 | 35 | 58 |

Preemergence

| | | | | | |
|---|---|---|---|---|---|
| Barley | 35 | 45 | 45 | 45 | — |
| Buckwheat, Wild | 95 | 60 | 65 | 65 | 100 |
| Chickweed | 65 | 60 | 65 | 100 | 75 |
| Galium | 100 | 100 | 100 | 100 | 100 |
| Kochia | 75 | 100 | 65 | 100 | 100 |
| Lambsquarters | 65 | 60 | 65 | 80 | 100 |
| Mustard, Wild | 65 | 60 | 65 | 75 | 100 |
| Pigweed | 100 | 80 | 90 | 85 | 100 |
| Russian Thistle | 100 | 100 | 85 | 100 | 70 |
| Wheat | 35 | 35 | 55 | 50 | 60 |

| | Compounds | | | | | | | |
|---|---|---|---|---|---|---|---|---|
| 125 g ai/ha | 1 | 2 | 4 | 9 | 26 | 28 | 33 | 35 | 58 |

Preemergence

| | | | | | | | | | |
|---|---|---|---|---|---|---|---|---|---|
| Barley | — | — | — | — | 25 | 25 | 35 | 45 | — |
| Buckwheat, Wild | 75 | 85 | 100 | 100 | 65 | 45 | 65 | 60 | 80 |
| Chickweed | 75 | 90 | 100 | 100 | 60 | 60 | — | 100 | — |
| Galium | 100 | 100 | 100 | 100 | 85 | 100 | 80 | 100 | 100 |
| Kochia | 100 | 100 | 100 | 100 | 55 | 80 | 65 | 100 | 95 |
| Lambsquarters | 100 | 100 | 100 | 100 | 60 | 60 | 65 | 75 | 100 |
| Mustard, Wild | 90 | 85 | 85 | 85 | 65 | 60 | 65 | 70 | 100 |

TABLE D-continued

| | | | | | | | | | |
|---|---|---|---|---|---|---|---|---|---|
| Pigweed | 100 | 100 | 100 | 100 | 65 | — | 70 | 80 | 100 |
| Russian Thistle | 100 | 100 | 100 | 100 | — | 80 | 60 | 100 | 65 |
| Wheat | 70 | 70 | 80 | — | 25 | 35 | 35 | 40 | 50 |

| | Compounds | | | | | | | |
|---|---|---|---|---|---|---|---|---|
| 62 g ai/ha | 1 | 2 | 4 | 9 | 28 | 33 | 35 | 58 |
| Preemergence | | | | | | | | |
| Barley | — | — | — | — | 10 | 10 | 40 | — |
| Buckwheat, Wild | 70 | 80 | 100 | 100 | 45 | 55 | 55 | 40 |
| Chickweed | 70 | 75 | 85 | 100 | 60 | — | 60 | 60 |
| Galium | 100 | 98 | 100 | 100 | 100 | 70 | 85 | 100 |
| Kochia | 100 | 100 | 100 | 100 | 45 | 60 | 75 | 35 |
| Lambsquarters | 85 | 95 | 100 | 100 | 60 | 60 | 65 | 60 |
| Mustard, Wild | 70 | 70 | 85 | 85 | 60 | 65 | 65 | 65 |
| Pigweed | 95 | 85 | 100 | 100 | 45 | 60 | 65 | 70 |
| Russian Thistle | 100 | 100 | 100 | 100 | 45 | 55 | 85 | 40 |
| Wheat | 70 | 70 | 80 | 75 | 20 | 15 | 35 | 25 |

| | Compounds | | | |
|---|---|---|---|---|
| 31 g ai/ha | 1 | 2 | 4 | 9 |
| Preemergence | | | | |
| Buckwheat, Wild | 60 | 65 | 80 | 85 |
| Chickweed | 65 | 60 | 70 | 95 |
| Galium | 80 | 90 | 100 | 100 |
| Kochia | 75 | 70 | 100 | 98 |
| Lambsquarters | 75 | 85 | 80 | 100 |
| Mustard, Wild | 65 | 70 | 85 | 70 |
| Pigweed | 70 | 70 | 90 | 80 |
| Russian Thistle | 100 | 100 | 100 | 100 |
| Wheat | 70 | 60 | 70 | 75 |

| | Compounds | | | |
|---|---|---|---|---|
| 16 g ai/ha | 1 | 2 | 4 | 9 |
| Preemergence | | | | |
| Buckwheat, Wild | 45 | 45 | 60 | 60 |
| Chickweed | 60 | 60 | 65 | 65 |
| Galium | 80 | 80 | 90 | 85 |
| Kochia | 65 | 55 | 85 | 70 |
| Lambsquarters | 65 | — | 70 | 65 |
| Mustard, Wild | 50 | 50 | 65 | 60 |
| Pigweed | 60 | 65 | 70 | 65 |
| Russian Thistle | 100 | 85 | 90 | 100 |
| Wheat | 35 | 45 | — | 60 |

Test E

Three plastic pots (ca. 16-cm diameter) per rate were partially filled with sterilized Tama silt loam soil comprising a 35:50:15 ratio of sand, silt and clay and 2.6% organic matter. Separate plantings for each of the three pots were as follows. Seeds from the U.S. of ducksalad (*Heteranthera limosa*), smallflower umbrella sedge (*Cyperus difformis*) and purple redstem (*Ammannia coccinea*), were planted into one 16-cm pot for each rate. Seeds from the U.S. of rice flatsedge (*Cyperus iria*), bearded (brdd.) sprangletop (*Leptochloa fusca* ssp. *fascicularis*), one stand of 9 or 10 water seeded rice seedlings (*Oryza sativa* cv. 'Japonica-M202'), and one stand of 6 transplanted rice seedlings (*Oryza sativa* cv. 'Japonica-M202') were planted into one 16-cm pot for each rate. Seeds from the U.S. of barnyardgrass (*Echinochloa crus-galli*), late watergrass (*Echinochloa oryzicola*), early watergrass (*Echinochloa oryzoides*) and junglerice (*Echinochloa colona*) were planted into one 16-cm pot for each rate. Plantings were sequential so that crop and weed species were at the 2.0 to 2.5-leaf stage at time of treatment.

Potted plants were grown in a greenhouse with day/night temperature settings of 29.5/26.7° C., and supplemental balanced lighting was provided to maintain a 16-hour photoperiod. Test pots were maintained in the greenhouse until test completion.

At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 days. Plant response ratings, summarized in Table E, are based on a scale of 0 to 100 where 0 is no effect and 100 is complete control. A dash (-) response means no test result.

TABLE E

| 500 g ai/ha | Compounds | | |
|---|---|---|---|
| | 44 | 61 | 62 |
| Flood | | | |
| Barnyardgrass | 10 | 65 | 100 |
| Ducksalad | 100 | 100 | 100 |
| Flatsedge, Rice | — | 95 | 100 |
| Junglerice | 20 | 25 | 65 |
| Redstem | 75 | 100 | 100 |
| Rice, Transplanted | 0 | 25 | 30 |
| Rice, Water Seeded | 20 | 35 | 60 |
| Sedge, Umbrella | 100 | 100 | 100 |
| Sprangletop, Brdd. | 95 | 65 | 75 |
| Watergrass, Early | 0 | 25 | 0 |
| Watergrass, Late | 20 | 25 | 20 |

| 250 g ai/ha | Compounds | | | | | | | | | | | | | |
|---|---|---|---|---|---|---|---|---|---|---|---|---|---|---|
| | 37 | 44 | 58 | 61 | 62 | 63 | 64 | 65 | 66 | 67 | 69 | 70 | 71 | 72 |
| Flood | | | | | | | | | | | | | | |
| Barnyardgrass | 0 | 0 | — | 0 | 50 | — | — | — | 35 | 40 | — | 0 | 60 | 0 |
| Ducksalad | 100 | 100 | 100 | 100 | 100 | 100 | 100 | 100 | 100 | 100 | 100 | 100 | 100 | 100 |
| Flatsedge, Rice | 90 | — | 100 | 40 | 65 | 85 | 100 | 100 | 0 | 60 | 100 | 65 | 0 | 100 |
| Junglerice | 0 | 20 | 0 | 25 | 50 | 30 | 0 | 40 | 0 | 65 | 0 | 0 | 45 | 0 |
| Redstem | 80 | 50 | 95 | 100 | 95 | 75 | 80 | 60 | 100 | 85 | 30 | 0 | 30 | 100 |
| Rice, Transplanted | 0 | 0 | 0 | 0 | 0 | 0 | 10 | 0 | 0 | 0 | 0 | 0 | 0 | 0 |
| Rice, Water Seeded | 0 | 0 | 20 | 10 | 10 | 30 | 0 | 10 | 0 | 0 | 0 | 0 | 0 | 0 |
| Sedge, Umbrella | 95 | 100 | 100 | 95 | 100 | 80 | 100 | 100 | 0 | 70 | 100 | 60 | 70 | 100 |
| Sprangletop, Brdd. | 0 | 50 | 60 | 65 | 45 | 65 | 0 | 40 | 0 | 30 | 0 | 0 | 60 | 0 |
| Watergrass, Early | — | 0 | — | 20 | 0 | 0 | 0 | 10 | 0 | 0 | 0 | 0 | 0 | 0 |
| Watergrass, Late | 0 | 0 | 0 | 20 | 20 | 0 | 20 | 25 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| | 73 | 74 | 84 | 88 | 91 | 94 | 95 | 96 | 98 | 99 | 111 | 117 | 118 | 128 |
| Flood | | | | | | | | | | | | | | |
| Barnyardgrass | 100 | 0 | 85 | 0 | 10 | 0 | 0 | 0 | 0 | 0 | 0 | 0 | 0 | 0 |
| Ducksalad | 100 | 100 | 100 | 100 | 100 | 100 | 100 | 100 | 100 | 100 | 100 | 100 | 100 | 100 |
| Flatsedge, Rice | 45 | 95 | 80 | 100 | — | 100 | 0 | 100 | 100 | 100 | 0 | 100 | 100 | 80 |
| Junglerice | 0 | 65 | 50 | 90 | 70 | 0 | 0 | 0 | 0 | 0 | 0 | 0 | 65 | 10 |
| Redstem | 100 | 25 | 100 | 65 | 50 | 100 | 80 | 100 | 40 | 45 | 75 | 30 | 85 | 90 |
| Rice, Transplanted | 0 | 0 | 20 | 0 | 10 | 20 | 15 | 20 | 0 | 20 | 0 | 20 | 0 | 0 |
| Rice, Water Seeded | 0 | 0 | 30 | 0 | 20 | 10 | 15 | 10 | 0 | 20 | 0 | 0 | 0 | 0 |
| Sedge, Umbrella | 85 | 100 | 100 | 95 | 100 | 100 | 95 | 100 | 60 | — | 75 | 100 | 100 | 100 |
| Sprangletop, Brdd. | 70 | 0 | 40 | 95 | 30 | 40 | 0 | 0 | 0 | 0 | 0 | 0 | 85 | 80 |
| Watergrass, Early | 0 | 0 | 30 | 50 | 0 | 0 | 0 | 0 | 0 | 0 | 0 | 0 | 0 | 0 |
| Watergrass, Late | 20 | 0 | 20 | 0 | 0 | 0 | 0 | 0 | 0 | 0 | 0 | 0 | 0 | 0 |

| 250 g ai/ha | Compounds | |
|---|---|---|
| | 129 | 133 |
| Flood | | |
| Barnyardgrass | 0 | 0 |
| Ducksalad | 100 | 100 |
| Flatsedge, Rice | 100 | 100 |
| Junglerice | 0 | 0 |
| Redstem | 95 | 85 |
| Rice, Transplanted | 0 | 0 |
| Rice, Water Seeded | 0 | 35 |
| Sedge, Umbrella | 100 | 100 |
| Sprangletop, Brdd. | 70 | 0 |
| Watergrass, Early | 0 | 0 |
| Watergrass, Late | 0 | 0 |

| 125 g ai/ha | Compounds | | | | | | | | | | | | | |
|---|---|---|---|---|---|---|---|---|---|---|---|---|---|---|
| | 37 | 44 | 58 | 61 | 62 | 63 | 64 | 65 | 66 | 67 | 69 | 70 | 71 | 72 |
| Flood | | | | | | | | | | | | | | |
| Barnyardgrass | 0 | 0 | — | 0 | 0 | — | — | — | 0 | 40 | 0 | 0 | 0 | 0 |
| Ducksalad | 100 | 100 | 100 | 100 | 100 | 100 | 100 | 100 | 100 | 100 | 100 | 100 | 100 | 100 |

TABLE E-continued

| | | | | | | | | | | | | | | |
|---|---|---|---|---|---|---|---|---|---|---|---|---|---|---|
| Flatsedge, Rice | 75 | — | 100 | 40 | 45 | 85 | 100 | 100 | 0 | 60 | 100 | 30 | 0 | 100 |
| Junglerice | 0 | 0 | 0 | 20 | 40 | 0 | 0 | 40 | 0 | 30 | 0 | 0 | 0 | 0 |
| Redstem | 40 | 20 | 95 | 80 | 85 | 75 | 60 | 50 | 40 | 0 | 0 | 0 | 0 | 35 |
| Rice, Transplanted | 0 | 0 | 0 | 0 | 0 | 0 | 10 | 0 | 0 | 0 | 0 | 0 | 0 | 0 |
| Rice, Water Seeded | 0 | 0 | 0 | 0 | 0 | 20 | 0 | 0 | 0 | 0 | 0 | 0 | 0 | 0 |
| Sedge, Umbrella | 65 | 90 | 95 | 85 | 95 | 75 | 100 | 100 | 0 | 40 | 90 | 0 | 30 | 90 |
| Sprangletop, Brdd. | 0 | 30 | 60 | 60 | 30 | 40 | 0 | 40 | 0 | 30 | 0 | 0 | 0 | 0 |
| Watergrass, Early | — | 0 | — | 0 | 0 | 0 | 0 | 0 | 0 | 0 | 0 | 0 | 0 | 0 |
| Watergrass, Late | 0 | 0 | 0 | 20 | 20 | 0 | 20 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 73 | 74 | 84 | 88 | 91 | 94 | 95 | 96 | 98 | 99 | 111 | 117 | 118 | 128 |
| Flood | | | | | | | | | | | | | | |
| Barnyardgrass | 90 | — | 20 | 0 | 10 | 0 | 0 | 0 | 0 | 0 | 0 | 0 | 0 | 0 |
| Ducksalad | 100 | 100 | 100 | 100 | 100 | 100 | 100 | 100 | 100 | 100 | 100 | 100 | 100 | 100 |
| Flatsedge, Rice | — | 90 | 60 | 100 | — | 100 | 0 | 100 | 100 | 100 | 0 | 100 | 95 | 60 |
| Junglerice | 0 | 0 | 50 | 0 | 0 | 0 | 0 | 0 | 0 | 0 | 0 | 0 | 65 | 0 |
| Redstem | 100 | 20 | 70 | 0 | 30 | 100 | 70 | 100 | 40 | 0 | 30 | 0 | 50 | 90 |
| Rice, Transplanted | 0 | 0 | 0 | 0 | 0 | 10 | 0 | 10 | 0 | 0 | 0 | 0 | 0 | 0 |
| Rice, Water Seeded | 0 | 0 | 0 | 0 | 10 | 10 | 0 | 10 | 0 | 20 | 0 | 0 | 0 | 0 |
| Sedge, Umbrella | 35 | 95 | 90 | 85 | 100 | 100 | 95 | 100 | 60 | — | 0 | 100 | 100 | 100 |
| Sprangletop, Brdd. | 50 | 0 | 0 | 85 | 30 | 20 | 0 | 0 | 0 | 0 | 0 | 70 | 0 | 0 |
| Watergrass, Early | 0 | 0 | 20 | 0 | 0 | 0 | 0 | 0 | 0 | 0 | 0 | 0 | 0 | 0 |
| Watergrass, Late | 0 | 0 | 0 | 0 | 0 | 0 | 0 | 0 | 0 | 0 | 0 | 0 | 0 | 0 |

| | Compounds | |
|---|---|---|
| 125 g ai/ha | 129 | 133 |
| Flood | | |
| Barnyardgrass | 0 | 0 |
| Ducksalad | 100 | 100 |
| Flatsedge, Rice | 100 | 95 |
| Junglerice | 0 | 0 |
| Redstem | 80 | 75 |
| Rice, Transplanted | 0 | 0 |
| Rice, Water Seeded | 0 | 0 |
| Sedge, Umbrella | 100 | 100 |
| Sprangletop, Brdd. | 0 | 0 |
| Watergrass, Early | 0 | 0 |
| Watergrass, Late | 0 | 0 |

| | Compounds | | | | | | | | | | | | | |
|---|---|---|---|---|---|---|---|---|---|---|---|---|---|---|
| 64 g ai/ha | 37 | 44 | 58 | 61 | 62 | 63 | 64 | 65 | 66 | 67 | 69 | 70 | 71 | 72 |
| Flood | | | | | | | | | | | | | | |
| Barnyardgrass | 0 | 0 | — | 0 | 0 | — | — | — | — | 0 | 0 | 0 | 0 | — |
| Ducksalad | 100 | 100 | 100 | 100 | 100 | 65 | 100 | 100 | 100 | 100 | 100 | 100 | 100 | 100 |
| Flatsedge, Rice | 0 | — | 100 | 0 | 0 | 75 | 90 | 100 | 0 | 30 | 100 | 0 | 0 | 100 |
| Junglerice | 0 | 0 | 0 | 20 | 30 | 0 | 0 | 0 | 0 | 0 | 0 | 0 | 0 | 0 |
| Redstem | 30 | 10 | 85 | 80 | 85 | 65 | 60 | 30 | 0 | 0 | 0 | 0 | 0 | 25 |
| Rice, Transplanted | 0 | 0 | 0 | 0 | 0 | 0 | 0 | 0 | 0 | 0 | 0 | 0 | 0 | 0 |
| Rice, Water Seeded | 0 | 0 | 0 | 0 | 0 | 0 | 0 | 0 | 0 | 0 | 0 | 0 | 0 | 0 |
| Sedge, Umbrella | 50 | 90 | 95 | 75 | 80 | 75 | 85 | 85 | 0 | 0 | 30 | 0 | 0 | 75 |
| Sprangletop, Brdd. | 0 | 30 | 60 | 35 | 0 | 40 | 0 | 0 | 0 | 0 | 0 | 0 | — | 0 |
| Watergrass, Early | — | 0 | — | 0 | 0 | 0 | 0 | 0 | 0 | 0 | 0 | 0 | 0 | 0 |
| Watergrass, Late | 0 | 0 | 0 | 20 | 20 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 64 g ai/ha | 73 | 74 | 84 | 88 | 91 | 94 | 95 | 96 | 98 | 99 | 111 | 117 | 118 | 128 |
| Flood | | | | | | | | | | | | | | |
| Barnyardgrass | 0 | 0 | 0 | 0 | 10 | 0 | 0 | 0 | 0 | 0 | 0 | 0 | 0 | 0 |
| Ducksalad | 100 | 100 | 100 | 100 | 100 | 100 | 100 | 100 | 100 | 100 | 85 | 100 | 100 | 100 |
| Flatsedge, Rice | 0 | 0 | 60 | 100 | — | 100 | 0 | 100 | 100 | 100 | 0 | 100 | 95 | 0 |
| Junglerice | 0 | 0 | 0 | 0 | 0 | 0 | 0 | 0 | 0 | 0 | 0 | 0 | 45 | 0 |
| Redstem | 90 | 0 | 20 | 0 | 0 | 75 | 30 | 90 | 0 | — | 30 | 0 | 30 | 80 |
| Rice, Transplanted | 0 | 0 | 0 | 0 | 0 | 10 | 0 | 0 | 0 | 0 | 0 | 0 | 0 | 0 |
| Rice, Water Seeded | 0 | 0 | 0 | 0 | 10 | — | 0 | 0 | 0 | 0 | 0 | 0 | 0 | 0 |
| Sedge, Umbrella | 0 | 80 | 80 | — | 30 | 100 | 95 | 100 | 60 | — | 0 | 100 | 100 | 70 |
| Sprangletop, Brdd. | 0 | 0 | 0 | 0 | 0 | 0 | 0 | 0 | 0 | 0 | 0 | 0 | 0 | 0 |

TABLE E-continued

| | | | | | | | | | | | | | | |
|---|---|---|---|---|---|---|---|---|---|---|---|---|---|---|
| Watergrass, Early | 0 | 0 | 10 | 0 | 0 | 0 | 0 | 0 | 0 | 0 | 0 | 0 | 0 | 0 |
| Watergrass, Late | 0 | 0 | 0 | 0 | 0 | 0 | 0 | 0 | 0 | 0 | 0 | 0 | 0 | 0 |

| | Compounds | |
|---|---|---|
| 64 g ai/ha | 129 | 133 |

Flood

| | | |
|---|---|---|
| Barnyardgrass | 0 | 0 |
| Ducksalad | 100 | 100 |
| Flatsedge, Rice | 100 | 95 |
| Junglerice | 0 | 0 |
| Redstem | 75 | 65 |
| Rice, Transplanted | 0 | 0 |
| Rice, Water Seeded | 0 | 0 |
| Sedge, Umbrella | 80 | 95 |
| Sprangletop, Brdd. | 0 | 0 |
| Watergrass, Early | 0 | 0 |
| Watergrass, Late | 0 | 0 |

| | Compounds | | | | | | | | | | | | |
|---|---|---|---|---|---|---|---|---|---|---|---|---|---|
| 32 g ai/ha | 37 | 44 | 58 | 61 | 62 | 63 | 64 | 65 | 66 | 67 | 69 | 70 | 71 | 72 |

Flood

| | 37 | 44 | 58 | 61 | 62 | 63 | 64 | 65 | 66 | 67 | 69 | 70 | 71 | 72 |
|---|---|---|---|---|---|---|---|---|---|---|---|---|---|---|
| Barnyardgrass | 100 | 0 | — | 0 | 0 | — | — | — | 0 | 0 | 0 | 0 | 0 | 0 |
| Ducksalad | 100 | 100 | 100 | 100 | 100 | 30 | 100 | 100 | 100 | 100 | 100 | 40 | 100 | 80 |
| Flatsedge, Rice | 0 | — | 100 | 0 | 0 | 75 | 85 | 80 | 0 | 0 | 70 | 0 | 0 | 100 |
| Junglerice | 0 | 0 | 0 | 0 | 20 | 0 | 0 | 0 | 0 | 0 | 0 | 0 | 0 | 0 |
| Redstem | 0 | 0 | 80 | 65 | 75 | 65 | 60 | 30 | 0 | 0 | 0 | 0 | 0 | 25 |
| Rice, Transplanted | 0 | 0 | 0 | 0 | 0 | 0 | 0 | 0 | 0 | 0 | 0 | 0 | 0 | 0 |
| Rice, Water Seeded | 0 | 0 | 0 | 0 | 0 | 0 | 0 | 0 | 0 | 0 | 0 | 0 | 0 | 0 |
| Sedge, Umbrella | 50 | 20 | 95 | 20 | 70 | 75 | 80 | 80 | 0 | 0 | 0 | 0 | 0 | 30 |
| Sprangletop, Brdd. | 0 | 20 | 40 | 35 | 0 | 0 | 0 | 0 | 0 | 0 | 0 | 0 | 0 | 0 |
| Watergrass, Early | — | 0 | — | 0 | 0 | 0 | 0 | 0 | 0 | 0 | 0 | 0 | 0 | 0 |
| Watergrass, Late | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 32 g ai/ha | 73 | 74 | 84 | 88 | 91 | 94 | 95 | 96 | 98 | 99 | 111 | 117 | 118 | 128 |

Flood

| | 73 | 74 | 84 | 88 | 91 | 94 | 95 | 96 | 98 | 99 | 111 | 117 | 118 | 128 |
|---|---|---|---|---|---|---|---|---|---|---|---|---|---|---|
| Barnyardgrass | — | 0 | 0 | 0 | 0 | 0 | 0 | 0 | 0 | 0 | 0 | 0 | 0 | 0 |
| Ducksalad | 100 | 100 | 100 | 100 | 100 | 100 | 100 | 100 | 100 | 100 | 0 | 100 | 100 | 100 |
| Flatsedge, Rice | 0 | 0 | 35 | 85 | — | 100 | 0 | 100 | 80 | — | 0 | 100 | 95 | 0 |
| Junglerice | 0 | 0 | 0 | 0 | 0 | 0 | 0 | 0 | 0 | 0 | 0 | 0 | 40 | 0 |
| Redstem | 0 | 0 | 20 | 0 | 0 | 65 | — | 85 | 0 | 0 | 20 | 0 | 20 | 75 |
| Rice, Transplanted | 0 | 0 | 0 | 0 | 0 | 0 | 0 | 0 | 0 | 0 | 0 | 0 | 0 | 0 |
| Rice, Water Seeded | 0 | 0 | 0 | 0 | 0 | 0 | 0 | 0 | 0 | 0 | 0 | 0 | 0 | 0 |
| Sedge, Umbrella | 0 | 0 | 80 | 40 | 0 | 100 | 95 | 100 | 60 | — | 0 | 85 | 95 | 60 |
| Sprangletop, Brdd. | 0 | 0 | 0 | 0 | 0 | 0 | 0 | 0 | 0 | 0 | 0 | 0 | 0 | 0 |
| Watergrass, Early | 0 | 0 | 0 | 0 | 0 | 0 | 0 | 0 | 0 | 0 | 0 | 0 | 0 | 0 |
| Watergrass, Late | 0 | 0 | 0 | 0 | 0 | 0 | 0 | 0 | 0 | 0 | 0 | 0 | 0 | 0 |

| | Compounds | |
|---|---|---|
| 32 g ai/ha | 129 | 133 |

Flood

| | | |
|---|---|---|
| Barnyardgrass | 0 | 0 |
| Ducksalad | 100 | 100 |
| Flatsedge, Rice | 100 | 65 |
| Junglerice | 0 | 0 |
| Redstem | 60 | 20 |
| Rice, Transplanted | 0 | 0 |
| Rice, Water Seeded | 0 | 0 |
| Sedge, Umbrella | 60 | 0 |
| Sprangletop, Brdd. | 0 | 0 |

TABLE E-continued

|  | | |
|---|---|---|
| Watergrass, Early | 0 | 0 |
| Watergrass, Late | 0 | 0 |

Compounds

| 16 g ai/ha | 37 | 58 | 63 | 64 | 65 | 66 | 67 | 69 | 70 | 71 | 72 | 73 | 74 | 84 |
|---|---|---|---|---|---|---|---|---|---|---|---|---|---|---|

Flood

| | 37 | 58 | 63 | 64 | 65 | 66 | 67 | 69 | 70 | 71 | 72 | 73 | 74 | 84 |
|---|---|---|---|---|---|---|---|---|---|---|---|---|---|---|
| Barnyardgrass | 0 | — | — | — | — | 0 | 0 | 0 | 0 | 0 | — | 0 | 0 | 0 |
| Ducksalad | 80 | 100 | 30 | 100 | 100 | 95 | 85 | 95 | 0 | 100 | 80 | 75 | 100 | 100 |
| Flatsedge, Rice | 0 | 40 | 60 | 75 | 0 | 0 | 0 | 65 | 0 | 0 | 90 | 0 | 0 | 25 |
| Junglerice | 0 | 0 | 0 | 0 | 0 | 0 | 0 | 0 | 0 | 0 | 0 | 0 | 0 | 0 |
| Redstem | 0 | 60 | 65 | 20 | 0 | 0 | 0 | 0 | 0 | 0 | 0 | 0 | 0 | 0 |
| Rice, Transplanted | 0 | 0 | 0 | 0 | 0 | 0 | 0 | 0 | 0 | 0 | 0 | 0 | 0 | 0 |
| Rice, Water Seeded | 0 | 0 | 0 | 0 | 0 | 0 | 0 | 0 | 0 | 0 | 0 | 0 | 0 | 0 |
| Sedge, Umbrella | 30 | 65 | 70 | 65 | 20 | 0 | 0 | 0 | 0 | 0 | 0 | 0 | 0 | 70 |
| Sprangletop, Brdd. | 0 | 20 | 0 | 0 | 0 | 0 | 0 | 0 | 0 | — | 0 | 0 | 0 | 0 |
| Watergrass, Early | — | — | 0 | 0 | 0 | 0 | 0 | 0 | 0 | 0 | 0 | 0 | 0 | 0 |
| Watergrass, Late | 0 | 0 | 0 | 0 | 0 | 0 | 0 | 0 | 0 | 0 | 0 | 0 | 0 | 0 |

Compounds

| 16 g ai/ha | 88 | 91 | 94 | 95 | 96 | 98 | 99 | 111 | 117 | 118 | 128 | 129 | 133 |
|---|---|---|---|---|---|---|---|---|---|---|---|---|---|

Flood

| | 88 | 91 | 94 | 95 | 96 | 98 | 99 | 111 | 117 | 118 | 128 | 129 | 133 |
|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 |
| Ducksalad | 95 | 100 | 100 | 100 | 100 | 0 | 95 | 0 | 100 | 100 | 95 | 100 | 100 |
| Flatsedge, Rice | 50 | — | 100 | 0 | 100 | 80 | 100 | 0 | 100 | 85 | 0 | 100 | 30 |
| Junglerice | 0 | 0 | 0 | 0 | 0 | 0 | 0 | 0 | 0 | 0 | 0 | 0 | 0 |
| Redstem | 0 | 0 | 0 | 30 | 0 | 0 | 0 | 0 | 0 | 0 | 0 | 30 | 0 |
| Rice, Transplanted | 0 | 0 | 0 | 0 | 0 | 0 | 0 | 0 | 0 | 0 | 0 | 0 | 0 |
| Rice, Water Seeded | 0 | 0 | 0 | 0 | 0 | 0 | 0 | 0 | 0 | 0 | 0 | 0 | 0 |
| Sedge, Umbrella | 40 | 0 | 100 | 0 | 100 | 60 | — | 0 | 60 | 85 | 0 | 0 | 0 |
| Sprangletop, Brdd. | 0 | — | 0 | 0 | 0 | 0 | 0 | 0 | 0 | 0 | 0 | 0 | 0 |
| Watergrass, Early | 0 | 0 | 0 | 0 | 0 | 0 | 0 | 0 | 0 | 0 | 0 | 0 | 0 |
| Watergrass, Late | 0 | 0 | 0 | 0 | 0 | 0 | 0 | 0 | 0 | 0 | 0 | 0 | 0 |

Test F

Seeds or nutlets of plant species selected from (turf) bermudagrass (*Cynodon dactylon*), Kentucky bluegrass (*Poa pratensis*), bentgrass (*Agrostis palustris*), hard fescue (*Festuca ovina*), large crabgrass (*Digitaria sanguinalis*), goosegrass (*Eleusine indica*), dallisgrass (*Paspalum dilatatum*), annual bluegrass (*Poa annua*), common chickweed (*Stellaria media*), dandelion (*Taraxacum officinale*), white clover (*Trifolium repens*), and yellow nutsedge (*Cyperus esculentus*) were planted and treated preemergence with the test chemical formulated in a non-phytotoxic solvent mixture which included a surfactant.

At the same time, plants selected from these crop and weed species were treated with postemergence applications of the test chemical formulated in the same manner. Plants ranged in height from 2 to 18 cm (1- to 4-leaf stage) for postemergence treatments. Treated plants and controls were maintained in a greenhouse for 12 to 14 days, after which time all species were compared to controls and visually evaluated. Plant response ratings, summarized in Table F, are based on a scale of 0 to 100 where 0 is no effect and 100 is complete control. A dash (-) response means no test result.

TABLE F

| | Compound 1 |
|---|---|
| Postemergence | |
| 500 g ai/ha | |
| Bentgrass | 70 |
| Bermudagrass, Turf | 70 |
| Bluegrass | 95 |
| Bluegrass, KY | 30 |
| Chickweed | 100 |
| Clover, White | 100 |
| Crabgrass, Large | 90 |
| Dallisgrass | 60 |
| Dandelion | 95 |
| Fescue, Hard | 0 |
| Goosegrass | 50 |
| Nutsedge, Yellow | 15 |
| 250 g ai/ha | |
| Bentgrass | 50 |
| Bermudagrass, Turf | 50 |
| Bluegrass | 70 |
| Bluegrass, KY | 0 |
| Chickweed | 85 |
| Clover, White | 100 |
| Crabgrass, Large | 75 |
| Dallisgrass | 75 |
| Dandelion | 85 |
| Fescue, Hard | 0 |
| Goosegrass | 40 |
| Nutsedge, Yellow | 15 |
| 125 g ai/ha | |
| Bentgrass | 50 |
| Bermudagrass, Turf | 40 |
| Bluegrass | 45 |
| Bluegrass, KY | 0 |
| Chickweed | 85 |
| Clover, White | 100 |
| Crabgrass, Large | 70 |
| Dallisgrass | 15 |
| Dandelion | 75 |
| Fescue, Hard | 0 |

TABLE F-continued

| | |
|---|---|
| Goosegrass | 35 |
| Nutsedge, Yellow | 10 |
| 62 g ai/ha | |
| Bentgrass | 30 |
| Bermudagrass, Turf | 20 |
| Bluegrass, KY | 0 |
| Chickweed | 80 |
| Clover, White | 90 |
| Crabgrass, Large | 45 |
| Dallisgrass | 0 |
| Dandelion | 75 |
| Fescue, Hard | 0 |
| Goosegrass | 10 |
| Nutsedge, Yellow | 10 |
| 31 g ai/ha | |
| Bentgrass | 0 |
| Bermudagrass, Turf | 0 |
| Bluegrass | 35 |
| Bluegrass, KY | 20 |
| Chickweed | 0 |
| Clover, White | 70 |
| Crabgrass, Large | 0 |
| Dallisgrass | 0 |
| Dandelion | 50 |
| Fescue, Hard | 0 |
| Goosegrass | 5 |
| Nutsedge, Yellow | 0 |

Preemergence 500 g ai/ha

| | |
|---|---|
| Bentgrass | 100 |
| Bermudagrass, Turf | 90 |
| Bluegrass | 70 |
| Bluegrass, KY | 80 |
| Chickweed | 100 |
| Clover, White | 100 |
| Crabgrass, Large | 100 |
| Dallisgrass | 95 |
| Dandelion | 100 |
| Fescue, Hard | 90 |
| Goosegrass | 85 |
| Nutsedge, Yellow | 70 |
| 250 g ai/ha | |
| Bentgrass | 90 |
| Bermudagrass, Turf | 80 |
| Bluegrass | 70 |
| Bluegrass, KY | 40 |
| Chickweed | 100 |
| Clover, White | 100 |
| Crabgrass, Large | 95 |
| Dallisgrass | 70 |
| Dandelion | 100 |
| Fescue, Hard | 60 |
| Goosegrass | 65 |
| Nutsedge, Yellow | 25 |
| 125 g ai/ha | |
| Bentgrass | 60 |
| Bermudagrass, Turf | 50 |
| Bluegrass | 45 |
| Bluegrass, KY | 30 |
| Chickweed | 100 |
| Clover, White | 100 |
| Crabgrass, Large | 85 |
| Dallisgrass | 45 |
| Dandelion | 100 |
| Fescue, Hard | 60 |
| Goosegrass | 30 |
| Nutsedge, Yellow | 30 |
| 62 g ai/ha | |
| Bentgrass | 60 |
| Bermudagrass, Turf | 40 |
| Bluegrass | 65 |
| Bluegrass, KY | 30 |
| Chickweed | 100 |
| Clover, White | 100 |
| Crabgrass, Large | 40 |
| Dallisgrass | 35 |
| Dandelion | 95 |
| Fescue, Hard | 60 |
| Goosegrass | 40 |
| Nutsedge, Yellow | 15 |
| 31 g ai/ha | |
| Bentgrass | 50 |
| Bermudagrass, Turf | 10 |
| Bluegrass | 20 |
| Bluegrass, KY | 0 |
| Chickweed | 80 |
| Clover, White | 80 |
| Crabgrass, Large | 15 |
| Dallisgrass | 10 |
| Dandelion | 35 |
| Fescue, Hard | 50 |
| Goosegrass | 30 |
| Nutsedge, Yellow | 0 |

Test G

Seeds or nutlets of plant species selected from bermudagrass (*Cynodon dactylon*), Surinam grass (*Brachiaria decumbens*), large crabgrass (*Digitaria sanguinalis*), green foxtail (*Setaria viridis*), goosegrass (*Eleusine indica*), johnsongrass (*Sorghum halepense*), kochia (*Kochia scoparia*), pitted morningglory (*Ipomoea lacunosa*), purple nutsedge (*Cyperus rotundus*), common ragweed (*Ambrosia elatior*), black mustard (*Brassica nigra*), guineagrass (*Panicum maximum*), dallisgrass (*Paspalum dilatatum*), barnyardgrass (*Echinochloa crus-galli*), southern sandbur (*Cenchrus echinatus*), common sowthistle (*Sonchus oleraceous*), prickly sida (*Sida spinosa*), Italian ryegrass (*Lolium multiflorum*), common purslane (*Portulaca oleracea*), broadleaf signalgrass (*Brachiaria platyphylla*), common groundsel (*Senecio vulgaris*), common chickweed (*Stellaria media*), tropical spiderwort (*Commelina benghalensis*), annual bluegrass (*Poa annua*), downy bromegrass (*Bromus tectorum*), itchgrass (*Rottboellia cochinchinensis*), quackgrass (*Elytrigia repens*), Canada horseweed (*Conyza canadensis*), field bindweed (*Convolvulus arvensis*), spanishneedles (*Bidens bipinnata*), common mallow (*Malva sylvestris*), and Russian thistle (*Salsola kali*) were planted and treated preemergence with test chemicals formulated in a non-phytotoxic solvent mixture which included a surfactant.

At the same time, plants selected from these weed species were treated with postemergence applications of some of the test chemicals formulated in the same manner. Plants ranged in height from 2 to 18 cm (1- to 4-leaf stage) for postemergence treatments. Treated plants and controls were maintained in a greenhouse for 12 to 21 days, after which time all species were compared to controls and visually evaluated.

At a different time, established container-grown grape (*Vitus vinifera*) vines, and olive (*Olea europaea*) and orange (*Citrus sinensis*) trees were treated with some of the test chemicals formulated in the same manner and applied to the soil surface and the lower 5 cm of the plant vines or trunks (post-directed application). Plants ranged in height from 30 to 100 cm. The applications were made using a hand sprayer delivering a volume of 990 L/ha. Treated plants and controls were maintained in a greenhouse for 28 days, after which time the treated plants were compared to controls and visually evaluated.

Also at a different time, seed pieces (nodes) of sugarcane (*Saccharum officinarum*) were planted and treated preemergence and/or postemergence with some of the test chemicals formulated in the same manner. Treated plants and controls were maintained in a greenhouse for 14 days, after which time the treated plants were compared to controls and visually evaluated.

Plant response ratings, summarized in Table G, are based on a scale of 0 to 100 where 0 is no effect and 100 is complete control. A dash (-) response means no test result.

TABLE G

| | Compound 1 |
|---|---|
| Postemergence | |
| 500 g ai/ha | |
| Barnyardgrass | 75 |
| Bermudagrass | 50 |
| Bindweed, Field | 95 |
| Black Mustard | 75 |
| Bluegrass | 50 |
| Bromegrass, Downy | 80 |
| Crabgrass, Large | 70 |
| Dallisgrass | 30 |
| Foxtail, Green | 60 |
| Goosegrass | 60 |
| Groundsel | 100 |
| Guineagrass | 95 |
| Horseweed | 100 |
| Itchgrass | 70 |
| Johnsongrass | 95 |
| Mallow | 95 |
| Morningglory | 100 |
| Nutsedge, Purple | 30 |
| Prickly Sida | 95 |
| Purslane | 100 |
| Quackgrass | 70 |
| Ragweed | 100 |
| Ryegrass, Italian | 40 |
| Sandbur | 95 |
| Signalgrass | 85 |
| Sowthistle | 100 |
| Spanishneedles | 95 |
| Spiderwort | 95 |
| Surinam Grass | 90 |
| 375 g ai/ha | |
| Barnyardgrass | 70 |
| Bermudagrass | 40 |
| Bindweed, Field | 95 |
| Black Mustard | 75 |
| Bluegrass | 50 |
| Bromegrass, Downy | 70 |
| Chickweed | 100 |
| Crabgrass, Large | 70 |
| Dallisgrass | 30 |
| Foxtail, Green | 50 |
| Goosegrass | 60 |
| Groundsel | 100 |
| Horseweed | 100 |
| Itchgrass | 60 |
| Johnsongrass | 95 |
| Kochia | 95 |
| Mallow | 95 |
| Morningglory | 100 |
| Nutsedge, Purple | 30 |
| Prickly Sida | 95 |
| Purslane | 100 |
| Quackgrass | 70 |
| Ragweed | 100 |
| Russian Thistle | 100 |
| Ryegrass, Italian | 40 |
| Sandbur | 95 |
| Signalgrass | 75 |
| Sowthistle | 95 |
| Spanishneedles | 95 |

TABLE G-continued

| | | | |
|---|---|---|---|
| Spiderwort | | 95 | |
| Surinam Grass | | 90 | |

| | Compound | | |
|---|---|---|---|
| 250 g ai/ha | 1 | 22 | 77 |
| Postemergence | | | |
| Barnyardgrass | 70 | 85 | 75 |
| Bermudagrass | 40 | 65 | 50 |
| Bindweed, Field | 95 | 100 | 100 |
| Black Mustard | 75 | 95 | 60 |
| Bluegrass | 40 | 75 | 40 |
| Bromegrass, Downy | 60 | 95 | 75 |
| Chickweed | 95 | 95 | 100 |
| Crabgrass, Large | 70 | 85 | 75 |
| Dallisgrass | 30 | 75 | 50 |
| Foxtail, Green | 30 | 75 | 40 |
| Goosegrass | 60 | 50 | 65 |
| Groundsel | 95 | — | 100 |
| Guineagrass | 95 | 100 | 75 |
| Horseweed | 100 | — | 80 |
| Itchgrass | 60 | 85 | 80 |
| Johnsongrass | 95 | — | 85 |
| Kochia | — | 100 | 98 |
| Mallow | 70 | 95 | 95 |
| Morningglory | 100 | 100 | 100 |
| Nutsedge, Purple | 20 | 15 | 40 |
| Prickly Sida | 90 | 95 | 80 |
| Purslane | 100 | 98 | 85 |
| Quackgrass | 60 | 85 | 60 |
| Ragweed | 95 | 100 | 100 |
| Russian Thistle | 100 | 100 | — |
| Ryegrass, Italian | 40 | 85 | 40 |
| Sandbur | 95 | 95 | 40 |
| Signalgrass | 75 | 85 | 70 |
| Sowthistle | 95 | 100 | 95 |
| Spanishneedles | 95 | — | 98 |
| Spiderwort | 95 | 98 | 100 |
| Surinam Grass | 85 | 95 | 70 |

| 125 g ai/ha | Compound 1 |
|---|---|
| Postemergence | |
| Barnyardgrass | 60 |
| Bermudagrass | 25 |
| Bindweed, Field | 95 |
| Black Mustard | 75 |
| Bluegrass | 30 |
| Bromegrass, Downy | 30 |
| Chickweed | 95 |
| Crabgrass, Large | 60 |
| Dallisgrass | 20 |
| Foxtail, Green | 20 |
| Goosegrass | 60 |
| Groundsel | 95 |
| Guineagrass | 70 |
| Horseweed | 70 |
| Itchgrass | 40 |
| Johnsongrass | 70 |
| Mallow | 60 |
| Morningglory | 100 |
| Nutsedge, Purple | 10 |
| Prickly Sida | 70 |
| Purslane | 100 |
| Quackgrass | 30 |
| Ragweed | 95 |
| Russian Thistle | 100 |
| Ryegrass, Italian | 10 |
| Sandbur | 60 |
| Signalgrass | 60 |

TABLE G-continued

| | |
|---|---|
| Sowthistle | 95 |
| Spanishneedles | 95 |
| Spiderwort | 95 |
| Surinam Grass | 60 |

| | Compound | |
|---|---|---|
| 125 g ai/ha | 22 | 77 |
| Postemergence | | |
| Barnyardgrass | 25 | 65 |
| Bermudagrass | 40 | 35 |
| Bindweed, Field | 100 | 100 |
| Black Mustard | 95 | 60 |
| Bluegrass | 40 | 40 |
| Bromegrass, Downy | 95 | 65 |
| Chickweed | 85 | 90 |
| Crabgrass, Large | 85 | 75 |
| Dallisgrass | 25 | 35 |
| Foxtail, Green | 50 | 40 |
| Goosegrass | 35 | 50 |
| Groundsel | 85 | 95 |
| Guineagrass | 95 | 65 |
| Horseweed | — | 80 |
| Itchgrass | 75 | 70 |
| Johnsongrass | — | 85 |
| Kochia | 100 | 98 |
| Mallow | 85 | 85 |
| Morningglory | 95 | 100 |
| Nutsedge, Purple | 0 | 0 |
| Prickly Sida | 95 | 80 |
| Purslane | 95 | 70 |
| Quackgrass | 75 | 60 |
| Ragweed | 98 | 98 |
| Russian Thistle | 100 | — |
| Ryegrass, Italian | 40 | 30 |
| Sandbur | 85 | 35 |
| Signalgrass | 50 | 60 |
| Sowthistle | 100 | 95 |
| Spanishneedles | — | 98 |
| Spiderwort | 95 | 90 |
| Surinam Grass | 65 | 65 |

| | Compound | | | |
|---|---|---|---|---|
| 62 g ai/ha | 1 | 22 | 64 | 77 |
| Postemergence | | | | |
| Barnyardgrass | 60 | 15 | 20 | 40 |
| Bermudagrass | 25 | 35 | 35 | 35 |
| Bindweed, Field | 90 | 100 | 90 | 98 |
| Black Mustard | 60 | 75 | 10 | 50 |
| Bluegrass | 20 | 15 | 0 | 0 |
| Bromegrass, Downy | 30 | 85 | 75 | 35 |
| Chickweed | — | 50 | — | 90 |
| Crabgrass, Large | 50 | 50 | 80 | 75 |
| Dallisgrass | 10 | 15 | 20 | 15 |
| Foxtail, Green | 10 | 25 | 0 | 35 |
| Goosegrass | 20 | 25 | 20 | 50 |
| Groundsel | 60 | 65 | 0 | 80 |
| Guineagrass | 60 | 65 | 0 | 65 |
| Horseweed | — | — | 60 | 75 |
| Itchgrass | 20 | 50 | 60 | 65 |
| Johnsongrass | 70 | — | 0 | 70 |
| Kochia | — | 98 | 90 | 98 |
| Mallow | 50 | — | 90 | 80 |
| Morningglory | 100 | 85 | 65 | 90 |
| Nutsedge, Purple | — | 0 | 35 | 0 |
| Prickly Sida | 70 | 90 | 75 | 80 |
| Purslane | 80 | 85 | 60 | 60 |

TABLE G-continued

| | | | | |
|---|---|---|---|---|
| Quackgrass | 10 | 65 | 35 | 40 |
| Ragweed | 75 | 98 | 100 | 95 |
| Russian Thistle | 100 | 100 | — | — |
| Ryegrass, Italian | 0 | 15 | 35 | 30 |
| Sandbur | 30 | 40 | 20 | 10 |
| Signalgrass | 20 | 25 | 30 | 50 |
| Sowthistle | 95 | 95 | 80 | 90 |
| Spanishneedles | 80 | — | 90 | 98 |
| Spiderwort | 95 | 85 | 90 | 75 |
| Surinam Grass | 30 | 35 | 10 | 25 |

| | Compound | | |
|---|---|---|---|
| | 22 | 64 | 77 |
| Postemergence | | | |
| 31 g ai/ha | | | |
| Barnyardgrass | 0 | 20 | 10 |
| Bermudagrass | 35 | 35 | 20 |
| Bindweed, Field | 100 | 80 | 98 |
| Black Mustard | 75 | 0 | 40 |
| Bluegrass | 0 | 0 | 0 |
| Bromegrass, Downy | 65 | 40 | 20 |
| Chickweed | 50 | — | 80 |
| Crabgrass, Large | 35 | 70 | 70 |
| Dallisgrass | 0 | 0 | 0 |
| Foxtail, Green | 15 | 0 | 0 |
| Goosegrass | 15 | 0 | 15 |
| Groundsel | 65 | 0 | 75 |
| Guineagrass | 55 | 0 | 0 |
| Horseweed | — | 60 | 50 |
| Itchgrass | 25 | 0 | 35 |
| Johnsongrass | — | 0 | 65 |
| Kochia | 98 | 85 | 95 |
| Mallow | 60 | 90 | 75 |
| Morningglory | 85 | 20 | 60 |
| Nutsedge, Purple | 0 | 35 | 0 |
| Prickly Sida | 85 | 75 | 75 |
| Purslane | 55 | 0 | 20 |
| Quackgrass | 40 | 20 | 10 |
| Ragweed | 85 | 100 | 75 |
| Russian Thistle | 100 | — | — |
| Ryegrass, Italian | 5 | 20 | 20 |
| Sandbur | 15 | 20 | 0 |
| Signalgrass | 15 | 0 | 30 |
| Sowthistle | 85 | 80 | 90 |
| Spanishneedles | — | 90 | 95 |
| Spiderwort | 40 | 80 | 50 |
| Surinam Grass | 15 | 0 | 10 |
| 16 g ai/ha | | | |
| Barnyardgrass | 0 | 20 | 0 |
| Bermudagrass | 15 | 20 | 10 |
| Bindweed, Field | 85 | 70 | 70 |
| Black Mustard | 50 | 0 | 25 |
| Bluegrass | 0 | 0 | 0 |
| Bromegrass, Downy | 15 | 20 | 0 |
| Chickweed | — | — | 10 |
| Crabgrass, Large | 15 | 50 | 60 |
| Dallisgrass | 0 | 0 | 0 |
| Foxtail, Green | 0 | 0 | 0 |
| Goosegrass | 5 | 0 | 0 |
| Groundsel | 65 | 0 | 40 |
| Guineagrass | 5 | 0 | 0 |
| Horseweed | — | 60 | 40 |
| Itchgrass | 15 | 0 | 0 |
| Johnsongrass | — | 0 | 20 |
| Kochia | 98 | 75 | 90 |
| Mallow | 40 | 80 | 65 |
| Morningglory | 50 | 0 | 50 |
| Nutsedge, Purple | 0 | 35 | 0 |
| Prickly Sida | 75 | 65 | 70 |

TABLE G-continued

| | | | |
|---|---|---|---|
| Purslane | 50 | 0 | 20 |
| Quackgrass | 15 | 20 | 0 |
| Ragweed | 65 | 75 | 75 |
| Russian Thistle | 95 | — | — |
| Ryegrass, Italian | 0 | 10 | 0 |
| Sandbur | 0 | 0 | 0 |
| Signalgrass | 5 | 0 | 0 |
| Sowthistle | 75 | 80 | 75 |
| Spanishneedles | — | 75 | 75 |
| Spiderwort | 15 | 80 | 10 |
| Surinam Grass | 0 | 0 | 0 |

| 8 g ai/ha | Compound 64 |
|---|---|

Postemergence

| | |
|---|---|
| Barnyardgrass | 0 |
| Bermudagrass | 0 |
| Bindweed, Field | 60 |
| Black Mustard | 0 |
| Bluegrass | 0 |
| Bromegrass, Downy | 0 |
| Crabgrass, Large | 30 |
| Dallisgrass | 0 |
| Foxtail, Green | 0 |
| Goosegrass | 0 |
| Groundsel | 0 |
| Guineagrass | 0 |
| Horseweed | 60 |
| Itchgrass | 0 |
| Johnsongrass | 0 |
| Kochia | 65 |
| Mallow | 65 |
| Morningglory | 0 |
| Nutsedge, Purple | 0 |
| Prickly Sida | 40 |
| Purslane | 0 |
| Quackgrass | 0 |
| Ragweed | 75 |
| Ryegrass, Italian | 0 |
| Sandbur | 0 |
| Signalgrass | 0 |
| Sowthistle | 65 |
| Spanishneedles | 65 |
| Spiderwort | 65 |
| Surinam Grass | 0 |

| | Compounds | |
|---|---|---|
| 1500 g ai/ha | 1 | 4 |

Post-Directed

| | | |
|---|---|---|
| Grape | 100 | 100 |
| Olive | 50 | — |
| Orange | 50 | 75 |

| 900 g ai/ha | Compound 4 |
|---|---|

Post-Directed

| | |
|---|---|
| Olive | 50 |

| | Compounds | |
|---|---|---|
| | 1 | 9 |

Postemergence

| 500 g ai/ha | | |
|---|---|---|
| Sugarcane | 38 | 17 |
| 250 g ai/ha | | |
| Sugarcane | 13 | 7 |
| 125 g ai/ha | | |
| Sugarcane | 3 | 0 |
| 62 g ai/ha | | |

TABLE G-continued

| | | |
|---|---|---|
| Sugarcane | 0 | 0 |
| 31 g ai/ha | | |
| Sugarcane | 0 | 0 |

| | Compounds | | |
|---|---|---|---|
| 500 g ai/ha | 1 | 4 | 9 |

Preemergence

| | | | |
|---|---|---|---|
| Barnyardgrass | 70 | 100 | 95 |
| Bermudagrass | 70 | 100 | 100 |
| Bindweed, Field | 100 | 100 | 100 |
| Black Mustard | 100 | 100 | 100 |
| Bluegrass | 85 | 100 | 100 |
| Bromegrass, Downy | 95 | 100 | 100 |
| Chickweed | 100 | 100 | 100 |
| Crabgrass, Large | 90 | 100 | 100 |
| Dallisgrass | 95 | 100 | 100 |
| Foxtail, Green | 90 | 100 | 100 |
| Goosegrass | 50 | 90 | 95 |
| Groundsel | 100 | 100 | — |
| Guineagrass | 100 | 100 | 100 |
| Horseweed | 100 | 100 | 100 |
| Itchgrass | 90 | 95 | 85 |
| Johnsongrass | 75 | 95 | 95 |
| Kochia | 100 | — | — |
| Mallow | 95 | 100 | 100 |
| Morningglory | 100 | 100 | 100 |
| Nutsedge, Purple | 100 | 100 | — |
| Prickly Sida | 100 | 100 | 100 |
| Purslane | 100 | 100 | — |
| Quackgrass | 95 | 100 | 100 |
| Ragweed | 100 | 100 | 100 |
| Russian Thistle | 100 | 100 | — |
| Ryegrass, Italian | 95 | 100 | 80 |
| Sandbur | 85 | 100 | 95 |
| Signalgrass | 95 | 95 | 100 |
| Sowthistle | 100 | 100 | — |
| Spanishneedles | 100 | 100 | 100 |
| Spiderwort | 100 | 100 | 100 |
| Surinam Grass | 100 | 95 | 90 |

| 375 g ai/ha | Compound 1 |
|---|---|

Preemergence

| | |
|---|---|
| Barnyardgrass | 70 |
| Bermudagrass | 70 |
| Bindweed, Field | 100 |
| Black Mustard | 100 |
| Bromegrass, Downy | 95 |
| Chickweed | 100 |
| Crabgrass, Large | 90 |
| Dallisgrass | 95 |
| Foxtail, Green | 90 |
| Goosegrass | 50 |
| Groundsel | 100 |
| Guineagrass | 100 |
| Horseweed | 100 |
| Itchgrass | 85 |
| Johnsongrass | 75 |
| Kochia | 100 |
| Mallow | 95 |
| Morningglory | 100 |
| Nutsedge, Purple | 100 |
| Prickly Sida | 100 |
| Purslane | 100 |
| Quackgrass | 95 |
| Ragweed | 100 |
| Russian Thistle | 100 |
| Ryegrass, Italian | 95 |
| Sandbur | 85 |
| Signalgrass | 75 |
| Sowthistle | 100 |
| Spanishneedles | 100 |
| Spiderwort | 100 |
| Surinam Grass | 95 |

TABLE G-continued

| | Compounds | | | | |
|---|---|---|---|---|---|
| | 1 | 4 | 9 | 22 | 77 |
| Preemergence | | | | | |
| 250 g ai/ha | | | | | |
| Barnyardgrass | 50 | 80 | 85 | 80 | 90 |
| Bermudagrass | 30 | 95 | 95 | 30 | 60 |
| Bindweed, Field | 100 | 100 | 100 | 100 | 100 |
| Black Mustard | 85 | 100 | 100 | 75 | 95 |
| Bluegrass | 85 | 80 | 95 | 60 | 40 |
| Bromegrass, Downy | 95 | 100 | 70 | 75 | 75 |
| Chickweed | 95 | 100 | 100 | 100 | 100 |
| Crabgrass, Large | 90 | 100 | 90 | 80 | 90 |
| Dallisgrass | 50 | 95 | 80 | 50 | 85 |
| Foxtail, Green | 50 | 100 | 100 | 20 | 90 |
| Goosegrass | 50 | 70 | 95 | 0 | 55 |
| Groundsel | 100 | 100 | — | 50 | 100 |
| Guineagrass | 85 | 100 | 100 | 95 | 95 |
| Horseweed | 100 | 100 | 100 | — | 100 |
| Itchgrass | 80 | 80 | 80 | 65 | 90 |
| Johnsongrass | 60 | 85 | 95 | 80 | 95 |
| Kochia | 100 | — | — | 100 | 100 |
| Mallow | 95 | 100 | 100 | 80 | 80 |
| Morningglory | 100 | 100 | 100 | 90 | 100 |
| Nutsedge, Purple | 100 | 100 | — | 50 | 100 |
| Prickly Sida | 100 | 100 | 100 | 95 | 95 |
| Purslane | 95 | 100 | — | 75 | 100 |
| Quackgrass | 90 | 100 | 70 | 30 | 80 |
| Ragweed | 100 | 100 | 100 | 100 | 100 |
| Russian Thistle | 100 | 100 | — | 100 | 100 |
| Ryegrass, Italian | 30 | 100 | 75 | 50 | 75 |
| Sandbur | 70 | 90 | 90 | 85 | 100 |
| Signalgrass | 75 | 95 | 80 | 80 | 95 |
| Sowthistle | 100 | 100 | — | 100 | 100 |
| Spanishneedles | 100 | 100 | 100 | — | — |
| Spiderwort | 100 | 100 | 100 | 100 | 100 |
| Surinam Grass | 95 | 80 | 80 | 90 | 100 |
| 125 g ai/ha | | | | | |
| Barnyardgrass | 20 | 70 | 70 | 70 | 85 |
| Bermudagrass | 20 | 90 | 95 | 0 | 10 |
| Bindweed, Field | 100 | 100 | 100 | 90 | 100 |
| Black Mustard | 80 | 95 | 75 | 65 | 90 |
| Bluegrass | 30 | 60 | 30 | 30 | 20 |
| Bromegrass, Downy | 20 | 70 | 50 | 20 | 10 |
| Chickweed | 95 | 100 | 100 | 90 | 100 |
| Crabgrass, Large | 30 | 75 | 90 | 80 | 85 |
| Dallisgrass | 10 | 50 | 70 | 40 | 30 |
| Foxtail, Green | 10 | 70 | 85 | 10 | 85 |
| Goosegrass | — | 60 | 60 | 0 | 25 |
| Groundsel | 100 | 95 | — | — | 80 |
| Guineagrass | 70 | 95 | 100 | 90 | 85 |
| Horseweed | 95 | 100 | 100 | — | 100 |
| Itchgrass | 30 | 70 | 60 | 40 | 85 |
| Johnsongrass | 40 | 75 | 80 | 50 | 85 |
| Kochia | 100 | — | — | 100 | 100 |
| Mallow | 80 | 100 | 100 | 80 | 80 |
| Morningglory | 100 | 100 | 100 | 90 | 100 |
| Nutsedge, Purple | 100 | 100 | — | 40 | 100 |
| Prickly Sida | 100 | 100 | 100 | 80 | 90 |
| Purslane | 60 | 100 | — | 70 | 100 |
| Quackgrass | 60 | 90 | — | 20 | 50 |
| Ragweed | 95 | 100 | 100 | 95 | 100 |
| Russian Thistle | 100 | 100 | — | 100 | — |
| Ryegrass, Italian | 10 | 60 | 50 | 0 | 40 |
| Sandbur | 30 | 80 | 80 | 70 | 100 |
| Signalgrass | 70 | 70 | 80 | 10 | 90 |
| Sowthistle | 100 | 100 | — | 100 | 100 |
| Spanishneedles | 100 | 100 | 100 | — | — |
| Spiderwort | 100 | 100 | 100 | 100 | 95 |
| Surinam Grass | 95 | 60 | 70 | 35 | 90 |

| | Compounds | | | | | |
|---|---|---|---|---|---|---|
| 62 g ai/ha | 1 | 4 | 9 | 22 | 64 | 77 |
| Preemergence | | | | | | |
| Barnyardgrass | 0 | 50 | 30 | 30 | 10 | 75 |
| Bermudagrass | 10 | 20 | 10 | 0 | 0 | 0 |
| Bindweed, Field | 95 | 100 | 95 | 90 | 65 | 95 |
| Black Mustard | 30 | 95 | 70 | 60 | 35 | 85 |
| Bluegrass | 10 | 10 | 10 | 0 | 0 | 5 |
| Bromegrass, Downy | 0 | 30 | 10 | 0 | 0 | 0 |
| Chickweed | 70 | 100 | — | — | 0 | 90 |
| Crabgrass, Large | 20 | 60 | 70 | 40 | 35 | 80 |
| Dallisgrass | 0 | 0 | 10 | 0 | 0 | 15 |
| Foxtail, Green | 10 | 20 | 20 | 0 | 0 | 65 |
| Goosegrass | 0 | 10 | 10 | 0 | 0 | 5 |
| Groundsel | 60 | 95 | — | — | 40 | — |
| Guineagrass | 70 | 95 | 90 | 75 | 0 | 85 |
| Horseweed | 95 | 100 | 100 | — | 95 | 100 |
| Itchgrass | 10 | 70 | 30 | 20 | 20 | 45 |
| Johnsongrass | 20 | 60 | 40 | 20 | 0 | 75 |
| Kochia | 100 | — | — | 98 | 15 | 95 |
| Mallow | 50 | 100 | 90 | 75 | 0 | 50 |
| Morningglory | 95 | 100 | 70 | 60 | 0 | 100 |
| Nutsedge, Purple | 10 | 40 | — | 30 | 0 | 100 |
| Prickly Sida | 70 | 85 | 95 | 65 | 50 | 85 |
| Purslane | 10 | 60 | — | 50 | 35 | 75 |
| Quackgrass | 10 | 60 | 70 | 20 | 0 | 10 |
| Ragweed | 50 | 80 | 95 | 90 | 95 | 100 |
| Russian Thistle | 100 | — | — | 95 | 0 | 100 |
| Ryegrass, Italian | 0 | 30 | 20 | 0 | 0 | 0 |
| Sandbur | 0 | 30 | — | 0 | 0 | 100 |
| Signalgrass | 10 | 50 | 20 | 0 | 0 | 75 |
| Sowthistle | 95 | 100 | — | 90 | 90 | 100 |
| Spanishneedles | 100 | 100 | 100 | — | 35 | — |
| Spiderwort | 70 | 100 | 100 | 95 | 90 | 95 |
| Surinam Grass | 95 | 30 | 40 | 0 | 0 | 70 |

| | Compounds | | |
|---|---|---|---|
| | 22 | 64 | 77 |
| Preemergence | | | |
| 31 g ai/ha | | | |
| Barnyardgrass | 20 | 0 | 55 |
| Bermudagrass | 0 | 0 | 0 |
| Bindweed, Field | 75 | 0 | 90 |
| Black Mustard | 35 | 20 | 60 |
| Bluegrass | 0 | 0 | 0 |
| Bromegrass, Downy | 0 | 0 | 0 |
| Chickweed | 50 | 0 | 70 |
| Crabgrass, Large | 40 | 0 | 45 |
| Dallisgrass | 0 | 0 | 5 |
| Foxtail, Green | 0 | 0 | 5 |
| Goosegrass | 0 | 0 | 5 |
| Groundsel | 0 | 10 | 60 |
| Guineagrass | 35 | 0 | 70 |
| Horseweed | — | 95 | 90 |
| Itchgrass | 0 | 0 | 10 |
| Johnsongrass | 0 | 0 | 65 |
| Kochia | 70 | 10 | 95 |
| Mallow | 50 | 0 | 40 |
| Morningglory | 50 | 0 | 90 |
| Nutsedge, Purple | 0 | 0 | 100 |
| Prickly Sida | 50 | 30 | 75 |
| Purslane | 0 | 0 | 60 |
| Quackgrass | 0 | 0 | 0 |
| Ragweed | 75 | 65 | 95 |
| Russian Thistle | 75 | 0 | — |
| Ryegrass, Italian | 0 | 0 | 0 |
| Sandbur | 0 | 0 | 20 |
| Signalgrass | 0 | 0 | 10 |
| Sowthistle | 75 | 35 | 100 |

TABLE G-continued

| | | | |
|---|---|---|---|
| Spanishneedles | — | 0 | — |
| Spiderwort | 50 | 75 | 85 |
| Surinam Grass | 0 | 0 | 5 |

| 16 g ai/ha | | | |
|---|---|---|---|
| Barnyardgrass | 10 | 0 | 50 |
| Bermudagrass | 0 | 0 | 0 |
| Bindweed, Field | 65 | 0 | 80 |
| Black Mustard | 30 | 0 | 60 |
| Bluegrass | 0 | 0 | 0 |
| Bromegrass, Downy | 0 | 0 | 0 |
| Chickweed | 0 | — | — |
| Crabgrass, Large | 0 | 0 | 45 |
| Dallisgrass | 0 | 0 | 0 |
| Foxtail, Green | 0 | 0 | 0 |
| Goosegrass | 0 | 0 | 0 |
| Groundsel | — | 0 | 50 |
| Guineagrass | 0 | 0 | 30 |
| Horseweed | — | 75 | 70 |
| Itchgrass | 0 | 0 | 0 |
| Johnsongrass | 0 | 0 | 10 |
| Kochia | 35 | 0 | 85 |
| Mallow | 50 | — | 30 |
| Morningglory | 20 | 0 | 70 |
| Nutsedge, Purple | 0 | 0 | 100 |
| Prickly Sida | 50 | 0 | 70 |
| Purslane | 0 | 0 | 45 |
| Quackgrass | 0 | 0 | 0 |
| Ragweed | 65 | 65 | 80 |
| Russian Thistle | 65 | — | 85 |
| Ryegrass, Italian | 0 | 0 | 0 |
| Sandbur | 0 | 0 | 0 |
| Signalgrass | 0 | 0 | 5 |
| Sowthistle | 35 | 0 | 80 |
| Spanishneedles | — | 0 | — |
| Spiderwort | 0 | 50 | 60 |
| Surinam Grass | 0 | 0 | 0 |

| 8 g ai/ha | Compound 64 |
|---|---|
| Preemergence | |
| Barnyardgrass | 0 |
| Bermudagrass | 0 |
| Bindweed, Field | 0 |
| Black Mustard | 0 |
| Bluegrass | 0 |
| Bromegrass, Downy | 0 |
| Chickweed | 0 |
| Crabgrass, Large | 0 |
| Dallisgrass | 0 |
| Foxtail, Green | 0 |
| Goosegrass | 0 |
| Groundsel | 0 |
| Guineagrass | 0 |
| Horseweed | 0 |
| Itchgrass | 0 |
| Johnsongrass | 0 |
| Kochia | 0 |
| Mallow | 0 |
| Morningglory | 0 |
| Nutsedge, Purple | 0 |
| Prickly Sida | 0 |
| Purslane | 0 |
| Quackgrass | 0 |
| Ragweed | 65 |
| Russian Thistle | 0 |
| Ryegrass, Italian | 0 |
| Sandbur | 0 |
| Signalgrass | 0 |
| Sowthistle | 0 |

TABLE G-continued

| | |
|---|---|
| Spanishneedles | 0 |
| Spiderwort | 0 |
| Surinam Grass | 0 |

| Compound 1 |
|---|
| Preemergence |

| 375 g ai/ha | |
|---|---|
| Sugarcane | 0 |

| 250 g ai/ha | |
|---|---|
| Sugarcane | 0 |

| 125 g ai/ha | |
|---|---|
| Sugarcane | 0 |

| 62 g ai/ha | |
|---|---|
| Sugarcane | 0 |

Test H

This test evaluated the effect of mixtures of compound 1 with diflufenzopyr on several plant species. Seeds of test plants consisting of large crabgrass (DIGSA, *Digitaria sanguinalis* (L.) Scop.), lambsquarters (CHEAL, *Chenopodium album* L.), redroot pigweed (AMARE, *Amaranthus retroflexus* L.), cocklebur (XANST, *Xanthium strumarium* L.), barnyardgrass (ECHCG; *Echinochloa crus-galli* (L.) Beauv.), corn (ZEAMD, *Zea mays* L. cv. 'Pioneer 33G26'), scarlet (red) morningglory (IPOCO, *Ipomoea coccinea* L.), giant foxtail (SETFA, *Setaria faberi* Herrm.) and velvetleaf (ABUTH, *Abutilon theophrasti* Medik.) were planted in pots containing Redi-Earth® planting medium (Scotts Company, 14111 Scottslawn Road, Marysville, Ohio 43041) comprising spaghnum peat moss, vermiculite, wetting agent and starter nutrients. Seeds of small-seeded species were planted about 1 cm deep; larger seeds were planted about 2.5 cm deep. Plants were grown in a greenhouse using supplemental lighting to maintain a photoperiod of about 14 hours; daytime and nighttime temperatures were about 25-30° C. and 22-25° C., respectively. Balanced fertilizer was applied through the watering system. The plants were grown for 7 to 11 days so that at time of treatment the plants ranged in height from 2 to 18 cm (1- to 4-leaf stage). Treatments consisted of Compound 1 and diflufenzopyr alone and in combination, suspended or dissolved in an aqueous solvent comprising glycerin and Tween nonionic surfactant and applied as a foliage spray using a volume of 541 L/ha. Each treatment was replicated four times. The application solvent was observed to have no effect compared to untreated check plants. Treated plants and controls were maintained in the greenhouse and watered as needed with care to not wet the foliage for the first 24 hours after treatment. The effects on the plants approximately 3 weeks after treatment were visually compared to untreated controls. Plant response ratings were calculated as the means of the four replicates, based on a scale of 0 to 100 where 0 is no effect and 100 is complete control. Colby's Equation was used to determine the herbicidal effects expected from the mixtures. Colby's Equation (Colby, S. R. "Calculating Synergistic and Antagonistic Responses of Herbicide Combinations," *Weeds,* 15(1), pp 20-22 (1967)) calculates the expected additive effect of herbicidal mixtures, and for two active ingredients is of the form:

$$P_{a+b}=P_a+P_b-(P_aP_b/100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

The results and additive effects expected from Colby's Equation are listed in Table H.

TABLE H

Observed and Expected Results from Compound 1 Alone and in Combination with Diflufenzopyr*

| Application Rate (g a.i./ha) | | DIGSA | | CHEAL | | AMARE | | XANST | | ECHCG | |
|---|---|---|---|---|---|---|---|---|---|---|---|
| Cmpd 1 | Diflufenzopyr | Obsd. | Exp. | Obsd. | Exp. | Obsd. | Exp. | Obsd. | Exp. | Obsd. | Exp. |
| 125 | — | 81 | — | 100 | — | 100 | — | 97 | — | 90 | — |
| 62 | — | 37 | — | 100 | — | 97 | — | 98 | — | 42 | — |
| 31 | — | 7 | — | 98 | — | 91 | — | 87 | — | 25 | — |
| — | 50 | 8 | — | 80 | — | 95 | — | 68 | — | 23 | — |
| — | 25 | 1 | — | 76 | — | 91 | — | 60 | — | 10 | — |
| — | 12 | 0 | — | 61 | — | 73 | — | 43 | — | 5 | — |
| 125 | 50 | 88 | 83 | 100 | 100 | 100 | 100 | 100 | 99 | 93 | 92 |
| 62 | 25 | 77 | 38 | 100 | 100 | 100 | 100 | 92 | 99 | 85 | 48 |
| 31 | 12 | 62 | 7 | 100 | 99 | 100 | 98 | 100 | 93 | 85 | 29 |

| Application Rate (g a.i./ha) | | ZEAMD | | IPOCO | | SETFA | | ABUTH | |
|---|---|---|---|---|---|---|---|---|---|
| Cmpd 1 | Diflufenzopyr | Obsd. | Exp. | Obsd. | Exp. | Obsd. | Exp. | Obsd. | Exp. |
| 125 | — | 22 | — | 100 | — | 65 | — | 93 | — |
| 62 | — | 5 | — | 97 | — | 4 | — | 26 | — |
| 31 | — | 2 | — | 92 | — | 2 | — | 14 | — |
| — | 50 | 0 | — | 82 | — | 59 | — | 68 | — |
| — | 25 | 0 | — | 83 | — | 58 | — | 78 | — |
| — | 12 | 0 | — | 77 | — | 41 | — | 50 | — |
| 125 | 50 | 56 | 22 | 100 | 100 | 89 | 86 | 100 | 98 |
| 62 | 25 | 32 | 5 | 100 | 99 | 72 | 60 | 92 | 84 |
| 31 | 12 | 8 | 2 | 99 | 98 | 73 | 42 | 62 | 57 |

*Application rates are grams of active ingredient per hectare (g a.i./ha).

"Obsd." is observed effect.

"Exp." is expected effect calculated from Colby's Equation.

As can be seen from the results listed in Table H, most of the observed results were greater than expected from the Colby Equation, and in some cases much greater. Most notable was the greater than additive effect observed on crabgrass, barnyardgrass, corn and giant foxtail. The increase was less noticeable for other test species, but primarily because the expected effect was already near 100% at the rates tested.

Test I

This test evaluated the effect of mixtures of compound 9 with metsulfuron-methyl and with a 5:1 by weight combination of chlorsulfuron and metsulfuron-methyl on several plant species. Seeds of test plants consisting of wheat (TRZAW; *Triticum aestivum*), wild buckwheat, (POLCO; *Polygonum convolvulus*), redroot pigweed (AMARE; *Amaranthus retroflexus*), wild mustard (SINAR; *Sinapis arvensis*), catchweed bedstraw (GALAP; *Galium aparine*), Russian thistle (SASKR; *Salsola kali*), common chickweed (STEME; *Stellaria media*), kochia (KCHSC; *Kochia scoparia*), and lambsquarters (CHEAL; *Chenopodium album*) were planted into a blend of loam soil and sand. Plants were grown in a greenhouse using supplemental lighting to maintain a photoperiod of about 14 hours; daytime and nighttime temperatures were about 23° C. and 16° C., respectively. Balanced fertilizer was applied through the watering system. The plants were grown for 10 to 23 days so that at time of treatment the plants ranged from 2- to 8-leaf stage. Treatments consisted of Compound 9, metsulfuron-methyl, and chlorsulfuron-metsulfuron-methyl (5:1) alone and in combination. The treatments were formulated in a non-phytotoxic solvent mixture which included a surfactant and applied as a foliage spray using a volume of 280-458 L/ha. Each treatment was replicated three times. The application solvent was observed to have no effect compared to untreated check plants. Treated plants and controls were maintained in the greenhouse and watered as needed with care to not wet the foliage for the first 24 hours after treatment. The effects on the plants approximately 17 days after treatment were visually compared to untreated controls. Plant response ratings were calculated as the means of the three replicates, based on a scale of 0 to 100 where 0 is no effect and 100 is complete control. Colby's Equation was used to determine the herbicidal effects expected from the mixtures. The results and additive effects expected from Colby's Equation are listed in Table I.

TABLE I

Observed and Expected Results from Compound 9 Alone and in Combination with Metsulfuron-Methyl and with Chlorsulfuron-Metsulfuron-Methyl (5:1)*

| Application Rate (g a.i./ha) | | POLCO | | AMARE | | SINAR | | GALAP | | KCHSC | |
|---|---|---|---|---|---|---|---|---|---|---|---|
| Compound 9 | Metsulfuron-Methyl | Obsd. | Exp. | Obsd. | Exp. | Obsd. | Exp. | Obsd. | Exp. | Obsd. | Exp. |
| 8 | — | 27 | — | 70 | — | 47 | — | 87 | — | 87 | — |
| 4 | — | 17 | — | 62 | — | 45 | — | 83 | — | 70 | — |
| — | 8 | 0 | — | 0 | — | 0 | — | 0 | — | 0 | — |
| — | 4 | 0 | — | 0 | — | 0 | — | 0 | — | 0 | — |
| 8 | 8 | 32 | 27 | 58 | 70 | 45 | 47 | 85 | 87 | 70 | 87 |
| 8 | 4 | 38 | 27 | 77 | 70 | 48 | 47 | 82 | 87 | 80 | 87 |
| 4 | 8 | 38 | 17 | 65 | 62 | 48 | 45 | 85 | 83 | 85 | 70 |
| 4 | 4 | 30 | 17 | 52 | 62 | 33 | 45 | 80 | 83 | 80 | 70 |

| Application Rate (g a.i./ha) | | SASKR | | STEME | | CHEAL | | TRZAW | |
|---|---|---|---|---|---|---|---|---|---|
| Compound 9 | Metsulfuron-Methyl | Obsd. | Exp. | Obsd. | Exp. | Obsd. | Exp. | Obsd. | Exp. |
| 8 | — | 73 | — | 55 | — | 83 | — | 12 | — |
| 4 | — | 50 | — | 47 | — | 45 | — | 8 | — |
| — | 8 | 0 | — | 0 | — | 0 | — | 0 | — |
| — | 4 | 0 | — | 0 | — | 0 | — | 0 | — |
| 8 | 8 | 68 | 73 | 43 | 55 | 73 | 83 | 8 | 12 |
| 8 | 4 | 67 | 73 | 55 | 55 | 88 | 83 | 7 | 12 |
| 4 | 8 | 55 | 50 | 50 | 47 | 60 | 45 | 8 | 8 |
| 4 | 4 | 55 | 50 | 52 | 47 | 48 | 45 | 3 | 8 |

| Application Rate (g a.i./ha) | | TRZAW | |
|---|---|---|---|
| Compound 9 | Chlorsulfuron-Metsulfuron-Methyl | Obsd. | Exp. |
| 16 | — | 43 | — |
| 8 | — | 30 | — |
| — | 20 | 35 | — |
| — | 10 | 3 | — |
| 16 | 20 | 42 | 63 |
| 16 | 10 | 33 | 45 |

TABLE I-continued

Observed and Expected Results from Compound 9 Alone and in Combination with
Metsulfuron-Methyl and with Chlorsulfuron-Metsulfuron-Methyl (5:1)*

| 8 | 20 | 33 | 55 |
| 8 | 10 | 22 | 32 |

*Application rates are grams of active ingredient per hectare (g a.i./ha).
"Obsd." is observed effect.
"Exp." is expected effect calculated from Colby's Equation.

As can be seen from the results listed in Table I, some of the observed results for weeds were greater than expected from the Colby Equation. Most notable was the greater than additive effect observed on wild buckwheat, kochia, and lambsquarters.

In addition, observed results for nearly all treatments on wheat were less than expected from the Colby Equation, suggesting crop safening.

Test J

This test evaluated the effect of mixtures of compound 58 with azimsulfuron on several plant species. Three plastic pots (ca. 16-cm diameter) per rate were partially filled with sterilized Tama silt loam soil comprising a 35:50:15 ratio of sand, silt and clay and 2.6% organic matter. Separate plantings for each of the three pots were as follows. Seeds from the U.S. of ducksalad (HETLI; *Heteranthera limosa*), smallflower umbrella sedge (CYPDI; *Cyperus difformis*) and purple redstem (AMMCO; *Ammannia coccinea*), were planted into one 16-cm pot for each rate. Seeds from the U.S. of bearded sprangletop (LEFUF; *Leptochloa fusca* ssp. *fascicularis*), one stand of 9 or 10 water-seeded rice seedlings (ORYSW; *Oryza sativa* cv. 'Japonica-M202'), and one stand of 6 transplanted rice seedlings (ORYSP; *Oryza sativa* cv. 'Japonica-M202') were planted into one 16-cm pot for each rate. Seeds from the U.S. of barnyardgrass (ECHCG; *Echinochloa crusgalli*), late watergrass (ECOR2; *Echinochloa oryzicola*), early watergrass (ECHOR; *Echinochloa oryzoides*) and junglerice (ECHCO; *Echinochloa colona*) were planted into one 16-cm pot for each rate. Plantings were sequential so that crop and weed species were at the 2.0 to 2.5-leaf stage at time of treatment.

Potted plants were grown in a greenhouse with day/night temperature settings of 29.5/26.7° C., and supplemental balanced lighting was provided to maintain a 16-hour photoperiod. Test pots were maintained in the greenhouse until test completion.

At time of treatment, test pots were flooded to 3 cm above the soil surface and then treated by application directly to the paddy water of test compounds formulated in a non-phytotoxic solvent mixture which included a surfactant. The pots were maintained at the 3-cm water depth for the duration of the test. Treatments consisted of compound 58 and azimsulfuron alone and in combination. Effects of treatments on rice and weeds were visually evaluated by comparison to untreated controls after 21 days. Plant response ratings were calculated as the means of the three replicates and are summarized in Table J. The ratings are based on a scale of 0 to 100 where 0 is no effect and 100 is complete control. A dash (-) response means no test result. Colby's Equation was used to determine the herbicidal effects expected from the mixtures. The results and additive effects expected from Colby's Equation are listed in Table J.

TABLE J

Observed and Expected Results from Compound 58 Alone and in Combination with Azimsulfuron*

| Application Rate (g a.i./ha) | | ORYSW | | ORYSP | | AMMCO | | HETLI | | CYPDI | |
|---|---|---|---|---|---|---|---|---|---|---|---|
| Cmpd 58 | Azimsulfuron | Obsd. | Exp. | Obsd. | Exp. | Obsd. | Exp. | Obsd. | Exp. | Obsd. | Exp. |
| 64 | — | 20 | — | 0 | — | 90 | — | 100 | — | 100 | — |
| 32 | — | 10 | — | 0 | — | 30 | — | 100 | — | 100 | — |
| 16 | — | 10 | — | 0 | — | 0 | — | 100 | — | 100 | — |
| — | 8 | 10 | — | 0 | — | 95 | — | 100 | — | 100 | — |
| — | 4 | 0 | — | 0 | — | 0 | — | 30 | — | 100 | — |
| — | 2 | 0 | — | 0 | — | 0 | — | 30 | — | 95 | — |
| 64 | 8 | 10 | 28 | 15 | 0 | 95 | 100 | 100 | 100 | 100 | 100 |
| 32 | 8 | 0 | 19 | 10 | 0 | 95 | 97 | 100 | 100 | 100 | 100 |
| 16 | 8 | 10 | 19 | 10 | 0 | 80 | 95 | 100 | 100 | 100 | 100 |
| 64 | 4 | 0 | 20 | 0 | 0 | 70 | 90 | 100 | 100 | 100 | 100 |
| 32 | 4 | 0 | 10 | 0 | 0 | 70 | 30 | 100 | 100 | 100 | 100 |
| 16 | 4 | 15 | 10 | 0 | 0 | 70 | 0 | 100 | 100 | 100 | 100 |
| 64 | 2 | 0 | 20 | 0 | 0 | 70 | 90 | 100 | 100 | 100 | 100 |
| 32 | 2 | 0 | 10 | 0 | 0 | 30 | 30 | 100 | 100 | 100 | 100 |
| 16 | 2 | 0 | 10 | 0 | 0 | 0 | 0 | 100 | 100 | 100 | 100 |

| Application Rate (g a.i./ha) | | LEFUF | | ECHCG | | ECOR2 | | ECHOR | | ECHCO | |
|---|---|---|---|---|---|---|---|---|---|---|---|
| Compound 58 | Azimsulfuron | Obsd. | Exp. | Obsd. | Exp. | Obsd. | Exp. | Obsd. | Exp. | Obsd. | Exp. |
| 64 | — | 20 | — | 0 | — | 0 | — | 0 | — | 0 | — |
| 32 | — | 0 | — | 0 | — | 0 | — | 0 | — | 0 | — |
| 16 | — | 0 | — | 0 | — | 0 | — | 0 | — | 0 | — |
| — | 8 | 0 | — | 30 | — | 50 | — | 40 | — | 40 | — |

TABLE J-continued

Observed and Expected Results from Compound 58 Alone and in Combination with Azimsulfuron*

| | | | | | | | | | | | |
|---|---|---|---|---|---|---|---|---|---|---|---|
| — | 4 | 0 | — | 0 | — | 0 | — | 0 | — | 0 | — |
| — | 2 | 0 | — | 0 | — | 0 | — | 0 | — | 0 | — |
| 64 | 8 | 0 | 20 | 55 | 30 | 60 | 50 | 55 | 40 | 60 | 40 |
| 32 | 8 | 0 | 0 | 45 | 30 | 45 | 50 | 65 | 40 | 55 | 40 |
| 16 | 8 | 0 | 0 | 30 | 30 | 45 | 50 | 30 | 40 | 40 | 40 |
| 64 | 4 | 0 | 20 | 35 | 0 | 50 | 0 | 20 | 0 | 30 | 0 |
| 32 | 4 | 0 | 0 | 10 | 0 | 30 | 0 | 20 | 0 | 20 | 0 |
| 16 | 4 | 0 | 0 | 20 | 0 | 0 | 0 | 20 | 0 | 20 | 0 |
| 64 | 2 | 0 | 20 | 20 | 0 | 0 | 0 | 0 | 0 | 0 | 0 |
| 32 | 2 | 0 | 0 | 0 | 0 | 0 | 0 | 0 | 0 | 0 | 0 |
| 16 | 2 | 0 | 0 | 0 | 0 | 0 | 0 | 0 | 0 | 0 | 0 |

*Application rates are grams of active ingredient per hectare (g a.i./ha).
"Obsd." is observed effect.
"Exp." is expected effect calculated from Colby's Equation.

Test K

Seeds of plant species selected from sulfonylurea herbicide-susceptible (SU-susceptible) and sulfonylurea herbicide-resistant (SU-resistant) catchweed bedstraw (GALAP; *Galium aparine*) and wheat (TRZAW; *Triticum aestivum*) were treated with postemergence applications of test chemicals formulated in a non-phytotoxic solvent mixture which included a surfactant. Plants were treated at the 2-3 leaf stage and 2 whorl stage for wheat and catchweed bedstraw, respectively. Treated plants and controls were maintained in a controlled growth environment for 15 days after which time all species were compared to controls and visually evaluated. Plant response ratings, summarized in Table K, are based on a scale of 0 to 100 where 0 is no effect and 100 is complete control. A dash (-) response means no test result.

As can be seen from Table K, while chlorosulfuron had little effect on the sulfonylurea-resistant biotype of *Galium aparine* in this test, Compounds 1 and 9 gave good control of both resistant and susceptible biotypes.

Test L

This field study included treatments that consisted of Compound 1 and nicosulfuron alone and in combination on Canada thistle (*Cirsium arvense*) and daisy fleabane (*Erigeron* spp.). The plants ranged from 20 to 30 cm in height at the time of application during the month of May in the vicinity of Newark, Del. Compound 1 was formulated as a wettable powder containing 25% active ingredient by weight. Nicosulfuron was in the form of Accent® Herbicide, a water-dispersible granule formulation containing 75% active ingredient by weight. The formulations were dispersed in water in

TABLE K

Results from Treatment of Wheat and Sulfonylurea Susceptible and Resistant Catchweed Bedstraw with Compounds 1 and 9 and Chlorsulfuron

| Application Rate (g a.i./ha) | | | | GALAP | GALAP |
|---|---|---|---|---|---|
| Compound 1 | Compound 9 | Chlorsulfuron | TRZAW | SU-Susceptible | SU-Resistant |
| 125 | — | — | 38 | 100 | 100 |
| 62 | — | — | 30 | 100 | 100 |
| 31 | — | — | 25 | 98 | 100 |
| 16 | — | — | 0 | 98 | 100 |
| 8 | — | — | 0 | 80 | 100 |
| 4 | — | — | 0 | 63 | 100 |
| — | 125 | — | 40 | 100 | 100 |
| — | 62 | — | 38 | 100 | 100 |
| — | 31 | — | 38 | 100 | 100 |
| — | 16 | — | 25 | 100 | 100 |
| — | 8 | — | 20 | 100 | 100 |
| — | 4 | — | 0 | 75 | 100 |
| — | — | 16 | 20 | 100 | 5 | the sprayer tank before treatment. The treatments were made using a backpack sprayer calibrated to deliver 24 gallons per acre (224 L per hectare) to a 10 ft×30 ft (3 m×9 m) plot. Each treatment was replicated two times. The effects on the plants approximately 56 days after treatment were visually compared to untreated controls. Plant response ratings were calculated as the means of the two replicates, based on a scale of 0 to 100 where 0 is no effect and 100 is complete control. Colby's Equation was used to determine the herbicidal effects expected from the mixture. The results and additive effects expected from Colby's Equation are listed in Table L.

TABLE L

Observed (Obsd.) and Expected (Exp.) Results from Compound 1 Alone and in Combination with Nicosulfuron*

| Application Rate (g a.i./ha) | | Cirsium arvense | | Erigeron spp. | |
|---|---|---|---|---|---|
| Compound 1 | Nicosulfuron | Obsd. | Exp. | Obsd. | Exp. |
| 125 | — | 73 | — | 53 | — |
| — | 18 | 15 | — | 28 | — |
| 125 | 18 | 98 | 77 | 85 | 66 |

*Application rates are grams of active ingredient per hectare (g a.i./ha).
"Obsd." is observed effect.
"Exp." is expected effect calculated from Colby's Equation.

Table L shows that a synergistic effect was apparent in this test from the combination of compound 1 and nicosulfuron.

What is claimed is:

1. A compound selected from Formula I, an N-oxide or an agriculturally suitable salt thereof,

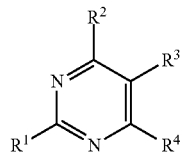

I wherein
$R^1$ is phenyl optionally substituted with 1-3 $R^7$;
$R^2$ is $((O)_jC(R^{15})(R^{16}))_kR$;
R is $CO_2H$ or a herbicidally effective derivative of $CO_2H$;
$R^3$ is halogen, nitro, $OR^{20}$, $SR^{21}$ or $N(R^{22})R^{23}$;
$R^4$ is —$N(R^{24})R^{25}$ or —$NO_2$;
each $R^7$ is independently halogen, cyano, nitro, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ hydroxyalkyl, $C_2$-$C_4$ alkoxyalkyl, $C_2$-$C_4$ haloalkoxyalkyl, $C_2$-$C_4$ alkenyl, $C_2$-$C_4$ haloalkenyl, $C_3$-$C_4$ alkynyl, $C_3$-$C_4$ haloalkynyl, hydroxy, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkenylthio, $C_2$-$C_4$ haloalkenylthio, $C_2$-$C_4$ alkenylsulfinyl, $C_2$-$C_4$ haloalkenylsulfinyl, $C_2$-$C_4$ alkenylsulfonyl, $C_2$-$C_4$ haloalkenylsulfonyl, $C_3$-$C_4$ alkynylthio, $C_3$-$C_4$ haloalkynylthio, $C_3$-$C_4$ alkynylsulfinyl, $C_3$-$C_4$ haloalkynylsulfinyl, $C_3$-$C_4$ alkynylsulfonyl, $C_3$-$C_4$ haloalkynylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl, phenyl, phenoxy and 5- or 6-membered heteroaromatic rings, each phenyl, phenoxy and 5- or 6-membered heteroaromatic ring optionally substituted with one to three substituents independently selected from $R^{45}$; or two adjacent $R^7$ are taken together as —$OCH_2O$—, —$CH_2CH_2O$—, —$OCH(CH_3)O$—, —$OC(CH_3)_2O$—, —$OCF_2O$—, —$CF_2CF_2O$—, —$OCF_2CF_2O$— or —$CH$=$CH$—$CH$=$CH$—;

$R^{15}$ is H, halogen, $C_1$-$C_4$ alkyl, $C_1$-$C_4$ haloalkyl, hydroxy, $C_1$-$C_4$ alkoxy or $C_2$-$C_4$ alkylcarbonyloxy;
$R^{16}$ is H, halogen, $C_1$-$C_4$ alkyl or $C_1$-$C_4$ haloalkyl; or
$R^{15}$ and $R^{16}$ are taken together as an oxygen atom to form, with the carbon atom to which they are attached, a carbonyl moiety;
$R^{20}$ is H, $C_1$-$C_4$ alkyl or $C_1$-$C_3$ haloalkyl;
$R^{21}$ is H, $C_1$-$C_4$ alkyl or $C_1$-$C_3$ haloalkyl;
$R^{22}$ and $R^{23}$ are independently H or $C_1$-$C_4$ alkyl;
$R^{24}$ is H, $C_1$-$C_4$ alkyl optionally substituted with 1-2 $R^{30}$, $C_2$-$C_4$ alkenyl optionally substituted with 1-2 $R^{31}$, or $C_2$-$C_4$ alkynyl optionally substituted with 1-2 $R^{32}$; or
$R^{24}$ is $C$(=$O$)$R^{33}$, nitro, $OR34$, $S(O)_2R^{35}$, $N(R^{36})R^{37}$ or $N$=$C(R^{62})R^{63}$;
$R^{25}$ is H, $C_1$-$C_4$ alkyl optionally substituted with 1-2 $R^{30}$ or $C$(=$O$)$R^{33}$; or
$R^{24}$ and $R^{25}$ are taken together as a radical selected from —$(CH_2)_4$—, —$(CH_2)_5$—, —$CH_2CH$=$CHCH_2$— and —$(CH_2)_2O(CH_2)_2$—, each radical optionally substituted with 1-2 $R^{38}$; or
$R^{24}$ and $R^{25}$ are taken together as =$C(R^{39})N(R^{40})R^{41}$ or =$C(R^{42})OR^{43}$;
each $R^{30}$, $R^{31}$ and $R^{32}$ is independently halogen, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl;
each $R^{33}$ is independently H, $C_1$-$C_{14}$ alkyl, $C_1$-$C_3$ haloalkyl, $C_1$-$C_4$ alkoxy, phenyl, phenoxy or benzyloxy;
$R^{34}$ is H, $C_1$-$C_4$ alkyl, $C_1$-$C_3$ haloalkyl or $CHR^{66}C(O)OR^{67}$;
$R^{35}$ is $C_1$-$C_4$ alkyl or $C_1$-$C_3$ haloalkyl;
$R^{36}$ is H, $C_1$-$C_4$ alkyl or $C$(=$O$)$R^{64}$;
$R^{37}$ is H or $C_1$-$C_4$ alkyl;
each $R^{38}$ is independently halogen, $C_1$-$C_3$ alkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl;
$R^{39}$ is H or $C_1$-$C_4$ alkyl;
$R^{40}$ and $R^{41}$ are independently H or $C_1$-$C_4$ alkyl; or
$R^{40}$ and $R^{41}$ are taken together as —$(CH_2)_4$—, —$(CH_2)_5$—, —$CH_2CH$=$CHCH_2$— or —$(CH_2)_2O(CH_2)_2$—;
$R^{42}$ is H or $C_1$-$C_4$ alkyl;
$R^{43}$ is $C_1$-$C_4$ alkyl;
each $R^{45}$ is independently halogen, cyano, nitro, $C_1$-$C_4$ alkyl, $C_1$-$C_4$ haloalkyl, $C_3$-$C_6$ cycloalkyl, $C_3$-$C_6$ halocycloalkyl, $C_2$-$C_4$ alkenyl, $C_2$-$C_4$ haloalkenyl, $C_3$-$C_4$ alkynyl, $C_3$-$C_4$ haloalkynyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{62}$ is H, $C_1$-$C_4$ alkyl or phenyl optionally substituted with 1-3 $R^{65}$;

$R^{63}$ is H or $C_1$-$C_4$ alkyl; or $R^{62}$ and $R^{63}$ are taken together as —$(CH_2)_4$— or —$(CH_2)_5$—;

$R^{64}$ is H, $C_1$-$C_{14}$ alkyl, $C_1$-$C_3$ haloalkyl, $C_1$-$C_4$ alkoxy, phenyl, phenoxy or benzyloxy;

each $R^{65}$ is independently $CH_3$, Cl or $OCH_3$;

$R^{66}$ is H, $C_1$-$C_4$ alkyl or $C_1$-$C_4$ alkoxy;

$R^{67}$ is H, $C_1$-$C_4$ alkyl or benzyl;

j is 0 or 1; and k is 0 or 1;

provided that:

(a) when k is 0, then j is 0;

(b) when $R^1$ is phenyl substituted by Cl in each of the meta positions, the phenyl is also substituted by $R^7$ in the para position;

(c) when $R^1$ is phenyl substituted by $R^7$ in the para position, said $R^7$ is other than tert-butyl, cyano or optionally substituted phenyl; and (d) the compound of Formula I is other than diethyl 6-amino-5-nitro-2-phenyl-4-pyrimidinemalonate.

2. The compound of claim 1 wherein $R^2$ is $CO_2R^{12}$, $CH_2OR^{13}$, $CH(OR^{46})(OR^{47})$, CHO, C(=NOR$^{14}$)H, C(=NNR$^{48}$R$^{49}$)H, (O)$_j$C(R$^{15}$)(R$^{16}$)CO$_2$R$^{17}$, C(=O)N(R$^{18}$)R$^{19}$, C(=S)OR$^{50}$, C(=O)SR$^{51}$, C(=S)SR$^{52}$ or C(=NR$^{53}$)YR$^{54}$;

$R^{12}$ is H, —CH$\vdash$C(O)O(CH$_2$)$_m$$\dashv$—, —N=C(R$^{55}$)R$^{56}$; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl, $C_2$-$C_{14}$ alkynyl and phenyl, each radical optionally substituted with 1-3 $R^{27}$; or $R^{12}$ is a divalent radical linking the carboxylic ester function $CO_2R^{12}$ of each of two pyrimidine ring systems of Formula I, the divalent radical selected from —CH$_2$—, —(CH$_2$)$_2$—, —(CH$_2$)$_3$— and —CH(CH$_3$)CH$_2$—;

$R^{13}$ is H, $C_1$-$C_{10}$ alkyl optionally substituted with 1-3 $R^{28}$, or benzyl;

$R^{14}$ is H, $C_1$-$C_4$ alkyl, $C_1$-$C_4$ haloalkyl or benzyl;

$R^{17}$ is $C_1$-$C_{10}$ alkyl optionally substituted with 1-3 $R^{29}$, or benzyl;

$R^{18}$ is H, $C_1$-$C_4$ alkyl, hydroxy, $C_1$-$C_4$ alkoxy or S(O)$_2$R$^{57}$;

$R^{19}$ is H or $C_1$-$C_4$ alkyl;

each $R^{27}$ is independently halogen, cyano, hydroxycarbonyl, $C_2$-$C_4$ alkoxycarbonyl, hydroxy, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ dialkylamino, —CH$\vdash$[ O(CH$_2$)$_n$$\dashv$] or phenyl optionally substituted with 1-3 $R^{44}$; or two $R^{27}$ are taken together as —OC(O)O— or —O(C(R$^{58}$)(R$^{58}$))$_{1-2}$O—; or two $R^{27}$ are taken together as an oxygen atom to form, with the carbon atom to which they are attached, a carbonyl moiety;

each $R^{28}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino; or two $R^{28}$ are taken together as an oxygen atom to form, with the carbon atom to which they are attached, a carbonyl moiety;

each $R^{29}$ is independently halogen, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino or $C_2$-$C_4$ dialkylamino;

each $R^{44}$ is independently halogen, $C_1$-$C_4$ alkyl, $C_1$-$C_3$ haloalkyl, hydroxy, $C_1$-$C_4$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or nitro;

$R^{46}$ and $R^{47}$ are independently $C_1$-$C_4$ alkyl or $C_1$-$C_3$ haloalkyl; or $R^{46}$ and $R^{47}$ are taken together as —$CH_2CH_2$—, —$CH_2CH(CH_3)$— or —$(CH_2)_3$—;

$R^{48}$ is H, $C_1$-$C_4$ alkyl, $C_1$-$C_4$ haloalkyl, $C_2$-$C_4$ alkylcarbonyl, $C_2$-$C_4$ alkoxycarbonyl or benzyl;

$R^{49}$ is H, $C_1$-$C_4$ alkyl or $C_1$-$C_4$ haloalkyl;

$R^{50}$, $R^{51}$ and $R^{52}$ are H; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl and $C_2$-$C_{14}$ alkynyl, each radical optionally substituted with 1-3 $R^{27}$;

Y is O, S or NR$^{61}$;

$R^{53}$ is H, $C_1$-$C_3$ alkyl, $C_1$-$C_3$ haloalkyl, $C_2$-$C_4$ alkoxyalkyl, OH or $C_1$-$C_3$ alkoxy;

$R^{54}$ is $C_1$-$C_3$ alkyl, $C_1$-$C_3$ haloalkyl or $C_2$-$C_4$ alkoxyalkyl; or $R^{53}$ and $R^{54}$ are taken together as —(CH$_2$)$_2$—, —CH$_2$CH(CH$_3$)—or —(CH$_2$)$_3$—;

$R^{55}$ and $R^{56}$ are independently $C_1$-$C_4$ alkyl;

$R^{57}$ is $C_1$-$C_4$ alkyl, $C_1$-$C_3$ haloalkyl or NR$^{59}$R$^{60}$;

each $R^{58}$ is independently selected from H and $C_1$-$C_4$ alkyl;

$R^{59}$ and $R^{60}$ are independently H or $C_1$-$C_4$ alkyl;

$R^{61}$ is H, $C_1$-$C_3$ alkyl, $C_1$-$C_3$ haloalkyl or $C_2$-$C_4$ alkoxyalkyl;

m is an integer from 2 to 3; and n is an integer from 1 to 4.

3. The compound of claim 2 wherein $R^3$ is halogen.

4. The compound of claim 2 wherein $R^1$ is phenyl substituted with a halogen, methyl or methoxy radical in the para position and optionally with 1-2 radicals selected from halogen and methyl in other positions; and $R^4$ is —N(R$^{24}$)R$^{25}$.

5. The compound of claim 4 wherein $R^2$ is $CO_2R^{12}$, $CH_2OR^{13}$, CHO or $CH_2CO_2R^{17}$.

6. The compound of claim 5 wherein $R^{24}$ is H, C(O)R$^{33}$ or $C_1$-$C_4$ alkyl optionally substituted with R$^{30}$; R$^{25}$ is H or $C_1$-$C_2$ alkyl; or R$^{24}$ and R$^{25}$ are taken together as =C(R$^{39}$)N(R$^{40}$)R$^{41}$.

7. The compound of claim 6 wherein $R^2$ is $CO_2R^{12}$; and $R^{24}$ and $R^{25}$ are H.

8. The compound of claim 7 wherein $R^{12}$ is H, $C_1$-$C_4$ alkyl or benzyl.

9. The compound of claim 1 selected from the group consisting of:

methyl 6-amino-5-chloro-2-(4-chlorophenyl)-4-pyrimidinecarboxylate, ethyl 6-amino-5-chloro-2-(4-chlorophenyl)-4-pyrimidinecarboxylate, 6-amino-5-chloro-2-(4-chlorophenyl)-4-pyrimidinecarboxylic acid, ethyl 6-amino-2-(4-bromophenyl)-5-chloro-4-pyrimidinecarboxylate, methyl 6-amino-2-(4-bromophenyl)-5-chloro-4-pyrimidinecarboxylate, and 6-amino-2-(4-bromophenyl)-5-chloro-4-pyrimidinecarboxylic acid.

10. A herbicidal mixture comprising a herbicidally effective amount of a compound of claim 1 and an effective amount of at least one additional active ingredient selected from the group consisting of an other herbicide and a herbicide safener.

11. A herbicidal mixture comprising synergistically effective amounts of a compound of claim 1 and an auxin transport inhibitor.

12. A herbicidal composition comprising a herbicidally effective amount of a compound of claim 1 and at least one of a surfactant, a solid diluent or a liquid diluent.

13. A method for controlling the growth of undesired vegetation comprising contacting the vegetation or its environment with a herbicidally effective amount of a compound of claim 1.

14. A herbicidal composition comprising a herbicidally effective amount of a compound of claim 1, an effective amount of at least one additional active ingredient selected from the group consisting of an other herbicide and a herbicide safener, and at least one of a surfactant, a solid diluent or a liquid diluent.

15. The compound of claim 1 selected from the group consisting of:
methyl 6-amino-5-chloro-2-(4-chlorophenyl)-4-pyrimidinecarboxylate,
ethyl 6-amino-5-chloro-2-(4-chlorophenyl)-4-pyrimidinecarboxylate,
6-amino-5-chloro-2-(4-chlorophenyl)-4-pyrimidinecarboxylic acid,
ethyl 6-amino-2-(4-bromophenyl)-5-chloro-4-pyrimidinecarboxylate,
methyl 6-amino-2-(4-bromophenyl)-5-chloro-4-pyrimidinecarboxylate, and
6-amino-2-(4-bromophenyl)-5-chloro-4-pyrimidinecarboxylic acid.

16. The compound of claim 15 selected from the group consisting of:
methyl 6-amino-5-chloro-2-(4-chlorophenyl)-4-pyrimidinecarboxylate,
ethyl 6-amino-5-chloro-2-(4-chlorophenyl)-4-pyrimidinecarboxylate,
6-amino-5-chloro-2-(4-chlorophenyl)-4-pyrimidinecarboxylic acid,
ethyl 6-amino-2-(4-bromophenyl)-5-chloro-4-pyrimidinecarboxylate,
6-amino-2-(4-bromophenyl)-5-chloro-4-pyrimidinecarboxylic acid, and
methyl 6-amino-2-(4-bromophenyl)-5-chloro-4-pyrimidinecarboxylate.

17. A compound of claim 1 which is methyl 6-amino-5-chloro-2-(4-chlorophenyl)-4-pyrimidinecarboxylate.

18. A compound of claim 1 which is ethyl 6-amino-5-chloro-2-(4-chlorophenyl)-4-pyrimidinecarboxylate.

19. A compound of claim 1 which is 6-amino-5-chloro-2-(4-chlorophenyl)-4-pyrimidinecarboxylic acid.

20. A herbicidal mixture comprising a herbicidally effective amount of a compound of claim 15, and an effective amount of at least one additional active ingredient selected from the group consisting of an other herbicide and a herbicide safener.

21. The herbicidal mixture of claim 10 wherein the additional active ingredient is selected from the group consisting of:
amidosulfuron, azimsulfuron, bensulfuron-methyl, bispyribac, bispyribac-sodium, chlorimuron-ethyl, chlorsulfuron, cinosulfuron, cloransulam-methyl, cyclosulfamuron, diclosulam, ethametsulfuron-methyl, ethoxysulfuron, flazasulfuron, florasulam, flucarbazone, flucarbazone-sodium, flucetosulfuron, flumetsulam, flupyrsulfuron-methyl, flupyrsulfuron-methyl-sodium, foramsulfuron, halosulfuron-methyl, imazamethabenz-methyl, imazamox, imazapic, imazapyr, imazaquin, imazaquin-ammonium, imazethapyr, imazosulfuron, iodosulfuron-methyl, mesosulfuron-methyl, metosulam, metsulfuron-methyl, nicosulfuron, oxasulfuron, penoxsulam, primisulfuron-methyl, propoxycarbazone, propoxycarbazone-sodium, prosulfuron, pyrazosulfuron-ethyl, pyribenzoxim, pyriftalid, pyriminobac-methyl, pyrithiobac, pyrithiobac-sodium, rimsulfuron, sulfometuron-methyl, sulfosulfuron, thifensulfuron-methyl, triasulfuron, tribenuron-methyl, trifloxysulfuron, triflusulfuron-methyl and tritosulfuron.

22. The herbicidal mixture of claim 21 wherein the additional active ingredient is in combination with at least one other active ingredient to form a combination of active ingredients selected from the group consisting of:
chlorsulfuron and flucarbazone-sodium;
chlorsulfuron and sulfometuron-methyl;
flumetsulam, nicosulfuron and rimsulfuron;
mesosulfuron-methyl and iodosulfuron-methyl;
metsulfuron-methyl and chlorsulfuron;
metsulfuron-methyl and sulfometuron-methyl;
metsulfuron-methyl, thifensulfuron-methyl and tribenuron-methyl;
imazapyr and metsulfuron-methyl;
imazapyr, metsulfuron-methyl and sulfometuron-methyl;
imazapyr and sulfometuron-methyl;
rimsulfuron and nicosulfuron;
rimsulfuron and thifensulfuron-methyl;
thifensulfuron-methyl and metsulfuron-methyl;
tribenuron-methyl and metsulfuron-methyl;
tribenuron-methyl and thifensulfuron-methyl;
bensulfuron-methyl and metsulfuron-methyl; and
metsulfuron-methyl and chlorimuron-ethyl.

23. The herbicidal mixture of claim 20 wherein the additional active ingredient is selected from the group consisting of:
amidosulfuron, azimsulfuron, bensulfuron-methyl, bispyribac, bispyribac-sodium, chlorimuron-ethyl, chlorsulfuron, cinosulfuron, cloransulam-methyl, cyclosulfamuron, diclosulam, ethametsulfuron-methyl, ethoxysulfuron, flazasulfuron, florasulam, flucarbazone, flucarbazone-sodium, flucetosulfuron, flumetsulam, flupyrsulfuron-methyl, flupyrsulfuron-methyl-sodium, foramsulfuron, halosulfuron-methyl, imazamethabenz-methyl, imazamox, imazapic, imazapyr, imazaquin, imazaquin-ammonium, imazethapyr, imazosulfuron, iodosulfuron-methyl, mesosulfuron-methyl, metosulam, metsulfuron-methyl, nicosulfuron, oxasulfuron, penoxsulam, primisulfuron-methyl, propoxycarbazone, propoxycarbazone-sodium, prosulfuron, pyrazosulfuron-ethyl, pyribenzoxim, pyriftalid, pyriminobac-methyl, pyrithiobac, pyrithiobac-sodium, rimsulfuron, sulfometuron-methyl, sulfosulfuron, thifensulfuron-methyl, triasulfuron, tribenuron-methyl, trifloxysulfuron, triflusulfuron-methyl and tritosulfuron.

24. The herbicidal mixture of claim 23 wherein the additional active ingredient is in combination with at least one other active ingredient to form a combination of active ingredients selected from the group consisting of:
chlorsulfuron and flucarbazone-sodium;
chlorsulfuron and sulfometuron-methyl;
flumetsulam, nicosulfuron and rimsulfuron;
mesosulfuron-methyl and iodosulfuron-methyl;
metsulfuron-methyl and chlorsulfuron;
metsulfuron-methyl and sulfometuron-methyl;
metsulfuron-methyl, thifensulfuron-methyl and tribenuron-methyl;
imazapyr and metsulfuron-methyl;
imazapyr, metsulfuron-methyl and sulfometuron-methyl;
imazapyr and sulfometuron-methyl;
rimsulfuron and nicosulfuron;
rimsulfuron and thifensulfuron-methyl;

thifensulfuron-methyl and metsulfuron-methyl;
tribenuron-methyl and metsulfuron-methyl;
tribenuron-methyl and thifensulfuron-methyl;
bensulfuron-methyl and metsulfuron-methyl; and
metsulfuron-methyl and chlorimuron-ethyl.

25. A herbicidal mixture comprising synergistically effective amounts of a compound of claim 15 and an auxin transport inhibitor.

26. The herbicidal mixture of claim 11 wherein the compound is selected from the group consisting of:
methyl 6-amino-5-chloro-2-(4-chlorophenyl)-4-pyrimidinecarboxylate,
ethyl 6-amino-5-chloro-2-(4-chlorophenyl)-4-pyrimidinecarboxylate,
6-amino-5-chloro-2-(4-chlorophenyl)-4-pyrimidinecarboxylic acid,
ethyl 6-amino-2-(4-bromophenyl)-5-chloro-4-pyrimidinecarboxylate,
6-amino-2-(4-bromophenyl)-5-chloro-4-pyrimidinecarboxylic acid, and
methyl 6-amino-2-(4-bromophenyl)-5-chloro-4-pyrimidinecarboxylate
and the auxin transport inhibitor is diflufenzopyr.

27. The herbicidal mixture of claim 11 wherein the compound is ethyl 6-amino-5-bromo-2-cyclopropyl-4-pyrimidinecarboxylate and the auxin transport inhibitor is diflufenzopyr.

28. The herbicidal mixture of claim 20 further comprising at least one of a surfactant, a solid diluent or a liquid diluent.

29. The herbicidal mixture of claim 25 further comprising at least one of a surfactant, a solid diluent or a liquid diluent.

30. The herbicidal mixture of claim 28 wherein the additional active ingredient is selected from the group consisting of:
amidosulfuron, azimsulfuron, bensulfuron-methyl, bispyribac, bispyribac-sodium, chlorimuron-ethyl, chlorsulfuron, cinosulfuron, cloransulam-methyl, cyclosulfamuron, diclosulam, ethametsulfuron-methyl, ethoxysulfuron, flazasulfuron, florasulam, flucarbazone, flucarbazone-sodium, flucetosulfuron, flumetsulam, flupyrsulfuron-methyl, flupyrsulfuron-methyl-sodium, foramsulfuron, halosulfuron-methyl, imazamethabenz-methyl, imazamox, imazapic, imazapyr, imazaquin, imazaquin-ammonium, imazethapyr, imazosulfuron, iodosulfuron-methyl, mesosulfuron-methyl, metosulam, metsulfuron-methyl, nicosulfuron, oxasulfuron, penoxsulam, primisulfuron-methyl, propoxycarbazone, propoxycarbazone-sodium, prosulfuron, pyrazosulfuron-ethyl, pyribenzoxim, pyriftalid, pyriminobac-methyl, pyrithiobac, pyrithiobac-sodium, rimsulfuron, sulfometuron-methyl, sulfosulfuron, thifensulfuron-methyl, triasulfuron, tribenuron-methyl, trifloxysulfuron, triflusulfuron-methyl and tritosulfuron.

31. The herbicidal mixture of claim 30 wherein the additional active ingredient is in combination with at least one other active ingredient to form a combination of active ingredients selected from the group consisting of:
chlorsulfuron and flucarbazone-sodium;
chlorsulfuron and sulfometuron-methyl;
flumetsulam, nicosulfuron and rimsulfuron;
mesosulfuron-methyl and iodosulfuron-methyl;
metsulfuron-methyl and chlorsulfuron;
metsulfuron-methyl and sulfometuron-methyl;
metsulfuron-methyl, thifensulfuron-methyl and tribenuron-methyl;
imazapyr and metsulfuron-methyl;
imazapyr, metsulfuron-methyl and sulfometuron-methyl;
imazapyr and sulfometuron-methyl;
rimsulfuron and nicosulfuron;
rimsulfuron and thifensulfuron-methyl;
thifensulfuron-methyl and metsulfuron-methyl;
tribenuron-methyl and metsulfuron-methyl;
tribenuron-methyl and thifensulfuron-methyl;
bensulfuron-methyl and metsulfuron-methyl; and
metsulfuron-methyl and chlorimuron-ethyl.

32. A method for controlling the growth of undesired vegetation comprising contacting the vegetation or its environment with the herbicidal mixture of claim 23.

33. A method for controlling the growth of undesired vegetation comprising contacting the vegetation or its environment with the herbicidal mixture of claim 24.

34. A method for controlling the growth of undesired vegetation comprising contacting the vegetation or its environment with the herbicidal mixture of claim 25.

35. A herbicidal mixture comprising a herbicidally effective amount of a compound of claim 16, and an effective amount of at least one additional active ingredient selected from the group consisting of an other herbicide and a herbicide safener.

36. A herbicidal mixture comprising synergistically effective amounts of a compound of claim 16 and an auxin transport inhibitor.

37. A compound of claim 1 wherein each $R^7$ is independently selected from halogen, $C_1$-$C_2$ alkyl, $C_1$ fluoroalkyl, $C_1$-$C_2$ alkoxy or $C_1$ fluoroalkoxy.

38. A compound of claim 1 wherein each $R^7$ is independently selected from halogen, methyl and methoxy.

* * * * *